(12) United States Patent
Bauer et al.

(10) Patent No.: US 6,361,977 B1
(45) Date of Patent: *Mar. 26, 2002

(54) METHODS OF USING MULTIVARIANT IL-3 HEMATOPOIESIS FUSION PROTEIN

(76) Inventors: S. Christopher Bauer, 4656 Orchard, New Haven, MO (US) 63068; Mark Allen Abrams, 7723 Blackberry Ave., St. Louis, MO (US) 63130; Sarah Ruth Braford-Goldberg, 4111 W. Pine #10, St. Louis, MO (US) 63108; Maire Helena Caparon, 109 Beechwood Ct., Chesterfield, MO (US) 63017; Alan Michael Easton, 2317 Seven Pines Dr. #7, Maryland Heights, MO (US) 63146; Barbara Kure Klein, 12917 Topping Estates, St. Louis, MO (US) 63131; John P. McKearn, 18612 Babler Meadows Dr., St. Louis; Peter O. Olins, 17507 Summit View, Glencoe, both of MO (US) 63038; Kumnan Paik, 1021 Alpine Ridge, Ballwin, MO (US) 63021; John W. Thomas, 13426 Mason Valley, Town & Country, MO (US) 63131

(*) Notice: Subject to any disclaimer, the term of this patent is extended or adjusted under 35 U.S.C. 154(b) by 0 days.

This patent is subject to a terminal disclaimer.

(21) Appl. No.: 08/446,872
(22) PCT Filed: Feb. 2, 1995
(86) PCT No.: PCT/US95/01185
  § 371 Date: Jun. 6, 1995
  § 102(e) Date: Jun. 6, 1995
(87) PCT Pub. No.: WO95/21254
  PCT Pub. Date: Aug. 10, 1995

Related U.S. Application Data

(63) Continuation-in-part of application No. 08/192,325, filed on Feb. 4, 1994, now Pat. No. 6,097,133, which is a continuation-in-part of application No. PCT/US93/11197, filed on Nov. 22, 1993, which is a continuation-in-part of application No. 07/981,044, filed on Nov. 24, 1992.

(51) Int. Cl.$^7$ ............................ C12P 21/04; A61K 45/00
(52) U.S. Cl. .................. 435/69.52; 435/69.7; 424/85.1; 424/85.2
(58) Field of Search .............................. 435/69.52, 69.7; 424/85.1, 85.2; 536/23.4, 23.5

(56) References Cited

U.S. PATENT DOCUMENTS

| 4,438,032 A | 3/1984 | Golde et al. |
| 4,810,643 A | 3/1989 | Souza |
| 4,877,729 A | 10/1989 | Clark et al. |
| 4,959,455 A | 9/1990 | Clark et al. |
| 4,999,291 A | 3/1991 | Souza |
| 5,032,395 A | 7/1991 | Clark et al. |
| 5,073,627 A | 12/1991 | Curtis et al. |
| 5,108,910 A | 4/1992 | Curtis et al. |
| 5,218,092 A | 6/1993 | Sasaki et al. |
| 5,376,367 A | 12/1994 | Williams ............... 424/85 |
| 5,516,512 A | * 5/1996 | Dorssers et al. ........... 424/85.2 |

FOREIGN PATENT DOCUMENTS

| EP | A 85306827.8 | 6/1986 |
| EP | A 89106339.8 | 10/1989 |
| EP | 0413383 | * 2/1991 |
| JP | 4-63595 | * 2/1992 |
| WO | WO 88/05469 | 7/1988 |
| WO | WO 90/01039 | 2/1990 |
| WO | WO 90/12877 | 11/1990 |
| WO | WO 91/02754 | 3/1991 |
| WO | WO 92/06166 | 2/1992 |
| WO | WO 92/04455 | 3/1992 |
| WO | 93/07171 | * 4/1993 |

OTHER PUBLICATIONS

Dorssers, L. C. J., et al. (1991) *J. Biol. Chem.* 266: 21310–317.*
Fojo et al., *Biochem.* vol. 17—No. 15:3109 (1978).
Park et al., *Biotech.* vol. 11:Nov. (1993).
Curtis et al., *Proc.Natl.Acad.Sci.* USA 88:5809 (1991).
Welch et al., Exp.Hem 21:647–655 (1993).
Williams et al., *Proc.Natl.Acad.Sci.* USA 88:5809 (1991).

* cited by examiner

Primary Examiner—Gary L. Kunz
Assistant Examiner—Robert S. Landsman
(74) Attorney, Agent, or Firm—S. Christopher Bauer

(57) ABSTRACT

The present invention relates to human interleukin-3 (hIL-3) variant or mutant proteins (muteins) fused with other colony stimulating factors (CSF), cytokines, lymphokines, interleukins, hematopoietic growth factors or IL-3 variants.

62 Claims, 6 Drawing Sheets

FIG. 1

```
     1                   5                         10
ATG GCT CCA ATG ACT CAG ACT ACT TCT CTT AAG ACT TCT
Met Ala Pro Met Thr Gln Thr Thr Ser Leu Lys Thr Ser
         15                  20                  25
TGG GTT AAC TGC TCT AAC ATG ATC GAT GAA ATT ATA ACA
Trp Val Asn Cys Ser Asn Met Ile Asp Glu Ile Ile Thr
             30                  35
CAC TTA AAG CAG CCA CCT TTG CCT TTG CTG GAC TTC AAC
His Leu Lys Gln Pro Pro Leu Pro Leu Leu Asp Phe Asn
     40              45                  50
AAC CTC AAT GGG GAA GAC CAA GAC ATT CTG ATG GAA AAT
Asn Leu Asn Gly Glu Asp Gln Asp Ile Leu Met Glu Asn
             55                  60
AAC CTT CGA AGG CCA AAC CTG GAG GCA TTC AAC AGG GCT
Asn Leu Arg Arg Pro Asn Leu Glu Ala Phe Asn Arg Ala
65                   70                  75
GTC AAG AGT TTA CAG AAT GCA TCA GCA ATT GAG AGC ATT
Val Lys Ser Leu Gln Asn Ala Ser Ala Ile Glu Ser Ile
             80                  85                  90
CTT AAA AAT CTC CTG CCA TGT CTG CCC CTG GCC ACG GCC
Leu Lys Asn Leu Leu Pro Cys Leu Pro Leu Ala Thr Ala
                 95                  100
GCA CCC ACG CGA CAT CCA ATC CAT ATC AAG GAC GGT GAC
Ala Pro Thr Arg His Pro Ile His Ile Lys Asp Gly Asp
    105                 110                 115
TGG AAT GAA TTC CGT CGT AAA CTG ACC TTC TAT CTG AAA
Trp Asn Glu Phe Arg Arg Lys Leu Thr Phe Tyr Leu Lys
            120                 125
ACC TTG GAG AAC GCG CAG GCT CAA CAG ACC ACT CTG TCG
Thr Leu Glu Asn Ala Gln Ala Gln Gln Thr Thr Leu Ser
130
CTA GCG ATC TTT TAA TAA          (SEQ ID NO: 197)
Leu Ala Ile Phe END END          (SEQ ID NO: 49)
```

METHODS OF USING MULTIVARIANT IL-3 HEMATOPOIESIS FUSION PROTEIN

This is a continuation-in-part of U.S. Ser. No. 08/192,325, filed Feb. 4, 1994, now U.S. Pat. No. 6,097,133; which is a continuation-in-part of international application PCT/US93/11197, filed on Nov. 22, 1993; which is a continuation-in-part of U.S. Ser. No. 07/981,044, filed Nov. 24, 1992, which is abandoned. The noted applications are incorporated herein by reference.

FIELD OF THE INVENTION

The present invention relates to fusion molecules composed of mutants or variants of human interleukin-3 (hIL-3) fused to a second colony stimulating factor (CSF) including cytokine, lymphokine, interleukin, hematopoietic growth factor or IL-3 variant with or without a linker

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies.

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and/or chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 307:233 (1984) and Yokota, et al., PROC. NATL. ACAD. SCI. USA 81:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. Nos. 4,877,729 and 4,959,454 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogs synthesized with an automated peptide synthesizer. The authors concluded that the stable tertiary structure of the complete molecule was required for full activity. A study on the role of the disulfide bridges showed that replacement of all four cysteines by alanine gave a molecule with ⅕₀₀th the activity as the native molecule. Replacement of two of the four Cys residues by Ala($Cys^{79}$, $Cys^{140}$→$Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA 85:7897 (1988)).

International Patent Application (PCT) WO 88/00598 discloses gibbon- and human-like IL-3. The hIL-3 contains a $Ser^8$→$Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1$→$Asp^1$, $Trp^{13}$→$Arg^{13}$ (pGB/IL-302) and $Ala^1$→$Asp^1$, $Met^3$→$Thr^3$ (pGB/IL-304) and one triple mutant $Ala^1$→$Asp^1$, $Leu^9$→$Pro^9$, $Trp^{13}$→$Arg^{13}$ (pGB/IL-303).

WO 88/05469 describes how deglycosylation mutants can be obtained and suggests mutants of $Arg^{54}Arg^{55}$ and $Arg^{108}Arg^{109}Lys^{110}$ might avoid proteolysis upon expression in Saccharomyces cerevisiae by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are $Met^2$→$Ile^2$ and $Ile^{131}$→$Leu^{131}$. It is not disclosed whether the contemplated neutralities were obtained for these two mutations.

WO 91/00350 discloses nonglycosylated hIL-3 analog proteins, for example, hIL-3 ($Pro^8Asp^{15}Asp^{70}$), $Met^3$ rhuIl-3

(Pro⁸Asp¹⁵Asp⁷⁰); Thr⁴ rhuIL-3 (Pro⁸Asp¹⁵Asp⁷⁰) and Thr⁶ rhuIL-3 (Pro⁸Asp¹⁵Asp⁷⁰). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met³, Thr⁴, or Thr⁶.

WO 91/12874 discloses cysteine added variants (CAVs) of IL-3 which have at least one Cys residue substituted for a naturally occurring amino acid residue.

U.S. Pat. No. 4,810,643 discloses the DNA sequence encoding human G-CSF.

WO 91/02754 discloses a fusion protein composed of GM-CSF and IL-3 which has increased biological activity compared to GM-CSF or IL-3 alone. Also disclosed are nonglycosylated IL-3 and GM-CSF analog proteins as components of the fusion.

WO 92/04455 discloses fusion proteins composed of IL-3 fused to a lymphokine selected from the group consisting of IL-3, IL-6, IL-7, IL-9, IL-11, EPO and G-CSF.

SUMMARY OF THE INVENTION

The present invention encompasses recombinant human interleukin-3 (hIL-3) variant or mutant proteins (muteins) fused to a second colony stimulating factor (CSF) include, cytokine, lymphokine, interleukin, hematopoietic growth factor (herein collectively referred to as "colony stimulating factors") or IL-3 variant with or without a linker. These hIL-3 muteins contain amino acid substitutions and may also have amino acid deletions at either/or both the N- and C-termini. This invention encompasses mixed function colony stimulating factors formed from covalently linked polypeptides, each of which may act through a different and specific cell receptor to initiate complementary biological activities.

Novel compounds of this invention are represented by the formulas

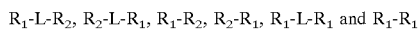

$R_1$-L-$R_2$, $R_2$-L-$R_1$, $R_1$-$R_2$, $R_2$-$R_1$, $R_1$-L-$R_1$ and $R_1$-$R_1$ where R1 is a hIL-3 variant which contains multiple amino acid substitutions and which may have portions of the hIL-3 molecule deleted, R2 is an Il-3, Il-3 variant or CSF with a different but complementary activity. The R1 polypeptide is fused either directly or through a linker segment to the R2 polypeptide. Thus L represents a chemical bond or polypeptide segment to which both R1 and R2 are fused. Preferably, these mutant IL-3 polypeptides of the present invention contain four or more amino acids which differ from the amino acids found at the corresponding positions in the native hIL-3 polypeptide. The invention also relates to pharmaceutical compositions containing the fusion molecules, DNA coding for the fusion molecules, and methods for using the fusion molecules. Additionally, the present invention relates to recombinant expression vectors comprising nucleotide sequences encoding the hIL-3 fusion molecules, related microbial expression systems, and processes for making the fusion molecules using the microbial expression systems.

These fusion molecules may be characterized by having the usual activity of both of the peptides forming the fusion molecule or it may be further characterized by having a biological or physiological activity greater than simply the additive function of the presence of IL-3 or the second colony stimulating factor alone. The fusion molecule may also unexpectedly provide an enhanced effect on the activity or an activity different from that expected by the presence of IL-3 or the second colony stimulating factor or IL-3 variant. The fusion molecule may also have an improved activity profile which may include reduction of undesirable biological activities associated with native hIL-3.

The present invention also includes mutants of hIL-3 in which from 1 to 14 amino acids have been deleted from the N-terminus and/or from 1 to 15 amino acids have been deleted from the C-terminus, containing multiple amino acid substitutions, to which a second colony stimulating factor or IL-3 variant has been fused. Preferred fusion molecules of the present invention are composed of hIL-3 variants in which amino acids 1 to 14 have been deleted from the N-terminus, amino acids 126 to 133 have been deleted from the C-terminus, and contains from about four to about twenty-six amino acid substitutions in the polypeptide sequence fused to second colony stimulating factor or IL-3 variant.

The present invention also provides fusion molecules which may function as IL-3 antagonists or as discrete antigenic fragments for the production of antibodies useful in immunoassay and immunotherapy protocols.

Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hemopoietins including and not limited to IL-3, GM-CSF and IL-5, which might trigger or augment the growth of cancer cells by virtue of their ability to bind to the IL-3 receptor complex while intrinsic activation properties of the ligand are diminished. IL-3, GM-CSF and/or IL-5 also play a role in certain asthmatic responses. An antagonist of the IL-3 receptor may have the utility in this disease by blocking receptor-mediated activation and recruitment of inflammatory cells.

In addition to the use of the fusion molecules of the present invention in vivo, it is envisioned that in vitro uses would include the ability to stimulate bone marrow and blood cell activation and growth before infusion into patients.

BRIEF DESCRIPTION OF THE DRAWINGS

FIG. 1 is the human IL-3 gene for E. coli expression (pMON5873), encoding the polypeptide sequence of natural (wild type) human IL-3 [SEQ ID NO:49], plus an initiator methionine, as expressed in E. coli, with the amino acids numbered from the N-terminus of the natural hIL-3.

DETAILED DESCRIPTION OF THE INVENTION

Figure 2:
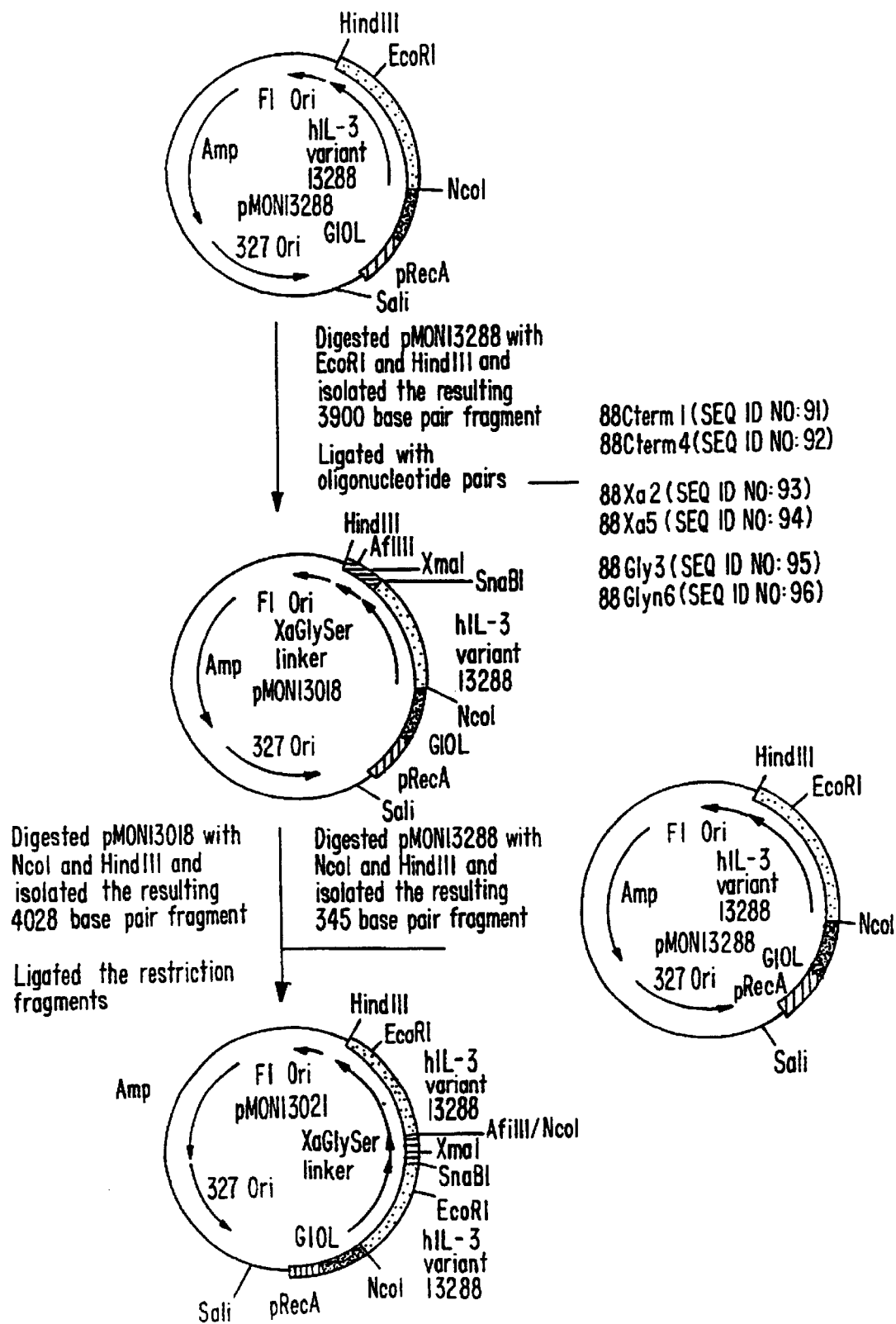
FIG. 2 is the construction of plasmids pMON13018 and pMON13021. The plasmid pMON13018 is an intermediate plasmid used to construct the plasmid pMON13021 which encodes the polypeptide fusion pMON13021.
Figure 3:
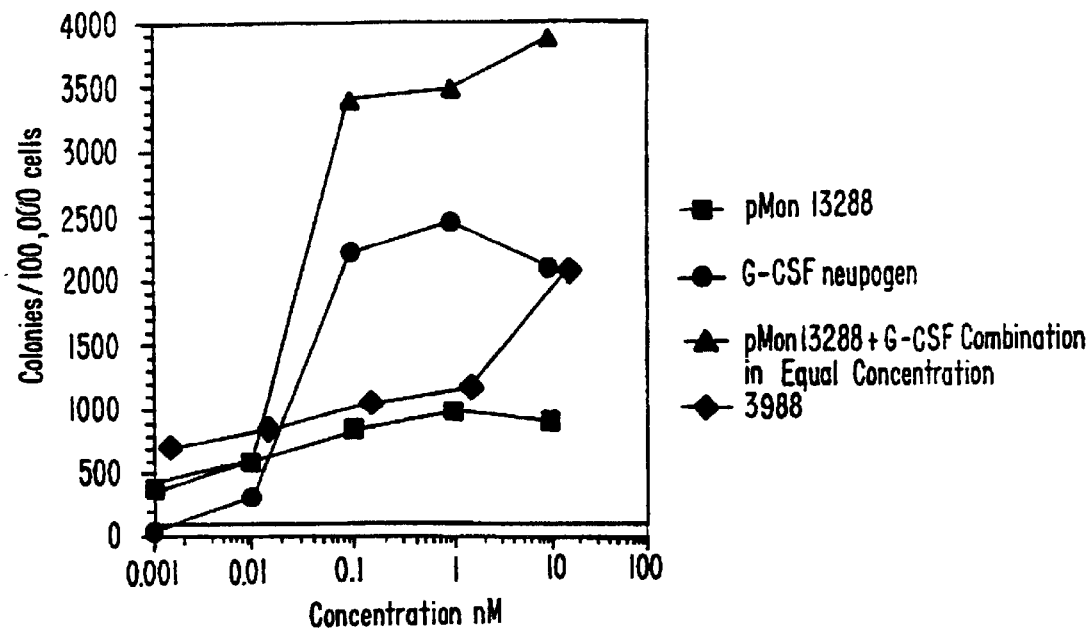
FIG. 3 is the bioactivity, as measured in the methylcellulose assay, of the polypeptide fusion pMON3988.
Figure 4:
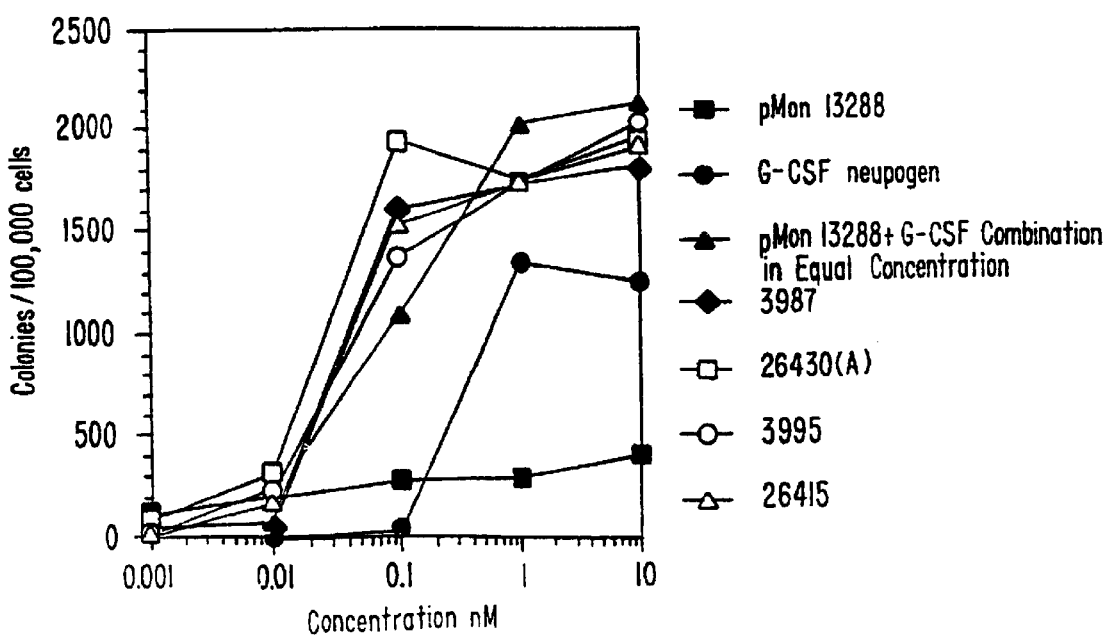
FIG. 4 is the bioactivity, as measured in the methylcellulose assay, of the polypeptide fusions pMON3987 and pMON26430, pMON3995 and pMON26415.
Figure 5:
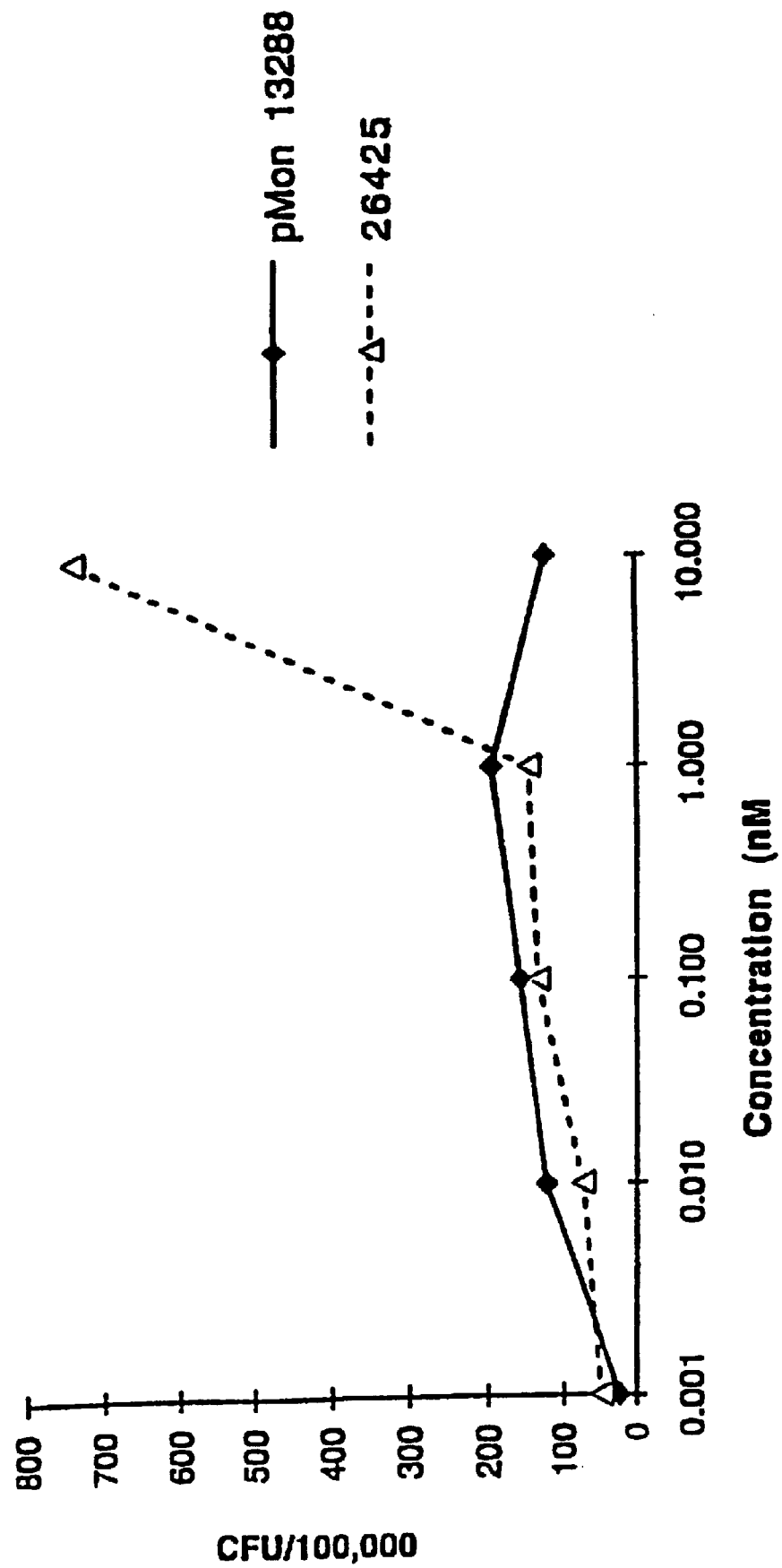
FIG. 5 is the bioactivity, as measured in the methylcellulose assay, of the polypeptide fusion pMON26425.
Figure 6:
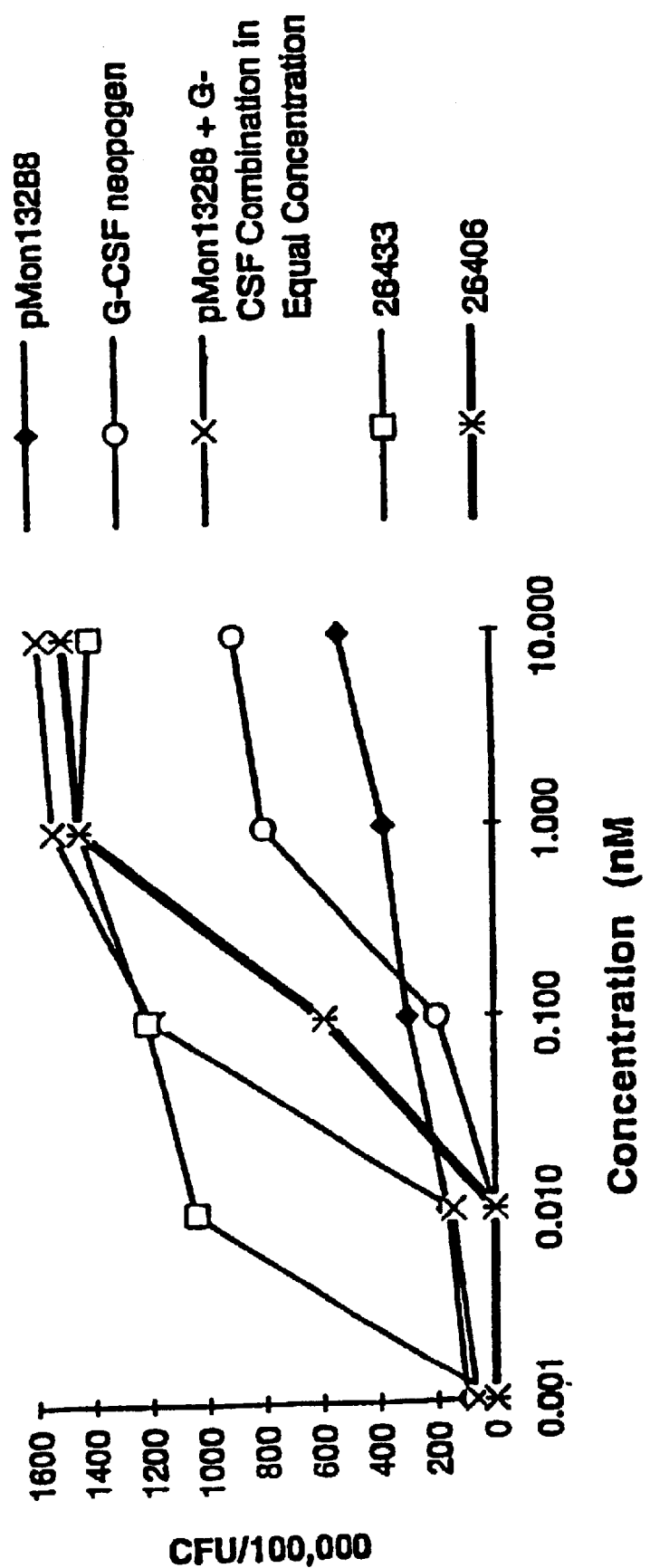
FIG. 6 is the bioactivity, as measured in the methylcellulose assay, of the polypeptide fusions pMON26406 and pMON26433.
Figure 7:
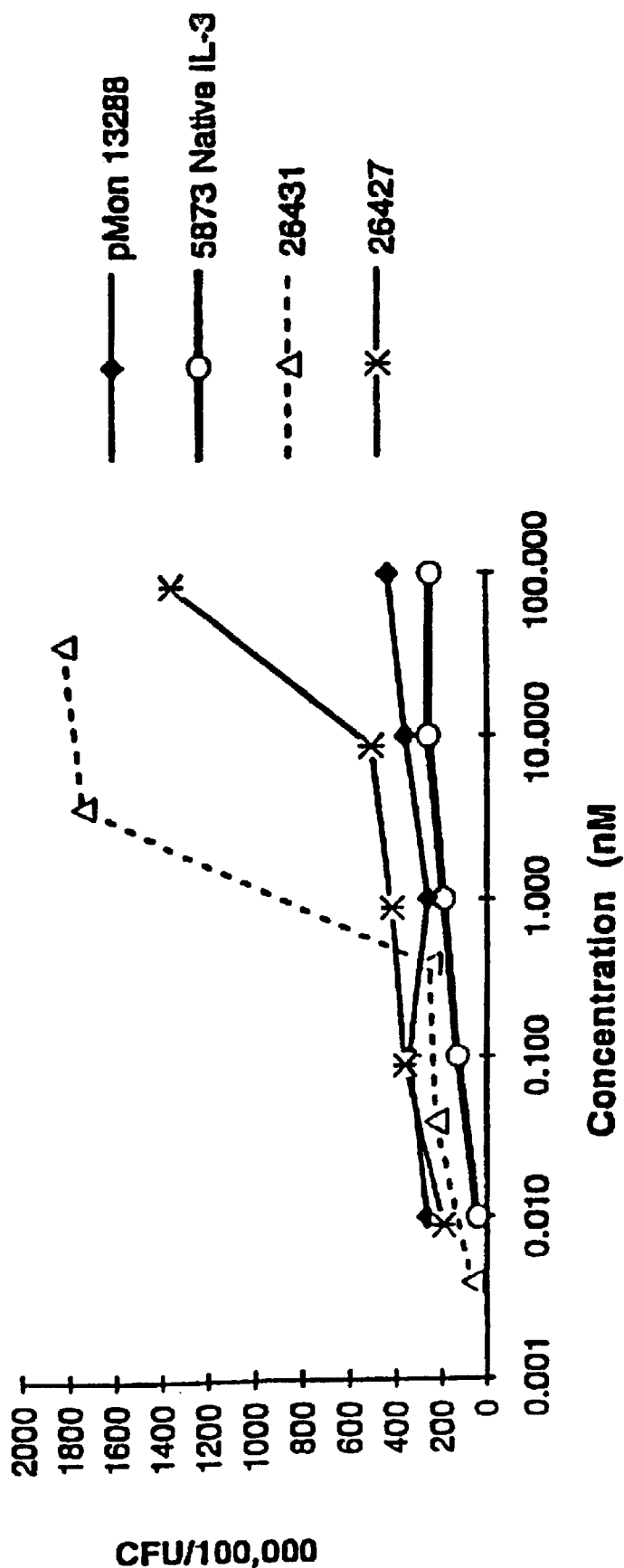
FIG. 7 is the bioactivity, as measured in the methylcellulose assay, of the polypeptide fusions pMON26431 and pMON26427.

The present invention encompasses recombinant human interleukin-3 (hIL-3) variants or mutant proteins (muteins) fused to itself, Il-3 or a second colony stimulating factor (CSF) including but not limited to cytokine, lymphokine, interleukin, hematopoietic growth factor or IL-3 variant with or without a linker. This invention encompasses mixed function colony stimulating factors formed from covalently linked polypeptides, each of which may act through a different and specific cell receptor to initiate complementary biological activities. Hematopoiesis requires a complex series of cellular events in which stem cells generate continuously into large populations of maturing cells in all major lineages. There are currently at least 20 known regulators with hematopoietic proliferative activity. Most of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, 1989). Other mechanisms could explain synergy. For example, if one signaling pathway is limited by an intermediate activation of an additional signaling pathway by a second factor may result in a superadditive response. In some cases, activation of one receptor type can induce a enhanced expression of other receptors (Metcalf, 1993). Two or more factors may result in a different pattern of cell lineages then from a single factor. The use of fusion molecules may have the potential clinical advantage resulting from a proliferative response that is not possible by any single factor.

Hematopoietic and other growth factors can be grouped in to two distinct families of related receptors: (1) tyrosine kinase receptors, including those for epidermal growth factor, M-CSF (Sherr, 1990) and SCF (Yarden et al., 1987): and (2) hematopoietic receptors, not containing a tyrosine kinase domain, but exhibiting obvious homology in their extracellular domain (Bazan, 1990). Included in this later group are erythropoietin (EPO) (D'Andrea et al., 1989), GM-CSF (Gearing et al., 1989), IL-3 (Kitamura et al., 1991), G-CSF (Fukunaga et al., 1990), IL-4 (Harada et al., 1990), IL-5 ((Takaki et al., 1990), IL-6 (Yamasaki et al., 1988), IL-7 (Goodwin et al., 1990), LIF (Gearing et al., 1991) and IL-2 (Cosman et al., 1987). Most of the later group of receptors exists in high-affinity form as a heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Kitamura et al., 1991 Takaki et al., 1991) and receptor complexes for IL-6, LIF and IL-11 share a common β-chain (gp130) (Taga et al., 1989; Gearing et al., 1992). The receptor complexes of IL-2, IL-4 and IL-7 share a common γ-chain (Kondo et al., 1993; Russell et al., 1993; Noguchi et al., 1993).

The use of multiple factors may also have potential advantage by lowering the demands placed on factor-producing cells and their induction systems. If there are limitations in the ability of a cell to produce a factor then by lowering the required concentrations of each of the factors by using them in combination may usefully reduce demands on the factor-producing cells. The use of multiple factors may lower the amount of the factors that would be needed, probably reducing the likelihood of adverse responses.

Novel compounds of this invention are represented by a formula selected from the group consisting of

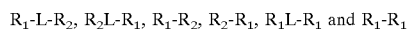

$R_1$-L-$R_2$, $R_2$L-$R_1$, $R_1$-$R_2$, $R_2$-$R_1$, $R_1$L-$R_1$ and $R_1$-$R_1$ where R1 is a hIL-3 variant which contains multiple amino acid substitutions and which may have portions of the hIL-3 molecule deleted as is disclosed in co-pending U.S. patent application Ser. No. PCT/US93/11197, R2 is Il-3, Il-3 variant or a colony stimulating factor with a different but complementary activity. By complementary activity is meant activity which enhances or changes the response to another cell modulator. The R1 polypeptide is fused either directly or through a linker segment to the R2 polypeptide. The term "directly" defines fusions in which the polypeptides are joined without a peptide linker. Thus L represents a chemical bound or polypeptide segment to which both R1 and R2 are fused in frame, most commonly L is a linear peptide to which R1 and R2 are bound by amide bonds linking the carboxy terminus of R1 to the amino terminus of L and carboxy terminus of L to the amino terminus of R2. By "fused in frame" is meant that there is no translation termination or disruption between the reading frames of R1 and R2. A nonexclusive list of other growth factors, colony stimulating factors (CSFs), cytokine, lymphokine, interleukin, hematopoietic growth factor within the definition of R2, which can be fused to a hIL-3 variant of the present invention include GM-CSF, CSF-1, G-CSF, Meg-CSF (more recently referred to as c-mpl ligand), M-CSF, erythropoietin (EPO), IL-1, IL-4, IL-2, IL-5, IL-6,-IL-7, IL-8, IL-9, IL-10, IL-11, IL-12, IL-13, LIF, flt3 ligand human growth hormone, B-cell growth factor, B-cell differentiation factor, eosinophil differentiation factor and stem cell factor (SCF) also known as steel factor or c-kit ligand. Additionally, this invention encompasses the use of modified R2 molecules or mutated or modified DNA sequences encoding these R2 molecules. The present invention also includes fusion molecules in which R2 is a hIL-3 variant which means an IL-3 in which has amino acid substitutions and which may have portions of the hIL-3 molecule deleted such as what is disclosed in PCT/US93/11197 and PCT/US93/11198 as well as other variants known in the art.

The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of R1 and R2 such that R1 and R2 could interact simultaneously with their corresponding receptors on a single cell.

Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

Preferred linkers of the present invention include sequences selected from the group of formulas:

$(Gly_3Ser)_n$, $(Gly_4Ser)_n$, $(Gly_5Ser)_n$, $(Gly_nSer)_n$ or $(AlaGlySer)_n$

One example of a highly-flexible linker is the (GlySer)-rich spacer region present within the pIII protein of the filamentous bacteriophages, e.g. bacteriophages M13 or fd (Schaller et al., 1975). This region provides a long, flexible spacer region between two domains of the pIII surface protein. The spacer region consists of the amino acid sequence:
GlyGlyGlySerGlyGlyGlySerGlyGlyGlySerGluGlyGly-GlySerGluGlyGlyGlySerGluGlyGlyGlySerGluGlyGly-GlySerGlyGlyGlySer [SEQ ID NO:50]

The present invention also includes linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikrein, Urokinase, Tissue Plasminogen activator, clostripain, Chymosin, Collagenase, Russell's Viper Venom Protease, Postproline cleavage enzyme, V8 protease, Thrombin and factor Xa.

Peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Preferred linkers of the present invention include sequences derived from murine IgG gamma 2b hinge region in which the cysteins have been changed to serines. These linkers may also include an endopeptidase cleavage site. Examples of such linkers include the following sequences selected from the group of sequences
IleSerGluProSerGlyProIleSerThrIleAsnProSerProProSer-LysGluSerHisLysSerPro [SEQ ID NO:51]
IleGluGlyArgIleSerGluProSerGlyProIleSerThrIleAsnPro-SerProProSerLysGluSerHisLysSerPro [SEQ ID NO:52]

The present invention is, however, not limited by the form, size or number of linker sequences employed and the only requirement of the linker is that functionally it does not interfere adversely with the folding and function of the individual molecules of the fusion.

An alternative method for connecting two hematopoietic growth factors is by means of a non-covalent interaction. Such complexed proteins can be described by one the formulae:

R1-C1+R2-C2; or C1-R1+C2-R2; C1-R1+R2-R2; or C1-R1+R2-C2.

where R1 is a hIL-3 variant which contains multiple amino acid substitutions and which may have portions of the hIL-3 molecule deleted, R2 is a colony stimulating factor with a different but complementary activity. A nonexclusive list of other growth hormones, colony stimulating factors (CSFs), cytokine, lymphokine, interleukin, hematopoietic growth factor within the definition of R2, which can be fused to a hIL-3 variant of the present invention include GM-CSF, CSF-1, G-CSF, Meg-CSF (more recently referred to as c-mpl ligand), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF) also known as steel factor or c-kit ligand. Domains C1 and C2 are either identical or non-identical chemical structures, typically proteinaceous, which can form a non-covalent, specific association. Complexes between C1 and C2 result in a one-to-one stoichiometric relationship between R1 and R2 for each complex. Examples of domains which associate are "leucine zipper" domains of transcription factors, dimerization domains of bacterial transcription repressors and immunoglobulin constant domains. Covalent bonds link R1 and C1, and R2 and C2, respectively. As indicated in the formulae, the domains C1 and C2 can be present either at the N-terminus or C-terminus of their corresponding hematopoietic growth factor (R). These multimerization domains (C1 and C2) include those derived from the bZIP family of proteins (Abel et al., 1989; Landshulz et al., 1988; Pu et al., 1993; Kozarides et al., 1988) as well as multimerization domains of the helix-loop-helix family of proteins (Abel et al., 1989; Murre et al., 1989; Tapscott et al., 1988; Fisher et al., 1991). Preferred fusions of the present invention include colony stimulating factors dimerized by virtue of their incorporation as translational fusions the leucine zipper dimerization domains of the bZIP family proteins Fos and Jun. The leucine zipper domain of Jun is capable of interacting with identical domains. On the other hand, the leucine zipper domain of Fos interacts with the Jun leucine zipper domain, but does not interact with other Fos leucine zipper domains. Mixtures of Fos and Jun predominantly result in formation of FOS-Jun heterodimers. Consequently, when fused to colony stimulating factors, the Jun domain can be used to direct the formation of either homo or heterodimers. Preferential formation of heterodimers can be achieved if one of the colony stimulating factor partner is engineered to possess the Jun leucine zipper domain while the other is engineered to possess the Fos zipper.

Peptides may also be added to facilitate purification or identification of fusion proteins (e.g., poly-His). A highly antigenic peptide may also be added that would enable rapid assay and facile purification of the fusion protein by a specific monoclonal antibody.

The present invention relates to novel fusion molecules composed of novel variants of human interleukin-3 (hIL-3) in which amino acid substitutions have been made at four or more positions in amino acid sequence of the polypeptide fused to second colony stimulating factor or IL-3 variant. Preferred fusion molecules of the present invention are (15–125)hIL-3 deletion mutants which have deletions of amino acids 1 to 14 at the N-terminus and 126 to 133 at the C-terminus and which also have four or more amino acid substitutions in the polypeptide fused to second colony stimulating factor or IL-3 variant. The present invention includes mutant polypeptides comprising minimally amino acids residues 15 to 118 of hIL-3 with or without additional amino acid extensions to the N-terminus and/or C-terminus which further contain four or more amino acid substitutions in the amino acid sequence of the polypeptide fused to another colony stimulating factor or IL-3 variant.

As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A, et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involve signal transduction and high affinity receptor binding. Fusion molecules of the present invention may exhibit useful properties such as having similar or greater biological activity when compared to native hIL-3 or by having improved half-life or decreased adverse side effects, or a combination of these properties. They may also be useful as antagonists. Fusion molecules which have little or no activity when compared to native hIL-3 may still be useful as antagonists, as antigens for the production of antibodies for use in immunology or immunotherapy, as genetic probes or as intermediates used to construct other useful hIL-3 muteins.

The novel fusion molecules of the present invention will preferably have at least one biological property of human IL-3 and the other colony stimulating factor or IL-3 variant to which it is fused and may have more than one IL-3-like biological property, or an improved property, or a reduction in an undesirable biological property of human IL-3. Some mutant polypeptides of the present invention may also exhibit an improved side effect profile. For example, they may exhibit a decrease in leukotriene release or histamine release when compared to native hIL-3 or (15–125) hIL-3. Such hIL-3 or hIL-3-like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, and erythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 fusion proteins of the present invention is determined by DNA synthesis by human acute myelogenous leukemia cells (AML). The factor-dependent cell line AML 193 was adapted for use in testing biological activity. The biological activity of hIL-3 and hIL-3 fusion proteins of the present invention is also determined by counting the colony forming units in a bone marrow assay.

Other in vitro cell based assays may also. be useful to determine the activity of the fusion molecules depending on the colony stimulating factors that comprise the fusion. The following are examples of other useful assays.

TF-1 proliferation assay: The TF-1 cell line was derived from bone marrow of a patient with erythroleukemia (Kitamura et al., 1989). TF-1 cells respond to IL-3, GM-CSF, EPO and IL-5.

32D proliferation assay: 32D is a murine IL-3 dependent cell line which does not respond to human IL-3 but does respond to human G-CSF which is not species restricted.

T1165 proliferation assay: T1165 cells are a IL-6 dependent murine cell line (Nordan et al., 1986) which respond to IL-6 and IL-11.

Human Plasma Clot meg-CSF Assay: Used to assay megakaryocyte colony formation activity (Mazur et al., 1981).

One object of the present invention is to provide hIL-3 variant with four or more amino acid substitutions in the polypeptide sequence fused to a second colony stimulating factor or IL-3 variant, which have similar or improved biological activity in relation to native hIL-3 or the second colony stimulating factor or IL-3 variant.

The hIL-3 variant fusion molecules of the present invention may have hIL-3 or hIL-3-like activity. For example, they may possess one or more of the biological activities of native hIL-3 and may be useful in stimulating the production of hematopoietic cells by human or primate progenitor cells. The fusion molecules of the present invention and pharmaceutical compositions containing them may be useful in the treatment of conditions in which hematopoietic cell populations have been reduced or destroyed due to disease or to treatments such as radiation or chemotherapy. Pharmaceutical compositions containing fusion molecules of the present invention can be administered parenterally, intravenously, or subcutaneously.

Native hIL-3 possesses considerable inflammatory activity and has been shown to stimulate synthesis of the arachidonic acid metabolites $LTC_4$, $LTD_4$, and $LTE_4$; histamine synthesis and histamine release. Human clinical trials with native hIL-3 have documented inflammatory responses (Biesma, et al., BLOOD, 80:1141–1148 (1992) and Postmus, et al., J. CLIN. ONCOL., 10:1131–1140 (1992)). A recent study indicates that leukotrienes are involved in IL-3 actions in vivo and may contribute significantly to the biological effects of IL-3 treatment (Denzlinger, C., et al., BLOOD, 81:2466–2470 (1993))

Some fusion molecules of the present invention may have an improved therapeutic profile as compared to native hIL-3. For example, some fusion molecules of the present invention may have a similar or more potent growth factor activity relative to native hIL-3 without having a similar or corresponding increase in the stimulation of leukotriene or histamine. These fusion molecules would be expected to have a more favorable therapeutic profile since the amount of polypeptide which needs to be given to achieve the desired growth factor activity (e. g. cell proliferation) would have a lesser leukotriene or histamine stimulating effect. In studies with native hIL-3, the stimulation of inflammatory factors has been an undesirable side effect of the treatment. Reduction or elimination of the stimulation of mediators of inflammation would provide an advantage over the use of native hIL-3.

Novel fusion molecules of the present invention may also be useful as antagonists which block the hIL-3 receptor by binding specifically to it and preventing binding of the agonist.

One potential advantage of the novel fusion molecules of the present invention, particularly those which retain activity similar to or better than that of native hIL-3, is that it may be possible to use a smaller amount of the biologically active mutein to produce the desired therapeutic effect. This may make it possible to reduce the number of treatments necessary to produce the desired therapeutic effect. The use of smaller amounts may also reduce the possibility of any potential antigenic effects or other possible undesirable side effects. For example, if a desired therapeutic effect can be achieved with a smaller amount of polypeptide it may be possible to reduce or eliminate side effects associated with the administration of native IL-3 such as the stimulation of leukotriene and/or histamine release. The novel fusion molecules of the present invention may also be useful in the activation of stem cells or progenitors which-have low receptor numbers.

The present invention also includes the DNA sequences which code for the fusion proteins, DNA sequences which are substantially similar and perform substantially the same function, and DNA sequences which differ from the DNAs encoding the fusion molecules of the invention only due to the degeneracy of the genetic code. Also included in the present invention are; the oligonucleotide intermediates used to construct the mutant DNAS; and the polypeptides coded for by these oligonucleotides. These polypeptides may be useful as antagonists or as antigenic fragments for the production of antibodies useful in immunoassay and immunotherapy protocols.

Compounds of this invention are preferably made by genetic engineering techniques now standard in the art U.S. Pat. No. 4,935,233 and Sambrook et al., "Molecular Cloning. A Laboratory Manual", Cold Spring Harbor Laboratory (1989)]. One method of creating the preferred hIL-3 (15–125) mutant genes is cassette mutagenesis [Wells, et al. (1985)] in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis [Zoller and Smith (1982, 1983, 1984), Smith (1985), Kunkel (1985), Taylor, et al. (1985), Deng and Nickoloff (1992)] or polymerase chain reaction (PCR) techniques [Saiki, (1985)].

Pairs of complementary synthetic oligonucleotides encoding the desired gene can be made and annealed to each other. The DNA sequence of the oligonucleotide would encode sequence for amino acids of desired gene with the exception of those substituted and/or deleted from the sequence.

Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with the desired genes.

Fusing of the DNA sequences of the hIL-3 variant with the DNA sequence of the other colony stimulating factor or IL-3 variant may be accomplished by the use of intermediate vectors. Alternatively one gene can be cloned directly into a vector containing the other gene. Linkers and adapters can be used for joining the DNA sequences, as well as replacing lost sequences, where a restriction site was internal to the region of interest. Thus genetic material (DNA) encoding one polypeptide, peptide linker, and the other polypeptide is inserted into a suitable expression vector which is used to transform bacteria, yeast, insect cell or mammalian cells. The transformed organism is grown and the protein isolated by standard techniques. The resulting product is therefore a new protein which has a hIL-3 variant joined by a linker region to a second colony stimulating factor or IL-3 variant.

Another aspect of the present invention provides plasmid DNA vectors for use in the expression of these novel fusion molecules. These vectors contain the novel DNA sequences described above which code for the novel polypeptides of the invention. Appropriate vectors which can transform microorganisms capable of expressing the fusion molecules include expression vectors comprising nucleotide sequences coding for the fusion molecules joined to transcriptional and translational regulatory sequences which are selected according to the host cells used.

Vectors incorporating modified sequences as described above are included in the present invention and are useful in the production of the fusion polypeptides. The vector employed in the method also contains selected regulatory sequences in operative association with the DNA coding sequences of the invention and capable of directing the replication and expression thereof in selected host cells.

As another aspect of the present invention, there is provided a method for producing the novel fusion molecules. The method of the present invention involves culturing a suitable cell or cell line, which has been transformed with a vector containing a DNA sequence coding for expression of a novel hIL-3 variant fusion molecule. Suitable cells or cell lines may be bacterial cells. For example, the various strains of *E. coli* are well-known as host cells in the field of biotechnology. Examples of such strains include *E. coli* strains JM101 [Yanish-Perron, et al. (1985)] and MON105 [Obukowicz, et al. (1992)]. Also included in the present invention is the expression of the fusion protein utilizing a chromosomal expression vector for *E. coli* based on the bacteriophage Mu (Weinberg et al., 1993). Various strains of *B. subtilis* may also be employed in this method. Many strains of yeast cells known to those skilled in the art are also available as host cells for expression of the polypeptides of the present invention. When expressed in the *E. coli* cytoplasm, the above-mentioned mutant hIL-3 variant fusion molecules of the present invention may also be constructed with Met-Ala- at the N-terminus so that upon expression the Met is cleaved off leaving Ala at the N-terminus. The fusion molecules of the present invention may include fusion polypeptides having Met-, Ala- or Met-Ala-attached to the N-terminus. When the fusion molecules are expressed in the cytoplasm of *E. coli*, polypeptides with and without Met attached to the N-terminus are obtained. The N-termini of proteins made in the cytoplasm of *E. coli* are affected by posttranslational processing by methionine aminopeptidase (Ben-Bassat et al., 1987) and possibly by other peptidases. These mutant fusion molecules may also be expressed in *E. coli* by fusing a signal peptide to the N-terminus. This signal peptide is cleaved from the polypeptide as part of the secretion process. Secretion in *E. coli* can be used to obtain the correct amino acid at the N-terminus (e.g., Asn$^{15}$ in the (15–125) hIL-3 polypeptide) due to the precise nature of the signal peptidase. This is in contrast to the heterogeneity often observed at the N-terminus of proteins expressed in the cytoplasm in *E. coli*.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in *Genetic Engineering, Principles and Methods,* Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the fusion molecule. For example, plasmids such as pcDNA I/Neo, pRc/RSV, and pRc/CMV (obtained from Invitrogen Corp., San Diego, Calif.) can be used. The eukaryotic secretion signal peptide coding region can be from the hIL-3 gene itself or it can be from another secreted mammalian protein (Bayne, M. L. et al. (1987) *Proc. Natl. Acad. Sci. USA* 84, 2638–2642). After construction of the vector containing the hIL-3 variant gene, the vector DNA is transfected into mammalian cells. Such cells can be, for example, the COS7, HeLa, BHK, CHO, or mouse L lines. The cells can be cultured, for example, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7): 1750–1759 (1985) or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, *Genetic Engineering,* 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally fused to the coding region for the fusion polypeptide. For example, the plasmid pVL1392 (obtained from Invitrogen Corp., San Diego, Calif.) can be used. After construction of the vector carrying the gene encoding the fusion polypeptide, two micrograms of this DNA is cotransfected with one microgram of Baculovirus DNA (see Summers & Smith, 1987) into insect cells, strain SF9. Pure recombinant Baculovirus carrying the fusion molecule is used to infect cells cultured, for example, in Excell 401 serum-free medium (JRH Biosciences, Lenexa, Kans.). The fusion molecule secreted into the medium can be recovered by standard biochemical approaches. Supernatants from mammalian or insect cells expressing the fusion protein can be first concentrated using any of an number of commercial concentration units.

The fusion molecules of the present invention may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these fusion molecules of the present invention may avoid undesirable side effects caused by treatment with presently available drugs.

The fusion molecules of the present invention may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

The fusion molecule of the present invention may be useful in the treatment or prevention of thrombocytopenia. Currently the only therapy for thrombocytopenia is platelet transfusions which are costly and carry the significant risks of infection (HIV, HBV) and alloimunization. The fusion molecule may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis.

The fusion molecules of the present invention may be useful in the mobilization of hematopoietic progenitors and stem cells into peripheral blood. Peripheral blood derived progenitors have been shown to be effective in reconstituting patients in the setting of autologous marrow transplantation. Hematopoietic growth factors including G-CSF and GM-CSF have been shown to enhance the number of circulating progenitors and stem cells in the peripheral blood. This has simplified the procedure for peripheral stem cell collection and dramatically decreased the cost of the procedure by decreasing the number of pheresis required. The fusion molecule may be useful in mobilization of stem cells and further enhance the efficacy of peripheral stem cell transplantation.

Another projected clinical use of growth factors has been in the in vitro activation of hematopoietic progenitors and stem cells for gene therapy. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti convulsants such as phenytoin or carbamazepine, antithyroids such as propylthiouracil and methimazole and diuretics. The fusion molecules of the present invention may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. The fusion molecules of the present invention may be useful in treating such hematopoietic deficiency.

The treatment of hematopoietic deficiency may include administration of a pharmaceutical composition containing the fusion molecules to a patient. The fusion molecules of the present invention may also be useful for the activation and amplification of hematopoietic precursor cells by treating these cells in vitro with the fusion proteins of the present invention prior to injecting the cells into a patient.

Various immunodeficiencies e.g., in T and/or B lymphocytes, or immune disorders, e.g., rheumatoid arthritis, may also be beneficially affected by treatment with the fusion molecules of the present invention. Immunodeficiencies may be the result of viral infections e.g. HTLVI, HTLVII, HTLVIII, severe exposure to radiation, cancer therapy or the result of other medical treatment. The fusion molecules of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the fusion molecules of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.2–150 μg/kg of fusion protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given fusion protein vs. the activity of native (reference) IL-3 and it would not be unreasonable to note that dosage regimens may include doses as low as 0.1 microgram and as high as 1 milligram per kilogram of body weight per day. In addition, there may exist specific circumstances where dosages of fusion molecule would be adjusted higher or lower than the range of 10–200 micrograms per kilogram of body weight. These include co-administration with other colony stimulating factor or IL-3 variant or growth factors; co-administration with chemotherapeutic drugs and/or radiation; the use of glycosylated fusion protein; and various patient-related issues mentioned earlier in this section. As indicated above, the therapeutic method and compositions may also include co-administration with other human factors. A non-exclusive list of other appropriate hematopoietins, CSFS, cytokines, lymphokines, hematopoietic growth factors and interleukins for simultaneous or serial co-administration with the polypeptides of the present invention includes GM-CSF, CSF-1, G-CSF, Meg-CSF (more recently referred to as c-mpl ligand), M-CSF, erythropoietin (EPO), IL-1, IL-4, IL-2, IL-5, IL-6, L-7, IL-8, IL-9, IL-10, IL-11, IL-12, IL-13, LIF, flt3 ligand, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

The present invention is also directed to the following;

1. $R_1$-L-$R_2$, $R_2$-L-$R_1$, $R_1$-$R_2$, $R_2$-$R_1$, $R_1$-L-$R_1$ and $R_1$-$R_1$ wherein R1 is a human interleukin-3 mutant polypeptide of the Formula:

| Ala | Pro | Met | Thr | Gln | Thr | Thr | Ser | Leu | Lys | Thr | Ser | Trp | Val | Asn |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Cys | Xaa | Xaa | Xaa | Xaa | Xaa | Xaa | Xaa | Xaa | Xaa | Xaa | Xaa | Xaa | Xaa | Xaa |
|     |     |     |     | 20  |     |     |     |     | 25  |     |     |     |     | 30  |
| Xaa | Xaa | Xaa | Xaa | Xaa | Xaa | Xaa | Xaa | Asn | Xaa | Xaa | Xaa | Xaa | Xaa | Xaa |
|     |     |     |     | 35  |     |     |     |     | 40  |     |     |     |     | 45  |

-continued

| | | | | | | | | | | | | | | |
|---|---|---|---|---|---|---|---|---|---|---|---|---|---|---|
| Xaa | Xaa | Xaa | Xaa | Xaa 50 | Xaa | Xaa | Xaa | Xaa | Xaa 55 | Xaa | Xaa | Xaa | Xaa | Xaa 60 |
| Xaa | Xaa | Xaa | Xaa | Xaa 65 | Xaa | Xaa | Xaa | Xaa | Xaa 70 | Xaa | Xaa | Xaa | Xaa | Xaa 75 |
| Xaa | Xaa | Xaa | Xaa | Xaa 80 | Xaa | Xaa | Xaa | Xaa | Xaa 85 | Xaa | Xaa | Xaa | Xaa | Xaa 90 |
| Xaa | Xaa | Xaa | Xaa | Xaa 95 | Xaa | Xaa | Xaa | Xaa | Xaa 100 | Xaa | Xaa | Xaa | Xaa | Xaa 105 |
| Xaa | Phe | Xaa | Xaa | Xaa 110 | Xaa | Xaa | Xaa | Xaa | Xaa 115 | Xaa | Xaa | Xaa | Xaa | Xaa 120 |
| Xaa | Xaa | Xaa | Gln | Gln 125 | Thr | Thr | Leu | Ser | Leu 130 | Ala | Ile | Phe | | |

[SEQ ID NO:1]

wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Leu, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp, Pro, Met, Lys, His, Thr, Val, Tyr, Glu, Asn, Ser, Ala, Gly, Ile, Leu, or Gln;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133) human interleukin-3;

2. The fusion protein of 1 wherein said human interleukin-3 mutant polypeptide is of the Formula:

| Ala 1 | Pro | Met | Thr | Gln 5 | Thr | Thr | Ser | Leu | Lys 10 | Thr | Ser | Trp | Val | Asn 15 |
|---|---|---|---|---|---|---|---|---|---|---|---|---|---|---|
| Cys | Xaa | Xaa | Xaa | Ile 20 | Xaa | Glu | Xaa | Xaa | Xaa 25 | Xaa | Leu | Lys | Xaa | Xaa 30 |
| Xaa | Xaa | Xaa | Xaa | Xaa 35 | Asp | Xaa | Xaa | Asn | Leu 40 | Asn | Xaa | Glu | Xaa | Xaa 45 |
| Xaa | Ile | Leu | Met | Xaa 50 | Xaa | Asn | Leu | Xaa | Xaa 55 | Xaa | Asn | Leu | Glu | Xaa 60 |
| Phe | Xaa | Xaa | Xaa | Xaa 65 | Xaa | Xaa | Xaa | Xaa | Asn 70 | Xaa | Xaa | Xaa | Ile | Glu 75 |
| Xaa | Xaa | Leu | Xaa | Xaa 80 | Leu | Xaa | Xaa | Cys | Xaa 85 | Pro | Xaa | Xaa | Thr | Ala 90 |
| Xaa | Pro | Xaa | Arg | Xaa 95 | Xaa | Xaa | Xaa | Xaa | Xaa 100 | Xaa | Gly | Asp | Xaa | Xaa 105 |
| Xaa | Phe | Xaa | Xaa | Lys 110 | Leu | Xaa | Phe | Xaa | Xaa 115 | Xaa | Xaa | Leu | Glu | Xaa 120 |
| Xaa | Xaa | Xaa | Gln | Gln 125 | Thr | Thr | Leu | Ser | Leu 130 | Ala | Ile | Phe | | |

[SEQ ID NO:2]

wherein
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, Gly, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Leu, Arg, Gln, Leu, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp, Pro, Met, Lys, His, Thr, Pro, Asn, Ile, Leu or Tyr;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys, Thr, Val, Trp, Ser, Ala, His, Met, Phe, Tyr or Ile;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 35 of the amino acids designated by Xaa are different from the corresponding amino acids of native (1–133) human interleukin-3.

3. The fusion protein of 2 wherein said human interleukin-3 mutant polypeptide is of the Formula:

| Ala 1 | Pro | Met | Thr | Gln 5 | Thr | Thr | Ser | Leu | Lys 10 | Thr | Ser | Trp | Val | Asn 15 |
|---|---|---|---|---|---|---|---|---|---|---|---|---|---|---|
| Cys | Xaa | Xaa | Met | Ile 20 | Asp | Glu | Xaa | Ile | Xaa 25 | Xaa | Leu | Lys | Xaa | Xaa 30 |
| Pro | Xaa | Pro | Xaa | Xaa 35 | Asp | Phe | Xaa | Asn | Leu 40 | Asn | Xaa | Glu | Asp | Xaa 45 |
| Xaa | Ile | Leu | Met | Xaa 50 | Xaa | Asn | Leu | Arg | Xaa 55 | Xaa | Asn | Leu | Glu | Ala 60 |
| Phe | Xaa | Arg | Xaa | Xaa 65 | Lys | Xaa | Xaa | Xaa | Asn 70 | Ala | Ser | Ala | Ile | Glu 75 |

-continued

| Xaa | Xaa | Leu | Xaa | Xaa 80 | Leu | Xaa | Pro | Cys | Leu 85 | Pro | Xaa | Xaa | Thr | Ala 90 |
|---|---|---|---|---|---|---|---|---|---|---|---|---|---|---|
| Xaa | Pro | Xaa | Arg | Xaa 95 | Pro | Ile | Xaa | Xaa | Xaa 100 | Xaa | Gly | Asp | Trp | Xaa 105 |
| Glu | Phe | Xaa | Xaa | Lys 110 | Leu | Xaa | Phe | Tyr | Leu 115 | Xaa | Xaa | Leu | Glu | Xaa 120 |
| Xaa | Xaa | Xaa | Gln | Gln 125 | Thr | Thr | Leu | Ser | Leu 130 | Ala | Ile | Phe | | |

[SEQ ID NO:3]

wherein
   Xaa at position 17 is Ser, Gly, Asp, or Gln;
   Xaa at position 18 is Asn, His, or Ile;
   Xaa at position 23 is Ile, Ala, Leu, or Gly;
   Xaa at position 25 is Thr, His, or Gln;
   Xaa at position 26 is His or Ala;
   Xaa at position 29 is Gln or Asn;
   Xaa at position 30 is Pro or Gly;
   Xaa at position 32 is Leu, Arg, Asn, or Ala;
   Xaa at position 34 is Leu, Val, Ser, Ala, Arg, Gln, Glu, Ile, Phe, Thr, or Met;
   Xaa at position 35 is Leu, Ala, Asn, or Pro;
   Xaa at position 38 is Asn or Ala;
   Xaa at position 42 is Gly, Asp, Ser, Ala, Asn, Ile, Leu, Met, Tyr or Arg;
   Xaa at position 45 is Gln, Val, Met, Leu, Ala, Asn, Glu, or Lys;
   Xaa at position 46 is Asp, Phe, Ser, Gln, Glu, His, Val or Thr;
   Xaa at position 50 is Glu Asn, Ser or Asp;
   Xaa at position 51 is Asn, Arg, Pro, Thr, or His;
   Xaa at position 55 is Arg, Leu, or Gly;
   Xaa at position 56 is Pro, Gly, Ser, Ala, Asn, Val, Leu or Gln;
   Xaa at position 62 is Asn, Pro, or Thr;
   Xaa at position 64 is Ala or Asn;
   Xaa at position 65 is Val or Thr;
   Xaa at position 67 is Ser or Phe;
   Xaa at position 68 is Leu or Phe;
   Xaa at position 69 is Gln, Ala, Glu, or Arg;
   Xaa at position 76 is Ser, Val, Asn, Pro, or Gly;
   Xaa at position 77 is Ile or Leu;
   Xaa at position 79 is Lys, Gly, Asn, Met, Arg, Ile, or Gly;
   Xaa at position 80 is Asn, Gly, Glu, or Arg;
   Xaa at position 82 is Leu, Gln, Trp, Arg, Asp, Asn, Glu, His, Met, Phe, Ser, Thr, Tyr or Val;
   Xaa at position 87 is Leu or Ser;
   Xaa at position 88 is Ala or Trp;
   Xaa at position 91 is Ala or Pro;
   Xaa at position 93 is Thr, Asp, or Ala;
   Xaa at position 95 is His, Pro, Arg, Val, Gly, Asn, Ser or Thr;
   Xaa at position 98 is His, Ile, Asn, Ala, Thr, Gln, Glu, Lys, Met, Ser, Tyr, Val or Leu;
   Xaa at position 99 is Ile or Leu;
   Xaa at position 100 is Lys or Arg;
   Xaa at position 101 is Asp, Pro, Met, Lys, Thr, His, Pro, Asn, Ile, Leu or Tyr;
   Xaa at position 105 is Asn, Pro, Ser, Ile or Asp;
   Xaa at position 108 is Arg, Ala, or Ser;
   Xaa at position 109 is Arg, Thr, Glu, Leu, or Ser;
   Xaa at position 112 is Thr or Gln;
   Xaa at position 116 is Lys, Val, Trp, Ala, His, Phe, Tyr or Ile;
   Xaa at position 117 is Thr or Ser;
   Xaa at position 120 is Asn, Pro, Leu, His, Val, or Gln;
   Xaa at position 121 is Ala, Ser, Ile, Pro, or Asp;
   Xaa at position 122 is Gln, Met, Trp, Phe, Pro, His, Ile, or Tyr;
   Xaa at position 123 is Ala, Met, Glu, Ser, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133)human interleukin-3.

4. The fusion protein of 3 wherein said human interleukin-3 mutant polypeptide is of the Formula:
   Xaa at position 42 is Gly, Asp, Ser, Ile, Leu, Met, Tyr, or Ala;
   Xaa at position 45 is Gln, Val, Met or Asn;
   Xaa at position 46 is Asp, Ser, Gln, His or Val;
   Xaa at position 50 is Glu or Asp;
   Xaa at position 51 is Asn, Pro or Thr;
   Xaa at position 62 is Asn or Pro;
   Xaa at position 76 is Ser, or Pro;
   Xaa at position 82 is Leu, Trp, Asp, Asn Glu, His, Phe, Ser or Tyr;
   Xaa at position 95 is His, Arg, Thr, Asn or Ser;
   Xaa at position 98 is His, Ile, Leu, Ala, Gln, Lys, Met, Ser, Tyr or Val;
   Xaa at position 100 is Lys or Arg;
   Xaa at position 101 is Asp, Pro, His, Asn, Ile or Leu;
   Xaa at position 105 is Asn, or Pro;
   Xaa at position 108 is Arg, Ala, or Ser;
   Xaa at position 116 is Lys, Val, Trp, Ala, His, Phe, or Tyr;
   Xaa at position 121 is Ala, or Ile;
   Xaa at position 122 is Gln, or Ile; and
   Xaa at position 123 is Ala, Met or Glu.

6. A fusion protein having the formula selected from the group consisting of $R_1$-L-$R_2$, $R_2$L-$R_1$, $R_1$-$R_2$, $R_2$-$R_1$, $R_1$L-$R_1$ and $R_1$-$R_1$ wherein $R_1$ is a human interleukin-3 mutant polypeptide of the Formula:

| | | | | | | | | | | | | | | |
|---|---|---|---|---|---|---|---|---|---|---|---|---|---|---|
| Asn 1 | Cys | Xaa | Xaa | Xaa 5 | Xaa | Xaa | Xaa | Xaa | Xaa 10 | Xaa | Xaa | Xaa | Xaa | Xaa 15 |
| Xaa | Xaa | Xaa | Xaa | Xaa 20 | Xaa | Xaa | Xaa | Xaa | Asn 25 | Xaa | Xaa | Xaa | Xaa | Xaa 30 |
| Xaa | Xaa | Xaa | Xaa | Xaa 35 | Xaa | Xaa | Xaa | Xaa | Xaa 40 | Xaa | Xaa | Xaa | Xaa | Xaa 45 |
| Xaa | Xaa | Xaa | Xaa | Xaa 50 | Xaa | Xaa | Xaa | Xaa | Xaa 55 | Xaa | Xaa | Xaa | Xaa | Xaa 60 |
| Xaa | Xaa | Xaa | Xaa | Xaa 65 | Xaa | Xaa | Xaa | Xaa | Xaa 70 | Xaa | Xaa | Xaa | Xaa | Xaa 75 |
| Xaa | Xaa | Xaa | Xaa | Xaa 80 | Xaa | Xaa | Xaa | Xaa | Xaa 85 | Xaa | Xaa | Xaa | Xaa | Xaa 90 |
| Xaa | Xaa | Phe | Xaa | Xaa 95 | Xaa | Xaa | Xaa | Xaa | Xaa 100 | Xaa | Xaa | Xaa | Xaa | Xaa 105 |
| Xaa | Xaa | Xaa | Xaa | Gln 110 | Gln [SEQ ID NO:4] | | | | | | | | | | wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Leu, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, Met, or;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp, Pro, Met, Lys, His, Thr, Val, Tyr, Glu, Asn, Ser, Ala, Gly, Ile, Leu or Gln;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys, Leu, Pro, Thr, Met, Asp, Val, Glu, Arg, Trp, Ser, Asn, His, Ala, Tyr, Phe, Gln, or Ile;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gin, Ser, Met, Trp, Arg, Phe, Pro, His, Ile, Tyr, or Cys;

Xaa at position 109 is Ala, Met, Glu, His, Ser, Pro, Tyr, or Leu;

and which can additionally have Met- or Met-Ala- preceding the amino acid in position 1; and wherein from 4 to 44 of the amino acids designated by Xaa are different from the corresponding native amino acids of (1–133) human interleukin-3;

$R_2$ is a colony stimulating factor; and

L is a linker capable of Linking $R_1$ to $R_2$.

6. The fusion protein of 5 wherein said human interleukin-3 mutant polypeptide is of the Formula:

| Asn 1 | Cys | Xaa | Xaa | Xaa 5 | Ile | Xaa | Glu | Xaa | Xaa 10 | Xaa | Xaa | Leu | Lys | Xaa 15 |
|---|---|---|---|---|---|---|---|---|---|---|---|---|---|---|
| Xaa | Xaa | Xaa | Xaa | Xaa 20 | Xaa | Asp | Xaa | Xaa | Asn 25 | Leu | Asn | Xaa | Glu | Xaa 30 |
| Xaa | Xaa | Ile | Leu | Met 35 | Xaa | Xaa | Asn | Leu | Xaa 40 | Xaa | Xaa | Asn | Leu | Glu 45 |
| Xaa | Phe | Xaa | Xaa | Xaa 50 | Xaa | Xaa | Xaa | Xaa | Xaa 55 | Asn | Xaa | Xaa | Xaa | Ile 60 |
| Glu | Xaa | Xaa | Leu | Xaa 65 | Xaa | Leu | Xaa | Xaa | Cys 70 | Xaa | Pro | Xaa | Xaa | Thr 75 |
| Ala | Xaa | Pro | Xaa | Arg 80 | Xaa | Xaa | Xaa | Xaa | Xaa 85 | Xaa | Xaa | Gly | Asp | Xaa 90 |
| Xaa | Xaa | Phe | Xaa | Xaa 95 | Lys | Leu | Xaa | Phe | Xaa 100 | Xaa | Xaa | Xaa | Leu | Glu 105 |
| Xaa | Xaa | Xaa | Xaa | Gln 110 | Gln [SEQ ID NO:5] | | | | | | | | | | wherein

Xaa at position 3 is Ser, Gly, Asp, Met, or Gln;

Xaa at position 4 is Asn, His, or Ile;

Xaa at position 5 is Met or Ile;

Xaa at position 7 is Asp or Glu;

Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, Gly, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Leu, Arg, Gln, Leu, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp, Pro, Met, Lys, His, Thr, Asn, Ile, Leu or Tyr;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position,100 is Tyr or Trp;
Xaa at position 101 is Leu or Ala;
Xaa at position 102 is Lys, Thr, Val, Trp, Ser, Ala, His, Met, Phe, Tyr or Ile;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

which can additionally have Met- or Met-Ala- preceding the amino acid in position 1; and wherein from 4 to 35 of the amino acids designated by Xaa are different from the corresponding amino acids of native human interleukin-3.

7. The fusion protein of 6 wherein said human interleukin-3 mutant polypeptide is of the Formula:

| Asn 1 | Cys | Xaa | Xaa | Met 5 | Ile | Asp | Glu | Xaa | Ile 10 | Xaa | Xaa | Leu | Lys | Xaa 15 |
|---|---|---|---|---|---|---|---|---|---|---|---|---|---|---|
| Xaa | Pro | Xaa | Pro | Xaa 20 | Xaa | Asp | Phe | Xaa | Asn 25 | Leu | Asn | Xaa | Glu | Asp 30 |
| Xaa | Xaa | Ile | Leu | Met 35 | Xaa | Xaa | Asn | Leu | Arg 40 | Xaa | Xaa | Asn | Leu | Glu 45 |
| Ala | Phe | Xaa | Arg | Xaa 50 | Xaa | Lys | Xaa | Xaa | Xaa 55 | Asn | Ala | Ser | Ala | Ile 60 |
| Glu | Xaa | Xaa | Leu | Xaa 65 | Xaa | Leu | Xaa | Pro | Cys 70 | Leu | Pro | Xaa | Xaa | Thr 75 |
| Ala | Xaa | Pro | Xaa | Arg 80 | Xaa | Pro | Ile | Xaa | Xaa 85 | Xaa | Xaa | Gly | Asp | Trp 90 |
| Xaa | Glu | Phe | Xaa | Xaa 95 | Lys | Leu | Xaa | Phe | Tyr 100 | Leu | Xaa | Xaa | Leu | Glu 105 |
| Xaa | Xaa | Xaa | Xaa | Gln 110 | Gln | [SEQ ID NO:6] | | | | | | | | | wherein
Xaa at position 3 is Ser, Gly, Asp, or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp, Pro, Met, Lys, His, Pro, Asn, Ile, Leu or Tyr;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys, Val, Trp, or Ile;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu; and which can additionally have Met- or Met-Ala- preceding the amino acid in position 1; and wherein from 4 to 26 of the amino acids designated by Xaa are different from the corresponding amino acids of native (1–133) human interleukin-3.

8. The fusion protein of 7 wherein said human interleukin-3 mutant polypeptide is of the Formula:
Xaa at position 17 is Ser, Lys, Asp, Met, Gln, or Arg;
Xaa at position 18 is Asn, His, Leu, Ile, Phe, Arg, or Gln;
Xaa at position 19 is Met, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, or Val;
Xaa at position 22 is Glu, Trp, Pro, Ser, Ala, His, or Gly;
Xaa at position 23 is Ile, Ala, Gly, Trp, Lys, Leu, Ser, or Arg;
Xaa at position 24 is Ile, Gly, Arg, or Ser;
Xaa at position 25 is Thr, His, Gly, Gln, Arg, Pro, or Ala;
Xaa at position 26 is His, Thr, Phe, Gly, Ala, or Trp;
Xaa at position 27 is Leu, Gly, Arg, Thr, Ser, or Ala;
Xaa at position 28 is Lys, Leu, Gln, Gly, Pro, Val or Trp;
Xaa at position 29 is Gln, Asn, Pro, Arg, or Val;
Xaa at position 30 is Pro, His, Thr, Gly, Asp, Gln, Ser, Leu, or Lys;
Xaa at position 31 is Pro, Asp, Gly, Arg, Leu, or Gln;
Xaa at position 32 is Leu, Arg, Gln, Asn, Gly, Ala, or Glu;
Xaa at position 33 is Pro, Leu, Gln, Thr, or Glu;
Xaa at position 34 is Leu, Gly, Ser, or Lys;
Xaa at position 35 is Leu, Ala, Gly, Asn, Pro, or Gln;
Xaa at position 36 is Asp, Leu, or Val;
Xaa at position 37 is Phe, Ser, or Pro;
Xaa at position 38 is Asn, or Ala;
Xaa at position 40 is Leu, Trp, or Arg;
Xaa at position 41 is Asn, Cys, Arg, Leu, His, Met, Pro;
Xaa at position 42 is Gly, Asp, Ser, Cys, or Ala;
Xaa at position 42 is Glu, Asn, Tyr, Leu, Phe, Asp, Ala, Cys, or Ser;
Xaa at position 44 is Asp, Ser, Leu, Arg, Lys, Thr, Met, Trp, or Pro;
Xaa at position 45 is Gln, Pro, Phe, Val, Met, Leu, Thr, Lys, or Trp;
Xaa at position 46 is Asp, Phe, Ser, Thr, Cys, or Gly;
Xaa at position 47 is Ile, Gly, Ser, Arg, Pro, or His;
Xaa at position 48 is Leu, Ser, Cys, Arg, His, Phe, or Asn;
Xaa at position 49 is Met, Arg, Ala, Gly, Pro, Asn, His, or Asp;
Xaa at position 50 is Glu, Leu, Thr, Asp, or Tyr;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or;
Xaa at position 54 is Arg, Asp, Ile, Ser, Val, Thr, Gln, or Leu;
Xaa at position 55 is Arg, Thr, Val, Ser, Leu, or Gly;
Xaa at position 56 is Pro, Gly, Cys, Ser, Gln, or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Tyr, Asn, or Thr;

Xaa at position 61 is Phe, Asn, Glu, Pro, Lys, Arg, or Ser;
Xaa at position 62 is Asn His, Val, Arg, Pro, Thr, or Ile;
Xaa at position 63 is Arg, Tyr, Trp, Ser, Pro, or Val;
Xaa at position 64 is Ala, Asn, Ser, or Lys;
Xaa at position 65 is Val, Thr, Pro, His, Leu, Phe, or Ser;
Xaa at position 66 is Lys, Ile, Val, Asn, Glu, or Ser;
Xaa at position 67 is Ser, Ala, Phe, Val, Gly, Asn, Ile, Pro, or His;
Xaa at position 68 is Leu, Val, Trp, Ser, Thr, or His;
Xaa at position 69 is Gln, Ala, Pro, Thr, Arg, Trp, Gly, or Leu;
Xaa at position 70 is Asn, Leu, Val, Trp, Pro, or Ala;
Xaa at position 71 is Ala, Met, Leu, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Thr, Pro, Arg, Gly, Ala;
Xaa at position 75 is Glu, Lys, Gly, Asp, Pro, Trp, Arg, Ser, or Leu;
Xaa at position 76 is Ser, Val, Ala, Asn, Trp, Glu, Pro, Gly, or Asp;
Xaa at position 77 is Ile, Ser, Arg, or Thr;
Xaa at position 78 is Leu, Ala, Ser, Glu, Gly, or Arg;
Xaa at position 79 is Lys, Thr, Gly, Asn, Met, Ile, or Asp;
Xaa at position 80 is Asn, Trp, Val, Gly, Thr, Leu, or Arg;
Xaa at position 81 is Leu, Gln, Gly, Ala, Trp, Arg, or Lys;
Xaa at position 82 is Leu, Gln, Lys, Trp, Arg, or Asp;
Xaa at position 83 is Pro, Thr, Trp, Arg, or Met;
Xaa at position 84 is Cys, Glu, Gly, Arg, Met, or Val;
Xaa at position 85 is Leu, Asn, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, or Asn;
Xaa at position 90 is Ala, Ser, Asp, Ile, or Met;
Xaa at position 91 is Ala, Ser, Thr, Phe, Leu, Asp, or His;
Xaa at position 92 is Pro, Phe, Arg, Ser, Lys, His, or Leu;
Xaa at position 93 is Thr, Asp, Ser, Asn, Pro, Ala, Leu, or Arg;
Xaa at position 94 is Arg, Ile, Ser, Glu, Leu, Val, or Pro;
Xaa at position 95 is His, Gln, Pro, Val, Leu, Thr or Tyr;
Xaa at position 96 is Pro, Lys, Tyr, Gly, Ile, or Thr;
Xaa at position 97 is Ile, Lys, Ala, or Asn;
Xaa at position 98 is His, Ile, Asn, Leu, Asp, Ala, Thr, or Pro;
Xaa at position 99 is Ile, Arg, Asp, Pro, Gln, Gly, Phe, or His;
Xaa at position 100 is Lys, Tyr, Leu, His, Ile, Ser, Gln, or Pro;
Xaa at position 101 is Asp, Pro, Met, Lys, His, Thr, Val, Tyr, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, or His;
Xaa at position 106 is Glu, Ser, Ala, Lys, Thr, Ile, Gly, or Pro;
Xaa at position 108 is Arg, Asp, Leu, Thr, Ile, or Pro;
Xaa at position 109 is Arg, Thr, Pro, Glu, Tyr, Leu, Ser, or Gly.

9. The fusion protein of 8 wherein said human interleukin-3 mutant polypeptide is of the Formula:

| | 1 | | | | 5 | | | | | 10 | |
|---|---|---|---|---|---|---|---|---|---|---|---|
| | (Met)$_m$-Ala | Pro | Met | Thr | Gln | Thr | Thr | Ser | Leu | Lys | Thr |
| | | 15 | | | | | | 20 | | | |
| Ser | Trp | Val | Asn | Cys | Ser | Xaa | Xaa | Xaa | Asp | Glu | Ile | Ile |
| 25 | | | | | | 30 | | | | | 35 |
| Xaa | His | Leu | Lys | Xaa | Pro | Pro | Xaa | Pro | Xaa | Leu | Asp | Xaa |
| | | 40 | | | | | 45 | | | 50 | | |
| Xaa | Asn | Leu | Asn | Xaa | Glu | Asp | Xaa | Asp | Ile | Leu | Xaa | Glu |
| | | | | | 55 | | | | | | 60 | |
| Xaa | Asn | Leu | Arg | Xaa | Xaa | Asn | Leu | Xaa | Xaa | Phe | Xaa | Xaa |
| | 65 | | | | | | 70 | | | | | 75 |
| Ala | Xaa | Lys | Xaa | Leu | Xaa | Asn | Ala | Ser | Xaa | Ile | Glu | Xaa |
| | | | 80 | | | | | | 85 | | | |
| Ile | Leu | Xaa | Asn | Leu | Xaa | Pro | Cys | Xaa | Pro | Xaa | Xaa | Thr |
| 90 | | | | | 95 | | | | | | | 100 |
| Ala | Xaa | Pro | Xaa | Arg | Xaa | Pro | Ile | Xaa | Ile | Xaa | Xaa | Gly |
| | | 105 | | | | | | 110 | | | | 115 |
| Asp | Trp | Xaa | Glu | Phe | Arg | Xaa | Lys | Leu | Xaa | Phe | Tyr | Leu |
| | | | | | 120 | | | | | | 125 | |
| Xaa | Xaa | Leu | Glu | Xaa | Ala | Gln | Xaa | Gln | Gln | Thr | Thr | Leu |
| | 130 | | | | | | | | | | | |
| Ser | Leu | Ala | Ile | Phe | [SEQ ID NO:7] | | | | | | | | wherein m is 0 or 1; Xaa at position 18 is Asn or Ile; Xaa at position 19 is Met, Ala or Ile; Xaa at position 20 is Ile, Pro or Ile; Xaa at position 23 is Ile, Ala or Leu; Xaa at position 25 is Thr or His; Xaa at position 29 is Gln, Arg, Val or Ile; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gln; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Tyr; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Glu; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from four to forty-four of the amino acids designated by Xaa are different from the corresponding amino acids of native human interleukin-3.

10. The fusion protein of 9 wherein said human interleukin-3 mutant polypeptide is of the Formula:

```
                    1                       5                      10         [SEQ ID NO:8]
    (Met_m-Ala_n)_p-Asn Cys Ser Xaa Xaa Xaa Asp Glu Xaa Ile 15                      20
    Xaa His Leu Lys Xaa Pro Pro Xaa Pro Xaa Leu Asp Xaa 25                      30                      35
    Xaa Asn Leu Asn Xaa Glu Asp Xaa Xaa Ile Leu Xaa Glu 40                      45
    Xaa Asn Leu Arg Xaa Xaa Asn Leu Xaa Xaa Phe Xaa Xaa 50                      55                      60
    Ala Xaa Lys Xaa Leu Xaa Asn Ala Ser Xaa Ile Glu Xaa 65                      70                      75
    Ile Leu Xaa Asn Xaa Xaa Pro Cys Xaa Pro Xaa Ala Thr 80                      85
    Ala Xaa Pro Xaa Arg Xaa Pro Ile Xaa Ile Xaa Xaa Gly 90                      95                          100
    Asp Trp Xaa Glu Phe Arg Xaa Lys Leu Xaa Phe Tyr Leu 105                     110
    Xaa Xaa Leu Glu Xaa Ala Gln Xaa Gln Gln
``` wherein m is 0 or 1; n is 0 or 1; p is 0 or 1; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Ile; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gln; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Tyr; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to forty-four of the amino acids designated by Xaa are different from the corresponding amino acids of native (15–125)human interleukin-3.

11. The fusion protein of 10 wherein said human interleukin-3 mutant polypeptide is of the Formula:

|     | Asn | Cys | Ser | Ile | Met | Ile | Asp | Glu | Ile | Ile | His | His | Leu |
|-----|-----|-----|-----|-----|-----|-----|-----|-----|-----|-----|-----|-----|-----|
| Lys | Arg | Pro | Pro | Ala | Pro | Leu | Leu | Asp | Pro | Asn | Asn | Leu | Asn |
| Ala | Glu | Asp | Val | Asp | Ile | Leu | Met | Glu | Asn | Asn | Leu | Arg | Arg |
| Pro | Asn | Leu | Glu | Ala | Phe | Asn | Arg | Ala | Val | Lys | Ser | Leu | Gln |
| Asn | Ala | Ser | Ala | Ile | Glu | Ser | Ile | Leu | Lys | Asn | Leu | Leu | Pro |
| Cys | Leu | Pro | Leu | Ala | Thr | Ala | Ala | Pro | Thr | Arg | His | Pro | Ile |
| His | Ile | Lys | Asp | Gly | Asp | Trp | Asn | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 9];

|     | Asn | Cys | Ser | Ile | Met | Ile | Asp | Glu | Ile | Ile | His | His | Leu |
|-----|-----|-----|-----|-----|-----|-----|-----|-----|-----|-----|-----|-----|-----|
| Lys | Arg | Pro | Pro | Asn | Pro | Leu | Leu | Asp | Pro | Asn | Asn | Leu | Asn |
| Ser | Glu | Asp | Met | Asp | Ile | Leu | Met | Glu | Asn | Asn | Leu | Arg | Arg |
| Pro | Asn | Leu | Glu | Ala | Phe | Asn | Arg | Ala | Val | Lys | Ser | Leu | Gln |
| Asn | Ala | Ser | Ala | Ile | Glu | Ser | Ile | Leu | Lys | Asn | Leu | Leu | Pro |
| Cys | Leu | Pro | Leu | Ala | Thr | Ala | Ala | Pro | Thr | Arg | His | Pro | Ile |
| His | Ile | Lys | Asp | Gly | Asp | Trp | Asn | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 10];

|     | Asn | Cys | Ser | Ile | Met | Ile | Asp | Glu | Ile | Ile | His | His | Leu |
|-----|-----|-----|-----|-----|-----|-----|-----|-----|-----|-----|-----|-----|-----|
| Lys | Val | Pro | Pro | Ala | Pro | Leu | Leu | Asp | Ser | Asn | Asn | Leu | Asn |
| Ser | Glu | Asp | Met | Asp | Ile | Leu | Met | Glu | Asn | Asn | Leu | Arg | Arg |
| Pro | Asn | Leu | Glu | Ala | Phe | Asn | Arg | Ala | Val | Lys | Ser | Leu | Gln |
| Asn | Ala | Ser | Ala | Ile | Glu | Ser | Ile | Leu | Lys | Asn | Leu | Leu | Pro |
| Cys | Leu | Pro | Leu | Ala | Thr | Ala | Ala | Pro | Thr | Arg | His | Pro | Ile |
| His | Ile | Lys | Asp | Gly | Asp | Trp | Asn | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 11];

|     | Asn | Cys | Ser | Asn | Met | Ile | Asp | Glu | Ile | Ile | Thr | His | Leu |
|-----|-----|-----|-----|-----|-----|-----|-----|-----|-----|-----|-----|-----|-----|
| Lys | Gln | Pro | Pro | Leu | Pro | Leu | Leu | Asp | Phe | Asn | Asn | Leu | Asn |
| Gly | Glu | Asp | Gln | Asp | Ile | Leu | Met | Glu | Arg | Asn | Leu | Arg | Leu |
| Pro | Asn | Leu | Leu | Ala | Phe | Val | Arg | Ala | Val | Lys | Ser | Leu | Glu |
| Asn | Ala | Ser | Ala | Ile | Glu | Ser | Ile | Leu | Lys | Asn | Leu | Leu | Pro |
| Cys | Leu | Pro | Leu | Ala | Thr | Ala | Ala | Pro | Thr | Arg | His | Pro | Ile |
| His | Ile | Lys | Asp | Gly | Asp | Trp | Asn | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 12];

|     | Asn | Cys | Ser | Asn | Met | Ile | Asp | Glu | Ile | Ile | Thr | His | Leu |
|-----|-----|-----|-----|-----|-----|-----|-----|-----|-----|-----|-----|-----|-----|
| Lys | Gln | Pro | Pro | Leu | Pro | Leu | Leu | Asp | Phe | Asn | Asn | Leu | Asn |
| Gly | Glu | Asp | Gln | Asp | Ile | Leu | Met | Glu | Arg | Asn | Leu | Arg | Leu |
| Pro | Asn | Leu | Glu | Ser | Phe | Val | Arg | Ala | Val | Lys | Asn | Leu | Glu |
| Asn | Ala | Ser | Ala | Ile | Glu | Ser | Ile | Leu | Lys | Asn | Leu | Leu | Pro |
| Cys | Leu | Pro | Leu | Ala | Thr | Ala | Ala | Pro | Thr | Arg | His | Pro | Ile |
| His | Ile | Lys | Asp | Gly | Asp | Trp | Asn | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 13];

|     | Asn | Cys | Ser | Asn | Met | Ile | Asp | Glu | Ile | Ile | Thr | His | Leu |
|-----|-----|-----|-----|-----|-----|-----|-----|-----|-----|-----|-----|-----|-----|
| Lys | Gln | Pro | Pro | Leu | Pro | Leu | Leu | Asp | Phe | Asn | Asn | Leu | Asn |
| Gly | Glu | Asp | Gln | Asp | Ile | Leu | Met | Glu | Arg | Asn | Leu | Arg | Thr |
| Pro | Asn | Leu | Leu | Ala | Phe | Val | Arg | Ala | Val | Lys | His | Leu | Glu |
| Asn | Ala | Ser | Ala | Ile | Glu | Ser | Ile | Leu | Lys | Asn | Leu | Leu | Pro |
| Cys | Leu | Pro | Leu | Ala | Thr | Ala | Ala | Pro | Thr | Arg | His | Pro | Ile |
| His | Ile | Lys | Asp | Gly | Asp | Trp | Asn | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 14];

|     | Asn | Cys | Ser | Asn | Met | Ile | Asp | Glu | Ile | Ile | Thr | His | Leu |
|-----|-----|-----|-----|-----|-----|-----|-----|-----|-----|-----|-----|-----|-----|
| Lys | Gln | Pro | Pro | Leu | Pro | Leu | Leu | Asp | Phe | Asn | Asn | Leu | Asn |
| Gly | Glu | Asp | Gln | Asp | Ile | Leu | Met | Glu | Asn | Asn | Leu | Arg | Arg |
| Pro | Asn | Leu | Glu | Ala | Phe | Asn | Arg | Ala | Val | Lys | Ser | Leu | Gln |
| Asn | Ala | Ser | Gly | Ile | Glu | Ala | Ile | Leu | Arg | Asn | Leu | Gln | Pro |
| Cys | Leu | Pro | Ser | Ala | Thr | Ala | Ala | Pro | Ser | Arg | His | Pro | Ile |
| Ile | Ile | Lys | Ala | Gly | Asp | Trp | Gln | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 15];

|     | Asn | Cys | Ser | Asn | Met | Ile | Asp | Glu | Ile | Ile | Thr | His | Leu |
|-----|-----|-----|-----|-----|-----|-----|-----|-----|-----|-----|-----|-----|-----|
| Lys | Gln | Pro | Pro | Leu | Pro | Leu | Leu | Asp | Phe | Asn | Asn | Leu | Asn |
| Gly | Glu | Asp | Gln | Asp | Ile | Leu | Met | Glu | Asn | Asn | Leu | Arg | Arg |
| Pro | Asn | Leu | Glu | Ala | Phe | Asn | Arg | Ala | Val | Lys | Ser | Leu | Gln |
| Asn | Ala | Ser | Gly | Ile | Glu | Ala | Ile | Leu | Arg | Asn | Leu | Val | Pro |
| Cys | Leu | Pro | Ser | Ala | Thr | Ala | Ala | Pro | Ser | Arg | His | Pro | Ile |
| Thr | Ile | Lys | Ala | Gly | Asp | Trp | Gln | Glu | Phe | Arg | Arg | Lys | Leu |
| Thr | Phe | Tyr | Leu | Lys | Thr | Leu | Glu | Asn | Ala | Gln | Ala | Gln | Gln |

[SEQ ID NO: 16];

|     | Asn | Cys | Ser | Asn | Met | Ile | Asp | Glu | Ile | Ile | Thr | His | Leu |
|-----|-----|-----|-----|-----|-----|-----|-----|-----|-----|-----|-----|-----|-----|
| Lys | Gln | Pro | Pro | Leu | Pro | Leu | Leu | Asp | Phe | Asn | Asn | Leu | Asn |
| Gly | Glu | Asp | Gln | Asp | Ile | Leu | Met | Glu | Asn | Asn | Leu | Arg | Arg |

```
       Pro  Asn  Leu  Glu  Ala  Phe  Asn  Arg  Ala  Val  Lys  Ser  Leu  Gln
       Asn  Ala  Ser  Ala  Ile  Glu  Ser  Ile  Leu  Lys  Asn  Leu  Val  Pro
       Cys  Leu  Pro  Leu  Ala  Thr  Ala  Ala  Pro  Thr  Arg  His  Pro  Ile
       His  Ile  Lys  Asp  Gly  Asp  Trp  Asn  Glu  Phe  Arg  Glu  Lys  Leu
       Thr  Phe  Tyr  Leu  Val  Thr  Leu  Glu  Gln  Ala  Gln  Glu  Gln  Gln
       [SEQ ID NO: 17];
            Asn  Cys  Ser  Asn  Met  Ile  Asp  Glu  Ile  Ile  Thr  His  Leu
       Lys  Gln  Pro  Pro  Leu  Pro  Leu  Leu  Asp  Phe  Asn  Asn  Leu  Asn
       Gly  Glu  Asp  Gln  Asp  Ile  Leu  Met  Glu  Asn  Asn  Leu  Arg  Arg
       Pro  Asn  Leu  Glu  Ala  Phe  Asn  Arg  Ala  Val  Lys  Ser  Leu  Gln
       Asn  Ala  Ser  Ala  Ile  Glu  Ser  Ile  Leu  Lys  Asn  Leu  Leu  Pro
       Cys  Leu  Pro  Leu  Ala  Thr  Ala  Ala  Pro  Thr  Arg  His  Pro  Ile
       His  Ile  Lys  Asp  Gly  Asp  Trp  Asn  Glu  Phe  Arg  Glu  Lys  Leu
       Thr  Phe  Tyr  Leu  Val  Ser  Leu  Glu  His  Ala  Gln  Glu  Gln  Gln
       [SEQ ID NO: 18];
            Asn  Cys  Ser  Asn  Met  Ile  Asp  Glu  Ile  Ile  Thr  His  Leu
       Lys  Gln  Pro  Pro  Leu  Pro  Leu  Leu  Asp  Phe  Asn  Asn  Leu  Asn
       Gly  Glu  Asp  Gln  Asp  Ile  Leu  Met  Glu  Asn  Asn  Leu  Arg  Arg
       Pro  Asn  Leu  Glu  Ala  Phe  Asn  Arg  Ala  Val  Lys  Ser  Leu  Gln
       Asn  Ala  Ser  Gly  Ile  Glu  Ala  Ile  Leu  Arg  Asn  Leu  Gln  Pro
       Cys  Leu  Pro  Ser  Ala  Thr  Ala  Ala  Pro  Ser  Arg  His  Pro  Ile
       Ile  Ile  Lys  Ala  Gly  Asp  Trp  Gln  Glu  Phe  Arg  Glu  Lys  Leu
       Thr  Phe  Tyr  Leu  Val  Thr  Leu  Glu  Gln  Ala  Gln  Glu  Gln  Gln
       [SEQ ID NO: 19];
            Asn  Cys  Ser  Asn  Met  Ile  Asp  Glu  Ile  Ile  Thr  His  Leu
       Lys  Gln  Pro  Pro  Leu  Pro  Leu  Leu  Asp  Phe  Asn  Asn  Leu  Asn
       Gly  Glu  Asp  Gln  Asp  Ile  Leu  Met  Glu  Asn  Asn  Leu  Arg  Arg
       Pro  Asn  Leu  Glu  Ala  Phe  Asn  Arg  Ala  Val  Lys  Ser  Leu  Gln
       Asn  Ala  Ser  Gly  Ile  Glu  Ala  Ile  Leu  Arg  Asn  Leu  Val  Pro
       Cys  Leu  Pro  Ser  Ala  Thr  Ala  Ala  Pro  Ser  Arg  His  Pro  Ile
       Thr  Ile  Lys  Ala  Gly  Asp  Trp  Gln  Glu  Phe  Arg  Glu  Lys  Leu
       Thr  Phe  Tyr  Leu  Val  Thr  Leu  Glu  Gln  Ala  Gln  Glu  Gln  Gln
       [SEQ ID NO: 20];
            Asn  Cys  Ser  Asn  Met  Ile  Asp  Glu  Ile  Ile  Thr  His  Leu
       Lys  Gln  Pro  Pro  Leu  Pro  Leu  Leu  Asp  Phe  Asn  Asn  Leu  Asn
       Gly  Glu  Asp  Gln  Asp  Ile  Leu  Met  Glu  Asn  Asn  Leu  Arg  Arg
       Pro  Asn  Leu  Glu  Ala  Phe  Asn  Arg  Ala  Val  Lys  Ser  Leu  Gln
       Asn  Ala  Ser  Gly  Ile  Glu  Ala  Ile  Leu  Arg  Asn  Leu  Val  Pro
       Cys  Leu  Pro  Ser  Ala  Thr  Ala  Ala  Pro  Ser  Arg  His  Pro  Ile
       Thr  Ile  Lys  Ala  Gly  Asp  Trp  Gln  Glu  Phe  Arg  Glu  Lys  Leu
       Thr  Phe  Tyr  Leu  Val  Ser  Leu  Glu  His  Ala  Gln  Glu  Gln  Gln
       [SEQ ID NO: 21];
            Asn  Cys  Ser  Ile  Met  Ile  Asp  Glu  Ile  Ile  His  His  Leu
       Lys  Arg  Pro  Pro  Ala  Pro  Leu  Leu  Asp  Pro  Asn  Asn  Leu  Asn
       Ala  Glu  Asp  Val  Asp  Ile  Leu  Met  Glu  Arg  Asn  Leu  Arg  Leu
       Pro  Asn  Leu  Glu  Ser  Phe  Val  Arg  Ala  Val  Lys  Asn  Leu  Glu
       Asn  Ala  Ser  Ala  Ile  Glu  Ser  Ile  Leu  Lys  Asn  Leu  Leu  Pro
       Cys  Leu  Pro  Leu  Ala  Thr  Ala  Ala  Pro  Thr  Arg  His  Pro  Ile
       His  Ile  Lys  Asp  Gly  Asp  Trp  Asn  Glu  Phe  Arg  Arg  Lys  Leu
       Thr  Phe  Tyr  Leu  Lys  Thr  Leu  Glu  Asn  Ala  Gln  Ala  Gln  Gln
       [SEQ ID NO: 22];
            Asn  Cys  Ser  Ile  Met  Ile  Asp  Glu  Ile  Ile  His  His  Leu
       Lys  Arg  Pro  Pro  Asn  Pro  Leu  Leu  Asp  Pro  Asn  Asn  Leu  Asn
       Ser  Glu  Asp  Met  Asp  Ile  Leu  Met  Glu  Arg  Asn  Leu  Arg  Thr
       Pro  Asn  Leu  Leu  Ala  Phe  Val  Arg  Ala  Val  Lys  His  Leu  Glu
       Asn  Ala  Ser  Ala  Ile  Glu  Ser  Ile  Leu  Lys  Asn  Leu  Leu  Pro
       Cys  Leu  Pro  Leu  Ala  Thr  Ala  Ala  Pro  Thr  Arg  His  Pro  Ile
       His  Ile  Lys  Asp  Gly  Asp  Trp  Asn  Glu  Phe  Arg  Arg  Lys  Leu
       Thr  Phe  Tyr  Leu  Lys  Thr  Leu  Glu  Asn  Ala  Gln  Ala  Gln  Gln
       [SEQ ID NO: 23];
            Asn  Cys  Ser  Ile  Met  Ile  Asp  Glu  Ile  Ile  His  His  Leu
       Lys  Val  Pro  Pro  Ala  Pro  Leu  Leu  Asp  Ser  Asn  Asn  Leu  Asn
       Ser  Glu  Asp  Met  Asp  Ile  Leu  Met  Glu  Arg  Asn  Leu  Arg  Leu
       Pro  Asn  Leu  Leu  Ala  Phe  Val  Arg  Ala  Val  Lys  His  Leu  Glu
       Asn  Ala  Ser  Ala  Ile  Glu  Ser  Ile  Leu  Lys  Asn  Leu  Leu  Pro
       Cys  Leu  Pro  Leu  Ala  Thr  Ala  Ala  Pro  Thr  Arg  His  Pro  Ile
       His  Ile  Lys  Asp  Gly  Asp  Trp  Asn  Glu  Phe  Arg  Arg  Lys  Leu
       Thr  Phe  Tyr  Leu  Lys  Thr  Leu  Glu  Asn  Ala  Gln  Ala  Gln  Gln
       [SEQ ID NO: 24];
       Met  Ala  Asn  Cys  Ser  Asn  Met  Ile  Asp  Glu  Ile  Ile  Thr  His
       Leu  Lys  Gln  Pro  Pro  Leu  Pro  Leu  Leu  Asp  Phe  Asn  Asn  Leu
       Asn  Gly  Glu  Asp  Gln  Asp  Ile  Leu  Met  Glu  Asn  Asn  Leu  Arg
       Arg  Pro  Asn  Leu  Glu  Ala  Phe  Asn  Arg  Ala  Val  Lys  Ser  Leu
       Gln  Asn  Ala  Ser  Gly  Ile  Glu  Ala  Ile  Leu  Arg  Asn  Leu  Gln
       Pro  Cys  Leu  Pro  Ser  Ala  Thr  Ala  Ala  Pro  Ser  Arg  His  Pro
       Ile  Ile  Ile  Lys  Ala  Gly  Asp  Trp  Gln  Glu  Phe  Arg  Glu  Lys
       Leu  Thr  Phe  Tyr  Leu  Val  Thr  Leu  Glu  Gln  Ala  Gln  Glu  Gln
       Gln  [SEQ ID NO: 25];
       Met  Ala  Asn  Cys  Ser  Asn  Met  Ile  Asp  Glu  Ile  Ile  Thr  His
```

-continued

```
Leu  Lys  Gln  Pro  Pro  Leu  Pro  Leu  Leu  Asp  Phe  Asn  Asn  Leu
Asn  Gly  Glu  Asp  Gln  Asp  Ile  Leu  Met  Glu  Asn  Asn  Leu  Arg
Arg  Pro  Asn  Leu  Glu  Ala  Phe  Asn  Arg  Ala  Val  Lys  Ser  Leu
Gln  Asn  Ala  Ser  Gly  Ile  Glu  Ala  Ile  Leu  Arg  Asn  Leu  Val
Pro  Cys  Leu  Pro  Ser  Ala  Thr  Ala  Ala  Pro  Ser  Arg  His  Pro
Ile  Thr  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  [SEQ ID NO: 26];
Met  Ala  Asn  Cys  Ser  Asn  Met  Ile  Asp  Glu  Ile  Ile  Thr  His
Leu  Lys  Gln  Pro  Pro  Leu  Pro  Leu  Leu  Asp  Phe  Asn  Asn  Leu
Asn  Gly  Glu  Asp  Gln  Asp  Ile  Leu  Met  Glu  Asn  Asn  Leu  Arg
Arg  Pro  Asn  Leu  Glu  Ala  Phe  Asn  Arg  Ala  Val  Lys  Ser  Leu
Gln  Asn  Ala  Ser  Gly  Ile  Glu  Ala  Ile  Leu  Arg  Asn  Leu  Val
Pro  Cys  Leu  Pro  Ser  Ala  Thr  Ala  Ala  Pro  Ser  Arg  His  Pro
Ile  Thr  Ile  Lys  Ala  Gly  Asp  Trp  Gln  Glu  Phe  Arg  Glu  Lys
Leu  Thr  Phe  Tyr  Leu  Val  Ser  Leu  Glu  His  Ala  Gln  Glu  Gln
Gln  [SEQ ID NO: 27];
Met  Ala  Asn  Cys  Ser  Ile  Met  Ile  Asp  Glu  Ile  Ile  His  His
Leu  Lys  Gln  Pro  Pro  Leu  Pro  Leu  Leu  Asp  Phe  Asn  Asn  Leu
Asn  Ala  Glu  Asp  Val  Asp  Ile  Leu  Met  Glu  Arg  Asn  Leu  Arg
Leu  Pro  Asn  Leu  Glu  Ser  Phe  Val  Arg  Ala  Val  Lys  Asn  Leu
Gln  Asn  Ala  Ser  Ala  Ile  Glu  Ser  Ile  Leu  Lys  Asn  Leu  Leu
Pro  Cys  Leu  Pro  Leu  Ala  Thr  Ala  Ala  Pro  Thr  Arg  His  Pro
Ile  His  Ile  Lys  Asp  Gly  Asp  Trp  Asn  Glu  Phe  Arg  Arg  Lys
Leu  Thr  Phe  Tyr  Leu  Lys  Thr  Leu  Glu  Asn  Ala  Gln  Ala  Gln
Gln  [SEQ ID NO: 28];
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Ala  Ile  Glu  Ser  Ile  Leu  Lys  Asn  Leu  Leu
Pro  Cys  Leu  Pro  Leu  Ala  Thr  Ala  Ala  Pro  Thr  Arg  His  Pro
Ile  His  Ile  Lys  Asp  Gly  Asp  Trp  Asn  Glu  Phe  Arg  Arg  Lys
Leu  Thr  Phe  Tyr  Leu  Lys  Thr  Leu  Glu  Asn  Ala  Gln  Ala  Gln
Gln  [SEQ ID NO: 29];
Met  Ala  Asn  Cys  Ser  Ile  Met  Ile  Asp  Glu  Ile  Ile  His  His
Leu  Lys  Val  Pro  Pro  Ala  Pro  Leu  Leu  Asp  Ser  Asn  Asn  Leu
Asn  Ser  Glu  Asp  Met  Asp  Ile  Leu  Met  Glu  Arg  Asn  Leu  Arg
Leu  Pro  Asn  Leu  Leu  Ala  Phe  Val  Arg  Ala  Val  Lys  Asn  Leu
Glu  Asn  Ala  Ser  Ala  Ile  Glu  Ser  Ile  Leu  Lys  Asn  Leu  Leu
Pro  Cys  Leu  Pro  Leu  Ala  Thr  Ala  Ala  Pro  Thr  Arg  His  Pro
Ile  His  Ile  Lys  Asp  Gly  Asp  Trp  Asn  Glu  Phe  Arg  Arg  Lys
Leu  Thr  Phe  Tyr  Leu  Lys  Thr  Leu  Glu  Asn  Ala  Gln  Ala  Gln
Gln  [SEQ ID NO: 30];
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Ala  Glu  Asp  Val  Asp  Ile  Leu  Met  Glu  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  [SEQ ID NO: 31];
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  [SEQ ID NO: 32];
Met  Ala  Asn  Cys  Ser  Ile  Met  Ile  Asp  Glu  Ile  Ile  His  His
Leu  Lys  Val  Pro  Pro  Ala  Pro  Leu  Leu  Asp  Ser  Asn  Asn  Leu
Asn  Ser  Glu  Asp  Met  Asp  Ile  Leu  Met  Glu  Arg  Asn  Leu  Arg
Leu  Pro  Asn  Leu  Leu  Ala  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  [SEQ ID NO: 33];
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Ala  Glu  Asp  Val  Asp  Ile  Leu  Met  Glu  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Val
Pro  Cys  Leu  Pro  Ser  Ala  Thr  Ala  Ala  Pro  Ser  Arg  His  Pro
Ile  Thr  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
```

-continued

Gln [SEQ ID NO: 34];
Met Ala Asn Cys Ser Ile Met Ile Asp Glu Ile Ile His His
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln [SEQ ID NO: 35];
Met Ala Asn Cys Ser Ile Met Ile Asp Glu Ile Ile His His
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln [SEQ ID NO: 36];
Met Ala Asn Cys Ser Ile Met Ile Asp Glu Ile Ile His His
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln [SEQ ID NO: 37];
Met Ala Asn Cys Ser Ile Met Ile Asp Glu Ile Ile His His
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln [SEQ ID NO: 38];
Met Ala Asn Cys Ser Ile Met Ile Asp Glu Ile Ile His His
Leu Lys Arg Pro Pro Ala Pro Leu Leu Asp Pro Asn Asn Leu
Asn Ala Glu Asp Val Asp Ile Leu Met Gln Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln [SEQ ID NO: 39].
Met Ala Asn Cys Ser Ile Met Ile Asp Glu Ile Ile His His
Leu Lys Arg Pro Pro Ala Pro Leu Leu Asp Pro Asn Asn Leu
Asn Ala Glu Asp Val Asp Ile Leu Met Asp Arg Asn Leu Arg
Leu Ser Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln [SEQ ID NO: 40]
Met Ala Asn Cys Ser Ile Met Ile Asp Glu Ala Ile His His
Leu Lys Arg Pro Pro Ala Pro Ser Leu Lys Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln [SEQ ID NO: 41]
Met Ala Asn Cys Ser Ile Met Ile Asp Glu Ile Ile His His
Leu Lys Arg Pro Pro Ala Pro Leu Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln [SEQ ID NO: 42]
Met Ala Asn Cys Ser Ile Met Ile Asp Glu Ile Ile His His
Leu Lys Arg Pro Pro Ala Pro Leu Leu Asp Pro Asn Asn Leu
Asn Asp Glu Asp Val Asp Ile Leu Met Asp Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro

-continued

| Ile | Ile | Ile | Lys | Ala | Gly | Asp | Trp | Gln | Glu | Phe | Arg | Glu | Lys |
|---|---|---|---|---|---|---|---|---|---|---|---|---|---|
| Leu | Thr | Phe | Tyr | Leu | Val | Thr | Leu | Glu | Gln | Ala | Gln | Glu | Gln |
| Gln [SEQ ID NO: 43] | | | | | | | | | | | | | |
| Met | Ala | Asn | Cys | Ser | Ile | Met | Ile | Asp | Glu | Ile | Ile | His | His |
| Leu | Lys | Arg | Pro | Pro | Ala | Pro | Leu | Leu | Asp | Pro | Asn | Asn | Leu |
| Asn | Asp | Glu | Asp | Val | Ser | Ile | Leu | Met | Glu | Arg | Asn | Leu | Arg |
| Leu | Pro | Asn | Leu | Glu | Ser | Phe | Val | Arg | Ala | Val | Lys | Asn | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln [SEQ ID NO: 44] | | | | | | | | | | | | | |
| Met | Ala | Asn | Cys | Ser | Ile | Met | Ile | Asp | Glu | Ile | Ile | His | His |
| Leu | Lys | Arg | Pro | Pro | Ala | Pro | Leu | Leu | Asp | Pro | Asn | Asn | Leu |
| Asn | Asp | Glu | Asp | Met | Ser | Ile | Leu | Met | Glu | Arg | Asn | Leu | Arg |
| Leu | Pro | Asn | Leu | Glu | Ser | Phe | Val | Arg | Ala | Val | Lys | Asn | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln [SEQ ID NO: 45] | | | | | | | | | | | | | |
| Met | Ala | Tyr | Pro | Glu | Thr | Asp | Asp | Asp | Asp | Ile | Ile | His | Lys |
| Asn | Cys | Ser | Ile | Met | Ile | Asp | Glu | Ile | Ile | His | His | Leu | Lys |
| Arg | Pro | Pro | Ala | Pro | Leu | Leu | Asp | Pro | Asn | Asn | Leu | Asn | Ala |
| Glu | Asp | Val | Asp | Ile | Leu | Met | Glu | Arg | Asn | Leu | Arg | Leu | Pro |
| Asn | Leu | Glu | Ser | Phe | Val | Arg | Ala | Val | Lys | Asn | Leu | Glu | Asn |
| Ala | Ser | Gly | Ile | Glu | Ala | Ile | Leu | Arg | Asn | Leu | Gln | Pro | Cys |
| Leu | Pro | Ser | Ala | Thr | Ala | Ala | Pro | Ser | Arg | His | Pro | Ile | Ile |
| Ile | Lys | Ala | Gly | Asp | Trp | Gln | Glu | Phe | Arg | Glu | Lys | Leu | Thr |
| Phe | Tyr | Leu | Val | Thr | Leu | Glu | Gln | Ala | Gln | Glu | Gln | Gln | |
| [SEQ ID NO: 46] | | | | | | | | | | | | | |
| Met | Ala | Tyr | Pro | Glu | Thr | Asp | Asp | Asp | Asp | Ile | Ile | His | Lys |
| Asn | Cys | Ser | Ile | Met | Ile | Asp | Glu | Ile | Ile | His | His | Leu | Lys |
| Arg | Pro | Pro | Asn | Pro | Leu | Leu | Asp | Pro | Asn | Asn | Leu | Asn | Ser |
| Glu | Asp | Met | Asp | Ile | Leu | Met | Glu | Arg | Asn | Leu | Arg | Thr | Pro |
| Asn | Leu | Leu | Ala | Phe | Val | Arg | Ala | Val | Lys | His | Leu | Glu | Asn |
| Ala | Ser | Gly | Ile | Glu | Ala | Ile | Leu | Arg | Asn | Leu | Gln | Pro | Cys |
| Leu | Pro | Ser | Ala | Thr | Ala | Ala | Pro | Ser | Arg | His | Pro | Ile | Ile |
| Ile | Lys | Ala | Gly | Asp | Trp | Gln | Glu | Phe | Arg | Glu | Lys | Leu | Thr |
| Phe | Tyr | Leu | Val | Thr | Leu | Glu | Gln | Ala | Gln | Glu | Gln | Gln | |
| [SEQ ID NO: 47] and | | | | | | | | | | | | | |
| Met | Ala | Asn | Cys | Ser | Ile | Met | Ile | Asp | Glu | Leu | Ile | His | His |
| Leu | Lys | Ile | Pro | Pro | Asn | Pro | Ser | Leu | Asp | Ser | Ala | Asn | Leu |
| Asn | Ser | Glu | Asp | Val | Ser | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln [SEQ ID NO: 48]. | | | | | | | | | | | | | |

The following are examples of the fusion proteins of the presents invention:

| Met | Ala | Asn | Cys | Ser | Ile | Met | Ile | Asp | Glu | Ile | Ile | His | His |
|---|---|---|---|---|---|---|---|---|---|---|---|---|---|
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Gly | Gly | Ser |
| Gly | Gly | Gly | Ser | Asn | Met | Ala | Thr | Pro | Leu | Gly | Pro | Ala | Ser |
| Ser | Leu | Pro | Gln | Ser | Phe | Leu | Leu | Lys | Cys | Leu | Glu | Gln | Val |
| Arg | Lys | Ile | Gln | Gly | Asp | Gly | Ala | Ala | Leu | Gln | Glu | Lys | Leu |
| Cys | Ala | Thr | Tyr | Lys | Leu | Cys | His | Pro | Glu | Glu | Leu | Val | Leu |
| Leu | Gly | His | Ser | Leu | Gly | Ile | Pro | Trp | Ala | Pro | Leu | Ser | Ser |
| Cys | Pro | Ser | Gln | Ala | Leu | Gln | Leu | Ala | Gly | Cys | Leu | Ser | Gln |
| Leu | His | Ser | Gly | Leu | Phe | Leu | Tyr | Gln | Gly | Leu | Leu | Gln | Ala |
| Leu | Glu | Gly | Ile | Ser | Pro | Glu | Leu | Gly | Pro | Thr | Leu | Asp | Thr |
| Leu | Gln | Leu | Asp | Val | Ala | Asp | Phe | Ala | Thr | Thr | Ile | Trp | Gln |
| Gln | Met | Glu | Glu | Leu | Gly | Met | Ala | Pro | Ala | Leu | Gln | Pro | Thr |

-continued

```
Gln  Gly  Ala  Met  Pro  Ala  Phe  Ala  Ser  Ala  Phe  Gln  Arg  Arg
Ala  Gly  Gly  Val  Leu  Val  Ala  Ser  His  Leu  Gln  Ser  Phe  Leu
Glu  Val  Ser  Tyr  Arg  Val  Leu  Arg  His  Leu  Ala  Gln  Pro
[SEQ ID NO:121]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Gln  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Arg  Ile  Ser  Pro  Gly  Gly  Gly  Ser
Gly  Gly  Gly  Ser  Asn  Met  Ala  Thr  Pro  Leu  Gly  Pro  Ala  Ser
Ser  Leu  Pro  Gln  Ser  Phe  Leu  Leu  Lys  Ser  Leu  Glu  Gln  Val
Arg  Lys  Ile  Gln  Gly  Asp  Gly  Ala  Ala  Leu  Gln  Glu  Lys  Leu
Cys  Ala  Thr  Tyr  Lys  Leu  Cys  His  Pro  Glu  Glu  Leu  Val  Leu
Leu  Gly  His  Ser  Leu  Gly  Ile  Pro  Trp  Ala  Pro  Leu  Ser  Ser
Cys  Pro  Ser  Gln  Ala  Leu  Gln  Leu  Ala  Gly  Cys  Leu  Ser  Gln
Leu  His  Ser  Gly  Leu  Phe  Leu  Tyr  Gln  Gly  Leu  Leu  Gln  Ala
Leu  Glu  Gly  Ile  Ser  Pro  Glu  Leu  Gly  Pro  Thr  Leu  Asp  Thr
Leu  Gln  Leu  Asp  Val  Ala  Asp  Phe  Ala  Thr  Thr  Ile  Trp  Gln
Gln  Met  Glu  Glu  Leu  Gly  Met  Ala  Pro  Ala  Leu  Gln  Pro  Thr
Gln  Gly  Ala  Met  Pro  Ala  Phe  Ala  Ser  Ala  Phe  Gln  Arg  Arg
Ala  Gly  Gly  Val  Leu  Val  Ala  Ser  His  Leu  Gln  Ser  Phe  Leu
Glu  Val  Ser  Tyr  Arg  Val  Leu  Arg  His  Leu  Ala  Gln  Pro
[SEQ ID NO:122]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Lys  Ile  Ser  Pro  Gly  Gly  Gly  Ser
Gly  Gly  Gly  Ser  Asn  Met  Ala  Thr  Pro  Leu  Gly  Pro  Ala  Ser
Ser  Leu  Pro  Gln  Ser  Phe  Leu  Leu  Lys  Ser  Leu  Glu  Gln  Val
Arg  Lys  Ile  Gln  Gly  Asp  Gly  Ala  Ala  Leu  Gln  Glu  Lys  Leu
Cys  Ala  Thr  Tyr  Lys  Leu  Cys  His  Pro  Glu  Glu  Leu  Val  Leu
Leu  Gly  His  Ser  Leu  Gly  Ile  Pro  Trp  Ala  Pro  Leu  Ser  Ser
Cys  Pro  Ser  Gln  Ala  Leu  Gln  Leu  Ala  Gly  Cys  Leu  Ser  Gln
Leu  His  Ser  Gly  Leu  Phe  Leu  Tyr  Gln  Gly  Leu  Leu  Gln  Ala
Leu  Glu  Gly  Ile  Ser  Pro  Glu  Leu  Gly  Pro  Thr  Leu  Asp  Thr
Leu  Gln  Leu  Asp  Val  Ala  Asp  Phe  Ala  Thr  Thr  Ile  Trp  Gln
Gln  Met  Glu  Glu  Leu  Gly  Met  Ala  Pro  Ala  Leu  Gln  Pro  Thr
Gln  Gly  Ala  Met  Pro  Ala  Phe  Ala  Ser  Ala  Phe  Gln  Arg  Arg
Ala  Gly  Gly  Val  Leu  Val  Ala  Ser  His  Leu  Gln  Ser  Phe  Leu
Glu  Val  Ser  Tyr  Arg  Val  Leu  Arg  His  Leu  Ala  Gln  Pro
[SEQ ID NO:123]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Gln  Phe  Arg  Glu  Lys
Leu  Thr  Phe  Tyr  Leu  Val  Thr  Leu  Glu  Gln  Ala  Gln  Glu  Gln
Gln  Tyr  Val  Glu  Gly  Gly  Gly  Gly  Ser  Pro  Gly  Gly  Gly  Ser
Gly  Gly  Gly  Ser  Asn  Met  Ala  Thr  Pro  Leu  Gly  Pro  Ala  Ser
Ser  Leu  Pro  Gln  Ser  Phe  Leu  Leu  Lys  Ser  Leu  Glu  Gln  Val
Arg  Lys  Ile  Gln  Gly  Asp  Gly  Ala  Ala  Leu  Gln  Glu  Lys  Leu
Cys  Ala  Thr  Tyr  Lys  Leu  Cys  His  Pro  Glu  Glu  Leu  Val  Leu
Leu  Gly  His  Ser  Leu  Gly  Ile  Pro  Trp  Ala  Pro  Leu  Ser  Ser
Cys  Pro  Ser  Gln  Ala  Leu  Gln  Leu  Ala  Gly  Cys  Leu  Ser  Gln
Leu  His  Ser  Gly  Leu  Phe  Leu  Tyr  Gln  Gly  Leu  Leu  Gln  Ala
Leu  Glu  Gly  Ile  Ser  Pro  Glu  Leu  Gly  Pro  Thr  Leu  Asp  Thr
Leu  Gln  Leu  Asp  Val  Ala  Asp  Phe  Ala  Thr  Thr  Ile  Trp  Gln
Gln  Met  Glu  Glu  Leu  Gly  Met  Ala  Pro  Ala  Leu  Gln  Pro  Thr
Gln  Gly  Ala  Met  Pro  Ala  Phe  Ala  Ser  Ala  Phe  Gln  Arg  Arg
Ala  Gly  Gly  Val  Leu  Val  Ala  Ser  His  Leu  Gln  Ser  Phe  Leu
Glu  Val  Ser  Tyr  Arg  Val  Leu  Arg  His  Leu  Ala  Gln  Pro
[SEQ ID NO:124]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
```

-continued

| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Gly | Gly | Ser |
| Gly | Gly | Gly | Ser | Asn | Met | Ala | Asn | Cys | Ser | Ile | Met | Ile | Asp |
| Glu | Ile | Ile | His | His | Leu | Lys | Arg | Pro | Pro | Asn | Pro | Leu | Leu |
| Asp | Pro | Asn | Asn | Leu | Asn | Ser | Glu | Asp | Met | Asp | Ile | Leu | Met |
| Glu | Arg | Asn | Leu | Arg | Thr | Pro | Asn | Leu | Leu | Ala | Phe | Val | Arg |
| Ala | Val | Lys | His | Leu | Glu | Asn | Ala | Ser | Gly | Ile | Glu | Ala | Ile |
| Leu | Arg | Asn | Leu | Gln | Pro | Cys | Leu | Pro | Ser | Ala | Thr | Ala | Ala |
| Pro | Ser | Arg | His | Pro | Ile | Ile | Ile | Lys | Ala | Gly | Asp | Trp | Gln |
| Glu | Phe | Arg | Glu | Lys | Leu | Thr | Phe | Tyr | Leu | Val | Thr | Leu | Glu |
| Gln | Ala | Gln | Glu | Gln | Gln | [SEQ ID NO:125] | | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Lys | Ile | Ser | Pro | Gly | Gly | Gly | Ser |
| Gly | Gly | Gly | Ser | Asn | Met | Ala | Asn | Cys | Ser | Ile | Met | Ile | Asp |
| Glu | Ile | Ile | His | His | Leu | Lys | Arg | Pro | Pro | Asn | Pro | Leu | Leu |
| Asp | Pro | Asn | Asn | Leu | Asn | Ser | Glu | Asp | Met | Asp | Ile | Leu | Met |
| Glu | Arg | Asn | Leu | Arg | Thr | Pro | Asn | Leu | Leu | AL | APhe | Val | Arg |
| Ala | Val | Lys | His | Leu | Glu | Asn | Ala | Ser | Gly | Ile | Glu | Ala | Ile |
| Leu | Arg | Asn | Leu | Gln | Pro | Cys | Leu | Pro | Ser | Ala | Thr | Ala | Ala |
| Pro | Ser | Arg | His | Pro | Ile | Ile | Ile | Lys | Ala | Gly | Asp | Trp | Gln |
| Glu | Phe | Arg | Glu | Lys | Leu | Thr | Phe | Tyr | Leu | Val | Thr | Leu | Glu |
| Gln | Ala | Gln | Glu | Gln | Gln | [SEQ ID NO.126] | | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Glu | Gly | Gly | Gly | Ser | Pro | Gly | Gly | Gly | Ser |
| Gly | Gly | Gly | Ser | Asn | Met | Ala | Asn | Cys | Ser | Ile | Met | Ile | Asp |
| Glu | Ile | Ile | His | His | Leu | Lys | Arg | Pro | Pro | Asn | Pro | Leu | Leu |
| Asp | Pro | Asn | Asn | Leu | Asn | Ser | Glu | Asp | Met | Asp | Ile | Leu | Met |
| Glu | Arg | Asn | Leu | Arg | Thr | Pro | Asn | Leu | Leu | Ala | Phe | Val | Arg |
| Ala | Val | Lys | His | Leu | Glu | Asn | Ala | Ser | Gly | Ile | Glu | Ala | Ile |
| Leu | Arg | Asn | Leu | Gln | Pro | Cys | Leu | Pro | Ser | Ala | Thr | Ala | Ala |
| Pro | Ser | Arg | His | Pro | Ile | Ile | Ile | Lys | Ala | Gly | Asp | Trp | Gln |
| Glu | Phe | Arg | Glu | Lys | Leu | Thr | Phe | Tyr | Leu | Val | Thr | Leu | Glu |
| Gln | Ala | Gln | Glu | Gln | Gln | [SEQ ID NO:127] | | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Thr | Pro | Leu | Gly | Pro | Ala |
| Ser | Ser | Leu | Pro | Gln | Ser | Phe | Leu | Leu | Lys | Cys | Leu | Glu | Gln |
| Val | Arg | Lys | Ile | Gln | Gly | Asp | Gly | Ala | Ala | Leu | Gln | Glu | Lys |
| Leu | Cys | Ala | Thr | Tyr | Lys | Leu | Cys | His | Pro | Glu | Glu | Leu | Val |
| Leu | Leu | Gly | His | Ser | Leu | Gly | Ile | Pro | Trp | Ala | Pro | Leu | Ser |
| Ser | Cys | Pro | Ser | Gln | Ala | Leu | Gln | Leu | Ala | Gly | Cys | Leu | Ser |
| Gln | Leu | His | Ser | Gly | Leu | Phe | Leu | Tyr | Gln | Gly | Leu | Leu | Gln |
| Ala | Leu | Glu | Gly | Ile | Ser | Pro | Glu | Leu | Gly | Pro | Thr | Leu | Asp |
| Thr | Leu | Gln | Leu | Asp | Val | Ala | Asp | Phe | Ala | Thr | Thr | Ile | Trp |
| Gln | Gln | Met | Glu | Glu | Leu | Gly | Met | Ala | Pro | Ala | Leu | Gln | Pro |
| Thr | Gln | Gly | Ala | Met | Pro | Ala | Phe | Ala | Ser | Ala | Phe | Gln | Arg |
| Arg | Ala | Gly | Gly | Val | Leu | Val | Ala | Ser | His | Leu | Gln | Ser | Phe |
| Leu | Glu | Val | Ser | Tyr | Arg | Val | Leu | Arg | His | Leu | Ala | Gln | Pro |
| [SEQ ID NO:128] | | | | | | | | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |

-continued

| Leu | Thr | Phe | Tyr | Leu | Val | Thr | Leu | Glu | Gln | Ala | Gln | Glu | Gln |
| Gln | Tyr | Val | Ile | Glu | Gly | Lys | Ile | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Thr | Pro | Leu | Gly | Pro | Ala |
| Ser | Ser | Leu | Pro | Gln | Ser | Phe | Leu | Leu | Lys | Cys | Leu | Glu | Gln |
| Val | Arg | Lys | Ile | Gln | Gly | Asp | Gly | Ala | Ala | Leu | Gln | Glu | Lys |
| Leu | Cys | Ala | Thr | Tyr | Lys | Leu | Cys | His | Pro | Glu | Glu | Leu | Val |
| Leu | Leu | Gly | His | Ser | Leu | Gly | Ile | Pro | Trp | Ala | Pro | Leu | Ser |
| Ser | Cys | Pro | Ser | Gln | Ala | Leu | Gln | Leu | Ala | Gly | Cys | Leu | Ser |
| Gln | Leu | His | Ser | Gly | Leu | Phe | Leu | Tyr | Gln | Gly | Leu | Leu | Gln |
| Ala | Leu | Glu | Gly | Ile | Ser | Pro | Glu | Leu | Gly | Pro | Thr | Leu | Asp |
| Thr | Leu | Gln | Leu | Asp | Val | Ala | Asp | Phe | Ala | Thr | Thr | Ile | Trp |
| Gln | Gln | Met | Glu | Gly | Leu | Gly | Met | Ala | Pro | Ala | Leu | Gln | Pro |
| Thr | Gln | Gly | Ala | Met | Pro | Ala | Phe | Ala | Ser | Ala | Phe | Gln | Arg |
| Arg | Ala | Gly | Gly | Val | Leu | Val | Ala | Ser | His | Leu | Gln | Ser | Phe |
| Leu | Glu | Val | Ser | Tyr | Arg | Val | Leu | Arg | His | Leu | Ala | Gln | Pro |

[SEQ ID NO:129]

| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Glu | Gly | Gly | Gly | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Thr | Pro | Leu | Gly | Pro | Ala |
| Ser | Ser | Leu | Pro | Gln | Ser | Phe | Leu | Leu | Lys | Cys | Leu | Glu | Gln |
| Val | Arg | Lys | Ile | Gln | Gly | Asp | Gly | Ala | Ala | Leu | Gln | Glu | Lys |
| Leu | Cys | Ala | Thr | Tyr | Lys | Leu | Cys | His | Pro | Glu | Glu | Leu | Val |
| Leu | LEY | Gly | His | Ser | Leu | Gly | Ile | Pro | Trp | Ala | Pro | Leu | Ser |
| Ser | Cys | Pro | Ser | Gln | Ala | Leu | Gln | Leu | Ala | Gly | Cys | Leu | Ser |
| Gln | Leu | His | Ser | Gly | Leu | Phe | Leu | Tyr | Gln | Gly | Leu | Leu | Gln |
| Ala | Leu | Glu | Gly | Ile | Ser | Pro | Glu | Leu | Gly | Pro | Thr | Leu | Asp |
| Thr | Leu | Gln | Leu | Asp | Val | Ala | Asp | Phe | Ala | Thr | Thr | Ile | Trp |
| Gln | Gln | Met | Glu | Glu | Leu | Gly | Met | Ala | Pro | Ala | Leu | Gln | Pro |
| Thr | Gln | Gly | Ala | Met | Pro | Ala | Phe | Ala | Ser | Ala | Phe | Gln | Arg |
| Arg | Ala | Gly | Gly | Val | Leu | Val | Ala | Ser | His | Leu | Gln | Ser | Phe |
| Leu | Glu | Val | Ser | Tyr | Arg | Val | Leu | Arg | His | Leu | Ala | Gln | Pro |

[SEQ ID NO:130]

| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Asn | Cys | Ser | Ile | Met | Ile |
| Asp | Glu | Ile | Ile | His | His | Leu | Lys | Arg | Pro | Pro | Asn | Pro | Leu |
| Leu | Asp | Pro | Asn | Asn | Leu | Asn | Ser | Glu | Asp | Met | Asp | Ile | Leu |
| Met | Glu | Arg | Asn | Leu | Arg | Thr | Pro | Asn | Leu | Leu | Ala | Phe | Val |
| Arg | Ala | Val | Lys | His | Leu | Glu | Asn | Ala | Ser | Gly | Ile | Glu | Ala |
| Ile | Leu | Arg | Asn | Leu | Gln | Pro | Cys | Leu | Pro | Ser | Ala | Thr | Ala |
| Ala | Pro | Ser | Arg | His | Pro | Ile | Ile | Ile | Lys | Ala | Gly | Asp | Trp |
| Gln | Glu | Phe | Arg | Glu | Lys | Leu | Thr | Phe | Tyr | Leu | Val | Thr | Leu |
| Glu | Gln | Ala | Gln | Glu | Gln | Gln | [SEQ ID NO:131] |

| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Lys | Ile | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Asn | Cys | Ser | Ile | Met | Ile |
| Asp | Glu | Ile | Ile | His | His | Leu | Lys | Arg | Pro | Pro | Asn | Pro | Leu |
| Leu | Asp | Pro | Asn | Asn | Leu | Asn | Ser | Glu | Asp | Met | Asp | Ile | Leu |
| Met | Glu | Arg | Asn | Leu | Arg | Thr | Pro | Asn | Leu | Leu | Ala | Phe | Val |
| Arg | Ala | Val | Lys | His | Leu | Glu | Asn | Ala | Ser | Gly | Ile | Glu | Ala |
| Ile | Leu | Arg | Asn | Leu | Gln | Pro | Cys | Leu | Pro | Ser | Ala | Thr | Ala |
| Ala | Pro | Ser | Arg | His | Pro | Ile | Ile | Ile | Lys | Ala | Gly | Asp | Trp |
| Gln | Glu | Phe | Arg | Glu | Lys | Leu | Thr | Phe | Tyr | Leu | Val | Thr | Leu |
| Glu | Gln | Ala | Gln | Glu | Gln | Gln | [SEQ ID NO:132] |

-continued

| Met | Ala | Asn | Cys | Ser | Ile | Met | Ile | Asp | Glu | Ile | Ile | His | His |
|---|---|---|---|---|---|---|---|---|---|---|---|---|---|
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Glu | Gly | Gly | Gly | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Asn | Cys | Ser | Ile | Met | Ile |
| Asp | Glu | Ile | Ile | His | His | Leu | Lys | Arg | Pro | Pro | Asn | Pro | Leu |
| Leu | Asp | Pro | Asn | Asn | Leu | Asn | Ser | Glu | Asp | Met | Asp | Ile | Leu |
| Met | Glu | Arg | Asn | Leu | Arg | Thr | Pro | Asn | Leu | Leu | Ala | Phe | Val |
| Arg | Ala | Val | Lys | His | Leu | Glu | Asn | Ala | Ser | Gly | Ile | Glu | Ala |
| Ile | Leu | Arg | Asn | Leu | Gln | Pro | Cys | Leu | Pro | Ser | Ala | Thr | Ala |
| Ala | Pro | Ser | Arg | His | Pro | Ile | Ile | Ile | Lys | Ala | Gly | Asp | Trp |
| Gln | Glu | Phe | Arg | Glu | Lys | Leu | Thr | Phe | Tyr | Leu | Val | Thr | Leu |
| Glu | Gln | Ala | Gln | Glu | Gln | [SEQ ID NO:133] | | | | | | | |
| Met | Ala | Asn | Cys | Ser | Ile | Met | Ile | Asp | Glu | Ile | Ile | His | His |
| Leu | Lys | Arg | Pro | Pro | Ala | Pro | Leu | Leu | Asp | Pro | Asn | Asn | Leu |
| Asn | Asp | Glu | Asp | Val | Ser | Ile | Leu | Met | Asp | Arg | Asn | Leu | Arg |
| Leu | Pro | Asn | Leu | Glu | Ser | Phe | Val | Arg | Ala | Val | Lys | Asn | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Gly | Gly | Ser |
| Gly | Gly | Gly | Ser | Asn | Met | Ala | Thr | Pro | Leu | Gly | Pro | Ala | Ser |
| Ser | Leu | Pro | Gln | Ser | Phe | Leu | Leu | Lys | Cys | Leu | Glu | Gln | Val |
| Arg | Lys | Ile | Gln | Gly | Asp | Gly | Ala | Ala | Leu | Gln | Glu | Lys | Leu |
| Cys | Ala | Thr | Tyr | Lys | Leu | Cys | His | Pro | Glu | Glu | Leu | Val | Leu |
| Leu | Gly | His | Ser | Leu | Gly | Ile | Pro | Trp | Ala | Pro | Leu | Ser | Ser |
| Cys | Pro | Ser | Gln | Ala | Leu | Gln | Leu | Ala | Gly | Cys | Leu | Ser | Gln |
| Leu | His | Ser | Gly | Leu | Phe | Leu | Tyr | Gln | Gly | Leu | Leu | Gln | Ala |
| Leu | Glu | Gly | Ile | Ser | Pro | Glu | Leu | Gly | Pro | Thr | Leu | Asp | Thr |
| Leu | Gln | Leu | Asp | Val | Ala | Asp | Phe | Ala | Thr | Thr | Ile | Trp | Gln |
| Gln | Met | Glu | Glu | Leu | Gly | Met | Ala | Pro | Ala | Leu | Gln | Pro | Thr |
| Gln | Gly | Ala | Met | Pro | Ala | Phe | Ala | Ser | Ala | Phe | Gln | Arg | Arg |
| Ala | Gly | Gly | Val | Leu | Val | Ala | Ser | His | Leu | Gln | Ser | Phe | Leu |
| Glu | Val | Ser | Tyr | Arg | Val | Leu | Arg | His | Leu | Ala | Gln | Pro | |
| [SEQ ID NO:134] | | | | | | | | | | | | | |
| Met | Ala | Asn | Cys | Ser | Ile | Met | Ile | Asp | Glu | Ile | Ile | His | His |
| Leu | Lys | Arg | Pro | Pro | Ala | Pro | Leu | Leu | Asp | Pro | Asn | Asn | Leu |
| Asn | Asp | Glu | Asp | Val | Ser | Ile | Leu | Met | Asp | Arg | Asn | Leu | Arg |
| Leu | Pro | Asn | Leu | Glu | Ser | Phe | Val | Arg | Ala | Val | Lys | Asn | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Gly | Gly | Ser |
| Gly | Gly | Gly | Ser | Asn | Met | Ala | Thr | Pro | Leu | Gly | Pro | Ala | Ser |
| Ser | Leu | Pro | Gln | Ser | Phe | Leu | Leu | Lys | Cys | Leu | Glu | Gln | Val |
| Arg | Lys | Ile | Gln | Gly | Asp | Gly | Ala | Ala | Leu | Gln | Glu | Lys | Leu |
| Cys | Ala | Thr | Tyr | Lys | Leu | Cys | His | Pro | Glu | Glu | Leu | Val | Leu |
| Leu | Gly | His | Ser | Leu | Gly | Ile | Pro | Trp | Ala | Pro | Leu | Ser | Ser |
| Cys | Pro | Ser | Gln | Ala | Leu | Gln | Leu | Ala | Gly | Cys | Leu | Ser | Gln |
| Leu | His | Ser | Gly | Leu | Phe | Leu | Tyr | Gln | Gly | Leu | Leu | Gln | Ala |
| Leu | Glu | Gly | Ile | Ser | Pro | Glu | Leu | Gly | Pro | Thr | Leu | Asp | Thr |
| Leu | Gln | Leu | Asp | Val | Ala | Asp | Phe | Ala | Thr | Thr | Ile | Trp | Gln |
| Gln | Met | Glu | Glu | Leu | Gly | Met | Ala | Pro | Ala | Leu | Gln | Pro | Thr |
| Gln | Gly | Ala | Met | Pro | Ala | Phe | Ala | Ser | Ala | Phe | Gln | Arg | Arg |
| Ala | Gly | Gly | Val | Leu | Val | Ala | Ser | His | Leu | Gln | Ser | Phe | Leu |
| Glu | Val | Ser | Tyr | Arg | Val | Leu | Arg | His | Leu | Ala | Gln | Pro | |
| [SEQ ID NO:135] | | | | | | | | | | | | | |
| Met | Ala | Asn | Cys | Ser | Ile | Met | Ile | Asp | Glu | Ile | Ile | His | His |
| Leu | Lys | Arg | Pro | Pro | Ala | Pro | Leu | Leu | Asp | Pro | Asn | Asn | Leu |
| Asn | Asp | Glu | Asp | Val | Ser | Ile | Leu | Met | Asp | Arg | Asn | Leu | Arg |
| Leu | Pro | Asn | Leu | Glu | Ser | Phe | Val | Arg | Ala | Val | Lys | Asn | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Gly | Gly | Ser |
| Gly | Gly | Gly | Ser | Asn | Met | Ala | Asn | Cys | Ser | Ile | Met | Ile | Asp |
| Glu | Ile | Ile | His | His | Leu | Lys | Arg | Pro | Pro | Ala | Pro | Leu | Leu |
| Asp | Pro | Asn | Asn | Leu | Asn | Asp | Glu | Asp | Val | Ser | Ile | Leu | Met |
| Asp | Arg | Asn | Leu | Arg | Leu | Pro | Asn | Leu | Glu | Ser | Phe | al | Arg |
| Ala | Val | Lys | Asn | Leu | Glu | Asn | Ala | Ser | Gly | Ile | Glu | Ala | Ile |

```
Leu  Arg  Asn  Leu  Gln  Pro  Cys  Leu  Pro  Ser  Ala  Thr  Ala  Ala
Pro  Ser  Arg  His  Pro  Ile  Ile  Ile  Lys  Ala  Gly  Asp  Trp  Gln
Glu  Phe  Arg  Glu  Lys  Leu  Thr  Phe  Tyr  Leu  Val  Thr  Leu  Glu
Gln  Ala  Gln  Glu  Gln  Gln  [SEQ ID NO:136]
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Asp  Glu  Asp  Val  Ser  Ile  Leu  Met  Asp  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Arg  Ile  Ser  Pro  Gly  Glu  Pro  Ser
Gly  Pro  Ile  Ser  Thr  Ile  Asn  Pro  Ser  Pro  Pro  Ser  Lys  Glu
Ser  His  Lys  Ser  Pro  Asn  Met  Ala  Asn  Cys  Ser  Ile  Met  Ile
Asp  Glu  Ile  Ile  His  His  Leu  Lys  Arg  Pro  Pro  Ala  Pro  Leu
Leu  Asp  Pro  Asn  Asn  Leu  Asn  Asp  Glu  Asp  Val  Ser  Ile  Leu
Met  Asp  Arg  Asn  Leu  Arg  Leu  Pro  Asn  Leu  Glu  Ser  Phe  Val
Arg  Ala  Val  Lys  Asn  Leu  Glu  Asn  Ala  Ser  Gly  Ile  Glu  Ala
Ile  Leu  Arg  Asn  Leu  Gln  Pro  Cys  Leu  Pro  Ser  Ala  Thr  Ala
Ala  Pro  Ser  Arg  His  Pro  Ile  Ile  Ile  Lys  Ala  Gly  Asp  Trp
Gln  Glu  Phe  Arg  Glu  Lys  Leu  Thr  Phe  Tyr  Leu  Val  Thr  Leu
Glu  Gln  Ala  Gln  Glu  Gln  Gln  [SEQ ID NO:137]
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Asp  Glu  Asp  Val  Ser  Ile  Leu  Met  Asp  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Arg  Ile  Ser  Pro  Gly  Glu  Pro  Ser
Gly  Pro  Ile  Ser  Thr  Ile  Asn  Pro  Ser  Pro  Pro  Ser  Lys  Glu
Ser  His  Lys  Ser  Pro  Asn  Met  Ala  Thr  Pro  Leu  Gly  Pro  Ala
Ser  Ser  Leu  Pro  Gln  Ser  Phe  Leu  Leu  Lys  Ser  Leu  Glu  Gln
Val  Arg  Lys  Ile  Gln  Gly  Asp  Gly  Ala  Ala  Leu  Gln  Glu  Lys
Leu  Cys  Ala  Thr  Tyr  Lys  Leu  Cys  His  Pro  Glu  Glu  Leu  Val
Leu  Leu  Gly  His  Ser  Leu  Gly  Ile  Pro  Trp  Ala  Pro  Leu  Ser
Ser  Cys  Pro  Ser  Gln  Ala  Leu  Gln  Leu  Ala  Gly  Cys  Leu  Ser
Gln  Leu  His  Ser  Gly  Leu  Phe  Leu  Tyr  Gln  Gly  Leu  Leu  Gln
Ala  Leu  Glu  Gly  Ile  Ser  Pro  Glu  Leu  Gly  Pro  Thr  Leu  Asp
Thr  Leu  Gln  Leu  Asp  Val  Ala  Asp  Phe  Ala  Thr  Thr  Ile  Trp
Gln  Gln  Met  Glu  Glu  Leu  Gly  Met  Ala  Pro  Ala  Leu  Gln  Pro
Thr  Gln  Gly  Ala  Met  Pro  Ala  Phe  Ala  Ser  Ala  Phe  Gln  Arg
Arg  Ala  Gly  Gly  Val  Leu  Val  Ala  Ser  His  Leu  Gln  Ser  Phe
Leu  Glu  Val  Ser  Tyr  Arg  Val  Leu  Arg  His  Leu  Ala  Gln  Pro
[SEQ ID NO:138]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Arg  Ile  Ser  Pro  Gln  Pro  Pro  Val
Asn  Ala  Gly  Gly  Gly  Ser  Gly  Gly  Gly  Gly  Ser  Gly  Gly  Ser
Glu  Gly  Gly  Gly  Ser  Glu  Gly  Gly  Gly  Ser  Glu  Gly  Gly  Gly
Ser  Glu  Gly  Gly  Gly  Ser  Glu  Gly  Gly  Gly  Ser  Gly  Gly  Asp
Phe  Asp  Tyr  Glu  Asn  Met  Ala  Thr  Pro  Leu  Gly  Pro  Ala  Ser
Ser  Leu  Pro  Gln  Ser  Phe  Leu  Leu  Lys  Ser  Leu  Glu  Gln  Val
Arg  Lys  Ile  Gln  Gly  Asp  Gly  Ala  Ala  Leu  Gln  Glu  Lys  Leu
Cys  Ala  Thr  Tyr  Lys  Leu  Cys  His  Pro  Glu  Glu  Leu  Val  Leu
Leu  Gly  His  Ser  Leu  Gly  Ile  Pro  Trp  Ala  Pro  Leu  Ser  Ser
Cys  Pro  Ser  Gln  Ala  Leu  Gln  Leu  Ala  Gly  Cys  Leu  Ser  Gln
Leu  His  Ser  Gly  Leu  Phe  Leu  Tyr  Gln  Gly  Leu  Leu  Gln  Ala
Leu  Glu  Gly  Ile  Ser  Pro  Glu  Leu  Gly  Pro  Thr  Leu  Asp  Thr
Leu  Gln  Leu  Asp  Val  Ala  Asp  Phe  Ala  Thr  Thr  Ile  Trp  Gln
Gln  Met  Glu  Glu  Leu  Gly  Met  Ala  Pro  Ala  Leu  Gln  Pro  Thr
Gln  Gly  Ala  Met  Pro  Ala  Phe  Ala  Ser  Ala  Phe  Gln  Arg  Arg
Ala  Gly  Gly  Val  Leu  Val  Ala  Ser  His  Leu  Gln  Ser  Phe  Leu
Glu  Val  Ser  Tyr  Arg  Val  Leu  Arg  His  Leu  Ala  Gln  Pro
[SEQ ID NO:139]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
```

-continued

| Ile | Ile | Ile | Lys | Ala | Gly | Asp | Trp | Gln | Glu | Phe | Arg | Glu | Lys |
|---|---|---|---|---|---|---|---|---|---|---|---|---|---|
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Gly | Gly | Ser |
| Gly | Gly | Gly | Ser | Asn | Met | Ala | Pro | Ala | Arg | Ser | Pro | Ser | Pro |
| Ser | Thr | Gln | Pro | Trp | Glu | His | Val | Asn | Ala | Ile | Gln | Glu | Ala |
| Arg | Arg | Leu | Leu | Asn | Leu | Ser | Arg | Asp | Thr | Ala | Ala | Glu | Met |
| Asn | Glu | Thr | Val | Glu | Val | Ile | Ser | Glu | Met | Phe | Asp | Leu | Gln |
| Glu | Pro | Thr | Cys | Leu | Gln | Thr | Arg | Leu | Glu | Leu | Tyr | Lys | Gln |
| Gly | Leu | Arg | Gly | Ser | Leu | Thr | Lys | Leu | Lys | Gly | Pro | Leu | Thr |
| Met | Met | Ala | Ser | His | Tyr | Lys | Gln | His | Cys | Pro | Pro | Thr | Pro |
| Glu | Thr | Ser | Cys | Ala | Thr | Gln | Ile | Ile | Thr | Phe | Glu | Ser | Phe |
| Lys | Glu | Asn | Leu | Lys | Asp | Phe | Leu | Leu | Val | Ile | Pro | Phe | Asp |
| Cys | Trp | Glu | Pro | Val | Gln | Glu | [SEQ ID NO:141] | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gln | Pro | Pro | Val |
| Asn | Ala | Gly | Gly | Gly | Ser | Gly | Gly | Gly | Ser | Gly | Gly | Gly | Ser |
| Glu | Gly | Gly | Gly | Ser | Glu | Gly | Gly | Gly | Ser | Glu | Gly | Gly | Gly |
| Ser | Glu | Gly | Gly | Gly | Ser | Gly | Gly | Gly | Ser | Gly | Ser | Gly | Asp |
| Phe | Asp | Tyr | Glu | Asn | Met | Ala | Pro | Ala | Arg | Ser | Pro | Ser | Pro |
| Ser | Thr | Gln | Pro | Trp | Glu | His | Val | Asn | Ala | Ile | Gln | Glu | Ala |
| Arg | Arg | Leu | Leu | Asn | Leu | Ser | Arg | Asp | Thr | Ala | Ala | Glu | Met |
| Asn | Glu | Thr | Val | Glu | Val | Ile | Ser | Glu | Met | Phe | Asp | Leu | Gln |
| Glu | Pro | Thr | Cys | Leu | Gln | Thr | Arg | Leu | Glu | Leu | Tyr | Lys | Gln |
| Gly | Leu | Arg | Gly | Ser | Leu | Thr | Lys | Leu | Lys | Gly | Pro | Leu | Thr |
| Met | Met | Ala | Ser | His | Tyr | Lys | Gln | His | Cys | Pro | Pro | Thr | Pro |
| Glu | Thr | Ser | Cys | Ala | Thr | Gln | Ile | Ile | Thr | Phe | Glu | Ser | Phe |
| Lys | Glu | Asn | Leu | Lys | Asp | Phe | Leu | Leu | Val | Ile | Pro | Phe | Asp |
| Cys | Trp | Glu | Pro | Val | Gln | Glu | [SEQ ID NO:142] | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Pro | Val | Asn | Ala | Gly | Gly | Gly | Ser | Gly | Gly | Gly |
| Ser | Gly | Gly | Gly | Ser | Glu | Gly | Gly | Gly | Ser | Glu | Gly | Gly | Gly |
| Ser | Glu | Gly | Gly | Gly | Ser | Gly | Gly | Gly | Ser | Gly | Gly | Gly | Gly |
| Ser | Gly | Ser | Gly | Asn | Met | Ala | Thr | Pro | Leu | Gly | Pro | Ala | Ser |
| Ser | Leu | Pro | Gln | Ser | Phe | Leu | Leu | Lys | Cys | Leu | Glu | Gln | Val |
| Arg | Lys | Ile | Gln | Gly | Asp | Gly | Ala | Ala | Leu | Gln | Glu | Lys | Leu |
| Cys | Ala | Thr | Tyr | Lys | Leu | Cys | His | Pro | Glu | Glu | Leu | Val | Leu |
| Leu | Gly | His | Ser | Leu | Gly | Ile | Pro | Trp | Ala | Pro | Leu | Ser | Ser |
| Cys | Pro | Ser | Gln | Ala | Leu | Gln | Leu | Ala | Gly | Cys | Leu | Ser | Gln |
| Leu | His | Ser | Gly | Leu | Phe | Leu | Tyr | Gln | Gly | Leu | Leu | Gln | Ala |
| Leu | Glu | Gly | Ile | Ser | Pro | Glu | Leu | Gly | Pro | Thr | Leu | Asp | Thr |
| Leu | Gln | Leu | Asp | Val | Ala | Asp | Phe | Ala | Thr | Thr | Ile | Trp | Gln |
| Gln | Met | Glu | Glu | Leu | Gly | Met | Ala | Pro | Ala | Leu | Gln | Pro | Thr |
| Gln | Gly | Ala | Met | Pro | Ala | Phe | Ala | Ser | Ala | Phe | Gln | Arg | Arg |
| Ala | Gly | Gly | Val | Leu | Val | Ala | Ser | His | Leu | Gln | Ser | Phe | Leu |
| Glu | Val | Ser | Tyr | Arg | Val | Leu | Arg | His | Leu | Ala | Gln | Pro | |
| [SEQ ID NO:143] | | | | | | | | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Leu | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Ile | Glu | Gly | Arg | Ile | Ser | Pro | Gly | Glu | Pro | Ser |
| Gly | Pro | Ile | Ser | Thr | Ile | Asn | Pro | Ser | Pro | Ser | Lys | Glu |
| Ser | His | Lys | Ser | Pro | Asn | Met | Ala | Pro | Ala | Arg | Ser | Pro | Ser |
| Pro | Ser | Thr | Gln | Pro | Trp | Glu | His | Val | Asn | Ala | Ile | Gln | Glu |
| Ala | Arg | Arg | Leu | Leu | Asn | Leu | Ser | Arg | Asp | Thr | Ala | Ala | Glu |
| Met | Asn | Glu | Thr | Val | Glu | Val | Ile | Ser | Glu | Met | Phe | Asp | Leu |
| Gln | Glu | Pro | Thr | Cys | Leu | Gln | Thr | Arg | Leu | Glu | Leu | Tyr | Lys |
| Gln | Gly | Leu | Arg | Gly | Ser | Leu | Thr | Lys | Leu | Lys | Gly | Pro | Leu |
| Thr | Met | Met | Ala | Ser | His | Tyr | Lys | Gln | His | Cys | Pro | Pro | Thr |
| Pro | Glu | Thr | Ser | Cys | Ala | Thr | Gln | Ile | Ile | Thr | Phe | Glu | Ser |
| Phe | Lys | Glu | Asn | Leu | Lys | Asp | Phe | Leu | Leu | Val | Ile | Pro | Phe |

-continued

```
Asp Cys Trp Glu Pro Val Gln Glu  [SEQ ID NO:144]
Met Ala Asn Cys Ser Ile Met Ile Asp Glu Ile Ile His His
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln Tyr Val Ile Glu Gly Arg Ile Ser Pro Gly Gly Gly Ser
Gly Gly Gly Ser Asn Met Ala Pro Val Pro Pro Gly Glu Asp
Ser Lys Asp Val Ala Ala Pro His Arg Gln Pro Leu Thr Ser
Ser Glu Arg Ile Asp Lys Gln Ile Arg Tyr Ile Leu Asp Gly
Ile Ser Ala Leu Arg Lys Glu Thr Cys Asn Lys Ser Asn Met
Cys Glu Ser Ser Lys Glu Ala Leu Ala Glu Asn Asn Leu Asn
Leu Pro Lys Met Ala Glu Lys Asp Gly Cys Phe Gln Ser Gly
Phe Asn Glu Glu Thr Cys Leu Val Lys Ile Ile Thr Gly Leu
Leu Glu Phe Glu Val Tyr Leu Glu Tyr Leu Gln Asn Arg Phe
Glu Ser Ser Glu Glu Gln Ala Arg Ala Val Gln Met Ser Thr
Lys Val Leu Ile Gln Phe Leu Gln Lys Lys Ala Lys Asn Leu
Asp Ala Ile Thr Thr Pro Asp Pro Thr Thr Asn Ala Ser Leu
Leu Thr Lys Leu Gln Ala Gln Asn Gln Trp Leu Gln Asp Met
Thr Thr His Leu Ile Leu Arg Ser Phe Lys Glu Phe Leu Gln
Ser Ser Leu Arg Ala Leu Arg Gln Met  [SEQ ID NO:145]
Met Ala Thr Pro Leu Gly Pro Ala Ser Ser Leu Pro Gln Ser
Phe Leu Leu Lys Cys Leu Glu Gln Val Arg Lys Ile Gln Gly
Asp Gly Ala Ala Leu Gln Glu Lys Leu Cys Ala Thr Tyr Lys
Leu Cys His Pro Glu Glu Leu Val Leu Leu Gly His Ser Leu
Gly Ile Pro Trp Ala Pro Leu Ser Ser Cys Pro Ser Gln Ala
Leu Gln Leu Ala Gly Cys Leu Ser Gln Leu His Ser Gly Leu
Phe Leu Tyr Gln Gly Leu Leu Gln Ala Leu Glu Gly Ile Ser
Pro Glu Leu Gly Pro Thr Leu Asp Thr Leu Gln Leu Asp Val
Ala Asp Phe Ala Thr Thr Ile Trp Gln Gln Met Glu Glu Leu
Gly Met Ala Pro Ala Leu Gln Pro Thr Gln Gly Ala Met Pro
Ala Phe Ala Ser Ala Phe Gln Arg Arg Ala Gly Gly Val Leu
Val Ala Ser His Leu Gln Ser Phe Leu Glu Val Ser Tyr Arg
Val Leu Arg His Leu Ala Gln Pro Tyr Val Ile Glu Gly Arg
Ile Ser Pro Gly Gly Gly Ser Gly Gly Gly Ser Asn Met Ala
Asn Cys Ser Ile Met Ile Asp Glu Ile Ile His His Leu Lys
Arg Pro Pro Asn Pro Leu Leu Asp Pro Asn Asn Leu Asn Ser
Glu Asp Met Asp Ile Leu Met Glu Arg Asn Leu Arg Thr Pro
Asn Leu Leu Ala Phe Val Arg Ala Val Lys His Leu Glu Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Glu Lys Leu Thr
Phe Tyr Leu Val Thr Leu Glu Gln Ala Gln Glu Gln Gln
[SEQ ID NO:146]
Met Ala Thr Pro Leu Gly Pro Ala Ser Ser Leu Pro Gln Ser
Phe Leu Leu Lys Cys Leu Glu Gln Val Arg Lys Ile Gln Gly
Asp Gly Ala Ala Leu Gln Glu Lys Leu Cys Ala Thr Tyr Lys
Leu Cys His Pro Glu Glu Leu Val Leu Leu Gly His Ser Leu
Gly Ile Pro Trp Ala Pro Leu Ser Ser Cys Pro Ser Gln Ala
Leu Gln Leu Ala Gly Cys Leu Ser Gln Leu His Ser Gly Leu
Phe Leu Tyr Gln Gly Leu Leu Gln Ala Leu Glu Gly Ile Ser
Pro Glu Leu Gly Pro Thr Leu Asp Thr Leu Gln Leu Asp Val
Ala Asp Phe Ala Thr Thr Ile Trp Gln Gln Met Glu Glu Leu
Gly Met Ala Pro Ala Leu Gln Pro Thr Gln Gly Ala Met Pro
Ala Phe Ala Ser Ala Phe Gln Arg Arg Ala Gly Gly Val Leu
Val Ala Ser His Leu Gln Ser Phe Leu Glu Val Ser Tyr Arg
Val Leu Arg His Leu Ala Gln Pro Tyr Val Ile Glu Gly Arg
Ile Ser Pro Gly Gly Gly Ser Gly Gly Gly Ser Asn Met Ala
Asn Cys Ser Ile Met Ile Asp Glu Ile Ile His His Leu Lys
Arg Pro Pro Ala Pro Leu Leu Asp Pro Asn Asn Leu Asn Asp
Glu Asp Val Ser Ile Leu Met Asp Arg Asn Leu Arg Leu Pro
Asn Leu Glu Ser Phe Val Arg Ala Val Lys Ser Asn Leu Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Glu Lys Leu Thr
Phe Tyr Leu Val Thr Leu Glu Gln Ala Gln Glu Gln Gln
[SEQ ID NO:147]
Met Ala Thr Pro Leu Gly Pro Ala Ser Ser Leu Pro Gln Ser
Phe Leu Leu Lys Cys Leu Glu Gln Val Arg Lys Ile Gln Gly
Asp Gly Ala Ala Leu Gln Glu Lys Leu Cys Ala Thr Tyr Lys
Leu Cys His Pro Glu Glu Leu Val Leu Leu Gly His Ser Leu
Gly Ile Pro Trp Ala Pro Leu Ser Ser Cys Pro Ser Gln Ala
Leu Gln Leu Ala Gly Cys Leu Ser Gln Leu His Ser Gly Leu
Phe Leu Tyr Gln Gly Leu Leu Gln Ala Leu Glu Gly Ile Ser
Pro Glu Leu Gly Pro Thr Leu Asp Thr Leu Gln Leu Asp Val
Ala Asp Phe Ala Thr Thr Ile Trp Gln Gln Met Glu Glu Leu
```

-continued

| Gly | Met | Ala | Pro | Ala | Leu | Gln | Pro | Thr | Gln | Gly | Ala | Met | Pro |
|---|---|---|---|---|---|---|---|---|---|---|---|---|---|
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Pro | Gln | Pro | Pro |
| Val | Asn | Ala | Gly | Gly | Gly | Ser | Gly | Gly | Gly | Ser | Gly | Gly | Gly |
| Ser | Glu | Gly | Gly | Gly | Ser | Glu | Gly | Gly | Gly | Ser | Glu | Gly | Gly |
| Gly | Ser | Glu | Gly | Gly | Gly | Ser | Gly | Gly | Gly | Ser | Gly | Ser | Gly |
| Asp | Phe | Asp | Tyr | Glu | Asn | Met | Ala | Asn | Cys | Ser | Ile | Met | Ile |
| Asp | Glu | Ile | Ile | His | His | Leu | Lys | Arg | Pro | Pro | Ala | Pro | Leu |
| Leu | Asp | Pro | Asn | Asn | Leu | Asn | Asp | Glu | Asp | Val | Ser | Ile | Leu |
| Met | Asp | Arg | Asn | Leu | Arg | Leu | Val | Arg | Ala | Val | Lys | Asn | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | | | | | | | | | | | | | |

[SEQ ID NO:148]

| Met | Ala | Thr | Pro | Leu | Gly | Pro | Ala | Ser | Ser | Leu | Pro | Gln | Ser |
|---|---|---|---|---|---|---|---|---|---|---|---|---|---|
| Phe | Leu | Leu | Lys | Cys | Leu | Glu | Gln | Val | Arg | Lys | Ile | Gln | Gly |
| Asp | Gly | Ala | Ala | Leu | Gln | Glu | Lys | Leu | Cys | Ala | Thr | Tyr | Lys |
| Leu | Cys | His | Pro | Glu | Glu | Leu | Val | Leu | Leu | Gly | His | Ser | Leu |
| Gly | Ile | Pro | Trp | Ala | Pro | Leu | Ser | Ser | Cys | Pro | Ser | Gln | Ala |
| Leu | Gln | Leu | Ala | Gly | Cys | Leu | Ser | Gln | Leu | His | Ser | Gly | Leu |
| Phe | Leu | Tyr | Gln | Gly | Leu | Leu | Gln | Ala | Leu | Glu | Gly | Ile | Ser |
| Pro | Glu | Leu | Gly | Pro | Thr | Leu | Asp | Thr | Leu | Gln | Leu | Asp | Val |
| Ala | Asp | Phe | Ala | Thr | Thr | Ile | Trp | Gln | Gln | Met | Glu | Glu | Leu |
| Gly | Met | Ala | Pro | Ala | Leu | Gln | Pro | Thr | Gln | Gly | Ala | Met | Pro |
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Ile | Glu | Glu | Arg |
| Ile | Ser | Pro | Gly | Glu | Pro | Ser | Gly | Pro | Ile | Ser | Thr | Ile | Asn |
| Pro | Ser | Pro | Pro | Ser | Lys | Glu | Ser | His | Lys | Ser | Pro | Asn | Met |
| Ala | Asn | Cys | Ser | Ile | Met | Ile | Asp | Glu | Ile | Ile | His | His | Leu |
| Lys | Arg | Pro | Pro | Ala | Pro | Leu | Leu | Asp | Pro | Asn | Asn | Leu | Asn |
| Asp | Glu | Asp | Val | Ser | Ile | Leu | Met | Asp | Arg | Asn | Leu | Arg | Leu |
| Pro | Asn | Leu | Glu | Ser | Phe | Val | Arg | Ala | Val | Lys | Asn | Leu | Glu |
| Asn | Ala | Ser | Gly | Ile | Glu | Ala | Ile | Leu | Arg | Asn | Leu | Gln | Pro |
| Cys | Leu | Pro | Ser | Ala | Thr | Ala | Ala | Pro | Ser | Arg | His | Pro | Ile |
| Ile | Ile | Lys | Ala | Gly | Asp | Trp | Gln | Glu | Phe | Arg | Glu | Lys | Leu |
| Thr | Phe | Tyr | Leu | Val | Thr | Leu | Glu | Gln | Ala | Gln | Glu | Gln | Gln |

[SEQ ID NO:149]

| Met | Ala | Thr | Pro | Leu | Gly | Pro | Ala | Ser | Ser | Leu | Pro | Gln | Ser |
|---|---|---|---|---|---|---|---|---|---|---|---|---|---|
| Phe | Leu | Leu | Lys | Cys | Leu | Glu | Gln | Val | Arg | Lys | Ile | Gln | Gly |
| Asp | Gly | Ala | Ala | Leu | Gln | Glu | Lys | Leu | Cys | Ala | Thr | Tyr | Lys |
| Leu | Cys | His | Pro | Glu | Glu | Leu | Val | Leu | Leu | Gly | His | Ser | Leu |
| Gly | Ile | Pro | Trp | Ala | Pro | Leu | Ser | Ser | Cys | Pro | Ser | Gln | Ala |
| Leu | Gln | Leu | Ala | Gly | Cys | Leu | Ser | Gln | Leu | His | Ser | Gly | Leu |
| Phe | Leu | Tyr | Gln | Gly | Leu | Leu | Gln | Ala | Leu | Glu | Gly | Ile | Ser |
| Pro | Glu | Leu | Gly | Pro | Thr | Leu | Asp | Thr | Leu | Gln | Leu | Asp | Val |
| Ala | Asp | Phe | Ala | Thr | Thr | Ile | Trp | Gln | Gln | Met | Glu | Glu | Leu |
| Gly | Met | Ala | Pro | Ala | Leu | Gln | Pro | Thr | Gln | Gly | Ala | Met | Pro |
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Ile | Glu | Gly | Arg |
| Ile | Ser | Pro | Gly | Glu | Pro | Ser | Gly | Pro | Ile | Ser | Thr | Ile | Asn |
| Pro | Ser | Pro | Pro | Ser | Lys | Glu | Ser | His | Lys | Ser | Pro | Asn | Met |
| Ala | Asn | Cys | Ser | Ile | Met | Ile | Asp | Glu | Ile | Ile | His | His | Leu |
| Lys | Arg | Pro | Pro | Asn | Pro | Leu | Leu | Asp | Pro | Asn | Asn | Leu | Asn |
| Ser | Glu | Asp | Met | Asp | Ile | Leu | Met | Glu | Arg | Asn | Leu | Arg | Thr |
| Pro | Asn | Leu | Leu | Ala | Phe | Val | Arg | Ala | Val | Lys | His | Leu | Glu |
| Asn | Ala | Ser | Gly | Ile | Glu | Ala | Ile | Leu | Arg | Asn | Leu | Gln | Pro |
| Cys | Leu | Pro | Ser | Ala | Thr | Ala | Ala | Pro | Ser | Arg | His | Pro | Ile |
| Ile | Ile | Lys | Ala | Gly | Asp | Trp | Gln | Glu | Phe | Arg | Glu | Lys | Leu |
| Thr | Phe | Tyr | Leu | Val | Thr | Leu | Glu | Gln | Ala | Gln | Glu | Gln | Gln |

[SEQ ID NO:150]

| Met | Ala | Thr | Pro | Leu | Gly | Pro | Ala | Ser | Ser | Leu | Pro | Gln | Ser |
|---|---|---|---|---|---|---|---|---|---|---|---|---|---|
| Phe | Leu | Leu | Lys | Cys | Leu | Glu | Gln | Val | Arg | Lys | Ile | Gln | Gly |
| Asp | Gly | Ala | Ala | Leu | Gln | Glu | Lys | Leu | Cys | Ala | Thr | Tyr | Lys |
| Leu | Cys | His | Pro | Glu | Glu | Leu | Val | Leu | Leu | Gly | His | Ser | Leu |
| Gly | Ile | Pro | Trp | Ala | Pro | Leu | Ser | Ser | Cys | Pro | Ser | Gln | Ala |
| Leu | Gln | Leu | Ala | Gly | Cys | Leu | Ser | Gln | Leu | His | Ser | Gly | Leu |
| Phe | Leu | Tyr | Gln | Gly | Leu | Leu | Gln | Ala | Leu | Glu | Gly | Ile | Ser |
| Pro | Glu | Leu | Gly | Pro | Thr | Leu | Asp | Thr | Leu | Gln | Leu | Asp | Val |
| Ala | Asp | Phe | Ala | Thr | Thr | Ile | Trp | Gln | Gln | Met | Glu | Glu | Leu |
| Gly | Met | Ala | Pro | Ala | Leu | Gln | Pro | Thr | Gln | Gly | Ala | Met | Pro |
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Ile | Glu | Gly | Arg |
| Ile | Ser | Pro | Gln | Pro | Pro | Val | Asn | Ala | Gly | Gly | Gly | Ser | Gly |
| Gly | Gly | Ser | Gly | Gly | Gly | Ser | Glu | Gly | Gly | Gly | Ser | Glu | Gly |

-continued

```
Gly  Gly  Ser  Glu  Gly  Gly  Gly  Ser  Glu  Gly  Gly  Gly  Ser  Gly
Gly  Gly  Ser  Gly  Ser  Gly  Asp  Phe  Asp  Tyr  Glu  Asn  Met  Ala
Asn  Cys  Ser  Ile  Met  Ile  Asp  Glu  Ile  Ile  His  His  Leu  Lys
Arg  Pro  Pro  Asn  Pro  Leu  Leu  Asp  Pro  Asn  Asn  Leu  Asn  Ser
Glu  Asp  Met  Asp  Ile  Leu  Met  Glu  Arg  Asn  Leu  Arg  Thr  Pro
Asn  Leu  Leu  Ala  Phe  Val  Arg  Ala  Val  Lys  His  Leu  Glu  Asn
Ala  Ser  Gly  Ile  Glu  Ala  Ile  Leu  Arg  Asn  Leu  Gln  Pro  Cys
Leu  Pro  Ser  Ala  Thr  Ala  Ala  Pro  Ser  Arg  His  Pro  Ile  Ile
Ile  Lys  Ala  Gly  Asp  Trp  Gln  Glu  Phe  Arg  Glu  Lys  Leu  Thr
Phe  Tyr  Leu  Val  Thr  Leu  Glu  Gln  Ala  Gln  Glu  Gln  Gln
[SEQ ID NO:151]
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Asp  Glu  Asp  Val  Ser  Ile  Leu  Met  Asp  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Glu  Gly  Gly  Gly  Gly  Ser  Pro  Gly  Gly  Gly  Ser
Gly  Gly  Gly  Ser  Asn  Met  Ala  Thr  Pro  Leu  Gly  Pro  Ala  Ser
Ser  Leu  Pro  Gln  Ser  Phe  Leu  Leu  Lys  Ser  Leu  Glu  Gln  Val
Arg  Lys  Ile  Gln  Gly  Asp  Gly  Ala  Ala  Leu  Gln  Glu  Lys  Leu
Cys  Ala  Thr  Tyr  Lys  Leu  Cys  His  Pro  Glu  Glu  Leu  Val  Leu
Leu  Gly  His  Ser  Leu  Gly  Ile  Pro  Trp  Ala  Pro  Leu  Ser  Ser
Cys  Pro  Ser  Gln  Ala  Leu  Gln  Leu  Ala  Gly  Cys  Leu  Ser  Gln
Leu  His  Ser  Gly  Leu  Phe  Leu  Tyr  Gln  Gly  Leu  Leu  Gln  Ala
Leu  Glu  Gly  Ile  Ser  Pro  Glu  Leu  Gly  Pro  Thr  Leu  Asp  Thr
Leu  Gln  Leu  Asp  Val  Ala  Asp  Phe  Ala  Thr  Thr  Ile  Trp  Gln
Gln  Met  Glu  Glu  Leu  Gly  Met  Ala  Pro  Ala  Leu  Gln  Pro  Thr
Gln  Gly  Ala  Met  Pro  Ala  Phe  Ala  Ser  Ala  Phe  Gln  Arg  Arg
Ala  Gly  Gly  Val  Leu  Val  Ala  Ser  His  Leu  Gln  Ser  Phe  Leu
Glu  Val  Ser  Tyr  Arg  Val  Leu  Arg  His  Leu  Ala  Gln  Pro
[SEQ ID NO:152]
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Asp  Glu  Asp  Val  Ser  Ile  Leu  Met  Asp  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Glu  Gly  Gly  Gly  Gly  Ser  Pro  Gly  Gly  Gly  Ser
Gly  Gly  Gly  Ser  Asn  Met  Ala  Asn  Cys  Ser  Ile  Met  Ile  Asp
Glu  Ile  Ile  His  His  Leu  Lys  Arg  Pro  Pro  Ala  Pro  Leu  Leu
Asp  Pro  Asn  Asn  Leu  Asn  Asp  Glu  Asp  Val  Ser  Ile  Leu  Met
Asp  Arg  Asn  Leu  Arg  Leu  Pro  Asn  Leu  Glu  Ser  Phe  Val  Arg
Ala  Val  Lys  Asn  Leu  Glu  Asn  Ala  Ser  Gly  Ile  Glu  Ala  Ile
Leu  Arg  Asn  Leu  Gln  Pro  Cys  Leu  Pro  Ser  Ala  Thr  Ala  Ala
Pro  Ser  Arg  His  Pro  Ile  Ile  Ile  Lys  Ala  Gly  Asp  Trp  Gln
Glu  Phe  Arg  Glu  Lys  Leu  Thr  Phe  Tyr  Leu  Val  Thr  Leu  Glu
Gln  Ala  Gln  Glu  Gln  Gln  [SEQ ID NO:153]
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Asp  Glu  Asp  Val  Ser  Ile  Leu  Met  Asp  Arg  Asn  Leu  Arg
Leu  Pro  Asn  Leu  Glu  Ser  Phe  Val  Arg  Ala  Val  Lys  Asn  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Gly  Gly  Ser  Pro  Gly  Glu  Pro  Ser
Gly  Pro  Ile  Ser  Thr  Ile  Asn  Pro  Ser  Pro  Pro  Ser  Lys  Glu
Ser  His  Lys  Ser  Pro  Asn  Met  Ala  Thr  Pro  Leu  Gly  Pro  Ala
Ser  Ser  Leu  Pro  Gln  Ser  Phe  Leu  Leu  Lys  Ser  Leu  Glu  Gln
Val  Arg  Lys  Ile  Gln  Gly  Asp  Gly  Ala  Ala  Leu  Gln  Glu  Lys
Leu  Cys  Ala  Thr  Tyr  Lys  Leu  Cys  His  Pro  Glu  Glu  Leu  Val
Leu  Leu  Gly  His  Ser  Leu  Gly  Ile  Pro  Trp  Ala  Pro  Leu  Ser
Ser  Cys  Pro  Ser  Gln  Ala  Leu  Gln  Leu  Ala  Gly  Cys  Leu  Ser
Gln  Leu  His  Ser  Gly  Leu  Phe  Leu  Tyr  Gln  Gly  Leu  Leu  Gln
Ala  Leu  Glu  Gly  Ile  Ser  Pro  Glu  Leu  Gly  Pro  Thr  Leu  Asp
Thr  Leu  Gln  Leu  Asp  Val  Ala  Asp  Phe  Ala  Thr  Thr  Ile  Trp
Gln  Gln  Met  Glu  Glu  Leu  Gly  Met  Ala  Pro  Ala  Leu  Gln  Pro
Thr  Gln  Gly  Ala  Met  Pro  Ala  Phe  Ala  Ser  Ala  Phe  Gln  Arg
Arg  Ala  Gly  Gly  Val  Leu  Val  Ala  Ser  His  Leu  Gln  Ser  Phe
Leu  Glu  Val  Ser  Tyr  Arg  Val  Leu  Arg  His  Leu  Ala  Gln  Pro
[SEQ ID NO:154]
Met  Ala  Asn  Cys  Ser  Ile  Met  Ile  Asp  Glu  Ile  Ile  His  His
Leu  Lys  Arg  Pro  Pro  Ala  Pro  Leu  Leu  Asp  Pro  Asn  Asn  Leu
Asn  Asp  Glu  Asp  Val  Ser  Ile  Leu  Met  Asp  Arg  Asn  Leu  Arg
```

-continued

| Leu | Pro | Asn | Leu | Glu | Ser | Phe | Val | Arg | Ala | Val | Lys | Asn | Leu |
|---|---|---|---|---|---|---|---|---|---|---|---|---|---|
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Glu | Gly | Gly | Gly | Gly | Ser | Pro | Gly | Glu | Pro | Ser |
| Gly | Pro | Ile | Ser | Thr | Ile | Asn | Pro | Ser | Pro | Pro | Ser | Lys | Glu |
| Ser | His | Lys | Ser | Pro | Asn | Met | Ala | Asn | Cys | Ser | Ile | Met | Ile |
| Asp | Glu | Ile | Ile | His | His | Leu | Lys | Arg | Pro | Pro | Ala | Pro | Leu |
| Leu | Asp | Pro | Asn | Asn | Leu | Asn | Asp | Glu | Asp | Val | Ser | Ile | Leu |
| Met | Asp | Arg | Asn | Leu | Arg | Leu | Pro | Asn | Leu | Glu | Ser | Phe | Val |
| Arg | Ala | Val | Lys | Asn | Leu | Glu | Asn | Ala | Ser | Gly | Ile | Glu | Ala |
| Ile | Leu | Arg | Asn | Leu | Gln | Pro | Cys | Leu | Pro | Ser | Ala | Thr | Ala |
| Ala | Pro | Ser | Arg | His | Pro | Ile | Ile | Ile | Lys | Ala | Gly | Asp | Trp |
| Gln | Glu | Phe | Arg | Glu | Lys | Leu | Thr | Phe | Tyr | Leu | Val | Thr | Leu |
| Glu | Gln | Ala | Gln | Glu | Gln | Gln | [SEQ ID NO:155] | | | | | | |
| Met | Ala | Thr | Pro | Leu | Gly | Pro | Ala | Ser | Ser | Leu | Pro | Gln | Ser |
| Phe | Leu | Leu | Lys | Cys | Leu | Glu | Gln | Val | Arg | Lys | Ile | Gln | Gly |
| Asp | Gly | Ala | Ala | Leu | Gln | Glu | Lys | Leu | Cys | Ala | Thr | Tyr | Lys |
| Leu | Cys | His | Pro | Glu | Glu | Leu | Val | Leu | Leu | Gly | His | Ser | Leu |
| Gly | Ile | Pro | Trp | Ala | Pro | Leu | Ser | Ser | Cys | Pro | Ser | Gln | Ala |
| Leu | Gln | Leu | Ala | Gly | Cys | Leu | Ser | Gly | Leu | His | Ser | Gly | Leu |
| Phe | Leu | Tyr | Gln | Gly | Leu | Leu | Gln | Ala | Leu | Glu | Gly | Ile | Ser |
| Pro | Glu | Leu | Gly | Pro | Thr | Leu | Asp | Thr | Leu | Gln | Leu | Asp | Val |
| Ala | Asp | Phe | Ala | Thr | Thr | Ile | Trp | Gln | Gln | Met | Glu | Glu | Leu |
| Gly | Met | Ala | Pro | Ala | Leu | Gln | Pro | Thr | Gln | Gly | Ala | Met | Pro |
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Glu | Gly | Gly | Gly |
| Gly | Ser | Pro | Gly | Glu | Pro | Ser | Gly | Pro | Ile | Ser | Thr | Ile | Asn |
| Pro | Ser | Pro | Pro | Ser | Lys | Glu | Ser | His | Lys | Ser | Pro | Asn | Met |
| Ala | Asn | Cys | Ser | Ile | Met | Ile | Asp | Glu | Ile | Ile | His | His | Leu |
| Lys | Arg | Pro | Pro | Ala | Pro | Leu | Leu | Asp | Pro | Asn | Asn | Leu | Asn |
| Asp | Glu | Asp | Val | Ser | Ile | Leu | Met | Asp | Arg | Asn | Leu | Arg | Leu |
| Pro | Asn | Leu | Glu | Ser | Phe | Val | Arg | Ala | Val | Lys | Asn | Leu | Glu |
| Asn | Ala | Ser | Gly | Ile | Glu | Ala | Ile | Leu | Arg | Asn | Leu | Gln | Pro |
| Cys | Leu | Pro | Ser | Ala | Thr | Ala | Ala | Pro | Ser | Arg | His | Pro | Ile |
| Ile | Ile | Lys | Ala | Gly | Asp | Trp | Gln | Glu | Phe | Arg | Glu | Lys | Leu |
| Thr | Phe | Tyr | Leu | Val | Thr | Leu | Glu | Gln | Ala | Gln | Glu | Gln | Gln |
| [SEQ ID NO:156] | | | | | | | | | | | | | |
| Met | Ala | Thr | Pro | Leu | Gly | Pro | Ala | Ser | Ser | Leu | Pro | Gln | Ser |
| Phe | Leu | Leu | Lys | Ser | Leu | Glu | Gln | Val | Arg | Lys | Ile | Gln | Gly |
| Asp | Gly | Ala | Ala | Leu | Gln | Glu | Lys | Leu | Cys | Ala | Thr | Tyr | Lys |
| Leu | Cys | His | Pro | Glu | Glu | Leu | Val | Leu | Leu | Gly | His | Ser | Leu |
| Gly | Ile | Pro | Trp | Ala | Pro | Leu | Ser | Ser | Cys | Pro | Ser | Gln | Ala |
| Leu | Gln | Leu | Ala | Gly | Cys | Leu | Ser | Gly | Leu | His | Ser | Gly | Leu |
| Phe | Leu | Tyr | Gln | Gly | Leu | Leu | Gln | Ala | Leu | Glu | Gly | Ile | Ser |
| Pro | Glu | Leu | Gly | Pro | Thr | Leu | Asp | Thr | Leu | Gln | Leu | Asp | Val |
| Ala | Asp | Phe | Ala | Thr | Thr | Ile | Trp | Gln | Gln | Met | Glu | Glu | Leu |
| Gly | Met | Ala | Pro | Ala | Leu | Gln | Pro | Thr | Gln | Gly | Ala | Met | Pro |
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Glu | Gly | Gly | Gly |
| Gly | Ser | Pro | Gly | Glu | Pro | Ser | Gly | Pro | Ile | Ser | Thr | Ile | Asn |
| Pro | Ser | Pro | Pro | Ser | Lys | Glu | Ser | His | Lys | Ser | Pro | Asn | Met |
| Ala | Asn | Cys | Ser | Ile | Met | Ile | Asp | Glu | Ile | Ile | His | His | Leu |
| Lys | Arg | Pro | Pro | Ala | Pro | Leu | Leu | Asp | Pro | Asn | Asn | Leu | Asn |
| Asp | Glu | Asp | Val | Ser | Ile | Leu | Met | Asp | Arg | Asn | Leu | Arg | Leu |
| Pro | Asn | Leu | Glu | Ser | Phe | Val | Arg | Ala | Val | Lys | Asn | Leu | Glu |
| Asn | Ala | Ser | Gly | Ile | Glu | Ala | Ile | Leu | Arg | Asn | Leu | Gln | Pro |
| Cys | Leu | Pro | Ser | Ala | Thr | Ala | Ala | Pro | Ser | Arg | His | Pro | Ile |
| Ile | Ile | Lys | Ala | Gly | Asp | Trp | Gln | Glu | Phe | Arg | Glu | Lys | Leu |
| Thr | Phe | Tyr | Leu | Val | Thr | Leu | Glu | Gln | Ala | Gln | Glu | Gln | Gln |
| [SEQ ID NO:157] | | | | | | | | | | | | | |
| Met | Ala | Thr | Pro | Leu | Gly | Pro | Ala | Ser | Ser | Leu | Pro | Gln | Ser |
| Phe | Leu | Leu | Lys | Cys | Leu | Glu | Gln | Val | Arg | Lys | Ile | Gln | Gly |
| Asp | Gly | Ala | Ala | Leu | Gln | Glu | Lys | Leu | Cys | Ala | Thr | Tyr | Lys |
| Leu | Cys | His | Pro | Glu | Glu | Leu | Val | Leu | Leu | Gly | His | Ser | Leu |
| Gly | Ile | Pro | Trp | Ala | Pro | Leu | Ser | Ser | Cys | Pro | Ser | Gln | Ala |
| Leu | Gln | Leu | Ala | Gly | Cys | Leu | Ser | Gly | Leu | His | Ser | Gly | Leu |
| Phe | Leu | Tyr | Gln | Gly | Leu | Leu | Gln | Ala | Leu | Glu | Gly | Ile | Ser |
| Pro | Glu | Leu | Gly | Pro | Thr | Leu | Asp | Thr | Leu | Gln | Leu | Asp | Val |
| Ala | Asp | Phe | Ala | Thr | Thr | Ile | Trp | Gln | Gln | Met | Glu | Glu | Leu |
| Gly | Met | Ala | Pro | Ala | Leu | Gln | Pro | Thr | Gln | Gly | Ala | Met | Pro |
| Ala | Phe | Ala | Ser | Ala | Phe | Gln | Arg | Arg | Ala | Gly | Gly | Val | Leu |
| Val | Ala | Ser | His | Leu | Gln | Ser | Phe | Leu | Glu | Val | Ser | Tyr | Arg |
| Val | Leu | Arg | His | Leu | Ala | Gln | Pro | Tyr | Val | Glu | Gly | Gly | Gly |
| Gly | Ser | Pro | Gly | Gly | Gly | Ser | Gly | Gly | Gly | Ser | Asn | Met | Ala |
| Asn | Cys | Ser | Ile | Met | Ile | Asp | Glu | Ile | Ile | His | His | Leu | Lys |

-continued

```
Arg  Pro  Pro  Ala  Pro  Leu  Leu  Asp  Pro  Asn  Asn  Leu  Asn  Asp
Glu  Asp  Val  Ser  Ile  Leu  Met  Asp  Arg  Asn  Leu  Arg  Leu  Pro
Asn  Leu  Glu  Ser  Phe  Val  Arg  Ala  Val  Lys  Asn  Leu  Glu  Asn
Ala  Ser  Gly  Ile  Glu  Ala  Ile  Leu  Arg  Asn  Leu  Gln  Pro  Cys
Leu  Pro  Ser  Ala  Thr  Ala  Ala  Pro  Ser  Arg  His  Pro  Ile  Ile
Ile  Lys  Ala  Gly  Asp  Trp  Gln  Glu  Phe  Arg  Glu  Lys  Leu  Thr
Phe  Tyr  Leu  Val  Thr  Leu  Glu  Gln  Ala  Gln  Glu  Gln  Gln
[SEQ ID NO:158]
Met  Ala  Thr  Pro  Leu  Gly  Pro  Ala  Ser  Ser  Leu  Pro  Gln  Ser
Phe  Leu  Leu  Lys  Ser  Leu  Glu  Gln  Val  Arg  Lys  Ile  Gln  Gly
Asp  Gly  Ala  Ala  Leu  Gln  Glu  Lys  Leu  Cys  Ala  Thr  Tyr  Lys
Leu  Cys  His  Pro  Glu  Glu  Leu  Val  Leu  Leu  Gly  His  Ser  Leu
Gly  Ile  Pro  Trp  Ala  Pro  Leu  Ser  Ser  Cys  Pro  Ser  Gln  Ala
Leu  Gln  Leu  Ala  Gly  Cys  Leu  Ser  Gly  Leu  His  Ser  Gly  Leu
Phe  Leu  Tyr  Gln  Gly  Leu  Leu  Gln  Ala  Leu  Glu  Gly  Ile  Ser
Pro  Glu  Leu  Gly  Pro  Thr  Leu  Asp  Thr  Leu  Gln  Leu  Asp  Val
Ala  Asp  Phe  Ala  Thr  Thr  Ile  Trp  Gln  Gln  Met  Glu  Glu  Leu
Gly  Met  Ala  Pro  Ala  Leu  Gln  Pro  Thr  Gln  Gly  Ala  Met  Pro
Ala  Phe  Ala  Ser  Ala  Phe  Gln  Arg  Arg  Ala  Gly  Gly  Val  Leu
Val  Ala  Ser  His  Leu  Gln  Ser  Phe  Leu  Glu  Val  Ser  Tyr  Arg
Val  Leu  Arg  His  Leu  Ala  Gln  Pro  Tyr  Val  Glu  Gly  Gly  Gly
Gly  Ser  Pro  Gly  Gly  Gly  Ser  Gly  Gly  Gly  Ser  Asn  Met  Ala
Asn  Cys  Ser  Ile  Met  Ile  Asp  Glu  Ile  Ile  His  His  Leu  Lys
Arg  Pro  Pro  Ala  Pro  Leu  Leu  Asp  Pro  Asn  Asn  Leu  Asn  Asp
Glu  Asp  Val  Ser  Ile  Leu  Met  Asp  Arg  Asn  Leu  Arg  Leu  Pro
Asn  Leu  Glu  Ser  Phe  Val  Arg  Ala  Val  Lys  Asn  Leu  Glu  Asn
Ala  Ser  Gly  Ile  Glu  Ala  Ile  Leu  Arg  Asn  Leu  Gln  Pro  Cys
Leu  Pro  Ser  Ala  Thr  Ala  Ala  Pro  Ser  Arg  His  Pro  Ile  Ile
Ile  Lys  Ala  Gly  Asp  Trp  Gln  Glu  Phe  Arg  Glu  Lys  Leu  Thr
Phe  Tyr  Leu  Val  Thr  Leu  Glu  Gln  Ala  Gln  Glu  Gln  Gln
[SEQ ID NO:159]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Arg  Ile  Ser  Pro  Gly  Gly  Gly  Ser
Gly  Gly  Gly  Ser  Asn  Met  Ala  Ser  Pro  Ala  Pro  Pro  Ala  Cys
Asp  Leu  Arg  Val  Leu  Ser  Lys  Leu  Leu  Arg  Asp  Ser  His  Val
Leu  His  Ser  Arg  Leu  Ser  Gln  Cys  Pro  Glu  Val  His  Pro  Leu
Pro  Thr  Pro  Val  Leu  Leu  Pro  Ala  Val  Asp  Phe  Ser  Leu  Gly
Glu  Trp  Lys  Thr  Gln  Met  Glu  Glu  Thr  Lys  Ala  Gln  Asp  Ile
Leu  Gly  Ala  Val  Thr  Leu  Leu  Leu  Glu  Gly  Val  Met  Ala  Ala
Arg  Gln  Gln  Leu  Gly  Pro  Thr  Cys  Leu  Ser  Ser  Leu  Leu  Gly
Gln  Leu  Ser  Gly  Gln  Val  Arg  Leu  Leu  Leu  Gly  Ala  Leu  Gln
Ser  Leu  Leu  Gly  Thr  Gln  Leu  Pro  Pro  Gln  Gly  Arg  Thr  Thr
Ala  His  Lys  Asp  Pro  Asn  Ala  Ile  Phe  Leu  Ser  Phe  Gln  His
Leu  Leu  Arg  Gly  Lys  Val  Arg  Phe  Leu  Met  Leu  Val  Gly  Gly
Ser  Thr  Leu  Cys  Val  Arg  [SEQ ID NO:165]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Val  Ala  Ser  His  Leu  Gln  Ser  Phe  Leu  Glu  Val  Ser  Tyr  Arg
Val  Leu  Arg  His  Leu  Ala  Gln  Pro  Tyr  Val  Glu  Gly  Gly  Gly
Gly  Ser  Pro  Gly  Gly  Gly  Ser  Gly  Gly  Gly  Ser  Asn  Met  Ala
Asn  Cys  Ser  Ile  Met  Ile  Asp  Glu  Ile  Ile  His  His  Leu  Lys
Arg  Pro  Pro  Ala  Pro  Leu  Leu  Asp  Pro  Asn  Asn  Leu  Asn  Asp
Glu  Asp  Val  Ser  Ile  Leu  Met  Asp  Arg  Asn  Leu  Arg  Leu  Pro
Asn  Leu  Glu  Ser  Phe  Val  Arg  Ala  Val  Lys  Asn  Leu  Glu  Asn
Ala  Ser  Gly  Ile  Glu  Ala  Ile  Leu  Arg  Asn  Leu  Gln  Pro  Cys
Leu  Pro  Ser  Ala  Thr  Ala  Ala  Pro  Ser  Arg  His  Pro  Ile  Ile
Ile  Lys  Ala  Gly  Asp  Trp  Gln  Glu  Phe  Arg  Glu  Lys  Leu  Thr
Phe  Tyr  Leu  Val  Thr  Leu  Glu  Gln  Ala  Gln  Glu  Gln  Gln
[SEQ ID NO:159]
Met  Ala  Asn  Cys  Ser  Ile  Met  Ile  Asp  Glu  Ile  Ile  His  His
Leu  Lys  Arg  Pro  Pro  Asn  Pro  Leu  Leu  Asp  Pro  Asn  Asn  Leu
Asn  Ser  Glu  Asp  Met  Asp  Ile  Leu  Met  Glu  Arg  Asn  Leu  Arg
Thr  Pro  Asn  Leu  Leu  Ala  Phe  Val  Arg  Ala  Val  Lys  His  Leu
Glu  Asn  Ala  Ser  Gly  Ile  Glu  Ala  Ile  Leu  Arg  Asn  Leu  Gln
Pro  Cys  Leu  Pro  Ser  Ala  Thr  Ala  Ala  Pro  Ser  Arg  His  Pro
Ile  Ile  Ile  Lys  Ala  Gly  Asp  Trp  Gln  Glu  Phe  Arg  Glu  Lys
Leu  Thr  Phe  Tyr  Leu  Val  Thr  Leu  Glu  Gln  Ala  Gln  Glu  Gln
Gln  Tyr  Val  Ile  Glu  Gly  Arg  Ile  Ser  Pro  Gly  Gly  Gly  Ser
Gly  Gly  Gly  Ser  Asn  Met  Ala  Ser  Pro  Ala  Pro  Pro  Ala  Cys
Asp  Leu  Arg  Val  Leu  Ser  Lys  Leu  Leu  Arg  Asp  Ser  His  Val
Leu  His  Ser  Arg  Leu  Ser  Gln  Cys  Pro  Glu  Val  His  Pro  Leu
Pro  Thr  Pro  Val  Leu  Leu  Pro  Ala  Val  Asp  Phe  Ser  Leu  Gly
```

-continued

| | | | | | | | | | | | | |
|---|---|---|---|---|---|---|---|---|---|---|---|---|
| Glu | Trp | Lys | Thr | Gln | Met | Glu | Glu | Thr | Lys | Ala | Gln | Asp | Ile |
| Leu | Gly | Ala | Val | Thr | Leu | Leu | Leu | Glu | Gly | Val | Met | Ala | Ala |
| Arg | Gln | Gln | Leu | Gly | Pro | Thr | Cys | Leu | Ser | Ser | Leu | Leu | Gly |
| Gln | Leu | Ser | Gly | Gln | Val | Arg | Leu | Leu | Leu | Gly | Ala | Leu | Gln |
| Ser | Leu | Leu | Gly | Thr | Gln | Leu | Pro | Pro | Gln | Gly | Arg | Thr | Thr |
| Ala | His | Lys | Asp | Pro | Asn | Ala | Ile | Phe | Leu | Ser | Phe | Gln | His |
| Leu | Leu | Arg | Gly | Lys | Val | Arg | Phe | Leu | Met | Leu | Val | Gly | Gly |
| Ser | Thr | Leu | Cys | Val | Arg | [SEQ ID NO:165] | | | | | | |
| Met | Ala | Asn | Cys | Ser | Ile | Met | Ile | Asp | Glu | Ile | Ile | His | His |
| Leu | Lys | Arg | Pro | Pro | Asn | Pro | Leu | Leu | Asp | Pro | Asn | Asn | Leu |
| Asn | Ser | Glu | Asp | Met | Asp | Ile | Leu | Met | Glu | Arg | Asn | Asn | Arg |
| Thr | Pro | Asn | Leu | Leu | Ala | Phe | Val | Arg | Ala | Val | Lys | His | Leu |
| Glu | Asn | Ala | Ser | Gly | Ile | Glu | Ala | Ile | Leu | Arg | Asn | Leu | Gln |
| Pro | Cys | Leu | Pro | Ser | Ala | Thr | Ala | Ala | Pro | Ser | Arg | His | Pro |
| Ile | Ile | Ile | Lys | Ala | Gly | Asp | Trp | Gln | Glu | Phe | Arg | Glu | Lys |
| Leu | Thr | Phe | Tyr | Leu | Val | Thr | Leu | Glu | Gln | Ala | Gln | Glu | Gln |
| Gln | Tyr | Val | Glu | Gly | Gly | Gly | Ser | Pro | Gly | Gly | Gly | Ser |
| Gly | Gly | Gly | Ser | Asn | Met | Ala | Ser | Pro | Ala | Pro | Pro | Ala | Cys |
| Asp | Leu | Arg | Val | Leu | Ser | Lys | Leu | Leu | Arg | Asp | Ser | His | Val |
| Leu | His | Ser | Arg | Leu | Ser | Gln | Cys | Pro | Glu | Val | His | Pro | Leu |
| Pro | Thr | Pro | Val | Leu | Leu | Pro | Ala | Val | Asp | Phe | Ser | Leu | Gly |
| Glu | Trp | Lys | Thr | Gln | Met | Glu | Glu | Thr | Lys | Ala | Gln | Asp | Ile |
| Leu | Gly | Ala | Val | Thr | Leu | Leu | Leu | Glu | Gly | Val | Met | Ala | Ala |
| Arg | Gln | Gln | Leu | Gly | Pro | Thr | Cys | Leu | Ser | Ser | Leu | Leu | Gly |
| Gln | Leu | Ser | Gly | Gln | Val | Arg | Leu | Leu | Leu | Gly | Ala | Leu | Gln |
| Ser | Leu | Leu | Gly | Thr | Gln | Leu | Pro | Pro | Gln | Gly | Arg | Thr | Thr |
| Ala | His | Lys | Asp | Pro | Asn | Ala | Ile | Phe | Leu | Ser | Phe | Gln | His |
| Leu | Leu | Arg | LGY | Lys | Val | Arg | Phe | Leu | Met | Leu | Val | Gly | Gly |
| Ser | THE | Leu | Cys | Val | Arg | [SEQ ID NO:166] | | | | | | |
| Met | Ala | Ser | Pro | Ala | Pro | Pro | Ala | Cys | Asp | Leu | Arg | Val | Leu |
| Ser | Lys | Leu | Leu | Arg | Asp | Ser | His | Val | Leu | His | Ser | Arg | Leu |
| Ser | Gln | Cys | Pro | Glu | Val | His | Pro | Leu | Pro | Thr | Pro | Val | Leu |
| Leu | Pro | Ala | Val | Asp | Phe | Ser | Leu | Gly | Glu | Trp | Lys | Thr | Gln |
| Met | Glu | Glu | Thr | Lys | Ala | Gln | Asp | Ile | Leu | Gly | Ala | Val | Thr |
| Leu | Leu | Leu | Glu | Gly | Val | Met | Ala | Ala | Arg | Gln | Gln | Leu | Gly |
| Pro | Thr | Cys | Leu | Ser | Ser | Leu | Leu | Gly | Gln | Leu | Ser | Gly | Gln |
| Val | Arg | Leu | Leu | Leu | Gly | Ala | Leu | Gln | Ser | Leu | LEY | Gly | Thr |
| Gln | Leu | Pro | Pro | Gln | Gly | Arg | Thr | Thr | Ala | His | Lys | Asp | Pro |
| Asn | Ala | Ile | Phe | Leu | Ser | Phe | Gln | His | Leu | Leu | Arg | Gly | Lys |
| Val | Arg | Phe | Leu | Met | Leu | Val | Gly | Gly | Ser | Thr | Leu | Cys | Val |
| Arg | Tyr | Val | Ile | Glu | Gly | Arg | Ile | Ser | Pro | Gly | Gly | Gly | Ser |
| Gly | Gly | Gly | Ser | Asn | Met | Ala | Asn | Cys | Ser | Ile | Met | Ile | Asp |
| Glu | Ile | Ile | His | His | Leu | Lys | Arg | Pro | Pro | Asn | Pro | Leu | Leu |
| Asp | Pro | Asn | Asn | Leu | Asn | Ser | Glu | Asp | Met | Asp | Ile | Leu | Met |
| Glu | Arg | Asn | Leu | Arg | Thr | Pro | Asn | Leu | Leu | Ala | Phe | Val | Arg |
| Ala | Val | Lys | His | Leu | Glu | Asn | Ala | Ser | Gly | Ile | Glu | Ala | Ile |
| Leu | Arg | Asn | Leu | Gln | Pro | Cys | Leu | Pro | Ser | Ala | Thr | Ala | Ala |
| Pro | Ser | Arg | His | Pro | Ile | Ile | Ile | Lys | Ala | Gly | Asp | Trp | Gln |
| Glu | Phe | Arg | Glu | Lys | Leu | Thr | Phe | Tyr | Leu | Val | Thr | Leu | Glu |
| Gln | Ala | Gln | Glu | Gln | Gln | [SEQ ID NO:167] | | | | | | |
| Met | Ala | Ser | Pro | Ala | Pro | Pro | Ala | Cys | Asp | Leu | Arg | Val | Leu |
| Ser | Lys | Leu | Leu | Arg | Asp | Ser | His | Val | Leu | His | Ser | Arg | Leu |
| Ser | Gln | Cys | Pro | Glu | Val | His | Pro | Leu | Pro | Thr | Pro | Val | Leu |
| Leu | Pro | Ala | Val | Asp | Phe | Ser | Leu | Gly | Glu | Trp | Lys | Thr | Gln |
| Met | Glu | Glu | Thr | Lys | Ala | Gln | Asp | Ile | Leu | Gly | Ala | Val | Thr |
| Leu | Leu | Leu | Glu | Gly | Val | Met | Ala | Ala | Arg | Gln | Gln | Leu | Gly |
| Pro | Thr | Cys | Leu | Ser | Ser | Leu | Leu | Gly | Gln | Leu | Ser | Gly | Gln |
| Val | Arg | Leu | Leu | Leu | Gly | Ala | Leu | Gln | Ser | Leu | Leu | Gly | Thr |
| Gln | Leu | Pro | Pro | Gln | Gly | Arg | Thr | Thr | Ala | His | Lys | Asp | Pro |
| Asn | Ala | Ile | Phe | Leu | Ser | Phe | Gln | His | Leu | Leu | Arg | Gly | Lys |
| Val | Arg | Phe | Leu | Met | Leu | Val | Gly | Gly | Ser | Thr | Leu | Cys | Val |
| Arg | Glu | Phe | His | Ala | Tyr | Val | Glu | Gly | Gly | Gly | Gly | Ser | Pro |
| Gly | Gly | Gly | Ser | Gly | Gly | Gly | Ser | Asn | Met | Ala | Asn | Cys | Ser |
| Ile | Met | Ile | Asp | Glu | Ile | Ile | His | His | Leu | Lys | Arg | Pro | Pro |
| Asn | Pro | Leu | Leu | Asp | Pro | Asn | Asn | Leu | Asn | Ser | Glu | Asp | Met |
| Asp | Ile | Leu | Met | Glu | Arg | Asn | Leu | Arg | Thr | Pro | Asn | Leu | Leu |
| Ala | Phe | Val | Arg | Ala | Val | Lys | His | Leu | Glu | Asn | Ala | Ser | Gly |
| Ile | Glu | Ala | Ile | Leu | Arg | Asn | Leu | Gln | Pro | Cys | Leu | Pro | Ser |
| Ala | Thr | Ala | Ala | Pro | Ser | Arg | His | Pro | Ile | Ile | Ile | Lys | Ala |
| Gly | Asp | Trp | Gln | Glu | Phe | Arg | Glu | Lys | Leu | Thr | Phe | Tyr | Leu |
| Val | Thr | Leu | Glu | Gln | Ala | Gln | Glu | Gln | Gln | | | | |
| [SEQ ID NO:168] | | | | | | | | | | | | | |

Materials and Methods for Fusion Molecule Expression in E. coli

Unless noted otherwise, all specialty chemicals are obtained from Sigma Co., (St. Louis, Mo.). Restriction endonucleases, T4 poly-nucleotides kinase, E. coli DNA polymerase I large fragment (Klenow) and T4 DNA ligase are obtained from New England Biolabs (Beverly, Mass.).

*Escherichia coli* Strains

Strain JM101: delta (pro lac), supE, thi, F' (traD36, rpoAB, lacI-Q, lacZdeltaM15) (Messing, 1979). This strain can be obtained from the American Type Culture Collection (ATCC), 12301 Parklawn Drive, Rockville, Md. 20852, accession number 33876. MON105 (W3110 rpoH358) is a derivative of W3110 (Bachmann, 1972) and has been assigned ATCC accession number 55204. Strain GM48: dam-3, dcm-6, gal, ara, lac, thr, leu, tonA, tsx (Marinus, 1973) is used to make plasmid DNA that is not methylated at the sequence GATC.

Genes and Plasmids

The gene used for hIL-3 production in *E. coli* is obtained from British Biotechnology Incorporated, Cambridge, England, catalogue number BBG14. This gene is carried on a pUC based plasmid designated pP0518. Many other human CSF genes can be obtained from R&D Systems, Inc. (Minn, Minn.) including IL-1 alpha, IL-1 beta, IL-2, IL-4, IL-5, IL-6, IL-7, IL-8, G-CSF, GM-CSF and LIF.

The plasmids used for production of hIL-3 in *E. coli* contain genetic elements whose use has been described (Olins et al., 1988; Olins and Rangwala, 1990). The replicon used is that of pBR327 (Covarrubias, et al., 1981) which is maintained at a copy number of about 100 in the cell (Soberon et al., 1980). A gene encoding the beta-lactamase protein is present on the plasmids. This protein confers ampicillin resistance on the cell. This resistance serves as a selectable phenotype for the presence of the plasmid in the cell.

For cytoplasmic expression vectors the transcription promoter is derived from the recA gene of *E. coli* (Sancar et al., 1980). This promoter, designated precA, includes the RNA polymerase binding site and the lexA repressor binding site (the operator). This segment of DNA provides high level transcription that is regulated even when the recA promoter is on a plasmid with the pBR327 origin of replication (Olins et al., 1988) incorporated herein by reference.

The ribosome binding site used is that from gene 10 of phage T7 (Olins et al., 1988). This is encoded in a 100 base pair (bp) fragment placed adjacent to precA. In the plasmids used herein, the recognition sequence for the enzyme NcoI (CCATGG) follows the g10-L. It is at this NcoI site that the hIL-3 genes are joined to the plasmid. It is expected that the nucleotide sequence at this junction will be recognized in mRNA as a functional start site for translation (Olins et al., 1988). The hIL-3 genes used were engineered to have a HindIII recognition site (AAGCTT) downstream from the coding sequence of the gene. At this HindIII site is a 514 base pair RsaI fragment containing the origin of replication of the single stranded phage f1 (Dente et al., 1983; Olins, et al., 1990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

In secretion expression plasmids the transcription promoter is derived from the ara B, A, and D genes of *E. coli* (Greenfield et al., 1978). This promoter is designated pAra-BAD and is contained on a 323 base pair SacII, BglII restriction fragment. The LamB secretion leader (Wong et al., 1988, Clement et al., 1981) is fused to the N-terminus of the hIL-3 gene at the recognition sequence for the enzyme NcoI (5'CCATGG3'). The hIL-3 genes used were engineered to have a HindIII recognition site (5'AAGCTT3') following the coding sequence of the gene.

Recombinant DNA Methods

Synthetic Gene Assembly

The hIL-3 variant genes and other CSF genes can be constructed by the assembly of synthetic oligonucleotides.

Synthetic oligonucleotides are designed so that they would anneal in complementary pairs, with protruding single stranded ends, and when the pairs are properly assembled would result in a DNA sequence that encoded a portion of the desired gene. Amino acid substitutions in the hIL-3 gene are made by designing the oligonucleotides to encode the desired substitutions. The complementary oligonucleotides are annealed at concentration of 1 picomole per microliter in ligation buffer plus 50 mM NaCl. The samples are heated in a 100 ml beaker of boiling water and permitted to cool slowly to room temperature. One picomole of each of the annealed pairs of oligonucleotides are ligated with approximately 0.2 picomoles of plasmid DNA, digested with the appropriate restriction enzymes, in ligation buffer (25 mM Tris pH 8.0, 10 mM $MgCl_2$, 10 mM dithiothreitol, 1 mM ATP, 2mm spermidine) with T4 DNA ligase obtained from New England Biolabs (Beverly, Mass.) in a total volume of 20 µl at room temperature overnight.

Polymerase Chain Reaction

Polymerase Chain Reaction (hereafter referred to as PCR) techniques (Saiki, 1985) used the reagent kit and thermal cycler from Perkin-Elmer Cetus (Norwalk, Conn.). PCR is based on a thermostable DNA polymerase from *Thermus aguaticus*. The PCR technique is a DNA amplification method that mimics the natural DNA replication process in that the number of DNA molecules doubles after each cycle, in a way similar to in vivo replication. The DNA polymerase mediated extension is in a 5' to 3' direction. The term "primer" as used herein refers to an oligonucleotide sequence that provides an end to which the DNA polymerase can add nucleotides that are complementary to a nucleotide sequence. The latter nucleotide sequence is referred to as the "template", to which the primers are annealed. The amplified PCR product is defined as the region comprised between the 5' ends of the extension primers. Since the primers have defined sequences, the product will have discrete ends, corresponding to the primer sequences. The primer extension reaction is carried out using 20 picomoles (pmoles) of each of the oligonucleotides and 1 picogram of template plasmid DNA for 35 cycles (1 cycle is defined as 94 degrees C. for one minute, 50 degrees C. for two minutes and 72 degrees for three minutes.). The reaction mixture is extracted with an equal volume of phenol/chloroform (50% phenol and 50% chloroform, volume to volume) to remove proteins. The aqueous phase, containing the amplified DNA, and solvent phase are separated by centrifugation for 5 minutes in a microcentrifuge (Model 5414 Eppendorf Inc, Fremont Calif.). To precipitate the amplified DNA the aqueous phase is removed and transferred to a fresh tube to which is added 1/10 volume of 3M NaoAc (pH 5.2) and 2.5 volumes of ethanol (100% stored at minus 20 degrees C.). The solution is mixed and placed on dry ice for 20 minutes. The DNA is pelleted by centrifugation for 10 minutes in a microcentrifuge and the solution is removed from the pellet. The DNA pellet is washed with 70% ethanol, ethanol removed and dried in a speedvac concentrator (Savant, Farmingdale, N.Y.). The pellet is resuspended in 25 microliters of TE (20 mM Tris-HCl pH 7.9, 1 mM EDTA). Alternatively the DNA is precipitated by adding equal volume of 4M $NH_4OAc$ and one volume of isopropanol [Treco et al., (1988)]. The solution is mixed and incubated at room temperature for 10 minutes and centrifuged. These conditions selectively precipitate DNA fragments larger than ~20 bases and are used to remove oligonucleotide primers. One quarter of the reaction is digested with restriction enzymes [Higuchi, (1989)] an on completion heated to 70 degrees C. to inactivate the enzymes.

Recovery of Recombinant Plasmids from Ligation Mixes

E. coli JM101 cells are made competent to take up DNA. Typically, 20 to 100 ml of cells are grown in LB medium to a density of approximately 150 Klett units and then collected by centrifugation. The cells are resuspended in one half culture volume of 50 mm $CaCl_2$ and held at 4° C. for one hour. The cells are again collected by centrifugation and resuspended in one tenth culture volume of 50 mM $CaCl_2$. DNA is added to a 150 microliter volume of these cells, and the samples are held at 4° C. for 30 minutes. The samples are shifted to 42° C. for one minute, one milliliter of LB is added, and the samples are shaken at 37° C. for one hour. Cells from these samples are spread on plates containing ampicillin to select for transformants. The plates are incubated overnight at 37° C. Single colonies are picked, grown in LB supplemented with ampicillin overnight at 37° C. with shaking. From these cultures DNA is isolated for restriction analysis.

Culture Medium

LB medium (Maniatis et al., 1982) is used for growth of cells for DNA isolation. M9 minimal medium supplemented with 1.0% casamino acids, acid hydrolyzed casein, Difco (Detroit, Mich.) is used for cultures in which recombinant fusion molecule is produced. The ingredients in the M9 medium are as follows: 3 g/liter $KH_2PO_4$, 6 g/l $Na_2HPO_4$, 0.5 g/l NaCl, 1 g/l $NH_4Cl$, 1.2 mM $MgSO_4$, 0.025 mM $CaCl_2$, 0.2% glucose (0.2% glycerol with the AraBAD promoter), 1% casamino acids, 0.1 ml/l trace minerals (per liter 108 g $FeCl_3.6H_2O$, 4.0 g $ZnSO_4.7H_2O$, 7.0 $CoCl_2.2H_2O$, 7.0 g $Na_2MoO_4.2H_2O$, 8.0 g $CuSO_4.5H_2O$, 2.0 g $H_3BO_3$, 5.0 g $MnSO_4.H_2O$, 100 ml concentrated HCl). Bacto agar is used for solid media and ampicillin is added to both liquid and solid LB media at 200 micrograms per milliliter.

Production of Fusion Molecules in E. coli with Vectors Employing the recA Promoter E. coli strains harboring the plasmids of interest are grown at 37° C. in $M_9$ plus casamino acids medium with shaking in a Gyrotory water bath Model G76 from New Brunswick Scientific (Edison, N.J.). Growth is monitored with a Klett Summerson meter (green 54 filter), Klett Mfg. Co. (New York, N.Y.). At a Klett value of approximately 150, an aliquot of the culture (usually one milliliter) is removed for protein analysis. To the remaining culture, nalidixic acid (10 mg/ml) in 0.1 N NaOH is added to a final concentration of 50 µg/ml. The cultures are shaken at 37° C. for three to four hours after addition of nalidixic acid. A high degree of aeration is maintained throughout the bacterial growth in order to achieve maximal production of the desired gene product. The cells are examined under a light microscope for the presence of inclusion bodies. One milliliter aliquots of the culture are removed for analysis of protein content.

Fractionation of E. coli Cells Producing Fusion Proteins in the Cytoplasm

The first step in purification of the fusion molecules is to sonicate the cells. Aliquots of the culture are resuspended from cell pellets in sonication buffer: 10 mM Tris, pH 8.0, 1 mM EDTA, 50 mM NaCl and 0.1 mM PMSF. These resuspended cells are subjected to several repeated sonication bursts using the microtip from a Sonicator cell disrupter, Model W-375 obtained from Heat Systems-Ultrasonics Inc. (Farmingdale, N.Y.) The extent of sonication is monitored by examining the homogenates under a light microscope. When nearly all of the cells are broken, the homogenates are fractionated by centrifugation. The pellets, which contain most of the inclusion bodies, are highly enriched for fusion proteins.

Methods: Extraction, Refolding and Purification of Fusion Molecules Expressed as Inclusion Bodies in E. coli These fusion proteins can be purified by a variety of standard methods. Some of these methods are described in detail in Methods in Enzymology, Volume 182 'Guide to Protein Purification' edited by Murray Deutscher, Academic Press, San Diego, Calif. (1990).

Fusion proteins which are produced as insoluble inclusion bodies in E. coli can be solubilized in high concentrations of denaturant, such as Guanidine HCl or Urea including dithiothreitol or beta mercaptoethanol as a reducing agent. Folding of the protein to an active conformation may be accomplished via sequential dialysis to lower concentrations of denaturant without reducing agent.

In some cases the folded proteins can be affinity purified using affinity reagents such as mabs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

hIL-3 Sandwich ELISA

The fusion protein concentrations can be determined using a sandwich ELISA based on an appropriate affinity purified antibody. Microtiter plates (Dynatech Immulon II) are coated with 150 µl goat-anti-rhIL-3 at a concentration of approximately 1 µg/ml in 100 mM $NaHCO_3$, pH 8.2. Plates are incubated overnight at room temperature in a chamber maintaining 100% humidity. Wells are emptied and the remaining reactive sites on the plate are blocked with 200 µl of solution containing 10 mM PBS, 3% BSA and 0.05% Tween 20, pH 7.4 for 1 hour at 37° C. and 100% humidity. Wells are emptied and washed 4× with 150 mM NaCl containing 0.05% Tween 20 (wash buffer). Each well then receives 150 µl of dilution buffer (10 mM PBS containing 0.1% BSA, 0.01% Tween 20, pH 7.4), containing rhIL-3 standard, control, sample or dilution buffer alone. A standard curve is prepared with concentrations ranging from 0.125 ng/ml to 5 ng/ml using a stock solution of rhIL-3 (concentration determined by amino acid composition analysis). Plates are incubated 2.5 hours at 37° C. and 100% humidity. Wells are emptied and each plate is washed 4× with wash buffer. Each well then received 150 µl of an optimal dilution (as determined in a checkerboard assay format) of goat anti-rhIL-3 conjugated to horseradish peroxidase. Plates are incubated 1.5 hours at 37° C. and 100% humidity. Wells are emptied and each plate is washed 4× with wash buffer. Each well then received 150 µl of ABTS substrate solution (Kirkegaard and Perry). Plates are incubated at room temperature until the color of the standard wells containing 5 ng/ml rhIL-3 had developed enough to yield an absorbance between 0.5–1.0 when read at a test wavelength of 410 nm and a reference wavelength of 570 nm on a Dynatech microtiter plate reader. Concentrations of immunoreactive rhIL-3 in unknown samples are calculated from the standard curve using software supplied with the plate reader.

The following examples will illustrate the invention in greater detail although it will be understood that the invention is not limited to these specific examples.

EXAMPLE 1

Construction of Expression Plasmid for Fusion Molecules

Construction of a plasmid encoding a fusion protein composed of the IL-3 variant protein found in the plasmid, pMON13288 (U.S. patent application Ser. No. PCT/US93/11197), followed by a factor Xa proteolytic cleavage site, followed by murine IgG 2b hinge region, in which the cysteines have replaced with serines, as the polypeptide linker sequence between the two proteins of the fusion and followed by G-CSF. The plasmid, pMON13288, is digested with EcoRI (which is internal in the IL-3 variant gene) and HindIII (which is after the stop codons for the IL-3 variant) and the 3900 base pair EcoRI,HindIII restriction fragment is purified. The genetic elements derived from pMON13288 are the beta-lactamase gene (AMP), pBR327 origin of replication, recA promoter, g10L ribosome binding site, the bases encoding amino acids 15–105 of (15–125)IL-3 variant gene, and phage f1 origin of replication. Pairs of complementary synthetic oligonucleotides are designed to replace the portion of the IL-3 variant gene after the EcoRI site (bases encoding amino acids 106–125), DNA sequence encoding the factor Xa cleavage site, DNA sequence encoding the polypeptide linker and AflIII restriction site to allow for cloning of the second gene in the fusion. When properly assembled the oligonucleotides result in a DNA sequence, encoding the above mentioned components in-frame, with EcoRI and HindIII restriction ends. Within this DNA sequence unique restriction sites are also created to allow for the subsequent replacement of specific regions with a sequence that has similar function (e.g. alternative polypeptide linker region). A unique SnaBI restriction site is created at the end of the 13288 gene which allows for the cloning of other genes in the C-terminus position of the fusion. A unique XmaI site is created between sequence encoding the factor Xa cleavage site and the region encoding the polypeptide linker. A unique AflIII site is created after the linker region that allows for the cloning of the N-terminal protein of the fusion. The 3900 base pair fragment from pMON13288 is ligated with the assembled oligonucleotides and transformed into an appropriate E. coli strain. The resulting clones are screened by restriction analysis and DNA sequenced to confirm that the desired DNA sequence are created. The resulting plasmid is used as an intermediate into which other genes can be cloned as a NcoI,HindIII fragment into the AflIII and HindIII sites to create the desired fusion. The overhangs created by NcoI and AflIII are compatible but the flanking sequence of the restriction recognition sites are different. The NcoI and AflIII sites are lost as a result of the cloning. The above mentioned restriction sites are used as examples and are not limited to those described. other unique restriction site may also be engineered which serve the function of allowing the regions to be replaced. The plasmid encoding the resulting fusion is DNA sequenced to confirm that the desired DNA sequence is obtained. Other IL-3 variant genes or other colony stimulating factor genes can be altered in a similar manner by genetic engineering techniques to create the appropriate restriction sites which would allow for cloning either into the C-terminal or N-terminal position of the fusion construct described above. Likewise alternative peptidase cleavage sites or polypeptide linkers can be engineered into the fusion plasmids.

EXAMPLE 2

Expression, Extraction, Refolding and Purification of Fusion Proteins, Such as pMON13061, Expressed as Inclusion Bodies in E. coli E. coli strains harboring the plasmids of interest are grown overnight at 37° C. and diluted the following morning, approximately 1/50, in fresh M9 plus casamino acids medium. The culture is grown at 37° C. for three to four hours to mid-log (OD600=~1) with vigorous shaking. Nalidixic acid (10 mg/ml) in 0.1 N NaOH is added to a final concentration of 50 µg/ml. The cultures are grown at 37° C. for three to four hours after the addition of nalidixic acid. A high degree of aeration is maintained throughout the bacterial growth in order to achieve maximal production of the desired fusion protein. In cases where the fusion proteins are produced as insoluble inclusion bodies in E. coli the cells are examined under a light microscope for the presence of inclusion bodies.

E. coli cells containing fusion molecules in inclusion bodies were lysed by sonication. A 10% (w/v) suspension of the cells in 10 mM Tris-HCl pH 8.0 and 1 mM EDTA was subjected to three or four one minute bursts using a Sonicator cell disrupter, Model W-375, obtained from Heat Systems-Ultrasonics Inc. (Farmingdale, N.Y.). The extent of cell disruption was monitored by examining the cells under a light microscope. When essentially all of the cells had been lysed, the inclusion bodies were harvested by centrifugation at 2800×g for 20 min. The inclusion bodies were washed twice by suspending the inclusion body pellets to 10% in sonication buffer and centrifuging as above.

The fusion molecules were dissolved at one gram of inclusion bodies in 10 ml of 8 M urea with 50 mM Tris-HCl pH 9.5 and 5 mM DTT by blending with a Bio Homogenizer for 10–30 seconds and then gently stirring at 4° C. for 1–2 hours. The dissolved fusion protein was clarified by centrifugation at 47,000×g for 15 minutes.

Folding of the protein into an active conformation was done by diluting 8 fold with 2.3 M urea in 10 mM Tris-HCl pH 9.5 over 30 minutes to lower the concentration to 3 M urea. Folding of the fusion molecule was normally done between 2 and 3 M urea although higher concentrations of urea will also permit folding. The fusion was gently stirred under these conditions exposed to air until protein folding and formation of disulfide bonds was complete. The folding progress was monitored by reversed phase high performance liquid chromatography (RP-HPLC) using a 0.46×15 cm Vydac C 4 column (Hesperia, Calif.) with a linear 35% to 65% acetonitrile ($CH_3CN$)/0.1% trifluoroacetic acid (TFA) gradient over 25 minutes at 1 ml/minute.

After folding was complete, the pH of the fusion protein solution was lowered to 5.0 with glacial acetic acid and incubated at 4° C. After one hour, the solution was clarified by centrifugation at 47,000×g for 15 minutes. The pH of the supernatant was lowered to 4.0 with acetic acid and clarified by filtration using a 0.45 g filter. The filtrate was dialyzed versus two, 100-fold, changes of 10 mM ammonium acetate pH 4.0. The pH of the dialyzed solution was increased to 6.5 with NaOH. The neutralized solution was then loaded at 2 mg of fusion protein per 1 ml of resin on a DEAE Fast Flow column (Pharmacia Piscataway, N.J.) equilibrated with 10 mM Tris-Cl pH 6.5. The fusion protein was eluted using a linear gradient from 50 to 150 mM NaCl in equilibration buffer with a linear flow of 0.28 cm/min. for 12 hours. Using RP-HPLC analysis, fractions with a purity of 93% or better were pooled. The pooled fractions were dialyzed versus two, 100-fold, changes of 10 mM Tris-Cl pH 7.5. The dialyzed protein solution was sterile filtered, using a 0.45 µ filter, and stored at 4° C. RP-HPLC and cation exchange chromatography such as CM Fast Flow can also be used separately or in combination with DEAE chromatography to purify the fusion proteins.

The purified fusion protein was analyzed by RP-HPLC, electrospray mass spectrometry, IEF, and SDS-PAGE. The protein quantitation was done by amino acid composition and Bradford protein determination.

In some cases the folded proteins can be affinity purified using affinity reagents such as mAbs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

These and other protein purification methods are described in detail in Methods in Enzymology, Volume 182 'Guide to Protein Purification' edited by Murray Deutscher, Academic Press, San Diego, Calif. (1990).

EXAMPLE 3

Determination of the In Vitro Activity of Fusion Proteins

The protein concentration of the fusion protein can be determined using a sandwich ELISA based on an affinity purified polyclonal antibody. Alternatively the protein concentration can be determined by amino acid composition. The bioactivity of the fusion molecule can be determined in a number of in vitro assays compared with native IL-3, the IL-3 variant or G-CSF alone or together. One such assay is the AML-193 cell proliferation assay. AML-193 cells respond to IL-3 and G-CSF which allows for the combined bioactivity of the IL-3 variant/G-CSF fusion to be determined. In addition other factor dependent cell lines, such as M-NFS-60 (ATCC. CRL 1838) or 32D which are murine IL-3 dependent cell line, may be used. The activity of IL-3 is species specific whereas G-CSF is not, therefor the bioactivity of the G-CSF component of the IL-3 variant/G-CSF fusion can be determined independently. The methylcellulose assay can be used to determine the effect of the IL-3 variant/G-CSF fusion protein on the expansion of the hematopoietic progenitor cells and the pattern of the different types of hematopoietic colonies in vitro. The methylcellulose assay can provide an estimate of precursor frequency since one measures the frequency of progenitors per 100,000 input cells. Long term, stromal dependent cultures have been used to delineate primitive hematopoietic progenitors and stem cells. This assay can be used to determine whether the fusion molecule stimulates the expansion of very primitive progenitors and/or stem cells. In addition, limiting dilution cultures can be performed which will indicate the frequency of primitive progenitors stimulated by the fusion molecule.

The factor Xa cleavage site is useful to cleave the fusion protein after it is purified and re-folded to separate the IL-3 and G-CSF components of the fusion. After cleavage with factor Xa the IL-3 and G-CSF components of the fusion can be purified to homogeneity and assayed separately to demonstrate that both components are in an active conformation after being expressed, refolded and purified as a fusion.

EXAMPLE 4

Construction of pMON13018

Construction of pMON13018, an intermediate plasmid used for constructing plasmids containing DNA sequences encoding fusion proteins. The 3900 base pair EcoRI*, HindIII restriction fragment from pMON13288 was ligated with the following pairs of annealed complementary oligonucleotides:

Oligo #88Cterm1 [SEQ ID NO:91]
Oligo #88Cterm4 [SEQ ID NO:92]
Oligo #88Xa2 [SEQ ID NO:93]
Oligo #88Xa5 [SEQ ID NO:94]
Oligo #Glyn3 [SEQ ID NO:95]
Oligo #Glyn6 [SEQ ID NO:96]

The assembled oligonucleotides create EcoRI and HindIII restriction ends and the DNA sequence that encodes amino acids 106–125 of (15–125)hIL-3 variant 13288 and the polypeptide Linker 1 (Table 1) which is comprised of the factor Xa cleavage site and the amino acid sequence (Gly3Ser)$_2$. The ligation reaction was used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides. A schematic diagram of the construction of the plasmid, pMON13018, is shown in FIG. 2.

EXAMPLE 5

Construction of pMON13019

Construction of pMON13019, an intermediate plasmid used for constructing plasmids containing DNA sequences encoding fusion proteins. The 4014 base pair XmaI/AflIII restriction fragment from pMON13018 was ligated with the following pair of annealed complementary oligonucleotides:

Oligo #IgG2b1 [SEQ ID NO:97]
Oligo #IgG2b2 [SEQ ID NO:98]

The assembled oligonucleotides create XmaI and AflIII restriction ends and the DNA sequence that encodes amino acids 9–33 of the polypeptide Linker 4 (Table 1) which is comprised of the factor Xa cleavage site and the murine IgG2b hinge region. The ligation reaction was used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides.

EXAMPLE 6

Construction of pMON13024

Construction of pMON13024, an intermediate plasmid used for constructing plasmids containing DNA sequences encoding fusion proteins. The 4091 base pair NheI,HindIII restriction fragment from pMON13010 was ligated with the following pair of annealed complementary oligonucleotides:

Oligo #GCSFSna1 [SEQ ID NO:99]
Oligo #GCSFSna2 [SEQ ID NO:100]

The assembled oligonucleotides create NheI and HindIII restriction ends, create a SnaBI restriction site at the 3' end of the G-CSF gene, and the DNA sequence that encodes amino acids 155–175 of G-CSF. The stop codon after the G-CSF gene is eliminated and the DNA sequence of the SnaBI recognition site encodes amino acids Tyr Val in-frame at the C-terminus of G-CSF. The ligation reaction was used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides.

EXAMPLE 7

Construction of pMON13027

Construction of pMON13027, an intermediate plasmid used for constructing plasmids containing DNA sequences encoding fusion proteins. Plasmid, pMON13018, DNA was digested with restriction enzymes NcoI and SnaBI, resulting in a 3704 base pair NcoI,SnaBI fragment. Plasmid, pMON13024, DNA was digested with NcoI and SnaBI resulting in a 528 base pair NcoI, SnaBI fragment. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert.

EXAMPLE 8

Construction of pMON13032

Construction of pMON13032, an intermediate plasmid used for constructing plasmids containing DNA sequences encoding fusion proteins. Plasmid, pMON15930, DNA was digested with restriction enzymes NcoI and SnaBI, resulting in a 3829 base pair NcoI,SnaBI fragment. Plasmid, pMON13024, DNA was digested with NcoI and SnaBI, resulting in a 528 base pair NcoI, SnaBI fragment. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert.

EXAMPLE 9

Construction of pMON13041

Construction of pMON13041, an intermediate plasmid used for constructing plasmids containing DNA sequences encoding fusion proteins. The 4018 base pair SnaBI/XmaI restriction fragment from pMON13018 was ligated with the following pair of annealed complementary oligonucleotides:

Oligo #Lysxa1 [SEQ ID NO:101]

Oligo #Lysxa2 [SEQ ID NO:102]

The assembled oligonucleotides create SnaBI and XmaI restriction ends and the DNA sequence that encodes amino acids 1–8 of the polypeptide Linker 2 (Table 1) which is comprised of the factor Xa cleavage site in which the Arg is changed to Lys and the amino acid sequence (Gly3Ser)2. The ligation reaction was used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides.

EXAMPLE 10

Construction of pMON13042

Construction of pMON13042, an intermediate plasmid used for constructing plasmids containing DNA sequences encoding fusion proteins. The 4018 base pair SnaBI/XmaI restriction fragment from pMON13018 was ligated with the following pair of annealed complementary oligonucleotides:

Oligo #Glyxa1 [SEQ ID NO:103]

Oligo #Glyxa2 [SEQ ID NO:104]

The assembled oligonucleotides create SnaBI and XmaI restriction ends and the DNA sequence that encodes the polypeptide Linker 3 (Table 1). Polypeptide Linker 3 is comprised of the following amino acid sequence Tyr Val Glu Gly Gly Gly Gly Ser Pro (Gly3Ser)2 Asn [SEQ ID NO:190]. The ligation reaction was used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides.

EXAMPLE 11

Construction of pMON13046

Construction of pMON13046, an intermediate plasmid used for constructing plasmids containing DNA sequences encoding fusion proteins. Plasmid, pMON13018, DNA was digested with restriction enzymes NcoI and NsiI, resulting in a 3873 base pair NcoI,NsiI fragment. Plasmid, pMON13416 (U.S. patent application Ser. No. PCT/US93/11197) DNA, which encodes a hIL-3 variant, was digested with NcoI and NsiI, resulting in a 170 base pair NcoI, NsiI fragment. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert.

EXAMPLE 12

Construction of pMON13047

Construction of pMON13047, an intermediate plasmid used for constructing plasmids containing DNA sequences encoding fusion proteins. Plasmid, pMON13019, DNA was digested with restriction enzymes NcoI and NsiI, resulting in a 3918 base pair NcoI, NsiI fragment. Plasmid, pMON13416, DNA was digested with NcoI and NsiI, resulting in a 170 base pair NcoI,NsiI fragment. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert.

EXAMPLE 13

Construction of pMON13478

A pUC18 based plasmid containing the engineered gene encoding human granulocyte colony stimulating factor (hG-CSF) was obtained from R&D Systems (catalog # BBG13, Minneapolis Minn.). This plasmid was designated pMON13457. The 3157 base pair ApaI,HindIII fragment from pMON13457 was ligated with the following pair of annealed complementary oligonucleotides:

Oligo #hgcsfma1 [SEQ ID NO:111]

Oligo #hgcsfma2 [SEQ ID NO:112]

The assembled oligonucleotides create HindIII and ApaI restriction ends, an internal NcoI restriction site, the DNA sequence that encodes the first four amino acids of hG-CSF (Thr Pro Leu Gly) preceded by an initiator methionine followed by an alanine. The methionine and alanine were added for expression in E. coli. The ligation reaction mixture was used to transform E. coli K-12 strain JM101. Transformant bacteria were selected on ampicillin-containing plates. Plasmid DNA was isolated and sequenced to confirm the correct insert. The resulting plasmid was designated pMON13478.

EXAMPLE 14

Construction of DMON13498

The 3163 base pair NcoI,ApaI fragment from pMON13478 was ligated with the following pair of annealed complementary oligonucleotides:

Oligo #hgcsfat3 [SEQ ID NO:115]
Oligo #hgcsfat4 [SEQ ID NO:116]

The assembled oligonucleotides create NcoI and ApaI restriction ends, and maximizes A/T content of the DNA sequence that encodes the first four amino acids of mature hG-CSF (Thr Pro Leu Gly). The A/T content of the DNA sequence was changed to increase protein expression levels in E. coli. The ligation reaction mixture was used to transform E. coli K-12 strain JM101. Transformant bacteria were selected on ampicillin-containing plates. Plasmid DNA was isolated and sequenced to confirm the correct insert. The ApaI restriction end of the oligonucleotides is compatible with the ApaI site but ApaI recognition sequence is altered. The resulting plasmid was designated pMON13498. The foregoing modifications to the hG-CSF gene are found in the DNA sequence [SEQ ID NO:178].

EXAMPLE 15

Construction of pMON13010

Plasmid, pMON5743 (Olins and Rangwala [1990], DNA was digested with restriction enzymes NcoI and EcoRI, resulting in a 3633 base pair NcoI,EcoRI fragment. Plasmid, pMON13498, DNA was digested with NcoI and EcoRI, resulting in a 542 base pair NcoI, ECORI fragment. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The plasmid, pMON13010, encodes the following amino acid sequence:

EXAMPLE 16

Construction of pMON13499

The 3163 base pair NcoI,ApaI fragment from pMON13478 was ligated with the following pair of annealed complementary oligonucleotides:

Oligo #hgcsfat1 [SEQ ID NO:113]
Oligo #hgcsfat2 [SEQ ID NO:114]

The assembled oligonucleotides create NcoI and ApaI restriction ends, and maximizes A/T content of the DNA sequence that encodes the first three amino acids of hG-CSF (Thr Pro Leu). The A/T content of the DNA sequence was changed to increase expression levels in E. coli. The ligation reaction mixture was used to transform E. coli K-12 strain JM101. Transformant bacteria were selected on ampicillin-containing plates. Plasmid DNA was isolated and sequenced to confirm the correct insert. The resulting plasmid was designated pMON13499. The foregoing modifications to the hG-CSF gene are found in the DNA sequence [SEQ ID NO:177].

EXAMPLE 17

Construction of pMON13033

The 3117 base pair ApaI,BstXI fragment from pMON13499 was ligated with the following pair of annealed complementary oligonucleotides:

Oligo # gcys18 [SEQ ID NO:107]
Oligo # gcysl18lo [SEQ ID NO:108]

The assembled oligonucleotides create ApaI and BstXI restriction ends, and encodes amino acids 5 to 26 of hG-CSF except for amino acid 17 where the cysteine was replaced with serine. The cysteine was replaced with a serine to increase the in vitro refold efficiencies of the protein isolated from E. coli. The ligation reaction mixture was used to transform E. coli K-12 strain JM101. Transformant bacteria were selected on ampicillin-containing plates. Plasmid DNA was isolated and sequenced to confirm the correct insert. The

```
Peptide #                                                     [SEQ ID NO:161]
Met Ala Thr Pro Leu Gly Pro Ala Ser Ser Leu Pro Gln Ser Phe Leu Leu Lys Cys Leu Glu Gln Val Arg Lys Ile Gln Gly Asp Gly Ala Ala Leu Gln Glu Lys Leu Cys Ala Thr Tyr Lys Leu Cys His Pro Glu Glu Leu Val Leu Leu Gly His Ser Leu Gly Ile Pro Trp Ala Pro Leu Ser Ser Cys Pro Ser Gln Ala Leu Gln Leu Ala Gly Cys Leu Ser Gln Leu His Ser Gly Leu Phe Leu Tyr Gln Gly Leu Leu Gln Ala Leu Glu Gly Ile Ser Pro Glu Leu Gly Pro Thr Leu Asp Thr Leu Gln Leu Asp Val Ala Asp Phe Ala Thr Thr Ile Trp Gln Gln Met Glu Glu Leu Gly Met Ala Pro Ala Leu Gln Pro Thr Gln Gly Ala Met Pro Ala Phe Ala Ser Ala Phe Gln Arg Arg Ala Gly Gly Val Leu Val Ala Ser His Leu Gln Ser Phe Leu Glu Val Ser Tyr Arg Val Leu Arg His Leu Ala Gln Pro
```

DNA sequence # [SEQ ID NO:178] codes for the foregoing pMON13010 polypeptide.

resulting plasmid was designated pMON13033. The foregoing modifications to the hG-CSF gene are found in the DNA sequence [SEQ ID NO:179].

EXAMPLE 18

Construction of pMON13037

Plasmid, pMON5743, DNA was digested with restriction enzymes NcoI and EcoRI, resulting in a 3633 base pair NcoI,EcoRI fragment. Plasmid, pMON13033, DNA was digested with NcoI and EcoRI, resulting in a 542 base pair NcoI, EcoRI fragment. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON13037, encodes the following amino acid sequence:

```
Peptide #                                                       ]SEQ ID NO:162]
Met Ala Thr Pro Leu Gly Pro Ala Ser Ser Leu Pro Gln Ser Phe Leu Leu Lys Ser Leu Glu Gln Val Arg Lys Ile Gln Gly Asp Gly Ala Ala Leu Gln Glu Lys Leu Cys Ala Thr Tyr Lys Leu Cys His Pro Glu Glu Leu Val Leu Leu Gly His Ser Leu Gly Ile Pro Trp Ala Pro Leu Ser Ser Cys Pro Ser Gln Ala Leu Gln Leu Ala Gly Cys Leu Ser Gln Leu His Ser Gly Leu Phe Leu Tyr Gln Gly Leu Leu Gln Ala Leu Glu Gly Ile Ser Pro Glu Leu Gly Pro Thr Leu Asp Thr Leu Gln Leu Asp Val Ala Asp Phe Ala Thr Thr Ile Trp Gln Gln Met Glu Glu Leu Gly Met Ala Pro Ala Leu Gln Pro Thr Gln Gly Ala Met Pro Ala Phe Ala Ser Ala Phe Gln Arg Arg Ala Gly Gly Val Leu Val Ala Ser His Leu Gln Ser Phe Leu Glu Val Ser Tyr Arg Val Leu Arg His Leu Ala Gln Pro
```

DNA sequence # [SEQ ID NO:179] codes for the foregoing pMON13037 polypeptide.

EXAMPLE 19

Construction of pMON13011

A pUC18 based plasmid containing the engineered gene encoding human granulocyte macrophage colony stimulating factor (hGM-CSF) was obtained from R&D Systems (catalog # BBG12, Minneapolis Minn.). This plasmid was designated pMON13458. The 2986 base pair NcoI,BsmI fragment from pMON13458 was ligated with the following pair of annealed complementary oligonucleotides:
Oligo #gm-aup [SEQ ID NO:105]
Oligo #gm-alow [SEQ ID NO:106]

The assembled oligonucleotides create NcoI and BsmI restriction ends and the DNA sequence that encodes the first nineteen amino acids of hGM-CSF. The DNA sequence encoding amino acids 3, 4, 5, 7, 9, 11, 12, 13 and 15 were changed to *E. coli* preferred codons to increase expression levels in *E. coli*. The ligation reaction mixture was used to transform *E. coli* K-12 strain JM101. Transformant bacteria were selected on ampicillin-containing plates. Plasmid DNA was isolated and sequenced to confirm the correct insert. The resulting plasmid was designated pMON13011. The foregoing modifications to the hGM-CSF gene are found in the DNA sequence [SEQ ID NO:176].

EXAMPLE 20

Construction of pMON13012

Plasmid, pMON5743, DNA was digested with restriction enzymes NcoI and EcoRI, resulting in a 3633 base pair NcoI,EcoRI fragment. Plasmid, pMON13011, DNA was digested with NcoI and EcoRI, resulting in a 398 base pair NcoI, EcoRI fragment. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON13012, encodes the following amino acid sequence:

```
Peptide #                                                       [SEQ ID NO:160]
Met Ala Pro Ala Arg Ser Pro Ser Pro Ser Thr Gln Pro Trp Glu His Val Asn Ala Ile Gln Glu Ala Arg Arg Leu Leu Asn Leu Ser Arg Asp Thr Ala Ala Glu Met Asn Glu Thr Val Glu Val Ile Ser Glu Met Phe Asp Leu Gln Glu Pro Thr Cys Leu Gln Thr Arg Leu Glu Leu Tyr Lys Gln Gly Leu Arg Gly Ser Leu Thr Lys Leu Lys Gly Pro Leu Thr Met Met Ala Ser His Tyr Lys Gln His Cys Pro Pro Thr Pro Glu Thr Ser Cys Ala Thr Gln Ile Ile Thr Phe Glu Ser Phe Lys Glu Asn Leu Lys Asp Phe Leu Leu Val Ile Pro Phe Asp Cys Trp Glu Pro Val Gln Glu
```

DNA sequence # [SEQ ID NO:176] codes for the foregoing pMON13012 polypeptide.

confirm the correct insert. The plasmid, pMON13040, encodes the following amino acid sequence:

```
Peptide #                                                                    [SEQ ID NO:163]
Met Ala Pro Val Pro Pro Gly Glu Asp Ser Lys Asp Val Ala Ala Pro His Arg Gln Pro Leu Thr Ser Ser Glu Arg Ile Asp Lys Gln Ile Arg Tyr Ile Leu Asp Gly Ile Ser Ala Leu Arg Lys Glu Thr Cys Asn Lys Ser Asn Met Cys Glu Ser Ser Lys Glu Ala Leu Ala Glu Asn Asn Leu Asn Leu Pro Lys Met Ala Glu Lys Asp Gly Cys Phe Gln Ser Gly Phe Asn Glu Glu Thr Cys Leu Val Lys Ile Ile Thr Gly Leu Leu Glu Phe Glu Val Tyr Leu Glu Tyr Leu Gln Asn Arg Phe Glu Ser Ser Glu Glu Gln Ala Arg Ala Val Gln Met Ser Thr Lys Val Leu Ile Gln Phe Leu Gln Lys Lys Ala Lys Asn Leu Asp Ala Ile Thr Thr Pro Asp Pro Thr Thr Asn Ala Ser Leu Leu Thr Lys Leu Gln Ala Gln Asn Gln Trp Leu Gln Asp Met Thr Thr His Leu Ile Leu Arg Ser Phe Lys Glu Phe Leu Gln Ser Ser Leu Arg Ala Leu Arg Gln Met
```

EXAMPLE 21

Construction of pMON5865

A pUC18 based plasmid containing the engineered gene encoding human interleukin-6 (hIL-6) was obtained from British Biotech (catalog # BBG17). The 3170 base pair HindIII/BstXI fragment from this plasmid was ligated with the following pair of annealed complementary oligonucleotides:

Oligo #HIL6231 [SEQ ID NO:109]
Oligo #HIL6232 [SEQ ID NO:110]

The assembled oligonucleotides create HindIII and BstXI restriction ends and the DNA sequence that encodes the first ten amino acids of hIL-6 plus Met Ala at the N-terminus for E. coli protein expression. The oligonucleotides also create an NcoI site at the 5' end of the gene. The codons encoding the first ten amino acids were changed to E.coli preferred to increase expression levels in E. coli. The ligation reaction mixture was used to transform E. coli K-12 strain JM101. Transformant bacteria were selected on ampicillin-containing plates. Plasmid DNA was isolated and sequenced to confirm the correct insert. The resulting plasmid was designated pMON5865. The foregoing modifications to the hG-CSF gene are found in the DNA sequence [SEQ ID NO:175].

EXAMPLE 22

Construction of dMON13040

Plasmid pMON5743 DNA was digested with restriction enzymes NcoI and EcoRI, resulting in a 3633 base pair NcoI,EcoRI fragment. Plasmid, pMON5865, DNA was digested with NcoI and EcoRI, resulting in a 572 base pair NcoI, EcoRI fragment. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to DNA sequence # [SEQ ID NO:175] codes for the foregoing pMON13040 polypeptide.

EXAMPLE 23

Construction of pMON15931

Construction of pMON15931, an intermediate plasmid used for constructing plasmids containing DNA sequences encoding fusion proteins. The DNA sequence encoding the (Gly-Ser)-rich spacer region of the pIII protein of the filamentous bacteriophage fd (Schaller et al., 1975) was amplified using PCR techniques. A plasmid containing the gene encoding the pIII protein of the filamentous bacteriophage fd served as the template for the PCR reaction using the following oligonucleotides as primers:

Oligo # prefor [SEQ ID NO:117]
Oligo # revpre [SEQ ID NO:118]

The PCR primer extension reaction generated the following DNA sequence:

```
                                              [SEQ ID NO:181]
CCTGTCAACC CGGGCGGCGG CTCTGGTGGT GGTTCTGGTG

GCGGCTCTGA GGGTGGCGGC TCTGAGGGTG GCGGTTCTGA

GGGTGGCGGC TCTGAGGGTG GCGGTTCCGG TGGCGGCTCC

GGTTCCGGTA ACATGTATTA TGA
```

The foregoing DNA sequence encodes amino acids 9–49 of the polypeptide Linker 7 (Table 1) which is comprised of the factor Xa cleavage site and the (Gly-Ser)-rich region of the pIII protein of the fd bacteriophage. The PCR generated fragment was digested with XmaI and AflIII and ligated with the 4014 base pair XmaI,AflIII fragment from pMON13018. The ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert.

EXAMPLE 24

Construction of pMON15930

Construction of pMON15930, an intermediate plasmid used for constructing plasmids containing DNA sequences encoding fusion proteins. The DNA sequence encoding the (Gly-Ser)-rich spacer region with a few flanking amino acids of the pIII protein of the filamentous bacteriophage fd (Schaller et al., 1975) was amplified using PCR techniques. A plasmid containing the gene encoding the pIII protein of the filamentous bacteriophage fd served as the template for the PCR reaction using the following oligonucleotides as primers:

Oligo # forxtra [SEQ ID NO:119]

Oligo # xtrarev [SEQ ID NO:120]

The PCR primer extension reaction generated the following DNA sequence:

```
                                                [SEQ ID NO:182]
ATCGTCTGAC CTCCCGGGCC TCCTGTCAAT GCTGGCGGCG

GCTCTGGTGG TGGTTCTGGT GGCGGCTCTG AGGGTGGCGG

CTCTGAGGGT GGCGGTTCTG AGGGTGGCGG CTCTGAGGGT

GGCGGTTCCG GTGGCGGCTC CGGTTCCGGT GATTTTGATT

ATGAAAACAT GTCAAACGCT
```

The foregoing DNA sequence encodes amino acids 9–70 of the polypeptide Linker 8 (Table 1) which is comprised of the factor Xa cleavage site and the (Gly-Ser)-rich region of the pIII protein of the fd bacteriophage. The PCR generated fragment was digested with XmaI and AflIII and ligated with the 4014 base pair XmaI,AflIII fragment from pMON13018. The ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert.

EXAMPLE 25

Construction of pMON13038

Construction of pMON13038, an intermediate plasmid used for constructing plasmids containing DNA sequences encoding fusion proteins. Plasmid, pMON13019, DNA was digested with restriction enzymes NcoI and SnaBI, resulting in a 3749 base pair NcoI,SnaBI fragment. Plasmid, pMON13024, DNA was digested with NcoI and SnaBI, resulting in a 528 base pair NcoI, SnaBI fragment. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The resulting plasmid was designated pMON13038.

EXAMPLE 26

Construction of pMON13021

Plasmid, pMON13018, DNA was digested with restriction enzymes AflIII and HindIII, resulting in a 4023 base pair AflIII,HindIII fragment. Plasmid, pMON13288, DNA was digested with NcoI and HindIII, resulting in a 345 base pair NcoI, HindIII fragment. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. A schematic diagram of the construction of the plasmid, pMON13021, is shown in FIG. 2. The plasmid, pMON13021, encodes the fusion with the following amino acid sequence:

Peptide # [SEQ ID NO:125]

DNA sequence # [SEQ ID NO:54] codes for the foregoing pMON13021 polypeptide.

EXAMPLE 27

Construction of pMON13022

Plasmid, pMON13018, DNA was digested with restriction enzymes AflIII and HindIII, resulting in a 4023 base pair AflIII,HindIII fragment. Plasmid, pMON13012, DNA was digested with NcoI and HindIII, resulting in a 586 base pair NcoI, HindIII fragment. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The plasmid, pMON13022, encodes the fusion with the following amino acid sequence:

Peptide # [SEQ ID No:141]

DNA sequence # [SEQ ID NO:55] codes for the foregoing pMON13022 polypeptide.

EXAMPLE 28–62

Further examples of fusion proteins, comprised in part of hIL-3 variant(s) are shown in Table 2. The plasmids containing the genes encoding the fusion proteins in Table 2 were constructed by methods described in materials and methods and in Examples contained herein, particularly Examples 1, 9, 10, 26 and 27. DNA restriction fragments, indicated in Table 2 were ligated and the resulting *E. coli* expression plasmids (Table 2) contain DNA sequences which encode the indicated polypeptide fusions (Table 2). The polypeptide fusions are comprised of two colony stimulating factors ($R_1$ and $R_2$) fused through a polypeptide linker (L) (Table 1), represented by the formula, $R_1$-L-$R_2$. Some of the genes encoding the polypeptide fusions in Table 2 were transferred from the *E. coli* expression vector, as a NcoI, HindIII restriction fragment into a mammalian cell (BHK) expression vector pMON3934. The *E. coli* and BHK expression plasmids are shown in Table 2. The biological activity, growth promoting activity in AML193.1.3 cells, for some of the polypeptide fusions in Table 2 is shown in Table 3. The biological activity, as evaluated in the methylcellulose assay, for some of the fusions in Table 2 is shown in FIGS. 3–7.

TABLE 1

Polypeptide linker nomenclature and amino acid sequence.

| Polypeptide Linker Designation | Amino Acid Sequence |
|---|---|
| Linker 1 | YVIEGRISP(GGGS)$_2$N [SEQ ID NO: 188] |
| Linker 2 | YVIEGKISP(GGGS)$_2$N [SEQ ID NO: 189] |
| Linker 3 | YVEGGGGSP(GGGS)$_2$N [SEQ ID NO: 190] |

TABLE 1-continued

Polypeptide linker nomenclature and amino acid sequence.

| Polypeptide Linker Designation | Amino Acid Sequence |
|---|---|
| Linker 4 | YVIEGRISPGEPSGPISTINPSPPSKESHKSPN [SEQ ID NO: 191] |
| Linker 5 | YVIEGKISPGEPSGPISTINPSPPSKESHKSPN [SEQ ID NO: 192] |
| Linker 6 | YVEGGGGSPGEPSGPISTINPSPPSKESHKSPN [SEQ ID NO: 193] |
| Linker 7 | YVIEGRISP(GGGS)$_3$(EGGGS)$_4$GGGSGSGN [SEQ ID NO: 194] |
| Linker 8 | YVIEGRISPQPPVNA(GGGS)$_3$(EGGGS)$_4$GGGSGSGDFDYEN [SEQ ID NO: 195] |
| Linker 9 | EFHAYVEGGGGSP(GGGS)$_2$N [SEQ ID NO: 196] |

TABLE 2

| Example Number | vector fragment | insert pMON | E. coli pMON | BHK | R1 | Linker | R2 | DNA [SEQ ID NO:] | Polypeptide [SEQ ID NO:] |
|---|---|---|---|---|---|---|---|---|---|
| 28 | pMON13018 4023 bp Af1III/HindIII | pMON13010 556 bp NcoI, HindIII | 13023 | 3987 | 13288 | Linker 1 | G-CSF | [SEQ ID NO: 53] | [SEQ ID NO: 121] |
| 26 | pMON13018 4023 bp Af1III/HindIII | pMON13288 345 bp NcoI, HindIII | 13021 | 3988 | 13288 | Linker 1 | 13288 | [SEQ ID NO: 54] | [SEQ ID NO: 125] |
| 27 | pMON13018 4023 bp Af1III/HindIII | pMON13012 412 bp NcoI, HindIII | 13022 | 3989 | 13288 | Linker 1 | GM-CSF | [SEQ ID NO: 55] | [SEQ ID NO: 141] |
| 29 | pMON13021 4029 bp NcoI, SnaBI | pMON13024 528 bp NcoI, SnaBI | 13026 | 3995 | G-CSF | Linker 1 | 13288 | [SEQ ID NO: 72] | [SEQ ID NO: 146] |
| 30 | pMON15931 4148 bp Af1III/HindIII | pMON13037 556 bp NcoI, HindIII | 13062 | 26432 | 13288 | Linker 8 | G-CSF Ser17 | [SEQ ID NO: 65] | [SEQ ID NO: 139] |
| 31 | pMON15931 4148 bp Af1III/HindIII | pMON13012 412 bp NcoI, HindIII | 13031 | 3998 | 13288 | Linker 8 | GM-CSF | [SEQ ID NO: 66] | [SEQ ID NO: 142] |
| 32 | pMON15930 4119 bp Af1III/HindIII | pMON13010 556 bp NcoI, HindIII | 15937 | 26405 | 13288 | Linker 7 | G-CSF | [SEQ ID NO: 67] | [SEQ ID NO: 143] |
| 33 | pMON13019 4068 bp AflIII/HindIII | pMON13010 556 bp NcoI, HindIII | 13034 | 26406 | 13288 | Linker 4 | G-CSF | [SEQ ID NO: 68] | [SEQ ID NO: 128] |
| 34 | pMON13019 4068 bp AflIII/HindIII | pMON13012 412 bp NcoI, HindIII | 13035 | 26407 | 13288 | Linker 4 | GM-CSF | [SEQ ID NO: 69] | [SEQ ID NO: 144] |
| 35 | pMON13019 4068 bp AflIII/HindIII | pMON13288 345 bp NcoI, HindIII | 13036 | 26408 | 13288 | Linker 4 | 13288 | [SEQ ID NO: 62] | [SEQ ID NO: 131] |
| 36 | pMON13038 4257 bp Af1III/HindIII | pMON13288 345 bp NcoI, HindIII | 13063 | 26433 | G-CSF | Linker 4 | 13288 | [SEQ ID NO: 73] | [SEQ ID NO: 150] |
| 37 | pMON13032 4337 bp Af1III/HindIII | pMON13288 345 bp NcoI, HindIII | 13064 | 26434 | G-CSF | Linker 8 | 13288 | [SEQ ID NO: 74] | [SEQ ID NO: 151] |
| 38 | pMON13018 4023 bp Af1III/HindIII | pMON13037 556 bp NcoI, HindIII | 13039 | 26415 | 13288 | Linker 1 | G-CSF Ser17 | [SEQ ID NO: 56] | [SEQ ID NO: 122] |
| 39 | pMON13027 4212 bp Af1III/HindIII | pMON13416 345 bp NcoI, HindIII | 13043 | 26416 | G-CSF | Linker 1 | 13416 | [SEQ ID NO: 75] | [SEQ ID NO: 147] |
| 40 | pMON13032 4337 bp Af1III/HindIII | pMON13416 345 bp NcoI, HindIII | 13044 | 26417 | G-CSF | Linker 8 | 13416 | [SEQ ID NO: 76] | [SEQ ID NO: 148] |

TABLE 2-continued

| Example Number | vector fragment | insert pMON | E. coli pMON | BHK | R1 | Linker | R2 | DNA [SEQ ID NO:] | Polypeptide [SEQ ID NO:] |
|---|---|---|---|---|---|---|---|---|---|
| 41 | pMON13038 4257 bp AflIII/HindIII | pMON13416 345 bp NcoI, HindIII | 13045 | 26418 | G-CSF | Linker 4 | 13416 | [SEQ ID NO: 77] | [SEQ ID NO: 149] |
| 42 | pMON13041 4023 bp AflIII, HindIII | pMON13037 556 bp NcoI, HindIII | 13054 | 26424 | 13288 | Linker 2 | G-CSF Ser17 | [SEQ ID NO: 59] | [SEQ ID NO: 123] |
| 43 | pMON13042 4023 bp AflIII, HindIII | pMON13037 556 bp NcoI, HindIII | 13056 | 26426 | 13288 | Linker 3 | G-CSF Ser17 | [SEQ ID NO: 60] | [SEQ ID NO: 124] |
| 44 | pMON13041 4023 bp AflIII, HindIII | pMON13288 345 bp NcoI, HindIII | 13055 | 26425 | 13288 | Linker 2 | 13288 | [SEQ ID NO: 58] | [SEQ ID NO: 126] |
| 45 | pMON13042 4023 bp AflIII, HindIII | pMON13288 345 bp NcoI, HindIII | 13057 | 26427 | 13288 | Linker 3 | 13288 | [SEQ ID NO: 61] | [SEQ ID NO: 127] |
| 46 | pMON13047 4068 bp AflIII, HindIII | pMON13416 345 bp NcoI, HindIII | 13052 | 26422 | 13416 | Linker 4 | 13416 | [SEQ ID NO: 82] | [SEQ ID NO: 137] |
| 47 | pMON13047 4068 bp AflIII, HindIII | pMON13037 556 bp NcoI, HindIII | 13053 | 26423 | 13416 | Linker 4 | G-CSF Ser17 | [SEQ ID NO: 83] | [SEQ ID NO: 138] |
| 48 | pMON13023 4409 bp NsiI, NcoI | pMON13416 170 bp NcoI, NsiI | 13066 | 26436 | 13416 | Linker 1 | G-CSF | [SEQ ID NO: 84] | [SEQ ID NO: 134] |
| 49 | pMON13046 4023 bp AflIII, HindIII | pMON13037 556 bp NcoI, HindIII | 13051 | 26421 | 13416 | Linker 1 | G-CSF Ser17 | [SEQ ID NO: 85] | [SEQ ID NO: 135] |
| 50 | pMon13046 4023 bp AflIII, HindIII | pMON13416 345 bp NcoI, HindIII | 13050 | 26420 | 13416 | Linker 1 | 13416 | [SEQ ID NO: 86] | [SEQ ID NO: 136] |
| 51 | pMON13041 3994 bp XmaI, HindIII | pMON13034 630 bp XmaI, HindIII | 13058 | 26428 | 13288 | Linker 5 | G-CSF | [SEQ ID NO: 70] | [SEQ ID NO: 129] |
| 52 | pMON13042 3994 bp XmaI, HindIII | pMON13034 630 bp XmaI, HindIII | 13060 | 26430 | 13288 | Linker 6 | G-CSF | [SEQ ID NO: 71] | [SEQ ID NO: 130] |
| 53 | pMON13041 3994 bp XmaI, HindIII | pMON13036 419 bp XmaI, HindIII | 13059 | 26429 | 13288 | Linker 5 | 13288 | [SEQ ID NO: 63] | [SEQ ID NO: 132] |
| 54 | pMON13042 3994 bp XmaI, HindIII | pMON13036 419 bp XmaI, HindIII | 13061 | 25431 | 13288 | Linker 6 | 13288 | [SEQ ID NO: 64] | [SEQ ID NO: 133] |
| 55 | pMON13018 4023 bp AflIII, HindIII | pMON13040 586 bp NcoI, HindIII | 13049 | 26435 | 13288 | Linker 1 | IL-6 | [SEQ ID NO: 57] | [SEQ ID NO: 145] |
| 56 | pMON13056 4409 bp NcoI, NsiI | pMON13416 170 bp NcoI, NsiI | 13145 | | 13416 | Linker 3 | G-CSF Ser17 | [SEQ ID NO: 87] | [SEQ ID NO: 152] |
| 57 | pMON13053 4599 bp SnaBI, XmaI | GlyXa1 [SEQ ID NO: 103] GlyXa2 [SEQ ID NO: 104] | 13146 | | 13416 | Linker 6 | G-CSF Ser17 | [SEQ ID NO: 89] | [SEQ ID NO: 154] |
| 58 | pMON13050 4343 bp SnaBI, XmaI | GlyXa1 [SEQ ID NO: 103] GlyXa2 [SEQ ID NO: 104] | 13147 | | 13416 | Linker 3 | 13416 | [SEQ ID NO: 88] | [SEQ ID NO: 153] |
| 59 | pMON13052 4388 bp SnaBI, XmaI | GlyXa1 [SEQ ID NO: 103] GlyXa2 [SEQ ID NO: 104] | 13148 | | 13416 | Linker 6 | 13416 | [SEQ ID NO: 90] | [SEQ ID NO: 155] |
| 60 | pMON13043 4532 bp SnaBI, XmaI | GlyXa1 [SEQ ID NO: 103] GlyXa2 [SEQ ID NO: 104] | 13151 | | G-CSF | Linker 3 | 13416 | [SEQ ID NO: 78] | [SEQ ID NO: 158] |
| 61 | pMON13151 4479 bp NcoI, BstXI | pMON13037 78 bp NcoI, BstXI | 13149 | | G-CSF Ser17 | Linker 3 | 13416 | [SEQ ID NO: 80] | [SEQ ID NO: 159] |
| 62 | pMON13045 4577 bp SnaBI, XmaI | GlyXa1 [SEQ ID NO: 103] GlyXa2 [SEQ ID NO: 104] | 13152 | | G-CSF | Linker 6 | 13416 | [SEQ ID NO: 79] | [SEQ ID NO: 156] |
| 63 | pMON13152 4524 bp NcoI/BstXI | pMON13037 78 bp NcoI, BstXI | 13150 | | G-CSF Ser17 | Linker 6 | 13416 | [SEQ ID NO: 81] | [SEQ ID NO: 157] |

EXAMPLE 63

Isolation of 1–332 and 1–153 Amino Acid Forms of c-mpl Ligand (Meg-CSF)

A. Reverse Transcriptase Reaction (c-mpl ligand sequence based on Genbank accession #L33410)

Human fetal liver A+ RNA was obtained from Clontech (Palo Alto, Calif.). The first strand cDNA reactions was carried out using a cDNA Cycle™ Kit obtained from Invitrogen (San Diego, Calif.).

B. Polymerase Chain Reactions

Following the reverse transcriptase (RT) reaction, the 1–332 c-mpl ligand was amplified by PCR using the oligonucleotide primers c-mplNcoI [SEQ ID NO:169], which created an NcoI site immediately preceding the 5' end of the gene and c-mplEcoRI [SEQ ID NO:170] which created an EcoRI site immediately 3' to the stop codon. Following the RT reaction, the 1–153 c-mpl ligand was amplified using the c-mplNcoI [SEQ ID NO:169] primer and the 3' primer, c-mplHindIII [SEQ ID NO:171] which created a stop codon and an HindIII site immediately 3' to the codon for amino acid 153.

EXAMPLE 64

Construction of pMON26448

The 1–153 c-mpl ligand PCR product was digested with NcoI and HindIII restriction enzymes for subcloning into pMON3934. pMON3934, a mammalian expression vector, is derived from pMON3359 [Hippenmeyer et al., (1993)], but it contains a modified human IL 3 signal peptide sequence in addition to the IE110 promoter and poly-A signal. The signal peptide sequence is flanked by BamHI and NcoI restriction enzyme sites, which facilitates cloning and expression of genes as NcoI,HindIII fragments. The HindIII site is 3' to the NcoI site. The DNA sequence of the signal peptide is shown below (restriction enzyme sites are indicated above). The ATG (methionine) codon within the NcoI site is in-frame with the initiator ATG of the signal peptide (underlined);

BamHI
GGATCCACCATGAGCCGCCTGCCCGTC-CTGCTCCTGCTCCAACTCCTGGTCCGCCCC
MetSerArgLeuProV-alLeuLeuLeuLeuGlnLeuLeuValArgPro
NcoI
GCCATGG [SEQ ID NO:140]
AlaMet [SEQ ID NO:187]

The resulting plasmid was designated pMON26448. The plasmid, pMON26448, encodes the fusion with the following amino acid sequence:

| Peptide # |
|---|
| Met Ala Ser Pro Ala Pro Pro Ala Cys Asp Leu Arg Val Leu Ser Lys Leu Leu Arg Asp Ser His Val Leu His Ser Arg Leu Ser Gln Cys Pro Glu Val His Pro Leu Pro Thr Pro Val Leu Leu Pro Ala Val Asp Phe Ser Leu Gly Glu Trp Lys Thr Gln Met Glu Glu Thr Lys Ala Gln Asp Ile Leu Gly Ala Val Thr Leu Leu Leu Glu Gly Val Met Ala Ala Arg Gln Gln Leu Gly Pro Thr Cys Leu Ser Ser Leu Leu Gly Gln Leu Ser Gly Gln Val Arg Leu Leu Leu Gly Ala Leu Gln Ser Leu Leu Gly Thr Gln Leu Pro Pro Gln Gly Arg Thr Thr Ala His Lys Asp Pro Asn Ala Ile Phe Leu Ser Phe Gln His Leu Leu Arg Gly Lys Val Arg Phe Leu Met Leu Val Gly Gly Ser Thr Leu Cys Val Arg [SEQ ID NO: 164] |

DNA sequence # [SEQ ID NO:180] codes for the foregoing pMON26448 polypeptide.

EXAMPLE 65

Isolation of cDNA Sequence Amino Acid 1–153 RForm of c-mpl Ligand (Meg-CSF) with Modified C-terminus A. Reverse Transcriptase Reaction (c-mpl ligand sequence based on Genbank accession #L33410)

Human fetal liver A+ RNA was obtained from Clontech (Palo Alto, Calif.). The first strand cDNA reactions was carried out using a cDNA Cycle™ Kit obtained from Invitrogen (San Diego, Calif.).

B. Polymerase Chain Reactions

Following the reverse transcriptase (RT) reaction, the 1–332 c-mpl ligand was amplified by PCR using the oligonucleotide primers c-mplNcoI [SEQ ID NO:169], which created an NcoI site immediately proceeding the 5' end of the gene and c-mplEcoRI [SEQ ID NO:170] which created an EcoRI site immediately 3' to the stop condon. Using the above PCR reaction as the template, the 1–153 c-mpl ligand was amplified using the c-mplNcoI [SEQ ID NO:169] primer and the 3' primer, Eco-mpl [SEQ ID NO:172] which created an EcoRI site immediately 3' to the condon for amino acid 153 and encodes the amino acids Glu Phe in-frame at the C-terminus of the gene. The 1–153 c-mpl ligand PCR product was digested with NcoI and EcoRI. The resulting 467 base pair NcoI,EcoRI restriction fragment was subsequently cloned into intermediate plasmids, described in the examples herein, to create fusion polypeptides.

EXAMPLE 66

Construction of pMON26460

Plasmid, pMON13018, DNA was digested with restriction enzymes AflIII and HindIII, resulting in a 4023 base pair AflIII,HindIII fragment. Plasmid, pMON26448, DNA was digested with NcoI and HindIII, resulting in a 468 base pair NcoI,HindIII fragment. The restriction fragments were ligated, and the ligation reaction mixture was used to transform E. coli. Transformant bacteria were selected on ampicillin-containing plates. Plasmid DNA was isolated, analyzed by restriction analysis, and sequenced to confirm the correct insert. The E. coli expression plasmid, pMON26460, encodes the fusion with the following amino acid sequence:

Peptide # [SEQ ID NO:165]
DNA sequence # [SEQ ID NO:183] codes for the foregoing pMON26460 polypeptide.

The gene encoding the fusion was transferred as a NcoI, HindIII fragment to the mammalian expression vector, pMON3934, and the resulting plasmid was designated pMON26463.

EXAMPLE 67

Construction of pMON26461

The 4029 base pair NcoI,SnaBI fragment from, pMON13057, was ligated with the 467 base pair NcoI, EcoRI PCR generated fragment from Example 65 and two oligonucleotides (Ecosna1 [SEQ ID NO:173], Ecosna2 [SEQ ID NO:174]) The ligation reaction mixture was used to transform E. coli. Transformant bacteria were selected on ampicillin-containing plates. Plasmid DNA was isolated, analyzed by restriction analysis, and sequenced to confirm the correct insert. The E. coli expression plasmid, pMON26461, encodes the fusion with the following amino acid sequence:

Peptide # [SEQ ID NO:168]
DNA sequence # [SEQ ID NO:186] codes for the foregoing pMON26461 polypeptide.
The gene encoding the fusion was transferred as a NcoI, HindIII fragment to the mammalian expression vector, pMON3934, and the resulting plasmid was designated pMON26464.

EXAMPLE 68

Construction of pMON26471

The 3285 base pair NcoI,HindIII fragment from, pMON3935, was ligated with the 362 base pair NcoI,SmaI restriction fragment from pMON26426 and the 494 base pair SmaI,HindIII restriction fragment from pMON26460, and the ligation reaction mixture was used to transform *E. coli*. Transformant bacteria were selected on spectinomycin-containing plates. Plasmid DNA was isolated, analyzed by restriction analysis, and sequenced to confirm the correct insert. The *E. coli* expression plasmid, pMON26471, encodes the fusion with the following amino acid sequence:

Peptide # [SEQ ID NO:166]
DNA sequence # [SEQ ID NO:184] codes for the foregoing pMON26471 polypeptide.
The gene encoding the fusion was transferred as a NcoI, HindIII fragment to the mammalian expression vector, pMON3934, and the resulting plasmid was designated pMON26473.

EXAMPLE 69

Construction of pMON26472

The 3285 base pair NcoI,HindIII fragment from, pMON3935, was ligated with the 481 base pair NcoI,SnaBI restriction fragment from pMON26461 and the 399 base pair SnaBI,HindIII restriction fragment from pMON3988, and the ligation reaction mixture was used to transform *E. coli*. Transformant bacteria were selected on spectinomycin-containing plates. Plasmid DNA was isolated, analyzed by restriction analysis, and sequenced to confirm the correct insert. The *E. coli* expression plasmid, pMON26472, encodes the fusion with the following amino acid sequence:

Peptide # [SEQ ID NO:167]
DNA sequence # [SEQ ID NO:185] codes for the foregoing pMON26472 polypeptide.
The gene encoding the fusion was transferred as a NcoI, HindIII fragment to the mammalian expression vector, pMON3934, and the resulting plasmid was designated pMoN26474.

Various other examples will be apparent to the person skilled in the art after reading the present disclosure without departing from the spirit and scope of the invention. It is intended that all such other examples be included within the scope of the appended claims.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM-CSF supplemented medium (Lange, B., et al., (1987); Valtieri, M., et al., (1987). The ability of AML 193 cells to proliferate in the presence of human IL-3 has also been documented. (Santoli, D., et al., (1987)). A cell line variant was used, AML 193 1.3, which was adapted for long term growth in IL-3 by washing out the growth factors and starving the cytokine dependent AML 193 cells for growth factors for 24 hours. The cells are then replated at $1\times10^5$ cells/well in a 24 well plate in media containing 100 U/ml IL-3. It took approximately 2 months for the cells to grow rapidly in IL-3. These cells are maintained as AML 193 1.3 thereafter by supplementing tissue culture medium (see below) with human IL-3.

ANL 193 1.3 cells are washed 6 times in cold Hanks balanced salt solution (HBSS, Gibco, Grand Island, N.Y.) by centrifuging cell suspensions at 250×g for 10 minutes followed by decantation of the supernatant. Pelleted cells are resuspended in HBSS and the procedure is repeated until six wash cycles are completed. Cells washed six times by this procedure are resuspended in tissue culture medium at a density ranging from $2\times10^5$ to $5\times10^5$ viable cells/ml. This medium is prepared by supplementing Iscove's modified Dulbecco's Medium (IMDM, Hazelton, Lenexa, Kans.) with albumin, transferrin, lipids and 2-mercaptoethanol. Bovine albumin (Boehringer-Mannheim, Indianapolis, Ind.) is added at 500 $\mu$g/ml; human transferrin (Boehringer-Mannheim, Indianapolis, Ind.) is added at 100 $\mu$g/ml; soybean lipid (Boehringer-Mannheim, Indianapolis, Ind.) is added at 50 $\mu$g/ml; and 2-mercaptoethanol (Sigma, St. Louis, Mo.) is added at $5\times10^{-5}$ M.

Serial dilutions of human interleukin-3 or fusion protein (hIL-3 mutein) are made in triplicate series in tissue culture medium supplemented as stated above in 96 well Costar 3596 tissue culture plates. Each well contained 50 $\mu$l of medium containing interleukin-3 or fusion protein once serial dilutions are completed. Control wells contained tissue culture medium alone (negative control). AML 193 1.3 cell suspensions prepared as above are added to each well by pipetting 50 $\mu$l ($2.5\times10^4$ cells) into each well. Tissue culture plates are incubated at 37° C. with 5% $CO_2$ in humidified air for 3 days. On day 3, 0.5 $\mu$Ci $^3$H-thymidine (2 Ci/mM, New England Nuclear, Boston, Mass.) is added in 50 $\mu$l of tissue culture medium. Cultures are incubated at 37° C. with 5% $CO_2$ in humidified air for 18–24 hours. Cellular DNA is harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats are allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) is added. Beta emissions of samples from individual tissue culture wells are counted in a LKB Betaplate model 1205 scintillation counter (Pharmacia LKB, Gaithersburg, Md.) and data is expressed as counts per minute of $^3$H-thymidine incorporated into cells from each tissue culture well. Activity of each human interleukin-3 preparation or fusion protein preparation is quantitated by measuring cell proliferation ($^3$H-thymidine incorporation) induced by graded concentrations of interleukin-3 or fusion protein. Typically, concentration ranges from 0.05 pM–$10^5$ pM are quantitated in these assays. Activity is determined by measuring the dose of interleukin-3 or fusion molecule which provides 50% of maximal proliferation [$EC_{50}$=0.5× (maximum average counts per minute of $^3$H-thymidine incorporated per well among triplicate cultures of all concentrations of interleukin-3 tested—background proliferation measured by $^3$H-thymidine incorporation observed in triplicate cultures lacking interleukin-3]. This $EC_{50}$ value is also equivalent to 1 unit of bioactivity. Every assay is performed with native interleukin-3 as a reference standard so that relative activity levels could be assigned.

Typically, the protein fusions were tested in a concentration range of 2000 pM to 0.06 pM titrated in serial 2 fold dilutions. Biological activity of the fusion molecules was compared to the following standards as described below.

Protein fusions comprised in part of G-CSF, pMON3987, pMON3995, pMON3997, pMON26406, pMON26433, pMON26415, pMON26416, and pMON26430, were compared to the dose response curve of equal molar concentrations of hG-CSF and pMON13288 or pMON13416.

Protein fusions comprised in part of GM-CSF, pMON3989 and pMON3998 were compared to the dose response curve of equal molar concentrations of hGM-CSF and pMON13288.

Protein fusions comprised of dimers of hIL-3 variants, pMON3988, pMON26425, pMON26427, pMON26420, pMoN26429 and pMON26431 were compared to the dose response curve of pMON13288 or pMON13416.

Activity for each sample was determined by the concentration which gave 50% of the maximal response by fitting a four-parameter logistic model to the data. It was observed that the upper plateau (maximal response) for the sample and the standard with which it was compared did not differ. Therefore relative potency calculation for each sample was determined from EC50 estimations for the sample and the standard as indicated above. Relative potency (EC50 of standard divided by EC50 of sample) reported in Table 3 is the mean of at least two independent assays unless indicated. AML 193.1.3 cells proliferate in response to hIL-3, hGM-CSF and hG-CSF. Therefore the following additional assays were performed for some samples to demonstrate that the G-CSF or GM-CSF portion of the fusion proteins was active. Proliferation assay was performed using neutralizing polyclonal antibodies to pMON13288. In addition, a fusion molecule with the factor Xa cleavage site was cleaved then purified and the halves of the molecule were assayed for proliferative activity. These experiments showed that both components of the fusion protein were active.

TABLE 3

AML cell proliferation assay

| pMON | $R_1$ | Linker | $R_2$ | AML 193.1.3 Bioactivity (relative potency) |
|---|---|---|---|---|
| pMON3987 | 13288 | Linker 1 | G-CSF | 0.35 ± 0.11 |
| pMON3988 | 13288 | Linker 1 | 13288 | 0.64 ± 0.13 |
| pMON3989 | 13288 | Linker 1 | GM-CSF | 0.6 ± 0.09 |
| pMON3995 | G-CSF | Linker 1 | 13288 | 0.41 ± 0.44 |
| pMON3997 | 13288 | Linker 7 | G-CSF | 0.26 (n = 1) |
| pMON3998 | 13288 | Linker 7 | GM-CSF | 0.21 (n = 1) |
| pMON26406 | 13288 | Linker 4 | G-CSF | 0.37 ± 0.30 |
| pMON26433 | G-CSF | Linker 4 | 13288 | 0.79 ± 0.35 |
| pMON26415 | 13288 | Linker 1 | G-CSF Ser17 | 0.46 ± 0.08 |
| pMON26416 | G-CSF | Linker 1 | 13416 | 0.43 ± 0.02 |
| pMON26425 | 13288 | Linker 2 | 13288 | 1.32 ± 0.41 |
| pMON26427 | 13288 | Linker 3 | 13288 | 1.41 ± 0.91 |
| pMON26420 | 13416 | Linker 1 | 13416 | 2.09 ± 0.52 |
| pMON26430 | 13288 | Linker 6 | G-CSF | 1.04 ± 0.69 |
| pMON26429 | 13288 | Linker 5 | 13288 | 1.88 ± 0.09 |
| pMON26431 | 13288 | Linker 6 | 13288 | 0.66 ± 0.26 |

Methylcellulose Assay

This assay provides a reasonable approximation of the growth activity of colony stimulating factors to stimulate normal bone marrow cells to produce different types of hematopoietic colonies in vitro (Bradley et al., 1966, Pluznik et al., 1965).

Methods

Approximately 30 ml of fresh, normal, healthy bone marrow aspirate are obtained from individuals. Under sterile conditions samples are diluted 1:5 with a 1×PBS (#14040.059 Life Technologies, Gaithersburg, Md.) solution in a 50 ml conical tube (#25339–50 Corning, Corning Md.). Ficoll (Histopaque 1077 Sigma H-8889) is layered under the diluted sample and centrifuged, 300×g for 30 min. The mononuclear cell band is removed and washed two times in 1×PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen.

Cultures are set up in triplicate with a final volume of 1.0 ml in a 35×10 mm petri dish (Nunc#174926). Culture medium is purchased from Terry Fox Labs. (HCC-4230 medium (Terry Fox Labs, Vancouver, B.C., Canada) and erythropoietin (Amgen, Thousands Oaks, Calif.) is added to the culture media. 3,000–10,000 CD34+ cells are added per dish. Native IL-3 and fusion molecules are added to give final concentrations ranging from 0.001 nM 10 nM. Native IL-3 and fusion molecules are supplied in house. G-CSF (Neupogen) is from Amgen. Cultures are resuspended using a 3 cc syringe and 1.0 ml is dispensed per dish. Control (baseline response) cultures received no colony stimulating factors. Positive control cultures received conditioned media (PHA stimulated human cells:Terry Fox Lab. H2400). Cultures are incubated at 37° C., 5% $CO_2$ in humidified air. Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

Human Cord Blood Hemopoietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., 1992; Mayani et al., 1993). In contrast to bone marrow, cord blood is more readily available on a regular basis. There is also a potential to reduce assay variability by pooling cells obtained fresh from several donors, or to create a bank of cryopreserved cells for this purpose. By modifying the culture conditions, and/or analyzing for lineage specific markers, it should be possible to assay specifically for granulocyte/macrophage colonies (CFU-GM), for megakaryocyte CSF activity, or for high proliferative potential colony forming cell (HPP-CFC) activity.

Methods

Mononuclear cells (MNC) are isolated from cord blood within 24 hr. of collection, using a standard density gradient (1.077 g/ml Histopaque). Cord blood MNC have been further enriched for stem cells and progenitors by several procedures, including immunomagnetic selection for CD14−, CD34+ cells; panning for SBA−, CD34+ fraction using coated flasks from Applied Immune Science (Santa Clara, Calif.); and CD34+ selection using a CellPro (Bothell, Wash.) avidin column. Either freshly isolated or cryopreserved CD34+ cell enriched fractions are used for the assay. Duplicate cultures for each serial dilution of sample (concentration range from 1 pM to 1204 pM) are prepared with 1×104 cells in 1 ml of 0.9% methycellulose containing medium without additional growth factors (Methocult H4230 from Stem Cell Technologies, Vancouver, BC.). In some experiments, Methocult H4330 containing erythropoietin (EPO) was used instead of Methocult H4230, or Stem Cell Factor (SCF), 50 ng/ml (Biosource International, Camarillo, Calif.) was added. After culturing for 7–9 days, colonies containing >30 cells are counted. In order to rule out subjective bias in scoring, assays are scored blind.

Analysis of c-mpl Ligand Proliferative Activity

Methods

1. Bone Marrow Proliferation Assay a. CD34+ Cell Purification

Between 15–20 ml bone marrow aspirates were obtained from normal allogeneic marrow donors after informed consent. Cells were diluted 1:3 in phosphate buffered saline (PBS, Gibco-BRL), 30 ml were layered over 15 ml Histopaque-1077 (Sigma) and centrifuged for 30 minutes at 300 RCF. The mononuclear interface layer was collected and washed in PBS. CD34+ cells were enriched from the mononuclear cell preparation using an affinity column per manufacturers instructions (CellPro, Inc, Bothell Wash.). After enrichment, the purity of CD34+ cells was 70% on average as determined by using flow cytometric analysis using anti CD34 monoclonal antibody conjugated to fluorescein and anti CD38 conjugated to phycoerythrin (Becton Dickinson, San Jose Calif.).

Cells were resuspended at 40,000 cells/ml in X-Vivo 10 media (Bio-Whittaker, Walkersville, Md.) and 1 ml was plated in 12-well tissue culture plates (Costar). The growth factor rhIL-3 was added at 100 ng/ml (pMON5873) was added to some wells. hIL3 variant, pMON13288, was used at 10 ng/ml or 100 ng/ml. Conditioned media from BHK cells transfected with plasmid encoding c-mpl ligand were tested by addition of 100 µl of supernatant added to 1 ml cultures (approximately a 10% dilution). Cells were incubated at 37° C. for 8–14 days at 5% $CO_2$ in a 37° C. humidified incubator.

b. Cell Harvest and Analysis

At the end of the culture period a total cell count was obtained for each condition. For fluorescence analysis and ploidy determination cells were washed in megakaryocyte buffer (MK buffer, 13.6 mM Sodium Citrate, 1 mM Theophylline, 2.2 µm PGE1, 11 mM Glucose, 3% w/v BSA, in PBS, pH 7.4,) [Tomer et al., (1987)] resuspended in 500 µl of MK buffer containing anti-CD41a FITC antibody (1:200, AMAC, Westbrook, Me.) and washed in MK buffer. For DNA analysis cells were permeablized in MK buffer containing 0.5% Tween 20 (Fisher, Fair Lawn N.J.) for 20 min. on ice followed by fixation in 0.5% Tween-20 and 1% paraformaldehyde (Fisher Chemical) for 30 minutes followed by incubation in Propidium Iodide (Calbiochem La Jolla Calif.) (50 µg/ml) with RNA-ase (400 U/ml) in 55% v/v MK buffer (200 mOsm) for 1–2 hours on ice. Cells were analyzed on a FACScan or Vantage flow cytometer (Becton Dickinson, San Jose, Calif.). Green fluorescence (CD41a-FITC) was collected along with linear and log signals for red fluorescence (PI) to determine DNA ploidy. All cells were collected to determine the percent of cells that were CD41+. Data analysis was performed using software by LYSIS (Becton Dickinson, San Jose, Calif.). Percent of cells expressing the CD41 antigen was obtained from flow cytometry analysis(Percent). Absolute (Abs) number of CD41+ cells/ml was calculated by: (Abs)=(Cell Count)*(Percent)/100.

2. Megakaryocyte Fibrin Clot Assay

CD34+ enriched population were isolated as described above. Cells were suspended at 25,000 cells/ml with/without cytokine(s) in a media consisting of a base Iscoves IMDM media supplemented with 0.3% BSA, 0.4 mg/ml apo-transferrin, 6.67 µM $FeCl_2$, 25 µg/ml $CaCl_2$, 25 µg/ml L-asparagine, 500 µg/ml E-amino-n-caproic acid and Penicillin/Streptomycin. Prior to plating into 35 mm plates, thrombin was added (0.25 Units/ml) to initiate clot formation. Cells were incubated at 37° C. for 13 days at 5% $CO_2$ in a 37° C. humidified incubator.

At the end of the culture period plates were fixed with Methanol:Acetone (1:3), air dried and stored at −200 C. until staining. A peroxidase immunocytochemistry staining procedure was used (Zymed, Histostain-SP. San Francisco, Calif.) using a cocktail of primary monoclonal antibodies consisting of anti CD41a, CD42 and CD61. Colonies were counted after staining and classified as negative, CFU-MK (small colonies, 1–2 foci and less that approx. 25 cells), BFU-MK (large, multi-foci colonies with >25 cells) or mixed colonies (mixture of both positive and negative cells.

EXAMPLE 70

Administration of hIL-3 Variant, pMON13288, and c-mpl Ligand Fusion Molecule has a More than Additive Effect on Meakaryocyte Expansion than Either Cytokine Alone Megakaryocyte fibrin clot cultures were set up as described in methods section. pMON26448 is the 1–153 amino acid form of c-mpl ligand (Meg-CSF). pMON26463 is a fusion molecule consisting of hIL3 variant, pMON13288 and the 1–153 amino acid form of c-mpl ligand.

Incubation in the presence of hIL3 variant, pMON13288 gave rise to colonies that were predominantly negative for megakaryocyte markers (86/114, (Table 4)) except for number of small CFU-MK colonies (23/114). pMON26448 alone gave rise primarily to CFU-MK colonies (172/175) with only a few number of negative colonies (3/175). Combination of hIL3 variant, pMON13288 and pMON26448 gave rise to a large number of positive colonies (295/414) that were predominantly of the BFU-MK morphology. There were a negative colonies as well (119/414). Total number of positive colonies with co-administration was more than additive than with either cytokine alone. pMON26463, the fusion molecule gave results similar to the combination of hIL3 variant, pMON13288 and pMON26448. The number of negative cells is less than with hIL3 variant, pMON13288 which is probably due to a lower concentration of pMON13288 in the preparation (approximately 10 ng/ml as part of the fusion molecule vs. 100 ng/ml of hIL3 variant, pMON13288)

TABLE 4

| cytokine treatment | Negative | CFU-MK | BFU-MK | Mixed | Total |
|---|---|---|---|---|---|
| | | Colonies/Well | | | |
| pMON13288 | 86 | 23 | 0 | 5 | 114 |
| pMON26448 | 3 | 73 | 98 | 1 | 175 |
| pMON26448 + pMQN13288 | 119 | 29 | 244 | 22 | 414 |
| pMON26463 | 10 | 30 | 165 | 17 | 222 |
| | | Colonies/100,000 plated | | | |
| pMON13288 | 344 | 92 | 0 | 20 | 456 |
| pMON26448 | 12 | 292 | 392 | 4 | 700 |
| pMON26448 + pMON13288 | 476 | 116 | 976 | 88 | 1656 |
| pMON26463 | 40 | 120 | 660 | 68 | 888 |

IL-3 Mediated Sulfidoleukotriene Release from Human Mononuclear Cells

The following assay is used to measure IL-3 mediated sulfidoleukotriene release from human mononuclear cells.

Heparin-containing human blood is collected and layered onto an equal volume of Ficoll-Paque (Pharmacia #17-0840-02) ready to use medium (density 1.077 g/ml.). The Ficoll is warmed to room temperature prior to use and clear 50 ml polystyrene tubes are utilized. The Ficoll gradient is spun at 300×g for 30 minutes at room temperature using a H1000B rotor in a Sorvall RT6000B refrigerated centrifuge. The band containing the mononuclear cells is carefully removed, the volume adjusted to 50 mls with Dulbecco's phosphate-buffered saline (Gibco Laboratories cat. #310-4040PK), spun at 400×g for 10 minutes at 4° C. and the supernatant is carefully removed. The cell pellet is washed twice with HA Buffer [20 mM Hepes (Sigma # H-3375], 125 mM NaCl (Fisher # S271-500), 5 mM KCl (Sigma # P-9541), 0.5 mM glucose (Sigma # G-5000),0.025% Human Serum Albumin (Calbiochem #126654) and spun at 300×g, 10 min., 4° C. The cells are resuspended in HACM Buffer (HA buffer supplemented with 1 mM CaCl2 (Fisher # C79-500) and 1 mM MgC12 (Fisher # M-33) at a concentration of 1×106 cells/ml and 180 µl are transferred into each well of 96 well tissue culture plates. The cells are allowed to acclimate at 37° C. for 15 minutes. The cells are primed by adding 10 µls of a 20×stock of various concentrations of cytokine to each well (typically 100000, 20000, 4000, 800, 160, 32, 6.4, 1.28, 0 fM IL3). The cells are incubated for 15 minutes at 37° C. Sulfidoleukotriene release is activated by the addition of 10 µls of 20×(1000 nM) fmet-leu-phe (Calbiochem #344252) final concentration 50 nM FMLP and incubated for 10 minutes at 37° C. The plates are spun at 350×g at 4° C. for 20 minutes. The supernatants are removed and assayed for sulfidoleukotrienes using Cayman's Leukotriene C4 EIA kit (Cat. #420211) according to manufacturers', directions. Native hIL-3 is run as a standard control in each assay.

Further details known to those skilled in the art may be found in T. Maniatis, et al., *Molecular Cloning, A Laboratory Manual*, Cold Spring Harbor Laboratory (1982) and references cited therein, incorporated herein by reference; and in J. Sambrook, et al., *Molecular Cloning, A Laboratory Manual*, 2nd edition, Cold Spring Harbor Laboratory (1989) and references cited therein, incorporated herein by reference.

Additional details on the IL-3 variants of the present invention may be found in co-pending U.S. patent application Ser. No. PCT/US93/11197 which is hereby incorporated by reference in its entirety as if written herein.

Additional details on how to make the fusion protein can be found in WO 92/04455 and WO 91/02754.

Additional details about the lymphokine and the variants thereof can be found in U.S. Pat. Nos. 4,810,643, and 5,218,092 E.P. Application 02174004.

All references, patents or applications cited herein are incorporated by reference in their entirety as if written herein.

Amino acids are shown herein by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

TABLE 5

OLIGONUCLEOTIDES

88CTERM1.REQ  Length: 000041
AATTCCGGGA AAAACTGACG TTCTATCTGG TTACCCTTGA G [SEQ ID NO: 91]
88CTERM4.REQ  Length: 000046
CTGCGCTTGC TCAAGGGTAA CCAGATAGAA CGTCAGTTTT TCCCGG
[SEQ ID NO: 92]
88XA2.REQ  Length: 000039
CAAGCGCAGG AACAACAGTA CGTAATCGAG GGAAGGATT [SEQ ID NO: 93]
88XA5.REQ  Length: 000039
ACCCGGGGAA ATCCTTCCCT CGATTACGTA CTGTTGTTC [SEQ ID NO: 94]
GLYN3.REQ  Length: 000063
TCCCCGGGTG GTGGTTCTGG CGGCGGCTCC AACATGTAAG GTACCGCATG
CAAGCTTAGA TCT [SEQ ID NO: 95]
GLYN6.REQ  Length: 000058
AGCTAGATCT AAGCTTGCAT GCGGTACCTT ACATGTTGGA GCCGCCGCCA
GAACCACC [SEQ ID NO: 96]
IGG2B1.REQ  Length: 000074
CCGGGTGAAC CGTCTGGTCC AATCTCTACT ATCAACCCGT CTCCTCCGTC
TAAAGAATCT CATAAATCTC CAAA [SEQ ID NO: 97]
IGG2B2.REQ  Length: 000074
CATGTTTGGA GATTTATGAG ATTCTTTAGA CGGAGGAGAC GGGTTGATAG

TABLE 5-continued

OLIGONUCLEOTIDES

TAGAGATTGG ACCAGACGGT TCAC [SEQ ID NO: 98]
GCSFSNA1.REQ Length: 000068
CTAGCCATCT GCAGAGCTTC CTGGAGGTGT CGTACCGCGT TCTACGCCAC
CTTGCGCAGC CCTACGTA [SEQ ID NO: 99]
GCSFSNA2.REQ Length: 000068
AGCtTACGTA GGGCTGCGCA AGGTGGCGTA GAACGCGGTA CGACACCTCC
AGGAAGCTCT GCAGATGG [SEQ ID NO: 100]
LYSXA1.REQ Length: 000021
GTAATCGAGG GAAAGATTTC C [SEQ ID NO: 101]
LYSXA2.REQ Length: 000025
CCGGGGAAAT CTTTCCCTCG ATTAC [SEQ ID NO: 102]
GLYXA1.REQ Length: 000021
GTAGAGGGCG GTGGAGGCTC C [SEQ ID NO: 103]
GLYXA2.REQ Length: 000025
CCGGGGAGCC TCCACCGCCC TCTAC [SEQ ID NO: 104]
GM-AUP.REQ Length: 000058
CATGGCACCA GCAAGATCAC CATCACCATC AACTCAACCT TGGGAACATG
TGAATGCC [SEQ ID NO: 105]
GM-ALOW.REQ Length: 000052
CATTCACATG TTCCCAAGGT TGAGTTGATG GTGATGGTGA TCTTGCTGGT
GC [SEQ ID NO: 106]
G-CYS18.REQ Length: 000066
CTGCCAGCTC CCTGCCCCAG AGCTTCCTGC TCAAGTCTTT AGAGCAAGTG
AGGAAGATCC AGGGCG [SEQ ID NO: 107]
GCYS18LO.REQ Length: 000066
CTGGATCTTC CTCACTTGCT CTAAAGACTT GAGCAGGAAG CTCTGGGGCA
GGGAGCTGGC AGGGCC [SEQ ID NO: 108]
HIL6231.REQ Length: 000048
AGCTTACCTG CCATGGCTCC AGTACCACCA GGTGAAGATT CCAAAGAT
[SEQ ID NO: 109]
HIL6232.REQ Length: 000040
TTGGAATCTT CACCTGGTGG TACTGGAGCC ATGGCAGGTA [SEQ ID NO: 110]
HGCSFMA1.REQ Length: 000026
AGCTTCCATG GCTACCCCCC TGGGCC [SEQ ID NO: 111]
HGCSFMA2.REQ Length: 000018
CAGGGGGGTA GCCATGGA [SEQ ID NO: 112]
HGCSFAT1.REQ Length: 000020
CATGGCTACA CCATTGGGGCC [SEQ ID NO: 113]
HGCSFAT2.REQ Length: 000012
CAATGGTGTA GC [SEQ ID NO: 114]
HGCSFAT3.REQ Length: 000020
CATGGCTACA CCATTAGGAC [SEQ ID NO: 115]
HGCSFAT4.REQ Length: 000012
TAATGGTGTA GC [SEQ ID NO: 116]
PREFOR.REQ
CCTGTCAACC CGGGCGGCGG CTCTGGTGGT [SEQ ID NO: 117]
REVPRE.REQ
TCATAATACA TGTTACCGGA ACGGAGCCGC C [SEQ ID NO: 118]
FORXTRA.REQ
ATCGTCTGAC CTCCCGGGAC CTCCTGTCAA TGCT [SEQ ID NO: 119]
XTRAREV.REQ
AGCGTTTGAC ATGTTTTCAT AATCAAAATC [SEQ ID NO: 120]
c-mplNcoI
ACGTCCATGGCNTCNCCNGCNCCNCCTGCTTGTGACCTCCGAGTC [SEQ ID NO: 169
(where N = G, C, T or A)
c-mplEcoRI
AATAGCTGAATTCTTACCCTTCCTGAGACAGATT [SEQ ID NO: 170]
c-mplHindIII
TGACAAGCTTACCTGACGCAGAGGGTGGACCCT [SEQ ID NO: 171]
Eco-mp1
ATGCACGAATTCCCTGACGCAGAGGGTGGA [SEQ ID NO: 172]
EcoSna1
AATTCCATGCATAC [SEQ ID NO: 173]
ECOSNA2
GGTACGTATG [SEQ ID NO: 174]

TABLE 6

DNA SEQUENCES pMON13023
ATGGCTAACT GCTCTATAAT GATCGATGAA ATTATACATC ACTTAAAGAG [SEQ ID NO:53]

ACCACCTAAC CCTTTGCTGG ACCCGAACAA CCTCAATTCT GAAGACATGG

TABLE 6-continued

DNA SEQUENCES

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTA

CACCATTAGG CCCTGCCAGC TCCCTGCCCC AGAGCTTCCT GCTCAAGTGC

TTAGAGCAAG TGAGGAAGAT CCAGGGCGAT GGCGCAGCGC TCCAGGAGAA

GCTGTGTGCC ACCTACAAGC TGTGCCACCC CGAGGAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TAACTGGGAA TGGCCCCTGC CCTGCAGCCC ACCCAGGGTG CCATGCCGGC

CTTCGCCTCT GCTTTCCAGC GCCGGGCAGG AGGGGTCCTG GTTGCTAGCC

ATCTGCAGAG CTTCCTGGAG GTGTCGTACC GCGTTCTACG CCACCTTGCG

CAGCCC pMON13021
ATGGCTAACT GCTCTATAAT GATCGATGAA ATTATACATC ACTTAAAGAG [SEQ ID NO:54]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTA

ACTGCTCTAT AATGATCGAT GAAATTATAC ATCACTTAAA GAGACCACCT

AACCCTTTGC TGGACCCGAA CAACCTCAAT TCTGAAGACA TGGATATCCT

GATGGAACGA AACCTTCGAA CTCCAAACCT GCTCGCATTC GTAAGGGCTG

TCAAGCACTT AGAAAATGCA TCAGGTATTG AGGCAATTCT TCGTAATCTC

CAACCATGTC TGCCCTCTGC CACGGCCGCA CCCTCTCGAC ATCCAATCAT

CATCAAGGCA GGTGACTGGC AAGAATTCCG GGAAAAACTG ACGTTCTATC

TGGTTACCCT TGAGCAAGCG CAGGAACAAC AG pMON13022
ATGGCTAACT GCTCTATAAT GATCGATGAA ATTATACATC ACTTAAAGAG [SEQ ID NO:55]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

TABLE 6-continued

DNA SEQUENCES

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCAC

CGGCTCGTTC CCCGTCCCCG TCTACCCAGC CGTGGGAACA CGTGAATGCC

ATCCAGGAGG CCCGGCGTCT CCTGAACCTG AGTAGAGACA CTGCTGCTGA

GATGAATGAA ACAGTAGAAG TGATATCAGA AATGTTTGAC CTCCAGGAGC

CGACTTGCCT ACAGACCCGC CTGGAGCTGT ACAAGCAGGG CCTGCGGGGC

AGCCTCACCA AGTCAAGGG CCCCTTGACC ATGATGGCCA GCCACTACAA

GCAGCACTGC CCTCCAACCC CGGAAACTTC CTGTGCAACC CAGATTATCA

CCTTTGAAAG TTTCAAAGAG AACCTGAAGG ACTTCCTGCT TGTCATCCCC

TTTGACTGCT GGGAGCCAGT CCAGGAG pMON13039
ATGGCTAACT GCTCTATAAT GATCGATGAA ATTATACATC ACTTAAAGAG [SEQ ID NO:56]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTA

CACCATTGGG CCCTGCCAGC TCCCTGCCCC AGAGCTTCCT GCTCAAGTCT

TTAGAGCAAG TGAGGAAGAT CCAGGGCGAT GGCGCAGCGC TCCAGGAGAA

GCTGTGTGCC ACCTACAAGC TGTGCCACCC CGAGGAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TGGCAGCAGA TGGAAGAACT GGGAATGGCC CCTGCCCTGC AGCCCACCCA

GGGTGCCATG CCGGCCTTCG CCTCTGCTTT CCAGCGCCGG GCAGGAGGGG

TCCTGGTTGC TAGCCATCTG CAGAGCTTCC TGGAGGTGTC GTACCGCGTT

CTACGCCACC TTGCGCAGCC C pMON13049
ATGGCTAACT GCTCTATAAT GATCGATGAA ATTATACATC ACTTAAAGAG [SEQ ID NO:57]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTC

TABLE 6-continued

DNA SEQUENCES

CAGTACCACC AGGTGAAGAT TCCAAAGATG TGGCCGCCCC ACACAGACAG

CCACTCACCT CTTCAGAACG AATTGACAAA GAAATTCGGT ACATCCTCGA

CGGGATATCA GCCCTGAGAA AGGAGACATG TAACAAGAGT AACATGTGTG

AAAGCAGCAA AGAGGCGCTA GCAGAAAACA ACCTGAACCT TCCAAAGATG

GCTGAAAAAG ATGGATGCTT CCAATCCGGA TTCAATGAGG AGACTTGCCT

GGTGAAAATC ATCACTGGTC TTTTGGAGTT TGAGGTATAC CTCGAGTACC

TCCAGAACAG ATTTGAGAGT AGTGAGGAAC AAGCCAGAGC TGTGCAGATG

TCGACAAAAG TCCTGATCCA GTTCCTGCAG AAAAAGGCAA AGAATCTAGA

TGCAATAACC ACCCCTGACC CAACCACAAA TGCATCCCTG CTGACGAAGC

TGCAGGCACA GAACCAGTGG CTGCAGGACA TGACAACTCA TCTCATTCTG

CGCAGCTTTA AGGAGTTCCT GCAGTCCAGC CTGAGGGCTC TTCGGCAAAT

G pMON13055
ATGGCTAACT GCTCTATAAT GATCGATGAA ATTATACATC ACTTAAAGAG [SEQ ID NO:58]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAAGATT TCCCCGGGTG GTGGTTCTGG CGGCGGCTCC AACATGGCTA

ACTGCTCTAT AATGATCGAT GAAATTATAC ATCACTTAAA GAGACCACCT

AACCCTTTGC TGGACCCGAA CAACCTCAAT TCTGAAGACA TGGATATCCT

GATGGAACGA AACCTTCGAA CTCCAAACCT GCTCGCATTC GTAAGGGCTG

TCAAGCACTT AGAAAATGCA TCAGGTATTG AGGCAATTCT TCGTAATCTC

CAACCATGTC TGCCCTCTGC CACGGCCGCA CCCTCTCGAC ATCCAATCAT

CATCAAGGCA GGTGACTGGC AAGAATTCCG GGAAAAACTG ACGTTCTATC

TGGTTACCCT TGAGCAAGCG CAGGAACAAC AG pMON13054
ATGGCTAACT GCTCTATAAT GATCGATGAA ATTATACATC ACTTAAAGAG [SEQ ID NO:59]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAAGATT TCCCCGGGTG GTGGTTCTGG CGGCGGCTCC AACATGGCTA

CACCATTGGG CCCTGCCAGC TCCCTGCCCC AGAGCTTCCT GCTCAAGTCT

TTAGAGCAAG TGAGGAAGAT CCAGGGCGAT GGCGCAGCGC TCCAGGAGAA

TABLE 6-continued

DNA SEQUENCES

GCTGTGTGCC ACCTACAAGC TGTGCCACCC CGAGGAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TGGCAGCAGA TGGAAGAACT GGGAATGGCC CCTGCCCTGC AGCCCACCCA

GGGTGCCATG CCGGCCTTCG CCTCTGCTTT CCAGCGCCGG GCAGGAGGGG

TCCTGGTTGC TAGCCATCTG CAGAGCTTCC TGGAGGTGTC GTACCGCGTT

CTACGCCACC TTGCGCAGCC C pMON13056
ATGGCTAACT GCTCTATAAT GATCGATGAA ATTATACATC ACTTAAAGAG [SEQ ID NO:60]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG GTGGTTCTGG CGGCGGCTCC AACATGGCTA

CACCATTGGG CCCTGCCAGC TCCCTGCCCC AGAGCTTCCT GCTCAAGTCT

TTAGAGCAAG TGAGGAAGAT CCAGGGCGAT GGCGCAGCGC TCCAGGAGAA

GCTGTGTGCC ACCTACAAGC TGTGCCACCC CGAGGAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TGGCAGCAGA TGGAAGAACT GGGAATGGCC CCTGCCCTGC AGCCCACCCA

GGGTGCCATG CCGGCCTTCG CCTCTGCTTT CCAGCGCCGG GCAGGAGGGG

TCCTGGTTGC TAGCCATCTG CAGAGCTTCC TGGAGGTGTC GTACCGCGTT

CTACGCCACC TTGCGCAGCC C pMON13057
ATGGCTAACT GCTCTATAAT GATCGATGAA ATTATACATC ACTTAAAGAG [SEQ ID NO:61]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG GTGGTTCTGG CGGCGGCTCC AACATGGCTA

ACTGCTCTAT AATGATCGAT GAAATTATAC ATCACTTAAA GAGACCACCT

AACCCTTTGC TGGACCCGAA CAACCTCAAT TCTGAAGACA TGGATATCCT

TABLE 6-continued

DNA SEQUENCES

GATGGAACGA AACCTTCGAA CTCCAAACCT GCTCGCATTC GTAAGGGCTG

TCAAGCACTT AGAAAATGCA TCAGGTATTG AGGCAATTCT TCGTAATCTC

CAACCATGTC TGCCCTCTGC CACGGCCGCA CCCTCTCGAC ATCCAATCAT

CATCAAGGCA GGTGACTGGC AAGAATTCCG GGAAAAACTG ACGTTCTATC

TGGTTACCCT TGAGCAAGCG CAGGAACAAC AG pMON13036
ATGGCTAACT GCTCTATAAT GATCGATGAA ATTATACATC ACTTAAAGAG [SEQ ID NO:62]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG AACCGTCTGG TCCAATCTCT ACTATCAACC

CGTCTCCTCC GTCTAAAGAA TCTCATAAAT CTCCAAACAT GGCTAACTGC

TCTATAATGA TCGATGAAAT TATACATCAC TTAAAGAGAC CACCTAACCC

TTTGCTGGAC CCGAACAACC TCAATTCTGA AGACATGGAT ATCCTGATGG

AACGAAACCT TCGAACTCCA AACCTGCTCG CATTCGTAAG GGCTGTCAAG

CACTTAGAAA ATGCATCAGG TATTGAGGCA ATTCTTCGTA ATCTCCAACC

ATGTCTGCCC TCTGCCACGG CCGCACCCTC TCGACATCCA ATCATCATCA

AGGCAGGTGA CTGGCAAGAA TTCCGGGAAA AACTGACGTT CTATCTGGTT

ACCCTTGAGC AAGCGCAGGA ACAACAG pMON13059
ATGGCTAACT GCTCTATAAT GATCGATGAA ATTATACATC ACTTAAAGAG [SEQ ID NO:63]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAAGATT TCCCCGGGTG AACCGTCTGG TCCAATCTCT ACTATCAACC

CGTCTCCTCC GTCTAAAGAA TCTCATAAAT CTCCAAACAT GGCTAACTGC

TCTATAATGA TCGATGAAAT TATACATCAC TTAAAGAGAC CACCTAACCC

TTTGCTGGAC CCGAACAACC TCAATTCTGA AGACATGGAT ATCCTGATGG

AACGAAACCT TCGAACTCCA AACCTGCTCG CATTCGTAAG GGCTGTCAAG

CACTTAGAAA ATGCATCAGG TATTGAGGCA ATTCTTCGTA ATCTCCAACC

ATGTCTGCCC TCTGCCACGG CCGCACCCTC TCGACATCCA ATCATCATCA

AGGCAGGTGA CTGGCAAGAA TTCCGGGAAA AACTGACGTT CTATCTGGTT

ACCCTTGAGC AAGCGCAGGA ACAACAG

TABLE 6-continued

DNA SEQUENCES pMON13061
ATGGCTAACT GCTCTATAAT GATCGATGAA ATTATACATC ACTTAAAGAG [SEQ ID NO:64]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG AACCGTCTGG TCCAATCTCT ACTATCAACC

CGTCTCCTCC GTCTAAAGAA TCTCATAAAT CTCCAAACAT GGCTAACTGC

TCTATAATGA TCGATGAAAT TATACATCAC TTAAAGAGAC CACCTAACCC

TTTGCTGGAC CCGAACAACC TCAATTCTGA AGACATGGAT ATCCTGATGG

AACGAAACCT TCGAACTCCA AACCTGCTCG CATTCGTAAG GGCTGTCAAG

CACTTAGAAA ATGCATCAGG TATTGAGGCA ATTCTTCGTA ATCTCCAACC

ATGTCTGCCC TCTGCCACGG CCGCACCCTC TCGACATCCA ATCATCATCA

AGGCAGGTGA CTGGCAAGAA TTCCGGGAAA AACTGACGTT CTATCTGGTT

ACCCTTGAGC AAGCGCAGGA ACAACAG pMON13062
ATGGCTAACT GCTCTATAAT GATCGATGAA ATTATACATC ACTTAAAGAG [SEQ ID NO:65]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCCGGGC CTCCTGTCAA TGCTGGCGGC GGCTCTGGTG

GTGGTTCTGG TGGCGGCTCT GAGGGTGGCG GCTCTGAGGG TGGCGGTTCT

GAGGGTGGCG GCTCTGAGGG TGGCGGTTCC GGTGGCGGCT CCGGTTCCGG

TGATTTTGAT TATGAAAACA TGGCTACACC ATTGGGCCCT GCCAGCTCCC

TGCCCCAGAG CTTCCTGCTC AAGTCTTTAG AGCAAGTGAG GAAGATCCAG

GGCGATGGCG CAGCGCTCCA GGAGAAGCTG TGTGCCACCT ACAAGCTGTG

CCACCCCGAG GAGCTGGTGC TGCTCGGACA CTCTCTGGGC ATCCCCTGGG

CTCCCCTGAG CTCCTGCCCC AGCCAGGCCC TGCAGCTGGC AGGCTGCTTG

AGCCAACTCC ATAGCGGCCT TTTCCTCTAC CAGGGGCTCC TGCAGGCCCT

GGAAGGGATA TCCCCCGAGT TGGGTCCCAC CTTGGACACA CTGCAGCTGG

ACGTCGCCGA CTTTGCCACC ACCATCTGGC AGCAGATGGA AGAACTGGGA

ATGGCCCCTG CCCTGCAGCC CACCCAGGGT GCCATGCCGG CCTTCGCCTC

TGCTTTCCAG CGCCGGGCAG GAGGGGTCCT GGTTGCTAGC CATCTGCAGA

GCTTCCTGGA GGTGTCGTAC CGCGTTCTAC GCCACCTTGC GCAGCCC pMON13031

TABLE 6-continued

DNA SEQUENCES

ATGGCTAACT GCTCTATAAT GATCGATGAA ATTATACATC ACTTAAAGAG [SEQ ID NO:66]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCCGGGC CTCCTGTCAA TGCTGGCGGC GGCTCTGGTG

GTGGTTCTGG TGGCGGCTCT GAGGGTGGCG GCTCTGAGGG TGGCGGTTCT

GAGGGTGGCG GCTCTGAGGG TGGCGGTTCC GGTGGCGGCT CCGGTTCCGG

TGATTTTGAT TATGAAAACA TGGCACCGGC TCGTTCCCCG TCCCCGTCTA

CCCAGCCGTG GGAACACGTG AATGCCATCC AGGAGGCCCG GCGTCTCCTG

AACCTGAGTA GAGACACTGC TGCTGAGATG AATGAAACAG TAGAAGTGAT

ATCAGAAATG TTTGACCTCC AGGAGCCGAC TTGCCTACAG ACCCGCCTGG

AGCTGTACAA GCAGGGCCTG CGGGGCAGCC TCACCAAGCT CAAGGGCCCC

TTGACCATGA TGGCCAGCCA CTACAAGCAG CACTGCCCTC CAACCCCGGA

AACTTCCTGT GCAACCCAGA TTATCACCTT TGAAAGTTTC AAAGAGAACC

TGAAGGACTT CCTGCTTGTC ATCCCCTTTG ACTGCTGGGA GCCAGTCCAG

GAG

PMON15937
ATGGCTAACT GCTCTATAAT GATCGATGAA ATTATACATC ACTTAAAGAG [SEQ ID NO:67]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCCGGTG GCGGCGGCTC TGGTGGTGGT TCTGGTGGCG

GCTCTGAGGG TGGCGGCTCT GAGGGTGGCG GTTCTGAGGG TGGCGGCTCT

GAGGGTGGCG GTTCCGGTGG CGGCTCCGGT TCCGGTAACA TGGCTACACC

ATTAGGCCCT GCCAGCTCCC TGCCCCAGAG CTTCCTGCTC AAGTGCTTAG

AGCAAGTGAG GAAGATCCAG GGCGATGGCG CAGCGCTCCA GGAGAAGCTG

TGTGCCACCT ACAAGCTGTG CCACCCCGAG GAGCTGGTGC TGCTCGGACA

CTCTCTGGGC ATCCCCTGGG CTCCCCTGAG CTCCTGCCCC AGCCAGGCCC

TGCAGCTGGC AGGCTGCTTG AGCCAACTCC ATAGCGGCCT TTTCCTCTAC

CAGGGGCTCC TGCAGGCCCT GGAAGGGATA TCCCCCGAGT TGGGTCCCAC

CTTGGACACA CTGCAGCTGG ACGTCGCCGA CTTTGCCACC ACCATCTGGC

AGCAGATGGA AGAACTGGGA ATGGCCCCTG CCCTGCAGCC CACCCAGGGT

GCCATGCCGG CCTTCGCCTC TGCTTTCCAG CGCCGGGCAG GAGGGGTCCT

TABLE 6-continued

DNA SEQUENCES

GGTTGCTAGC CATCTGCAGA GCTTCCTGGA GGTGTCGTAC CGCGTTCTAC

GCCACCTTGC GCAGCCC

PMON13034
ATGGCTAACT GCTCTATAAT GATCGATGAA ATTATACATC ACTTAAAGAG [SEQ ID NO:68]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG AACCGTCTGG TCCAATCTCT ACTATCAACC

CGTCTCCTCC GTCTAAAGAA TCTCATAAAT CTCCAAACAT GGCTACACCA

TTAGGCCCTG CCAGCTCCCT GCCCCAGAGC TTCCTGCTCA AGTGCTTAGA

GCAAGTGAGG AAGATCCAGG GCGATGGCGC AGCGCTCCAG GAGAAGCTGT

GTGCCACCTA CAAGCTGTGC CACCCCGAGG AGCTGGTGCT GCTCGGACAC

TCTCTGGGCA TCCCCTGGGC TCCCCTGAGC TCCTGCCCCA GCCAGGCCCT

GCAGCTGGCA GGCTGCTTGA GCCAACTCCA TAGCGGCCTT TTCCTCTACC

AGGGGCTCCT GCAGGCCCTG GAAGGGATAT CCCCCGAGTT GGGTCCCACC

TTGGACACAC TGCAGCTGGA CGTCGCCGAC TTTGCCACCA CCATCTGGCA

GCAGATGGAA GAACTGGGAA TGGCCCCTGC CCTGCAGCCC ACCCAGGGTG

CCATGCCGGC CTTCGCCTCT GCTTTCCAGC GCCGGGCAGG AGGGGTCCTG

GTTGCTAGCC ATCTGCAGAG CTTCCTGGAG GTGTCGTACC GCGTTCTACG

CCACCTTGCG CAGCCC

PMON13035
ATGGCTAACT GCTCTATAAT GATCGATGAA ATTATACATC ACTTAAAGAG [SEQ ID NO:69]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG AACCGTCTGG TCCAATCTCT ACTATCAACC

CGTCTCCTCC GTCTAAAGAA TCTCATAAAT CTCCAAACAT GGCACCGGCT

CGTTCCCCGT CCCCGTCTAC CCAGCCGTGG AACACGTGA ATGCCATCCA

GGAGGCCCGG CGTCTCCTGA ACCTGAGTAG AGACACTGCT GCTGAGATGA

ATGAAACAGT AGAAGTGATA TCAGAAATGT TTGACCTCCA GGAGCCGACT

TGCCTACAGA CCCGCCTGGA GCTGTACAAG CAGGGCCTGC GGGGCAGCCT

CACCAAGCTC AAGGGCCCCT TGACCATGAT GGCCAGCCAC TACAAGCAGC

ACTGCCCTCC AACCCCGGAA ACTTCCTGTG CAACCCAGAT TATCACCTTT

GAAAGTTTCA AGAGAACCT GAAGGACTTC CTGCTTGTCA TCCCCTTTGA

TABLE 6-continued

DNA SEQUENCES

CTGCTGGGAG CCAGTCCAGG AG

PMON13058
ATGGCTAACT GCTCTATAAT GATCGATGAA ATTATACATC ACTTAAAGAG [SEQ ID NO:70]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAAGATT TCCCCGGGTG AACCGTCTGG TCCAATCTCT ACTATCAACC

CGTCTCCTCC GTCTAAAGAA TCTCATAAAT CTCCAAACAT GGCTACACCA

TTAGGCCCTG CCAGCTCCCT GCCCCAGAGC TTCCTGCTCA AGTGCTTAGA

GCAAGTGAGG AAGATCCAGG GCGATGGCGC AGCGCTCCAG GAGAAGCTGT

GTGCCACCTA CAAGCTGTGC CACCCCGAGG AGCTGGTGCT GCTCGGACAC

TCTCTGGGCA TCCCCTGGGC TCCCCTGAGC TCCTGCCCCA GCCAGGCCCT

GCAGCTGGCA GGCTGCTTGA GCCAACTCCA TAGCGGCCTT TTCCTCTACC

AGGGGCTCCT GCAGGCCCTG GAAGGGATAT CCCCCGAGTT GGGTCCCACC

TTGGACACAC TGCAGCTGGA CGTCGCCGAC TTTGCCACCA CCATCTGGCA

GCAGATGGAA GAACTGGGAA TGGCCCCTGC CCTGCAGCCC ACCCAGGGTG

CCATGCCGGC CTTCGCCTCT GCTTTCCAGC GCCGGGCAGG AGGGGTCCTG

GTTGCTAGCC ATCTGCAGAG CTTCCTGGAG GTGTCGTACC GCGTTCTACG

CCACCTTGCG CAGCCC

PMON13060
ATGGCTAACT GCTCTATAAT GATCGATGAA ATTATACATC ACTTAAAGAG [SEQ ID NO:71]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG AACCGTCTGG TCCAATCTCT ACTATCAACC

CGTCTCCTCC GTCTAAAGAA TCTCATAAAT CTCCAAACAT GGCTACACCA

TTAGGCCCTG CCAGCTCCCT GCCCCAGAGC TTCCTGCTCA AGTGCTTAGA

GCAAGTGAGG AAGATCCAGG GCGATGGCGC AGCGCTCCAG GAGAAGCTGT

GTGCCACCTA CAAGCTGTGC CACCCCGAGG AGCTGGTGCT GCTCGGACAC

TCTCTGGGCA TCCCCTGGGC TCCCCTGAGC TCCTGCCCCA GCCAGGCCCT

GCAGCTGGCA GGCTGCTTGA GCCAACTCCA TAGCGGCCTT TTCCTCTACC

AGGGGCTCCT GCAGGCCCTG GAAGGGATAT CCCCCGAGTT GGGTCCCACC

TTGGACACAC TGCAGCTGGA CGTCGCCGAC TTTGCCACCA CCATCTGGCA

TABLE 6-continued

DNA SEQUENCES

GCAGATGGAA GAACTGGGAA TGGCCCCTGC CCTGCAGCCC ACCCAGGGTG

CCATGCCGGC CTTCGCCTCT GCTTTCCAGC GCCGGGCAGG AGGGGTCCTG

GTTGCTAGCC ATCTGCAGAG CTTCCTGGAG GTGTCGTACC GCGTTCTACG

CCACCTTGCG CAGCCC

PMON13026
ATGGCTACAC CATTAGGCCC TGCCAGCTCC CTGCCCCAGA GCTTCCTGCT [SEQ ID NO:72]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAATCGAG GGAAGGATTT

CCCCGGGTGG TGGTTCTGGC GGCGGCTCCA ACATGGCTAA CTGCTCTATA

ATGATCGATG AAATTATACA TCACTTAAAG AGACCACCTA ACCCTTTGCT

GGACCCGAAC AACCTCAATT CTGAAGACAT GGATATCCTG ATGGAACGAA

ACCTTCGAAC TCCAAACCTG CTCGCATTCG TAAGGGCTGT CAAGCACTTA

GAAAATGCAT CAGGTATTGA GGCAATTCTT CGTAATCTCC AACCATGTCT

GCCCTCTGCC ACGGCCGCAC CCTCTCGACA TCCAATCATC ATCAAGGCAG

GTGACTGGCA AGAATTCCGG GAAAAACTGA CGTTCTATCT GGTTACCCTT

GAGCAAGCGC AGGAACAACA G

PMON13063
ATGGCTACAC CATTAGGCCC TGCCAGCTCC CTGCCCCAGA GCTTCCTGCT [SEQ ID NO:73]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAATCGAG GGAAGGATTT

CCCCGGGTGA ACCGTCTGGT CCAATCTCTA CTATCAACCC GTCTCCTCCG

TCTAAAGAAT CTCATAAATC TCCAAACATG GCTAACTGCT CTATAATGAT

CGATGAAATT ATACATCACT TAAAGAGACC ACCTAACCCT TTGCTGGACC

CGAACAACCT CAATTCTGAA GACATGGATA TCCTGATGGA ACGAAACCTT

TABLE 6-continued

DNA SEQUENCES

CGAACTCCAA ACCTGCTCGC ATTCGTAAGG GCTGTCAAGC ACTTAGAAAA

TGCATCAGGT ATTGAGGCAA TTCTTCGTAA TCTCCAACCA TGTCTGCCCT

CTGCCACGGC CGCACCCTCT CGACATCCAA TCATCATCAA GGCAGGTGAC

TGGCAAGAAT TCCGGGAAAA ACTGACGTTC TATCTGGTTA CCCTTGAGCA

AGCGCAGGAA CAACAG

PMON13064
ATGGCTACAC CATTAGGCCC TGCCAGCTCC CTGCCCCAGA GCTTCCTGCT [SEQ ID NO:74]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAATCGAG GGAAGGATTT

CCCCCGGGCC TCCTGTCAAT GCTGGCGGCG GCTCTGGTGG TGGTTCTGGT

GGCGGCTCTG AGGGTGGCGG CTCTGAGGGT GGCGGTTCTG AGGGTGGCGG

CTCTGAGGGT GGCGGTTCCG GTGGCGGCTC CGGTTCCGGT GATTTTGATT

ATGAAAACAT GGCTAACTGC TCTATAATGA TCGATGAAAT TATACATCAC

TTAAAGAGAC CACCTAACCC TTTGCTGGAC CCGAACAACC TCAATTCTGA

AGACATGGAT ATCCTGATGG AACGAAACCT TCGAACTCCA AACCTGCTCG

CATTCGTAAG GCTGTCAAG CACTTAGAAA ATGCATCAGG TATTGAGGCA

ATTCTTCGTA ATCTCCAACC ATGTCTGCCC TCTGCCACGG CCGCACCCTC

TCGACATCCA ATCATCATCA AGGCAGGTGA CTGGCAAGAA TTCCGGGAAA

AACTGACGTT CTATCTGGTT ACCCTTGAGC AAGCGCAGGA ACAACAG

PMON13043
ATGGCTACAC CATTAGGCCC TGCCAGCTCC CTGCCCCAGA GCTTCCTGCT [SEQ ID NO:75]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAATCGAG GGAAGGATTT

TABLE 6-continued

| DNA SEQUENCES |
|---|

CCCCGGGTGG TGGTTCTGGC GGCGGCTCCA ACATGGCTAA CTGCTCTATA

ATGATCGATG AAATTATACA TCACTTAAAG AGACCACCTG CACCTTTGCT

GGACCCGAAC AACCTCAATG ACGAAGACGT CTCTATCCTG ATGGAACGAA

ACCTTCGACT TCCAAACCTG GAGAGCTTCG TAAGGGCTGT CAAGAACTTA

GAAAATGCAT CAGGTATTGA GGCAATTCTT CGTAATCTCC AACCATGTCT

GCCCTCTGCC ACGGCCGCAC CCTCTCGACA TCCAATCATC ATCAAGGCAG

GTGACTGGCA AGAATTCCGG GAAAAACTGA CGTTCTATCT GGTTACCCTT

GAGCAAGCGC AGGAACAACA G

PMON13044
ATGGCTACAC CATTAGGCCC TGCCAGCTCC CTGCCCCAGA GCTTCCTGCT [SEQ ID NO:76]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAATCGAG GGAAGGATTT

CCCCCGGGCC TCCTGTCAAT GCTGGCGGCG GCTCTGGTGG TGGTTCTGGT

GGCGGCTCTG AGGGTGGCGG CTCTGAGGGT GGCGGTTCTG AGGGTGGCGG

CTCTGAGGGT GGCGGTTCCG GTGGCGGCTC CGGTTCCGGT GATTTTGATT

ATGAAAACAT GGCTAACTGC TCTATAATGA TCGATGAAAT TATACATCAC

TTAAAGAGAC CACCTGCACC TTTGCTGGAC CCGAACAACC TCAATGACGA

AGACGTCTCT ATCCTGATGG AACGAAACCT TCGACTTCCA AACCTGGAGA

GCTTCGTAAG GGCTGTCAAG AACTTAGAAA ATGCATCAGG TATTGAGGCA

ATTCTTCGTA ATCTCCAACC ATGTCTGCCC TCTGCCACGG CCGCACCCTC

TCGACATCCA ATCATCATCA AGGCAGGTGA CTGGCAAGAA TTCCGGGAAA

AACTGACGTT CTATCTGGTT ACCCTTGAGC AAGCGCAGGA ACAACAG

PMON13045
ATGGCTACAC CATTAGGCCC TGCCAGCTCC CTGCCCCAGA GCTTCCTGCT [SEQ ID NO:77]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

TABLE 6-continued

DNA SEQUENCES

```
GGAGGGGTCC TGGTTGCTAG CCATCTGCAG AGCTTCCTGG AGGTGTCGTA

CCGCGTTCTA CGCCACCTTG CGCAGCCCTA CGTAATCGAG GGAAGGATTT

CCCCGGGTGA ACCGTCTGGT CCAATCTCTA CTATCAACCC GTCTCCTCCG

TCTAAAGAAT CTCATAAATC TCCAAACATG GCTAACTGCT CTATAATGAT

CGATGAAATT ATACATCACT TAAAGAGACC ACCTGCACCT TTGCTGGACC

CGAACAACCT CAATGACGAA GACGTCTCTA TCCTGATGGA ACGAAACCTT

CGACTTCCAA ACCTGGAGAG CTTCGTAAGG GCTGTCAAGA ACTTAGAAAA

TGCATCAGGT ATTGAGGCAA TTCTTCGTAA TCTCCAACCA TGTCTGCCCT

CTGCCACGGC CGCACCCTCT CGACATCCAA TCATCATCAA GGCAGGTGAC

TGGCAAGAAT TCCGGGAAAA ACTGACGTTC TATCTGGTTA CCCTTGAGCA

AGCGCAGGAA CAACAG
```

PMON13151
```
ATGGCTACAC CATTAGGCCC TGCCAGCTCC CTGCCCCAGA GCTTCCTGCT   [SEQ ID NO 78]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAGAGGGC GGTGGAGGCT

CCCCGGGTGG TGGTTCTGGC GGCGGCTCCA ACATGGCTAA CTGCTCTATA

ATGATCGATG AAATTATACA TCACTTAAAG AGACCACCTG CACCTTTGCT

GGACCCGAAC AACCTCAATG ACGAAGACGT CTCTATCCTG ATGGAACGAA

ACCTTCGACT TCCAAACCTG GAGAGCTTCG TAAGGGCTGT CAAGAACTTA

GAAAATGCAT CAGGTATTGA GGCAATTCTT CGTAATCTCC AACCATGTCT

GCCCTCTGCC ACGGCCGCAC CCTCTCGACA TCCAATCATC ATCAAGGCAG

GTGACTGGCA AGAATTCCGG GAAAAACTGA CGTTCTATCT GGTTACCCTT

GAGCAAGCGC AGGAACAACA G
```

PMON13152
```
ATGGCTACAC CATTAGGCCC TGCCAGCTCC CTGCCCCAGA GCTTCCTGCT   [SEQ ID NO 79]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC
```

TABLE 6-continued

| DNA SEQUENCES |
|---|

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAGAGGGC GGTGGAGGCT

CCCCGGGTGA ACCGTCTGGT CCAATCTCTA CTATCAACCC GTCTCCTCCG

TCTAAAGAAT CTCATAAATC TCCAAACATG GCTAACTGCT CTATAATGAT

CGATGAAATT ATACATCACT TAAAGAGACC ACCTGCACCT TTGCTGGACC

CGAACAACCT CAATGACGAA GACGTCTCTA TCCTGATGGA ACGAAACCTT

CGACTTCCAA ACCTGGAGAG CTTCGTAAGG GCTGTCAAGA ACTTAGAAAA

TGCATCAGGT ATTGAGGCAA TTCTTCGTAA TCTCCAACCA TGTCTGCCCT

CTGCCACGGC CGCACCCTCT CGACATCCAA TCATCATCAA GGCAGGTGAC

TGGCAAGAAT TCCGGGAAAA ACTGACGTTC TATCTGGTTA CCCTTGAGCA

AGCGCAGGAA CAACAG

PMON13149
ATGGCTACAC CATTGGGCCC TGCCAGCTCC CTGCCCCAGA GCTTCCTGCT [SEQ ID NO:80]

CAAGTCTTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CGTCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAGAGGGC GGTGGAGGCT

CCCCGGGTGG TGGTTCTGGC GGCGGCTCCA ACATGGCTAA CTGCTCTATA

ATGATCGATG AAATTATACA TCACTTAAAG AGACCACCTG CACCTTTGCT

GGACCCGAAC AACCTCAATG ACGAAGACGT CTCTATCCTG ATGGAACGAA

ACCTTCGACT TCCAAACCTG GAGAGCTTCG TAAGGGCTGT CAAGAACTTA

GAAAATGCAT CAGGTATTGA GGCAATTCTT CGTAATCTCC AACCATGTCT

GCCCTCTGCC ACGGCCGCAC CCTCTCGACA TCCAATCATC ATCAAGGCAG

GTGACTGGCA AGAATTCCGG GAAAAACTGA CGTTCTATCT GGTTACCCTT

GAGCAAGCGC AGGAACAACA G

PMON13150
ATGGCTACAC CATTGGGCCC TGCCAGCTCC CTGCCCCAGA GCTTCCTGCT [SEQ ID NO:81]

CAAGTCTTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TABLE 6-continued

| DNA SEQUENCES |
| --- |

```
TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTA CGTAGAGGGC GGTGGAGGCT

CCCCGGGTGA ACCGTCTGGT CCAATCTCTA CTATCAACCC GTCTCCTCCG

TCTAAAGAAT CTCATAAATC TCCAAACATG GCTAACTGCT CTATAATGAT

CGATGAAATT ATACATCACT TAAAGAGACC ACCTGCACCT TTGCTGGACC

CGAACAACCT CAATGACGAA GACGTCTCTA TCCTGATGGA ACGAAACCTT

CGACTTCCAA ACCTGGAGAG CTTCGTAAGG GCTGTCAAGA ACTTAGAAAA

TGCATCAGGT ATTGAGGCAA TTCTTCGTAA TCTCCAACCA TGTCTGCCCT

CTGCCACGGC CGCACCCTCT CGACATCCAA TCATCATCAA GGCAGGTGAC

TGGCAAGAAT TCCGGGAAAA ACTGACGTTC TATCTGGTTA CCCTTGAGCA

AGCGCAGGAA CAACAG

PMON13052
ATGGCTAACT GCTCTATAAT GATCGATGAA ATTATACATC ACTTAAAGAG [SEQ ID NO:82]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG AACCGTCTGG TCCAATCTCT ACTATCAACC

CGTCTCCTCC GTCTAAAGAA TCTCATAAAT CTCCAAACAT GGCTAACTGC

TCTATAATGA TCGATGAAAT TATACATCAC TTAAAGAGAC CACCTGCACC

TTTGCTGGAC CCGAACAACC TCAATGACGA AGACGTCTCT ATCCTGATGG

AACGAAACCT TCGACTTCCA AACCTGGAGA GCTTCGTAAG GCTGTCAAG

AACTTAGAAA ATGCATCAGG TATTGAGGCA ATTCTTCGTA ATCTCCAACC

ATGTCTGCCC TCTGCCACGG CCGCACCCTC TCGACATCCA ATCATCATCA

AGGCAGGTGA CTGGCAAGAA TTCCGGGAAA ACTGACGTT CTATCTGGTT

ACCCTTGAGC AAGCGCAGGA ACAACAG

PMON13053
ATGGCTAACT GCTCTATAAT GATCGATGAA ATTATACATC ACTTAAAGAG [SEQ ID NO:83]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA
```

TABLE 6-continued

DNA SEQUENCES

GGGAAGGATT TCCCCGGGTG AACCGTCTGG TCCAATCTCT ACTATCAACC

CGTCTCCTCC GTCTAAAGAA TCTCATAAAT CTCCAAACAT GGCTACACCA

TTGGGCCCTG CCAGCTCCCT GCCCCAGAGC TTCCTGCTCA AGTCTTTAGA

GCAAGTGAGG AAGATCCAGG GCGATGGCGC AGCGCTCCAG GAGAAGCTGT

GTGCCACCTA CAAGCTGTGC CACCCCGAGG AGCTGGTGCT GCTCGGACAC

TCTCTGGGCA TCCCCTGGGC TCCCCTGAGC TCCTGCCCCA GCCAGGCCCT

GCAGCTGGCA GGCTGCTTGA GCCAACTCCA TAGCGGCCTT TTCCTCTACC

AGGGGCTCCT GCAGGCCCTG GAAGGGATAT CCCCCGAGTT GGGTCCCACC

TTGGACACAC TGCAGCTGGA CGTCGCCGAC TTTGCCACCA CCATCTGGCA

GCAGATGGAA GAACTGGGAA TGGCCCCTGC CCTGCAGCCC ACCCAGGGTG

CCATGCCGGC CTTCGCCTCT GCTTTCCAGC GCCGGGCAGG AGGGGTCCTG

GTTGCTAGCC ATCTGCAGAG CTTCCTGGAG GTGTCGTACC GCGTTCTACG

CCACCTTGCG CAGCCCTGAT AAGGATCCGA ATTC

PMON13066
ATGGCTAACT GCTCTATAAT GATCGATGAA ATTATACATC ACTTAAAGAG [SEQ ID NO:84]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTA

CACCATTAGG CCCTGCCAGC TCCCTGCCCC AGAGCTTCCT GCTCAAGTGC

TTAGAGCAAG TGAGGAAGAT CCAGGGCGAT GGCGCAGCGC TCCAGGAGAA

GCTGTGTGCC ACCTACAAGC TGTGCCACCC CGACCAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TGGCAGCAGA TGGAAGAACT GGGAATGGCC CTGCCCTGC AGCCCACCCA

GGGTGCCATG CCGGCCTTCG CCTCTGCTTT CCAGCGCCGG GCAGGAGGGG

TCCTGGTTGC TAGCCATCTG CAGAGCTTCC TGGAGGTGTC GTACCGCGTT

CTACGCCACC TTGCGCAGCC C

PMON13051
ATGGCTAACT GCTCTATAAT GATCGATGAA ATTATACATC ACTTAAAGAG [SEQ ID NO:85]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TABLE 6-continued

DNA SEQUENCES

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTA

CACCATTAGG CCCTGCCAGC TCCCTGCCCC AGAGCTTCCT GCTCAAGTCC

TTAGAGCAAG TGAGGAAGAT CCAGGGCGAT GGCGCAGCGC TCCAGGAGAA

GCTGTGTGCC ACCTACAAGC TGTGCCACCC CGAGGAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TGGCAGCAGA TGGAAGAACT GGGAATGGCC CCTGCCCTGC AGCCCACCCA

GGGTGCCATG CCGGCCTTCG CCTCTGCTTT CCAGCGCCGG GCAGGAGGGG

TCCTGGTTGC TAGCCATCTG CAGAGCTTCC TGGAGGTGTC GTACCGCGTT

CTACGCCACC TTGCGCAGCC C

PMON13050
ATGGCTAACT GCTCTATAAT GATCGATGAA ATTATACATC ACTTAAAGAG [SEQ ID NO:86]

ACCACCTGCA CCTTTGCTGG ACCCGAACAA CCTCAATGAC GAAGACGTCT

CTATCCTGAT GGAACGAAAC CTTCGACTTC AAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCTA

ACTGCTCTAT AATGATCGAT GAAATTATAC ATCACTTAAA GAGACCACCT

GCACCTTTGC TGGACCCGAA CAACCTCAAT GACGAAGACG TCTCTATCCT

GATGGAACGA AACCTTCGAC TTCCAAACCT GGAGAGCTTC GTAAGGGCTG

TCAAGAACTT AGAAAATGCA TCAGGTATTG AGGCAATTCT TCGTAATCTC

CAACCATGTC TGCCCTCTGC CACGGCCGCA CCCTCTCGAC ATCCAATCAT

CATCAAGGCA GGTGACTGGC AAGAATTCCG GGAAAAACTG ACGTTCTATC

TGGTTACCCT TGAGCAAGCG CAGGAACAAC AG

PMON13145
ATGGCTAACT GCTCTATAAT GATCGATGAA ATTATACATC ACTTAAAGAG [SEQ ID NO:87]

ACCACCTGCA CCTTTGCTGG ACCCGAACAA CCTCAATGAC GAAGACGTCT

CTATCCTGAT GGAACGAAAC CTTCGACTTC AAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG GTGGTTCTGG CGGCGGCTCC AACATGGCTA

CACCATTGGG CCCTGCCAGC TCCCTGCCCC AGAGCTTCCT GCTCAAGTCT

TABLE 6-continued

DNA SEQUENCES

TTAGAGCAAG TGAGGAAGAT CCAGGGCGAT GGCGCAGCGC TCCAGGAGAA

GCTGTGTGCC ACCTACAAGC TGTGCCACCC CGAGGAGCTG GTGCTGCTCG

GACACTCTCT GGGCATCCCC TGGGCTCCCC TGAGCTCCTG CCCCAGCCAG

GCCCTGCAGC TGGCAGGCTG CTTGAGCCAA CTCCATAGCG GCCTTTTCCT

CTACCAGGGG CTCCTGCAGG CCCTGGAAGG GATATCCCCC GAGTTGGGTC

CCACCTTGGA CACACTGCAG CTGGACGTCG CCGACTTTGC CACCACCATC

TGGCAGCAGA TGGAAGAACT GGGAATGGCC CCTGCCCTGC AGCCCACCCA

GGGTGCCATG CCGGCCTTCG CCTCTGCTTT CCAGCGCCGG GCAGGAGGGG

TCCTGGTTGC TAGCCATCTG CAGAGCTTCC TGGAGGTGTC GTACCGCGTT

CTACGCCACC TTGCGCAGCC C

PMON13147
ATGGCTAACT GCTCTATAAT GATCGATGAA ATTATACATC ACTTAAAGAG [SEQ ID NO:88]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG GTGGTTCTGG CGGCGGCTCC AACATGGCTA

ACTGCTCTAT AATGATCGAT GAAATTATAC ATCACTTAAA GAGACCACCT

GCACCTTTGC TGGACCCGAA CAACCTCAAT GACGAAGACG TCTCTATCCT

GATGGAACGA AACCTTCGAC TTCCAAACCT GGAGAGCTTC GTAAGGGCTG

TCAAGAACTT AGAAAATGCA TCAGGTATTG AGGCAATTCT TCGTAATCTC

CAACCATGTC TGCCCTCTGC CACGGCCGCA CCCTCTCGAC ATCCAATCAT

CATCAAGGCA GGTGACTGGC AAGAATTCCG GGAAAAACTG ACGTTCTATC

TGGTTACCCT TGAGCAAGCG CAGGAACAAC AG

PMON13146
ATGGCTAACT GCTCTATAAT GATCGATGAA ATTATACATC ACTTAAAGAG [SEQ ID NO:89]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG AACCGTCTGG TCCAATCTCT ACTATCAACC

CGTCTCCTCC GTCTAAAGAA TCTCATAAAT CTCCAAACAT GGCTACACCA

TTGGGCCCTG CCAGCTCCCT GCCCCAGAGC TTCCTGCTCA AGTCTTTAGA

GCAAGTGAGG AAGATCCAGG GCGATGGCGC AGCGCTCCAG GAGAAGCTGT

GTGCCACCTA CAAGCTGTGC CACCCCGAGG AGCTGGTGCT GCTCGGACAC

TCTCTGGGCA TCCCCTGGGC TCCCCTGAGC TCCTGCCCCA GCCAGGCCCT

TABLE 6-continued

DNA SEQUENCES

GCAGCTGGCA GGCTGCTTGA GCCAACTCCA TAGCGGCCTT TTCCTCTACC

AGGGGCTCCT GCAGGCCCTG GAAGGGATAT CCCCCGAGTT GGGTCCCACC

TTGGACACAC TGCAGCTGGA CGTCGCCGAC TTTGCCACCA CCATCTGGCA

GCAGATGGAA GAACTGGGAA TGGCCCCTGC CCTGCAGCCC ACCCAGGGTG

CCATGCCGGC CTTCGCCTCT GCTTTCCAGC GCCGGGCAGG AGGGGTCCTG

GTTGCTAGCC ATCTGCAGAG CTTCCTGGAG GTGTCGTACC GCGTTCTACG

CCACCTTGCG CAGCCC pMON13148
ATGGCTAACT GCTCTATAAT GATCGATGAA ATTATACATC ACTTAAAGAG [SEQ ID NO:90]

ACCACCTGCA CCTTTGCTGG ACCCGAACAA CCTCAATGAC GAAGACGTCT

CTATCCTGAT GGAACGAAAC CTTCGACTTC CAAACCTGGA GAGCTTCGTA

AGGGCTGTCA AGAACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAGAGGG

CGGTGGAGGC TCCCCGGGTG AACCGTCTGG TCCAATCTCT ACTATCAACC

CGTCTCCTCC GTCTAAAGAA TCTCATAAAT CTCCAAACAT GGCTAACTGC

TCTATAATGA TCGATGAAAT TATACATCAC TTAAAGAGAC CACCTGCACC

TTTGCTGGAC CCGAACAACC TCAATGACGA AGACGTCTCT ATCCTGATGG

AACGAAACCT TCGACTTCCA AACCTGGAGA GCTTCGTAAG GGCTGTCAAG

AACTTAGAAA ATGCATCAGG TATTGAGGCA ATTCTTCGTA ATCTCCAACC

ATGTCTGCCC TCTGCCACGG CCGCACCCTC TCGACATCCA ATCATCATCA

AGGCAGGTGA CTGGCAAGAA TTCCGGGAAA AACTGACGTT CTATCTGGTT

ACCCTTGAGC AAGCGCAGGA ACAACAG pMON13040
ATGGCTCCAG TACCACCAGG TGAAGATTCC AAAGATGTGG CCGCCCCACA [SEQ ID NO:175]

CAGACAGCCA CTCACCTCTT CAGAACGAAT TGACAAACAA ATTCGGTACA

TCCTCGACGG GATATCAGCC CTGAGAAAGG AGACATGTAA CAAGAGTAAC

ATGTGTGAAA GCAGCAAAGA GGCGCTAGCA GAAAACAACC TGAACCTTCC

AAAGATGGCT GAAAAAGATG GATGCTTCCA ATCCGGATTC AATGAGGAGA

CTTGCCTGGT GAAAATCATC ACTGGTCTTT TGGAGTTTGA GGTATACCTC

GAGTACCTCC AGAACAGATT TGAGAGTAGT GAGGAACAAG CCAGAGCTGT

GCAGATGTCG ACAAAAGTCC TGATCCAGTT CCTGCAGAAA AAGGCAAAGA

ATCTAGATGC AATAACCACC CCTGACCCAA CCACAAATGC ATCCCTGCTG

ACGAAGCTGC AGGCACAGAA CCAGTGGCTG CAGGACATGA CAACTCATCT

CATTCTGCGC AGCTTTAAGG AGTTCCTGCA GTCCAGCCTG AGGGCTCTTC

GGCAAATGTA G pMON13012
ATGGCACCGG CTCGTTCCCC GTCCCCGTCT ACCCAGCCGT GGGAACACGT [SEQ ID NO:176]

GAATGCCATC CAGGAGGCCC GGCGTCTCCT GAACCTGAGT AGAGACACTG

TABLE 6-continued

DNA SEQUENCES

CTGCTGAGAT GAATGAAACA GTAGAAGTGA TATCAGAAAT GTTTGACCTC

CAGGAGCCGA CTTGCCTACA GACCCGCCTG GAGCTGTACA AGCAGGGCCT

GCGGGGCAGC CTCACCAAGC TCAAGGGCCC CTTGACCATG ATGGCCAGCC

ACTACAAGCA GCACTGCCCT CCAACCCCGG AAACTTCCTG TGCAACCCAG

ATTATCACCT TTGAAAGTTT CAAAGAGAAC CTGAAGGACT TCCTGCTTGT

CATCCCCTTT GACTGCTGGG AGCCAGTCCA GGAGTGATAA GGATCCGAAT

TC pMON13499
ATGGCTACAC CATTAGGCCC TGCCAGCTCC CTGCCCCAGA GCTTCCTGCT [SEQ ID NO:177]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTG ATAAGGATCC GAATTC pMON13498/pMON13010
ATGGCTACAC CATTAGGACC TGCCAGCTCC CTGCCCCAGA GCTTCCTGCT [SEQ ID NO:178]

CAAGTGCTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTG ATAAGGATCC GAATTC pMON13033/pMON13037
ATGGCTACAC CATTGGGCCC TGCCAGCTCC CTGCCCCAGA GCTTCCTGCT [SEQ ID NO:179]

CAAGTCTTTA GAGCAAGTGA GGAAGATCCA GGGCGATGGC GCAGCGCTCC

AGGAGAAGCT GTGTGCCACC TACAAGCTGT GCCACCCCGA GGAGCTGGTG

CTGCTCGGAC ACTCTCTGGG CATCCCCTGG GCTCCCCTGA GCTCCTGCCC

CAGCCAGGCC CTGCAGCTGG CAGGCTGCTT GAGCCAACTC CATAGCGGCC

TTTTCCTCTA CCAGGGGCTC CTGCAGGCCC TGGAAGGGAT ATCCCCCGAG

TTGGGTCCCA CCTTGGACAC ACTGCAGCTG GACGTCGCCG ACTTTGCCAC

CACCATCTGG CAGCAGATGG AAGAACTGGG AATGGCCCCT GCCCTGCAGC

TABLE 6-continued

DNA SEQUENCES

CCACCCAGGG TGCCATGCCG GCCTTCGCCT CTGCTTTCCA GCGCCGGGCA

GGAGGGGTCC TGGTTGCTAG CCATCTGCAG AGCTTCCTGG AGGTGTCGTA

CCGCGTTCTA CGCCACCTTG CGCAGCCCTG ATAAGGATCC GAATTC pMON26448
ATGGCGTCTC CGGCGCCGCC TGCTTGTGAC CTCCGAGTCC TCAGTAAACT [SEQ ID NO:180]

GCTTCGTGAC TCCCATGTCC TTCACAGCAG ACTGAGCCAG TGCCCAGAGG

TTCACCCTTT GCCTACACCT GTCCTGCTGC CTGCTGTGGA CTTTAGCTTG

GGAGAATGGA AAACCCAGAT GGAGGAGACC AAGGCACAGG ACATTCTGGG

AGCAGTGACC CTTCTGCTGG AGGGAGTGAT GGCAGCACGG GGACAACTGG

GACCCACTTG CCTCTCATCC CTCCTGGGGC AGCTTTCTGG ACAGGTCCGT

CTCCTCCTTG GGGCCCTGCA GAGCCTCCTT GGAACCCAGC TTCCTCCACA

GGGCAGGACC ACAGCTCACA AGGATCCCAA TGCCATCTTC CTGAGCTTCC

AACACCTGCT CCGAGGAAAG GTGCGTTTCC TGATGCTTGT AGGAGGGTCC

ACCCTCTGCG TCAGG pMON26463
ATGGCTAACT GCTCTATAAT GATCGATGAA ATTATACATC ACTTAAAGAG [SEQ ID ON:183]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TTCTATCTGG TTACCCTTGA GCAAGCGCAG GAACAACAGT ACGTAATCGA

GGGAAGGATT TCCCCGGGTG GTGGTTCTGG CGGCGGCTCC AACATGGCGT

CTCCGGCGCC GCCTGCTTGT GACCTCCGAG TCCTCAGTAA ACTGCTTCGT

GACTCCCATG TCCTTCACAG CAGACTGAGC CAGTGCCCAG AGGTTCACCC

TTTGCCTACA CCTGTCCTGC TGCCTGCTGT GGACTTTAGC TTGGGAGAAT

GGAAAACCCA GATGGAGGAG ACCAAGGCAC AGGACATTCT GGGAGCAGTG

ACCCTTCTGC TGGAGGGAGT GATGGCAGCA CGGGGACAAC TGGGACCCAC

TTGCCTCTCA TCCCTCCTGG GGCAGCTTTC TGGACAGGTC CGTCTCCTCC

TTGGGGCCCT GCAGAGCCTC CTTGGAACCC AGCTTCCTCC ACAGGGCAGG

ACCACAGCTC ACAAGGATCC CAATGCCATC TTCCTGAGCT TCCAACACCT

GCTCCGAGGA AAGGTGCGTT TCCTGATGCT TGTAGGAGGG TCCACCCTCT

GCGTCAGG pMON26473
ATGGCTAACT GCTCTATAAT GATCGATGAA ATTATACATC ACTTAAAGAG [SEQ ID NO 184]

ACCACCTAAC CCTTTGCTGG ACCCGAACAA CCTCAATTCT GAAGACATGG

ATATCCTGAT GGAACGAAAC CTTCGAACTC CAAACCTGCT CGCATTCGTA

AGGGCTGTCA AGCACTTAGA AAATGCATCA GGTATTGAGG CAATTCTTCG

TAATCTCCAA CCATGTCTGC CCTCTGCCAC GGCCGCACCC TCTCGACATC

CAATCATCAT CAAGGCAGGT GACTGGCAAG AATTCCGGGA AAAACTGACG

TABLE 6-continued

DNA SEQUENCES

TTCTATCTGG TTACCCTTGA GCAAGCGCAG GAACAACAGT ACGTAGAGGG

CGGTGGAGGC TCCCCGGGTG GTGGTTCTGG CGGCGGCTCC AACATGGCGT

CTCCGGCGCC GCCTGCTTGT GACCTCCGAG TCCTCAGTAA ACTGCTTCGT

GACTCCCATG TCCTTCACAG CAGACTGAGC CAGTGCCCAG AGGTTCACCC

TTTGCCTACA CCTGTCCTGC TGCCTGCTGT GGACTTTAGC TTGGGAGAAT

GGAAAACCCA GATGGAGGAG ACCAAGGCAC AGGACATTCT GGGAGCAGTG

ACCCTTCTGC TGGAGGGAGT GATGGCAGCA CGGGGACAAC TGGGACCCAC

TTGCCTCTCA TCCCTCCTGG GGCAGCTTTC TGGACAGGTC CGTCTCCTCC

TTGGGGCCCT GCAGAGCCTC CTTGGAACCC AGCTTCCTCC ACAGGGCAGG

ACCACAGCTC ACAAGGATCC CAATGCCATC TTCCTGAGCT TCCAACACCT

GCTCCGAGGA AAGGTGCGTT TCCTGATGCT TGTAGGAGGG TCCACCCTCT

GCGTCAGG pMON26474
ATGGCGTCTC CGGCGCCGCC TGCTTGTGAC CTCCGAGTCC TCAGTAAACT [SEQ ID NO:185]

GCTTCGTGAC TCCCATGTCC TTCACAGCAG ACTGAGCCAG TGCCCAGAGG

TTCACCCTTT GCCTACACCT GTCCTGCTGC CTGCTGTGGA CTTTAGCTTG

GGAGAATGGA AAACCCAGAT GGAGGAGACC AAGGCACAGG ACATTCTGGG

AGCAGTGACC CTTCTGCTGG AGGGAGTGAT GGCAGCACGG GGACAACTGG

GACCCACTTG CCTCTCATCC CTCCTGGGGC AGCTTTCTGG ACAGGTCCGT

CTCCTCCTTG GGGCCCTGCA GAGCCTCCTT GGAACCCAGC TTCCTCCACA

GGGCAGGACC ACAGCTCACA AGGATCCCAA TGCCATCTTC CTGAGCTTCC

AACACCTGCT CCGAGGAAAG GTGCGTTTCC TGATGCTTGT AGGAGGGTCC

ACCCTCTGCG TCAGGATCGA GGGAAGGATT TCCCCGGGTG GTGGTTCTGG

CGGCGGCTCC AACATGGCTA ACTGCTCTAT AATGATCGAT GAAATTATAC

ATCACTTAAA GAGACCACCT AACCCTTTGC TGGACCCGAA CAACCTCAAT

TCTGAAGACA TGGATATCCT GATGGAACGA AACCTTCGAA CTCCAAACCT

GCTCGCATTC GTAAGGGCTG TCAAGCACTT AGAAAATGCA TCAGGTATTG

AGGCAATTCT TCGTAATCTC CAACCATGTC TGCCCTCTGC CACGGCCGCA

CCCTCTCGAC ATCCAATCAT CATCAAGGCA GGTGACTGGC AAGAATTCCG

GGAAAAACTG ACGTTCTATC TGGTTACCCT TGAGCAAGCG CAGGAACAAC

AG

PMON26464
ATGGCGTCTC CGGCGCCGCC TGCTTGTGAC CTCCGAGTCC TCAGTAAACT [SEQ ID NO:186]

GCTTCGTGAC TCCCATGTCC TTCACAGCAG ACTGAGCCAG TGCCCAGAGG

TTCACCCTTT GCCTACACCT GTCCTGCTGC CTGCTGTGGA CTTTAGCTTG

GGAGAATGGA AAACCCAGAT GGAGGAGACC AAGGCACAGG ACATTCTGGG

AGCAGTGACC CTTCTGCTGG AGGGAGTGAT GGCAGCACGG GGACAACTGG

GACCCACTTG CCTCTCATCC CTCCTGGGGC AGCTTTCTGG ACAGGTCCGT

CTCCTCCTTG GGGCCCTGCA GAGCCTCCTT GGAACCCAGC TTCCTCCACA

TABLE 6-continued

DNA SEQUENCES

```
GGGCAGGACC ACAGCTCACA AGGATCCCAA TGCCATCTTC CTGAGCTTCC

AACACCTGCT CCGAGGAAAG GTGCGTTTCC TGATGCTTGT AGGAGGGTCC

ACCCTCTGCG TCAGGGAATT CCATGCATAC GTAGAGGGCG GTGGAGGCTC

CCCGGGTGGT GGTTCTGGCG GCGGCTCCAA CATGGCTAAC TGCTCTATAA

TGATCGATGA AATTATACAT CACTTAAAGA GACCACCTAA CCCTTTGCTG

GACCCGAACA ACCTCAATTC TGAAGACATG GATATCCTGA TGGAACGAAA

CCTTCGAACT CCAAACCTGC TCGCATTCGT AAGGGCTGTC AAGCACTTAG

AAAATGCATC AGGTATTGAG GCAATTCTTC GTAATCTCCA ACCATGTCTG

CCCTCTGCCA CGGCCGCACC CTCTCGACAT CCAATCATCA TCAAGGCAGG

TGACTGGCAA GAATTCCGGG AAAAACTGAC GTTCTATCTG GTTACCCTTG

AGCAAGCGCA GGAACAACAG
```

REFERENCES

Abel, T. and T. Maniatis. *Nature* 341:24–25, (1989).

Adams, S. P., Kavka, K. S., Wykes, E. J., Holder, S. B. and Galluppi, G. R. Hindered Dialkyamino Nucleoside Phosphate reagents in the synthesis of two DNA 51-mers. *J. Am. Chem. Soc.*, 105, 661–663 (1983).

Atkinson, T. and Smith, M., in Gait, M. J., Oligonucleotide Synthesis (1984) (IRL Press, Oxford England).

Bachmann, B., Pedigrees of some mutant strains of *Escherichia coli* K-12, *Bacteriological Reviews*, 36:525–557 (1972).

Bayne, M. L., Expression of a synthetic gene encoding human insulin-like growth factor I in cultured mouse fibroblasts. *Proc. Natl. Acad. Sci. USA* 84, 2638–2642 (1987).

Bazan, J. F., Haemopoietic receptors and helical cytokines. *Proc. Natl. Acad. Sci. U.S.A.* 87(18):6934–8 (1990).

Ben-Bassat, A., K. Bauer, S-Y. Chang, K. Myambo, A. Boosman and S. Ching. Processing of the initiating methionine from proteins: properties of the *Escherichia coli* methionine aminopeptidase and its gene structure. *J. Bacteriol.*, 169: 751–757 (1987).

Biesma, B. et al., Effects of interleukin-3 after chemotherapy for advanced ovarian cancer. *Blood*, 80:1141–1148 (1992).

Birnboim, H. C. and J. Doly. A rapid alkaline extraction method for screening recombinant plasmid DNA. *Nucleic Acids Research*, 7(6): 1513–1523 (1979).

Bradford, M. M., A rapid and sensitive method for the quantitation of microgram quantities of protein utilizing the principle of protein-dye binding, *Analytical Biochemistry*, 72: 248–254 (1976).

Bradley, T R and Metcalf, D. The growth of mouse bone marrow cells in vitro. *Aust. Exp. Biol. Med. Sci.* 44:287–300, (1966).

Broxmeyer, H. E. et al, Growth characteristics and expansion of human umbilical cord blood and estimation of its potential for transplantation in adults, *Proc. Natl. Acad. Sci. USA*, 89:4109–4113, (1992).

Clark-Lewis, I., L. E. Hood and S. B. H. Kent. Role of disulfide bridges in determining the biological activity of interleukin 3, *Proc. Natl. Acad. Sci.*, 85: 7897–7901 (1988).

Clement, J. M. and Hofnung, M. Gene sequence of the receptor, an outer membrane protein of *E. coli* K12. *Cell*, 27: 507–514 (1981).

Covarrubias, L., L. Cervantes, A. Covarrubias, X. Soberon, I. Vichido, A. Blanco, Y. M. Kupersztoch-Portnoy and F. Bolivar. Construction and characterization of new cloning vehicles. V. Mobilization and coding properties of pBR322 and several deletion derivatives including pBR327 and pBR328. *Gene* 13: 25–35 (1981).

D'Andrea, A. D., Lodish, H. G., Wong, G. G.:Expression cloning of the murine erythropoietin receptor. Cell 57:277, 1989

Deng, W. P. & Nickoloff, J. A. Site-directed mutagenesis of virtually any plasmid by eliminating a unique site *Anal. Biochem.* 200:81 (1992).

Dente, L., G. Cesareni and R. Cortese, pEMBL: a new family of single stranded plasmids, *Nucleic Acids Research*, 11: 1645–1655 (1983).

Dunn, J. J. and Studier, F. W., Complete nucleotide sequence of bacteriophage T7 DNA and the locations of T7 genetic elements. *J. Mol. Biol.* 1:477–535 (1983).

Falk, S., G. Seipelt, A. Ganser, O. G. Ottmann, D. Hoelzer, H. J. Stutte and K. Hubner. *Hematopathology* 95: 355 (1991).

Farese, A. M., Williams, D. E., Seiler, F. R., and MacVittie, T. J., Combination protocols fo cytokine therapy with interleukin-3 and granulocyte-Macrophage colony-stimulating factor in a primate model of radiation-induced marrow aplasia. *Blood* 82(10):3012–3018 (1993).

Fisher, D. E., C. S. Carr, L. A. Parent and P. A. Sharp. *Genes and Development* 5:2342–2352, (1991).

Fling, M. E., et al. Nucleotide sequence of the transposon Tn7 gene encoding an aminoglycoside-modifying enzyme, 3"(9)-O-nucleotidyltransferase. *Nucl. Acids Res.* 13:7095–7106 (1985).

Fukunaga, R., Ishizaka-Ikeda, E., and Nagata, S., Purification and characterization of the recptor for murine granulocyte colonystimulating factor. *J. Biol. Chem.* 265(23):14008–15 (1990).

Ganser, A., A. Lindemann, G. Seipelt, O. G. Ottmann, F. Herrmann, M. Eder, J. Frisch, G. Schulz, R. Mertelsmann and D. Hoelzer. Effects of Recombinant Human Interleukin-3 in Patients With Normal Hematopoiesis and in Patients with Bone Marrow Failure, *Blood* 76: 666 (1990).

Gearing, D. P., King, J. A., Gough, N. M., Nicola, N. A.: Expression cloning of a receptor for human granulocyte-macrophage colony-stimulating factor. EMBO J 8:3667, 1989

Gearing, D. P., Thut, C. J., VandenBos, T., Gimpel, S. D., Delaney, P. B., King, J. A., Price V., Cosman, D., Beckmann MP: Leukemia inhibitory factor receptor is structurally related to the IL-6 signal transducer, gp130. EMBO J 10:2839, 1991

Gearing, D. P., Comeau, M. R., Friend, D. J., Gimpel, S. D., Thut, C. J., McGourty, J., Brasher, K. K., King. J. A., Gills, S., and Mosely, B., Ziegler, S. F., and Cosman, D., The IL-6 signal transducer, GP130: an oncostatin M recptor and affinty converter for the LIF recptor. Science 255(5050):1434–7 (1992).

Gething and Sambrook, Cell-surface expression of influenza haemagglutinin from a cloned DNA copy of the RNA gene, Nature, 293: 620–625 (1981).

Gillio, A. P., C. Gasparetto, J. Laver, M. Abboud, M. A. Bonilla, M. B. Garnick and R. J. O'Reilly. J. Clin. Invest. 85: 1560 (1990).

Goodwin, R. G., Friend, D. J., Ziegler, S. F., Jerry, R., Falk, B. A., Gimpel, S. D., Cosman, D., Dower, S. K., March, C. J., Namen, A. E., Cloning of the human and murine interleukin-7 receptors: demonstration of a sloble form and homology to a new receptor superfamily. Cell 60(6):941–51 (1990)

Gouy, M. and G. Gautier, Codon usage in bacteria: Correlation with gene expressivity, Nucleic Acids Research, 10: 7055–7074 (1982).

Greenfield, L., T. Boone, and G. Wilcox. DNA sequence of the araBAD promoter in Escherichia coli B/r. Proc. Natl. Acad. Sci. USA, 75: 4724–4728 (1978).

Harada, N., Castle, B. E., Gorman, D. M., Itoh, N., Schreurs, J., Barrett R. L., Howard, M., Miyajima, A.: Expression cloning of a cDNA encoding the murine interleukin 4 receptor based on ligand binding. Proc Natl Acad Sci USA 87:857, 1990

Higuchi, R., in PCR Technology, H. A. Erlich ed., Stockton Press, N.Y. chapter 2–6 (1989).

Hippenmeyer, P., and Highkin M. High level, stable production of recombinant proteins in mammalian cell culture using the herpesvirus VP16 transactivator. Bio/Technology 11: 1037–1041 (1993).

Hunkapiller, M. W., R. W. Hewick, R. J. Dreyer and L. E. Hood. High sensitivity sequencing with a gas-phase sequenator. Methods in Enzymology 153: 399–413 (1983).

Kaufman, et al., Coamplification and Coexpression of Human Tissue-Type Plasminogen Activator and Murine Dihydrofolate Reductase Sequences in Chinese Hamster Ovary Cells, Mol. Cell. Biol., 5(7): 1750–1759 (1985).

Kaufman, R. J. High level production of proteins in mammalian cells, in Genetic Engineering, Principles and Methods, Vol. 9, J. K. Setlow, editor, Plenum Press, New York (1987).

Kelso, A., Gough, N. M.: Coexpession of granulocyte-macrophage colony-stimulating factor. gamma-interferon and interleukins-3 and 4 is random in murine alloreactive T lymphocyte clones. Proc Natl Acad Sci USA 85:9189, 1988

Kitamura, T., Sato, N., Arai, K., Miyajima, A.: Expression cloning of the human IL-3 receptor cDNA reveals a shared beta subunit for the human IL-3 and GM-CSF receptors. Cell 66:1165, 1991

Kondo, M., Takeshita, T., Ishii, N., Nakamura, M., Watanabe, S., Arai, K-I, Sugamura, K.: Sharing of the Interleukin-2 (IL-2) Receptor g Chain Between Receptors for IL-2 and Il-4. Science 262:1874, Dec. 17, 1993.

Kozarides, T. and E. Ziff, Nature 336: 646–651, (1988).

Kunkel, T. A. Rapid and efficient site-specific mutagenesis without phenotypic selection. Proc. Natl. Acad. Sci. USA, 82: 488–492 (1985).

Laemmli, U. K., Cleavage of structural proteins during assembly of the head of bacteriophage T4, Nature, 227:680–685 (1970).

Landshulz, W. H., P. F. Johnson and S. L. Knight, Science 240: 1759–1764, (1988).

Lange, B., M. Valtieri, D. Santoli, D. Caracciolo, F. Mavilio, I. Gemperlein, C. Griffin, B. Emanuel, J. Finan, P. Nowell, and G. Rovera. Growth factor requirements of childhood acute leukemia: establishment of GM-CSF-dependent cell lines. Blood 70:192 (1987).

Maekawa, T., Metcalf, D., Gearing, D. P.: Enhanced suppression of human myeloid leukemic cell lines by combination of IL-6, LIF, GM-CSF and G-CSF, Int J Cancer 45:353, 1989

Mahler, H. R. and E. H. Cordes, in Biological Chemistry, p. 128, New York, Harper and Row (1966).

Maniatis, T., E. F. Fritsch and J. Sambrook, Molecular Cloning, A Laboratory Manual. Cold Spring Harbor Laboratory (1982).

Marinus, M. G. Location of DNA methylation genes on the Escherichia coli K-12 genetic map. Molec. Gen. Genet. 127: 47–55 (1973).

Mayani, H. et al, Cytokine-induced selective expansion and maturation of erythroid versus myeloid progenitors from purified cord blood precursor cells, Blood, vol. 81:3252–3258, (1993).

Mazur, E et al, Blood 57:277–286, (1981).

McBride, L. J. and Caruthers, M. H. An investigation of several deoxynucleoside phosphoramidites. Tetrahedron Lett., 24, 245–248 (1983).

Messing, J., A multipurpose cloning system based on the single-stranded DNA bacteriophage M13. Recombinant DNA Technical Bulletin, NIH Publication No. 79–99, Vol. 2, No. 2, pp. 43–48 (1979).

Metcalf, D., Begley, C. G., Williamson, D., Nice, E. C., DeLamarter, J., Mermod J-J, Thatcher, D., Schmidt, A.: Hemopoietic responses in mice injected with purified recombinant murine GM-CSF. Exp Hematol 15:1, 1987

Metcalf, D.: The molecular control of cell division, differentiation commitment and maturation in haemopoietic cells. Nature 339:27, 1989

Metcalf, D., Nicola, N. A.: Direct proliferative actions of stem cell factor on murine bone marrow cells in vitro. Effects of combinatin with colony-stimulating factors. Proc Natl Acad Sci USA 88:6239, 1991

Metcalf, D., Hematopoietic regulators: redundancy or subtlety? Blood 82(12):3515–3523 (1993).

Murre, C. S. P. S. McCaw and D. Baltimore. Cell 56:777–783, (1989).

Murre, C. S., P. S. McCaw, H. Vassin, M. Caudy, L. Y. Jan, Y. N. Jan, C. V. Cabrera, J. N. Bushkin, S. Hauschka, A. B. Lassar, H. Weintraub and D. Baltimore, Cell 58:537–544, (1989).

Neu, H. C. and L. A. Heppel. The release of enzymes from Escherichia coli by osmotic shock and during the formation of spheroplasts. J. Biol. Chem., 240: 3685–3692 (1965).

Noguchi, M., Nakamura, Y., Russell, S. M., Ziegler, S. F., Tsang, M., Xiqing, C., Leonard, W. J.: Interleukin-2 Receptor g Chain: A Functional Component of the Interleukin-7 Receptor. Science 262:1877, Dec. 17, 1993.

Nordon, P, and Potter, M, A Macrophage-Derived Factor Required by plasmacytomas for Survival and Proliferation in Vitro, *Science* 233:566, (1986).

Obukowicz, M. G., Staten, N. R. and Krivi, G. G., Enhanced Heterologous Gene Expression in Novel rpoH Mutants of *Escherichia coli. Applied and Environmental Microbiology* 58, No. 5, p. 1511–1523 (1992).

Olins, P. O., C. S. Devine, S. H. Rangwala and K. S. Kavka, The T7 phage gene 10 leader RNA, a ribosome-binding site that dramatically enhances the expression of foreign genes in *Escherichia coli, Gene,* 73:227–235 (1988).

Olins, P. O. and S. H. Rangwala, Vector for enhanced translation of foreign genes in *Escherichia coli, Methods in Enzymology,* 185: 115–119 (1990).

Pluznik, DH and Sachs, L. Cloning of normal "mast" cells in tissue culture. *J Cell Comp Physiol* 66:319–324 (1965).

Postmus, et al., Effects of recombinant human interleukin-3 in patients with relapsed small-cell lung cancer treated with chemotherapy: a dose-finding study. *J. Clin. Oncol.,* 10:1131–1140 (1992).

Prober, J. M., G. L. Trainor, R. J. Dam, F. W. Hobbs, C. W. Robertson, R. J. Zagursky, A. J. Cocuzza, M. A. Jensen and K. Baumeister. A system for rapid DNA sequencing with fluorescent chain-terminating dideoxynucleotides. *Science* 238: 336–341 (1987).

Pu, W. T. and K. Struhl, *Nucleic Acids Research* 21:4348–4355, (1993).

Renart J., J. Reiser and G. R. Stark, Transfer of proteins from gels to diazobenzyloxymethyl-paper and detection with anti-sera: a method for studying antibody specificity and antigen structure, *Proc. Natl. Acad. Sci. USA,* 76:3116–3120 (1979).

Russell, S. M., Keegan, A. D., Harada, N., Nakamura, Y., Noguchi, M., Leland, P., Friedmann, M. C., Miyajima, A., Puri, R. K., Paul, W. E., Leonard, W. J.: Interleukin-2 Receptor g Chain: A Functional Component of the Interleukin-4 Receptor. Science 262:1880, Dec. 17, 1993.

Saiki, R. K., Schorf, S., Faloona, F., Mullis, K. B., Horn, G. T., Erlich, H. A. and Arnheim, N., Enzymatic Amplification of β-Globin Genomic Sequences and Restriction Site Analysis for Diagnosis of Sickle Cell Anemia, *Science,* 230: 1350–1354 (1985).

Sambrook, J., et al., *Molecular Cloning, A Laboratory Manual,* 2nd edition, Cold Spring Harbor Laboratory (1989).

Sancar, A., C. Stachelek, W. Konigsberg and W. D. Rupp, Sequences of the recA gene and protein, *Proc. Natl. Acad. Sci.,* 77: 2611–2615 (1980).

Sanger, F., S. Nicklen and A. R. Coulson. DNA sequencing with chain-terminating inhibitors. *Proc. Natl. Acad. Sci. U.S.A.* 74: 5463–5467 (1977).

Santoli, D., Y. Yang, S. C. Clark, B. L. Kreider, D. Caracciolo, and G. Rovera. Synergistic and antagonistic effects of recombinant human interleukin (IL-3), IL-1, granulocyte and macrophage colony-stimulating factors (G-CSF and M-CSF) on the growth of GM-CSF-dependent leukemic cell lines. *J. Immunol.* 139:348 (1987).

Schaller et al., *PROC NATL ACAD SCI USA* 72:737–741, (1975).

Sherr, C. J.: Colony-stimulating factor-1 receptor. Blood 75:1, 1990

Smith, M. In vitro mutagenesis. *Ann. Rev. Genet.,* 19:423–462 (1985).

Soberon, X., L. Covarrubias and F. Bolivar, Construction and characterization of new cloning vehicles. IV. Deletion derivatives of pBR322 and pBR325, *Gene,* 9: 211–223 (1980).

Stader, J. A. and T. J. Silhavy. Engineering Escherichia coli to secrete heterologous gene products, *Methods in Enzymology,* 185: 166–87 (1990).

Summers, M. D. and G. E. Smith. A manual of methods for Baculovirus vectors and insect cell culture procedures. *Texas Agricultural Experiment Station Bulletin No.* 1555 (1987).

Taga, T., Hibi, M., Yamasaki, K., Yasukswa, K., Matsuda, T., Hirano, T., and Kishimoto, T. Interleukin-6 triggers the association of its receptor with a possibele signal transducer, gp130. *Cell* 58(3):573–81 (1989).

Takaki, S., Tominage, A., Hitoshi, Y., Mita S., Sonada, E., Yamaguchi, N., Takatsu, K.: Molecular cloning and expression of the murine interleukin-5 receptor. *EMBO J* 9:4367, 1990

Takaki, S., Mita, S., Kitamura, T., Yonehara, S., Yamaguchi, N., Tominaga, A., Miyajima, A., and Takatsu, S., Identification of the second subunit of the murine interleukin-5 receptor: interleukin-3 receptor-like protein, AIC2B is a component of the high affinty interleukin-5 recptor. *EMBO. J.:*10(10):2833–8 (1991).

Tapscott, S. J., R. L. Davis, M. J. Thayer, P. F. Cheng, H. Weintraub and A. B. Lassar, *Science* 242:405–411, (1988).

Taylor, J. W., Ott, J. and Eckstein, F. The rapid generation of oligonucleotide-directed mutants at high frequency using phosphorothioate modified DNA. *Nucl. Acids Res.,* 13:8764–8785 (1985).

Tomer, A., Harker, L. A., and Burstein, S. A. Purification of human megakaryocytes by Fluoresence-activated cell sorting. *Blood* 70(6):1735–1742 (1987).

Treco, D.A., (1989) in *Current protocols in Molecular Biology,* Seidman et al., eds. J Wiley N.Y., unit 2.1.

Valtieri, M., D. Santoli, D. Caracciolo, B. L. Kreider, S. W. Altmann, D. J. Tweardy, I. Gemperlein, F. Mavilio, B. J. Lange and G. Rovera. Establishment and characterization of an undifferentiated human T leukemia cell line which requires granulocyte-macrophage colony stimulating factor for growth. *J. Immunol.* 138:4042 (1987).

Voet, D., W. B. Gatzer, R. A. Cox, P. Doty. Absorption spectra of the common bases. *Biopolymers* 1: 193 (1963).

Weinberg, R. A., De Ciechi, P. A., Obukowicz, M.: A chromosomal expression vector for *Escherichia coli* based on the bacteriophage Mu. Gene 126 (1993) 25–33.

Wells, J. A., Vasser, M., and Powers, D. B. Cassette mutagenesis: an effective method for generation of multiple mutants at defined sites. *Gene,* 34:315–323 (1985).

Wong, Y. Y., R. Seetharam, C. Kotts, R. A. Heeren, B. K. Klein, S. B. Braford, K. J. Mathis, B. F. Bishop, N. R. Siegel, C. E. Smith and W. C. Tacon. Expression of secreted IGF-1 in *Escherichia coli. Gene,* 68: 193–203 (1988).

Yanisch-Perron, C., J. Viera and J. Messing. Improved M13 phage cloning vectors and host strains: nucleotide sequences of the M13mp18 and pUC19 vectors. *Gene* 33: 103–119 (1985).

Yamasaki, K., Taga, T., Hirata, Y., Yawata, H., Kawanishi, Y., Seed, B., Taniguchi, T., Hirano, T., Kishimoto, T.: Cloning and expression of the human interleukin-6 (BSF-2IFN beta 2) receptor. Science 241:825, 1988

Yarden Y., Kuang, W-J., Yang-Feng, T., Coussens, L., Munemitsu, S., Dull, T. J., Chen, E., Schlesinger, J., Francke, U., Ullrich, A., Human proto-oncogene c-kit: A new cell surface receptor tyrosine kinase for an unidentified ligand. EMBO J 6:3341, 1987

Zoller, M. J. and Smith, M. Oligonucleotide-directed mutagenesis using M13-derived vectors: an efficient and general procedure for the production of point mutations in any fragment of DNA. *Nucleic Acid Research,* 10: 6487–6500 (1982).

Zoller, M. J. and Smith, M. Oligonucleotide-directed mutagenesis of DNA fragments cloned into M13 vectors. *Methods in Enzymology,* 100:468–500 (1983).

Zoller, M. J. and Smith, M. oligonucleotide-directed Mutagenesis: A simple method using two oligonucleotide primers and a single-stranded DNA template. *DNA,* 3: 479 (1984).

What is claimed is:

1. A method of treating a patient having a hematopoietic disorder comprising;

administering a therapeutically effective amount of a fusion protein comprising;

a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;

to said patient.

2. A method of treating a patient having a hematopoietic disorder comprising;

administering a therapeutically effective amount of a fusion protein comprising a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133)

hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

3. A method of treating a patient having a hematopoietic disorder comprising;

administering a therapeutically effective amount of a fusion protein comprising;

a human interleukin-3 mutant polypeptide of SEQ ID NO:1;

wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 sell proliferation and Methylcellulose assay;

to said patient.

4. A method of treating a patient having an a hematopoietic disorder comprising;

administering a therapeutically effective amount of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:1;

wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser,, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

5. The method of claim 4, wherein in said fusion protein, $R_1$ is a human interleukin-3 mutant polypeptide of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 4 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

6. The method of claim 4, wherein in said human interleukin-3 mutant sequence the amino acids which differ from the corresponding residues in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;
position 108 wherein Xaa is Arg, Ala, or Ser;
position 121 wherein Xaa is Ala, or Ile;
position 122 wherein Xaa is Gln, or Ile; and
position 123 wherein Xaa is Ala, Met or Glu.

7. A method of treating a patient having a hematopoietic disorder comprising;
administering a therapeutically effective amount of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a human interleukin-3 mutant polypeptide sequence of SEQ ID NO:4;
wherein Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 4 to about 44 of the amino acids designated by Xaa are different from the corresponding native amino acids of (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

8. The method of claim 7, wherein in said fusion protein $R_1$ is a human interleukin-3 mutant polypeptide sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

Xaa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr, Tyr or Val;

Xaa at position 73 is Leu or Ser;

Xaa at position 74 is Ala or Trp;

Xaa at position 77 is Ala or Pro;

Xaa at position 79 is Thr, Asp, or Ala;

Xaa at position 81 is His, Pro, Arg, Val, Gly, Asn, Ser or Thr;

Xaa at position 84 is His, Ile, Asn, Ala, Thr, Arg, Gln, Glu, Lys, Met, Ser, Tyr, Val or Leu;

Xaa at position 85 is Ile or Leu;

Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 4 to about 44 of the amino acids designated by Xaa are different from the corresponding amino acids of native (1–133) human interleukin-3.

9. A method of treating a patient having a hematopoietic disorder comprising;
administering a therapeutically effective amount of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a human interleukin-3 mutant polypeptide sequence of SEQ ID NO:8;
wherein;
Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;
wherein from 4 to about 44 of the amino acids designated by Xaa are different from the corresponding amino acids of native (1–133) human interleukin-3; to said patient.

10. The method of claim 2, 4, 5, 6, 7, 8, or 9 wherein in said fusion protein $R_2$ is a factor selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7; IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

11. The method according to claim 1, 2, 3, 4, 5, 6, 7, 8, or 9 wherein said hematopoietic disorder is the result of a viral infection, bacterial infection or fungal infection.

12. The method according to claim 1, 2, 3, 4, 5, 6, 7, 8, or 9 wherein said hematopoietic disorder is a result of cancer radiation therapy or chemotherapy or a bone marrow suppressive drug.

13. The method according to claim 10 wherein said hematopoietic disorder is a result of a viral infection, bacterial infection or fungal infection.

14. The method according to claim 10 wherein said hematopoietic disorder is a result of cancer radiation therapy or chemotherapy or a bone marrow suppressive drug.

15. A method of treating a patient comprising the steps of:
(i) administering to said patient an amount, effective to promote proliferation and/or differentiation of hematopoietic cells in the patient, of a fusion protein comprising a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;
(ii) removing hematopoietic cells from said patient;

(iii) administering cancer radiation therapy or chemotherapy to said patient; and
(iv) returning said hematopoietic cells to said patient.

16. A method of treating a patient comprising the steps of:
(i) administering to said patient an amount, effective to promote proliferation and/or differentiation of hematopoietic cells in the patient, of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;
$R_2$ is a factor selected from the group consisting of: a colony stimulating factor, a cytokine, a lymphokine, and interleukin and a hematopoietic growth factor; and
L is a linker capable of linking $R_1$ to $R_2$;
(ii) removing hematopoietic cells from said patient;
(iii) administering cancer radiation therapy or chemotherapy to said patient; and
(iv) returning said hematopoietic cells to said patient.

17. A method of treating a patient comprising the steps of:
(i) administering to said patient an amount, effective to promote proliferation and/or differentiation of hematopoietic cells in the patient, of a fusion protein comprising a human interleukin-3 mutant polypeptide of SEQ ID NO:1;
wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;

Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;g wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

(ii) removing hematopoietic cells from said patient;

(iii) administering cancer radiation therapy or chemotherapy to said patient; and (iv) returning said hematopoietic cells to said patient.

18. A method of treating a patient comprising the steps of:

(i) administering to said patient an amount, effective to promote proliferation and/or differentiation of hematopoietic cells in the patient, of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:1;

wherein

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, and interleukin and a hematopoietic growth factor; and L is a linker capable of linking $R_1$ to $R_2$;

(ii) removing hematopoietic cells from said patient;

(iii) administering cancer radiation therapy or chemotherapy to said patient; and (iv) returning said hematopoietic cells to said patient.

19. The method of claim 18, wherein in said fusion protein, $R_1$ is a human interleukin-3 mutant polypeptide of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 4 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

20. The method of claim 18, wherein in said human interleukin-3 mutant sequence the amino acids which differ from the corresponding residues in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu.

21. A method of treating a patient comprising the steps of:

(i) administering to said patient an amount, effective to promote proliferation and/or differentiation of hematopoietic cells in the patient, of a fusion protein comprising a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide sequence of SEQ ID NO:4;

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala,Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro,

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 4 to about 44 of the amino acids designated by Xaa are different from the corresponding native amino acids of (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

(ii) removing hematopoietic cells from said patient;

(iii) administering cancer radiation therapy or chemotherapy to said patient; and (iv) returning said hematopoietic cells to said patient.

22. The method of claim 21, wherein in said protein fusion $R_1$ is a human interleukin-3 mutant polypeptide sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 4 to about 44 of the amino acids designated by Xaa are different from the corresponding amino acids of native (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

23. A method of treating a patient comprising the steps of:

(i) administering to said patient, an amount effective to promote proliferation and/or differentiation of hematopoietic cells in the patient of a fusion protein comprising a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide sequence of SEQ ID NO:8;

wherein;

Xaa at position 4 is Asn or Ile;

Xaa at position 5 is Met, Ala or Ile;

Xaa at position 6 is Ile, Pro or Leu;

Xaa at position 9 is Ile, Ala or Leu;

Xaa at position 11 is Thr or His;

Xaa at position 15 is Gln, Arg, Val or Leu;

Xaa at position 18 is Leu, Ala, Asn or Arg;

Xaa at position 20 is Leu or Ser;

Xaa at position 23 is Phe, Pro, or Ser;

Xaa at position 24 is Asn or Ala;

Xaa at position 28 is Gly, Ala, Ser, Asp or Asn;

Xaa at position 31 is Gln, Val, or Met;

Xaa at position 32 is Asp or Ser;

Xaa at position 35 is Met, Ile, Leu or Asp;

Xaa at position 36 is Glu or Asp;

Xaa at position 37 is Asn, Arg or Ser;

Xaa at position 41 is Arg, Leu, or Thr;

Xaa at position 42 is Pro or Ser;

Xaa at position 45 is Glu or Leu;

Xaa at position 46 is Ala or Ser;

Xaa at position 48 is Asn, Val or Pro;

Xaa at position 49 is Arg or His;

Xaa at position 51 is Val or Ser;

Xaa at position 53 is Ser, Asn, His or Gly;

Xaa at position 55 is Gln or Glu;

Xaa at position 59 is Ala or Gly;

Xaa at position 62 is Ser, Ala or Pro;

Xaa at position 65 is Lys, Arg or Ser;

Xaa at position 67 is Leu, Glu, or Val;

Xaa at position 68 is Leu, Glu, Val or Trp;

Xaa at position 71 is Leu or Val;

Xaa at position 73 is Leu, Ser or Trp;

Xaa at position 74 is Ala or Trp;

Xaa at position 77 is Ala or Pro;

Xaa at position 79 is Pro or Ser;

Xaa at position 81 is His or Thr;

Xaa at position 84 is His, Ile, or Thr;

Xaa at position 86 is Lys or Arg;

Xaa at position 87 is Asp;

Xaa at position 91 is Asn or Gln;

Xaa at position 95 is Arg, Glu, Leu;

Xaa at position 98 is Thr or Gln;

Xaa at position 102 is Lys;

Xaa at position 103 is Thr or Ser;

Xaa at position 106 is Asn, Gln, or His;

Xaa at position 109 is Ala or Glu;

wherein from 4 to about 44 of the amino acids designated by Xaa are different from the corresponding amino acids of native (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

R₂ is a factor selected from the group consisting of: a colony stimulating factor, a cytokine, a lymphokine, an interleukin, and a hematopoietic growth factor; and L is a linker capable of linking R₁ to R₂;

(ii) removing hematopoietic cells from said patient;

(iii) administering cancer radiation therapy or chemotherapy to said patient; and (iv) returning said hematopoietic cells to said patient.

24. The method of claim 16, 18, 19, 20, 21, 22, or 23, wherein in said fusion protein R₂ is a factor selected from the group consisting of; GM-CSF, CSF-1, G-CSF, G-CSF (Ser¹⁷), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

25. A method of treating a side effect of cancer chemotherapy or radiation therapy in a patient comprising;
administering a therapeutically effective amount of a fusion protein comprising a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;
to said patient.

26. A method of treating a side effect of cancer chemotherapy or radiation therapy in a patient comprising;
administering a therapeutically effective amount of a fusion protein comprising; a polypeptide having a sequence selected from the group consisting of:
R₁-L-R₂, R₂-L-R₁, R₁-R₂, R₂-L-R₁, Met-Ala-R₁-L-R₂, Met-Ala-R₂-L-R₁, Met-Ala-R₁-R₂, Met-Ala-R₂-R₁, Met-R₁-L-R₂, Met-R₂-L-R₁, Met-R₁-R₂, Met-R₂-R₁, Ala-R₁-L-R₂, Ala-R₂-L-R₁, Ala-R₁-R₂ and Ala-R₂-R₁;
wherein R₁ is a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;

R₂ is a factor selected from the group consisting of: a colony stimulating factor, a cytokine, a lymphokine, an interleukin, and a hematopoietic growth factor; and L is a linker capable of linking R₁ to R₂;

to said patient.

27. A method of treating a side effect of cancer chemotherapy or radiation therapy in a patient comprising;
administering a therapeutically effective amount of a fusion protein comprising a human interleukin-3 mutant polypeptide of SEQ ID NO:1;
wherein Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Her, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu, wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;
to said patient.

28. A method of treating a side effect of cancer chemotherapy or radiation therapy in a patient comprising;
administering a therapeutically effective amount of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a human interleukin-3 mutant polypeptide of SEQ ID NO:1;
wherein Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

29. The method of claim 28, wherein in said fusion protein, $R_1$ is a human interleukin-3 mutant polypeptide of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;
Xaa at position 100 is Lys or Arg;
Xaa at position 101 is Asp;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys;
Xaa at position 120 is Asn, Pro, Leu, His, Val, or Gln;
Xaa at position 121 is Ala, Ser, Ile, Pro, or Asp;
Xaa at position 122 is Gln, Met, Trp, Phe, Pro, His, Ile, or Tyr;
Xaa at position 123 is Ala, Met, Glu, Ser, or Leu;
wherein from 4 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

30. The method of claim 28, wherein in said human interleukin-3 mutant sequence the amino acids which differ from the corresponding residues in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu.

31. A method of treating a side effect of cancer chemotherapy or radiation therapy in a patient comprising;

administering a therapeutically effective amount of a fusion protein comprising a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide sequence of SEQ ID NO:4;

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr; Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 4 to about 44 of the amino acids designated by Xaa are different from the corresponding native amino acids of (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking R1 to R2;

to said patient.

32. The method of claim 31, wherein in said fusion protein, $R_1$ is a human interleukin-3 mutant polypeptide sequence of SEQ ID NO:6;

wherein

Xaa at position 3 is Ser, Gly, Asp, or Gln;

Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys,,
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 4 to about 44 of the amino acids designated by Xaa are different from the corresponding amino acids of native (1–133) human interleukin-3.

33. A method of treating a side effect of cancer chemotherapy or radiation therapy in a patient comprising;
a administering a therapeutically effective amount of a fusion protein comprising a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a human interleukin-3 mutant polypeptide sequence of SEQ ID NO:8;
wherein;
Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;

Xaa at position 109 is Ala or Glu;
wherein from 4 to about 44 of the amino acids designated by Xaa are different from the corresponding amino acids of native (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;
to said patient.

34. The method of claim 26, 28, 29, 30, 31, 32, or 33, wherein in said fusion protein $R_2$ is a factor selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

35. A method of treating a patient having a hematopoietic disorder consisting of:
administering a therapeutically effective amount of a fusion protein consisting of a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;
$R_2$ is a factor selected from the group consisting of: a colony stimulating factor, a cytokine, a lymphokine, an interleukin, and a hematopoietic growth factor; and
L is a linker capable of linking $R_1$ to $R_2$;
to said patient.

36. A method of treating a patient having a hematopoietic disorder consisting of:
administering a therapeutically effective amount of a fusion protein consisting of a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, -$R_2$-L-$R_1$, Met-Ala-$R_1$-$R_2$, Met-Ala-$R_2$-$R_1$Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;
wherein $R_1$ is a human interleukin-3 mutant polypeptide of SEQ ID NO:1;
wherein
Xaa at position 17 is Ser, Lys, Gly, Asp, Met, Gln, or Arg;

Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln,Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, * T Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;

Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln,Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

37. The method of claim 36, wherein in said fusion protein, $R_1$ is a human interleukin-3 mutant polypeptide of SEQ ID NO:3;

wherein

Xaa at position 17 is Ser, Gly, Asp, or Gln;

Xaa at position 18 is Asn, His, or Ile;
Xaa at position 23 is Ile, Ala, Leu, or Gly;
Xaa at position 25 is Thr, His, or Gln;
Xaa at position 26 is His or Ala;
Xaa at position 29 is Gln or Asn;
Xaa at position 30 is Pro or Gly;
Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp, Ser, Ala, Asn, Ile, Leu, Met, Tyr or Arg;
Xaa at position 45 is Gln, Val, Met, Leu, Ala, Asn, Glu, or Lys;
Xaa at position 46 is Asp, Phe, Ser, Gln, Glu, His, Val or Thr;
Xaa at position 50 is Glu, Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asn, Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gln, Ala, Glu, or Arg;
Xaa at position 76 is Ser, Val, Asn, Pro, or Gly;
Xaa at position 77 is Ile or Leu;
Xaa at position 79 is Lys, Asn, Met, Arg, Ile, or Gly;
Xaa at position 80 is Asn, Gly, Glu, or Arg;
Xaa at position 82 is Leu, Gln, Trp, Arg, Asp, Asn, Glu, His, Met, Phe, Ser, Thr, Tyr or Val;
Xaa at position 87 is Leu or Ser;
Xaa at position 88 is Ala or Trp;
Xaa at position 91 is Ala or Pro;
Xaa at position 93 is Thr, Asp, or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;
Xaa at position 100 is Lys or Arg;
Xaa at position 101 is Asp;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys;
Xaa at position 120 is Asn, Pro, Leu, His, Val, or Gln;
Xaa at position 121 is Ala, Ser, Ile, Pro, or Asp;
Xaa at position 122 is Gln, Met, Trp, Phe, Pro, His, Ile, or Tyr;
Xaa at position 123 is Ala, Met, Glu, Ser, or Leu;
wherein from 4 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

38. The method of claim 36, wherein in said human interleukin-3 mutant sequence the amino acids which differ from the corresponding residues in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu.

39. A method of treating a patient having a hematopoietic disorder consisting of:

administering a therapeutically effective amount of a fusion protein consisting of a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$ , Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide sequence of SEQ ID NO:4;

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp,

Xaa Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys; or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile,Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking R1 to R2;

to said patient.

40. The method of claim 39, wherein in said fusion protein $R_1$ is a human interleukin-3 mutant polypeptide sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

Xaa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr,Tyr or Val;

Xaa at position 73 is Leu or Ser;

Xaa at position 74 is Ala or Trp;

Xaa at position 77 is Ala or Pro;

Xaa at position 79 is Thr, Asp, or Ala;

Xaa at position 81 is His, Pro, Arg, Val, Gly, Asn, Ser or Thr;

Xaa at position 84 is His, Ile, Asn, Ala, Thr, Arg, Gln, Glu, Lys, Met, Ser, Tyr, Val or Leu;

Xaa at position 85 is Ile or Leu;

Xaa at position 86 is Lys or Arg;

Xaa at position 87 is Asp;

Xaa at position 91 is Asn, Pro, Ser, Ile or Asp;

Xaa at position 94 is Arg, Ala, or Ser;

Xaa at position 95 is Arg, Thr, Glu, Leu, or Ser;

Xaa at position 98 is Thr or Gln;

Xaa at position 102 is Lys;

Xaa at position 103 is Thr, Ala, His, Phe, Tyr or Ser;

Xaa at position 106 is Asn, Pro, Leu, His, Val, or Gln;

Xaa at position 107 is Ala, Ser, Ile, Pro, or Asp;

Xaa at position 108 is Gln, Met, Trp, Phe, Pro, His, Ile, or Tyr;

Xaa at position 109 is Ala, Met, Glu, Ser, or Leu;

wherein from 4 to about 44 of the amino acids designated by Xaa are different from the corresponding amino acids of native (1–133) human interleukin-3.

41. A method of treating a patient having a hematopoietic disorder consisting of:

administering a therapeutically effective amount of a fusion protein consisting of a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide-sequence of SEQ ID NO:8;

wherein;

Xaa at position 4 is Asn or Ile;

Xaa at position 5 is Met, Ala or Ile;

Xaa at position 6 is Ile, Pro or Leu;

Xaa at position 9 is Ile, Ala or Leu;

Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;
wherein from 4 to about 44 of the amino acids designated by Xaa are different from the corresponding amino acids of native (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

42. The method of claim 35, 36, 37, 38, 39, 40 or 41, wherein in said fusion protein $R_2$ is a factor selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

43. The method according to claim 35, 36, 37, 38, 39, 40, or 41, wherein said hematopoietic disorder is a result of a viral infection, bacterial infection or fungal infection.

44. The method according to claim 35, 36, 37, 38, 39, 40, or 41, wherein said hematopoietic disorder is a result of cancer radiation therapy or chemotherapy or a bone marrow suppressive drug.

45. The method according to claim 42 wherein said hematopoietic disorder is a result of a viral infection, bacterial infection or fungal infection.

46. The method according to claim 42 wherein said a hematopoietic disorder is a result of cancer radiation therapy or chemotherapy or a bone marrow suppressive drug.

47. A method of treating a patient consisting of the steps of:
(i) administering to said patient, an amount effective to promote proliferation and/or differentiation of hematopoietic cells in the patient of a fusion protein consisting of a polypeptide having a sequence selected from the group consisting of:
$R_1$-L-$R_2$, $R_2$-L-$R_1$, $R_1$-$R_2$, $R_2$-L-R-1, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, and interleukin and a hematopoietic growth factor; and L is a linker capable of linking $R_1$ to $R_2$;

(ii) removing hematopoietic cells from said patient;
(iii) administering cancer radiation therapy or chemotherapy to said patient; and
(iv) returning said hematopoietic cells to said patient.

48. A method of treating a patient consisting of the steps of:
(i) administering to said patient, an amount effective to promote proliferation and/or differentiation of hematopoietic cells in the patient of a fusion protein to said patient consisting of a polypeptide having a sequence selected from the group consisting of:
$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-R$_1$-L-R$_2$, Met-R$_2$-L-R$_1$, Met-R$_1$-R$_2$, Met-R$_2$-R$_1$, Ala-R$_1$-L-R$_2$, Ala-R$_2$-L-R$_1$, Ala-R$_1$-R$_2$ and Ala-R$_2$-R$_1$;

wherein R$_1$ is a human interleukin-3 mutant polypeptide of SEQ ID NO:1;

wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr,Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin and a hematopoietic growth factor; and L is a linker capable of linking $R_1$ to $R_2$;

(ii) removing hematopoietic cells from said patient;

(iii) administering cancer radiation therapy or chemotherapy to said patient; and (iv) returning said hematopoietic cells to said patient.

49. The method of claim 48, wherein in said fusion protein, $R_1$ is a human interleukin-3 mutant polypeptide of SEQ ID NQ:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;g wherein from 4 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

50. The method of claim 48, wherein in said human interleukin-3 mutant sequence the amino acids which differ from the corresponding residues in native human interleukin-3 are selected from the group consisting of:

wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu.

51. A method of treating a patient consisting of the steps of:

(i) administering to said patient, an amount effective to promote proliferation and/or differentiation of hematopoietic cells in the patient of a fusion protein consisting of a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide sequence of SEQ ID NO:4;

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 4 to about 44 of the amino acids designated by Xaa are different from the corresponding native amino acids of (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

(ii) removing hematopoietic cells from said patient;

(iii) administering cancer radiation therapy or chemotherapy to said patient; and (iv) returning said hematopoietic cells to said patient.

52. The method of claim 51, wherein in said protein fusion $R_1$ is a human interleukin-3 mutant polypeptide sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 4 to about 44 of the amino acids designated by Xaa are different from the corresponding amino acids of native (1–133) human interleukin-3 and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

53. A method of treating a patient consisting of the steps of:
(i) administering to said patient, an amount effective to promote proliferation and/or differentiation of hematopoietic cells in the patient of a fusion protein consisting of a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-R I, Met-R I-$R_2$, Met-$R_2$-$R_1$, Ala-$R_1$-L-$R_2$, Ala-$R_2$-L-$R_1$, Ala-$R_1$-$R_2$ and Ala-$R_{2g}$-$R_1$;

wherein $R_1$ is a human interleukin-3 mutant polypeptide sequence of SEQ ID NO:8;

wherein;

Xaa at position 4 is Asn or Ile;

Xaa at position 5 is Met, Ala or Ile;

Xaa at position 6 is Ile, Pro or Leu;

Xaa at position 9 is Ile, Ala or Leu;

Xaa at position 11 is Thr or His;

Xaa at position 15 is Gln, Arg, Val or Leu;

Xaa at position 18 is Leu, Ala, Asn or Arg;

Xaa at position 20 is Leu or Ser;

Xaa at position 23 is Phe, Pro, or Ser;

Xaa at position 24 is Asn or Ala;

Xaa at position 28 is Gly, Ala, Ser, Asp or Asn;

Xaa at position 31 is Gln, Val, or Met;

Xaa at position 32 is Asp or Ser;

Xaa at position 35 is Met, Ile, Leu or Asp;

Xaa at position 36 is Glu or Asp;

Xaa at position 37 is Asn, Arg or Ser;

Xaa at position 41 is Arg, Leu, or Thr;

Xaa at position 42 is Pro or Ser;

Xaa at position 45 is Glu or Leu;

Xaa at position 46 is Ala or Ser;

Xaa at position 48 is Asn, Val or Pro;

Xaa at position 49 is Arg or His;

Xaa at position 51 is Val or Ser;

Xaa at position 53 is Ser, Asn, His or Gly;

Xaa at position 55 is Gln or Glu;

Xaa at position 59 is Ala or Gly;

Xaa at position 62 is Ser, Ala or Pro;

Xaa at position 65 is Lys, Arg or Ser;

Xaa at position 67 is Leu, Glu, or Val;

Xaa at position 68 is Leu, Glu, Val or Trp;

Xaa at position 71 is Leu or Val;

Xaa at position 73 is Leu, Ser or Trp;

Xaa at position 74 is Ala or Trp;

Xaa at position 77 is Ala or Pro;

Xaa at position 79 is Pro or Ser;

Xaa at position 81 is His or Thr;

Xaa at position 84 is His, Ile, or Thr;

Xaa at position 86 is Lys or Arg;

Xaa at position 87 is Asp;

Xaa at position 91 is Asn or Gln;

Xaa at position 95 is Arg, Glu, Leu;

Xaa at position 98 is Thr or Gln;

Xaa at position 102 is Lys;

Xaa at position 103 is Thr or Ser;

Xaa at position 106 is Asn, Gln, or His;

Xaa at position 109 is Ala or Glu;

wherein from 4 to about 44 of the amino acids designated by Xaa are different from the corresponding amino acids of native (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

(ii) removing hematopoietic cells from said patient;

(iii) administering cancer radiation therapy or chemotherapy to said patient; and (iv) returning said hematopoietic cells to said patient.

54. The method of claim 47, 48, 49, 50, 51, 52, 53, wherein in said fusion protein $R_2$ is a factor selected from the group consisting of; GM-CSF, CSF-1, G-CSF, G-CSF ($Ser^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

55. A method of treating a side effect of cancer chemotherapy or radiation therapy in a patient consisting of;

administering a therapeutically effective amount of a fusion protein consisting of; a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, provided that the residues corresponding to positions 101 or 116 are not Ala or Val, respectively; wherein said modified sequence optionally 9 further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified human interleukin-3 (hIL-3) amino acid sequence has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

56. A method of treating a side effect of cancer chemotherapy or radiation therapy in a patient consisting of administering a therapeutically effective amount of a fusion protein consisting of a polypeptide having a sequence selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:1;

wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly,Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly; Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val,Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg,Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

R$_2$ is a factor selected from the group consisting of: a colony stimulating factor, a cytokine, a lymphokine, an interleukin, and a hematopoietic growth factor; and L is a linker capable of linking R$_1$ to R$_2$;

to said patient.

57. The method of claim 56, wherein in said fusion protein, R$_1$ is a human interleukin-3 mutant polypeptide of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, His, Pro, or Asp;

Xaa at position 122 is Gln, Met, Trp, Phe, Pro, His, Ile, or Tyr;

Xaa at position 123 is Ala, Met, Glu, Ser, or Leu;

wherein from 4 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said human interleukin-3 mutant polypeptide; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

58. The method of claim 56, wherein in said human interleukin-3 mutant sequence the amino acids which differ from the corresponding residues in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu.

59. A method of treating a side effect of cancer chemotherapy or radiation therapy in a patient consisting of administering a therapeutically effective amount of a fusion protein consisting of a polypeptide having a sequence selected from the group consisting of:

R$_1$-L-R$_2$, R$_2$-L-R$_1$, R$_1$-R$_2$, R$_2$-L-R$_1$, Met-Ala-R$_1$-L-R$_2$, Met-Ala-R$_2$-L-R$_1$, Met-Ala-R$_1$-R$_2$, Met-Ala-R$_2$-R$_1$, Met-R$_1$-L-R$_2$, Met-R$_2$-L-R$_1$, Met-R$_1$-R$_2$, Met-R$_2$-R$_1$, Ala-R$_1$-L-R$_2$, Ala-R$_2$-L-R$_1$, Ala-R$_1$-R$_2$ and Ala-R$_2$-R$_1$;

wherein R$_1$ is a human interleukin-3 mutant polypeptide sequence of SEQ ID NO:4;

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys; Xaa at position 109 is Ala, Met, Glu, His, Ser, Pro, Tyr, or Leu;

wherein from 4 to about 44 of the amino acids designated by Xaa are different from the corresponding native amino acids of (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

$R_2$ is a factor selected from the group consisting of: a colony stimulating factor, a cytokine, a lymphokine, an interleukin, and a hematopoietic growth factor; and L is a linker capable of linking $R_1$ to $R_2$;

to said patient.

60. The method of claim 59, wherein in said fusion protein, $R_1$ is a human interleukin-3 mutant polypeptide sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

aa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr, Tyr or Val;

Xaa at position 73 is Leu or Ser;

Xaa at position 74 is Ala or Trp;

Xaa at position 77 is Ala or Pro;

Xaa at position 79 is Thr, Asp, or Ala;

Xaa at position 81 is His, Pro, Arg, Val, Gly, Asn, Ser or Thr;

Xaa at position 84 is His, Ile, Asn, Ala, Thr, Arg, Gln, Glu, Lys, Met, Ser, Tyr, Val or Leu;

Xaa at position 85 is Ile or Leu;

Xaa at position 86 is Lys or Arg;

Xaa at position 87 is Asp;

Xaa at position 91 is Asn, Pro, Ser, Ile or Asp;

Xaa at position 94 is Arg, Ala, or Ser;

Xaa at position 95 is Arg, Thr, Glu, Leu, or Ser;

Xaa at position 98 is Thr or Gln;

Xaa at position 102 is Lys;

Xaa at position 103 is Thr, Ala, His, Phe, Tyr or Ser;

Xaa at position 106 is Asn, Pro, Leu, His, Val, or Gln;

Xaa at position 107 is Ala, Ser, Ile, Pro, or Asp;

Xaa at position 108 is Gln, Met, Trp, Phe, Pro, His, Ile, or Tyr;

Xaa at position 109 is Ala, Met, Glu, Ser, or Leu;

wherein from 4 to about 44 of the amino acids designated by Xaa are different from the corresponding amino acids of native (1–133) human-interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay.

61. A method of treating a side effect of cancer chemotherapy radiation therapy in a patient consisting of administering a therapeutically effective amount of a fusion protein consisting of a polypeptide having a sequence selected from the group consisting of:

R$_1$-L-R$_2$, R$_2$-L-R$_1$, R$_1$-R$_2$, R$_2$-L-R$_1$, Met-Ala-R$_1$-L-R$_2$, Met-Ala-R$_2$-L-R$_1$, Met-Ala-R$_1$-R$_2$, Met-Ala-R$_2$-R$_1$, Met-R$_1$-L-R$_2$, Met-R$_2$-L-R$_1$, Met-R$_1$-R$_2$, Met-R$_2$-R$_1$, Ala-R$_1$-L-R$_2$, Ala-R$_2$-L-R$_1$, Ala-R$_1$-R$_2$ and Ala-R$_2$-R$_1$;

wherein R$_1$ is a human interleukin-3-mutant polypeptide sequence of SEQ ID NO:8;

wherein;

Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln; Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;

wherein from 4 to about 44 of the amino acids designated by Xaa are different from the corresponding amino acids of native (1–133) human interleukin-3; and wherein a polypeptide having only said human interleukin-3 mutant polypeptide has at least three times greater activity than native human interleukin-3, in at least one assay selected from the group consisting of: AML cell proliferation, TF-1 cell proliferation and Methylcellulose assay;

R$_2$ is a factor selected from the group consisting of: a colony stimulating factor, a cytokine, a lymphokine, an interleukin, and a hematopoietic growth factor; and L is a linker capable of linking R1 to R2;

to said patient.

62. The method of claims 55, 56, 57, 58, 59, 60, or 61 wherein in said fusion protein R$_2$ is a factor selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

* * * * *

SEQUENCE LISTING (1) GENERAL INFORMATION:

(iii) NUMBER OF SEQUENCES: 197

(2) INFORMATION FOR SEQ ID NO:1:

(i) SEQUENCE CHARACTERISTICS:
       (A) LENGTH: 133 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Met- may or may not precede the
           amino acid in position 1"

(ix) FEATURE:
       (A) NAME/KEY: Modified-site
       (B) LOCATION: 17
       (D) OTHER INFORMATION: /note= "Xaa at position 17 is Ser,
           Lys, Gly, Asp, Met, Gln, or Arg"

(ix) FEATURE:
       (A) NAME/KEY: Modified-site
       (B) LOCATION: 18
       (D) OTHER INFORMATION: /note= "Xaa at position 18 is Asn,
           His, Leu, Ile, Phe, Arg, or Gln"

(ix) FEATURE:
       (A) NAME/KEY: Modified-site
       (B) LOCATION: 19
       (D) OTHER INFORMATION: /note= "Xaa at positiion 19 is Met,
           Phe, Ile, Arg, Gly, Ala, or Cys"

(ix) FEATURE:
       (A) NAME/KEY: Modified-site
       (B) LOCATION: 20
       (D) OTHER INFORMATION: /note= "Xaa at position 20 is Ile,
           Cys, Gln, Glu, Arg, Pro, or Ala"

(ix) FEATURE:
       (A) NAME/KEY: Modified-site
       (B) LOCATION: 21
       (D) OTHER INFORMATION: /note= "Xaa at position 21 is Asp,
           Phe, Lys, Arg, Ala, Gly, Glu, Gln, Asn, Thr, Ser,
           or Val"

(ix) FEATURE:
       (A) NAME/KEY: Modified-site
       (B) LOCATION: 22
       (D) OTHER INFORMATION: /note= "Xaa at position 22 is Glu,
           Trp, Pro, Ser, Ala, His, Asp, Asn, Gln, Leu, Val,
           or Gly"

(ix) FEATURE:
       (A) NAME/KEY: Modified-site
       (B) LOCATION: 23
       (D) OTHER INFORMATION: /note= "Xaa at position 23 is Ile,

```
                Val, Ala, Leu, Gly, Trp, Lys, Phe, Ser, or
                Arg"

(ix) FEATURE:
        (A) NAME/KEY: Modified-site
        (B) LOCATION: 24
        (D) OTHER INFORMATION: /note= "Xaa at position 24 is Ile,
                Gly, Val, Arg, Ser, Phe, or Leu"

(ix) FEATURE:
        (A) NAME/KEY: Modified-site
        (B) LOCATION: 25
        (D) OTHER INFORMATION: /note= "Xaa at position 25 is Thr,
                His, Gly, Gln, Arg, Pro, or Ala"

(ix) FEATURE:
        (A) NAME/KEY: Modified-site
        (B) LOCATION: 26
        (D) OTHER INFORMATION: /note= "Xaa at position 26 is His,
                Thr, Phe, Gly, Arg, Ala, or Trp"

(ix) FEATURE:
        (A) NAME/KEY: Modified-site
        (B) LOCATION: 27
        (D) OTHER INFORMATION: /note= "Xaa at position 27 is Leu,
                Gly, Arg, Thr, Ser, or Ala"

(ix) FEATURE:
        (A) NAME/KEY: Modified-site
        (B) LOCATION: 28
        (D) OTHER INFORMATION: /note= "Xaa at position 28 is Lys,
                Arg, Leu, Gln, Gly, Pro, Val, or Trp"

(ix) FEATURE:
        (A) NAME/KEY: Modified-site
        (B) LOCATION: 29
        (D) OTHER INFORMATION: /note= "Xaa at position 29 is Gln,
                Asn, Leu, Pro, Arg, or Val"

(ix) FEATURE:
        (A) NAME/KEY: Modified-site
        (B) LOCATION: 30
        (D) OTHER INFORMATION: /note= "Xaa at position 30 is Pro,
                His, Thr, Gly, Asp, Gln, Ser, Leu, or Lys"

(ix) FEATURE:
        (A) NAME/KEY: Modified-site
        (B) LOCATION: 31
        (D) OTHER INFORMATION: /note= "Xaa at position 31 is Pro,
                Asp, Gly, Ala, Arg, Leu, or Gln"

(ix) FEATURE:
        (A) NAME/KEY: Modified-site
        (B) LOCATION: 32
        (D) OTHER INFORMATION: /note= "Xaa at position 32 is Leu,
                Val, Arg, Gln, Asn, Gly, Ala, or Glu"

(ix) FEATURE:
        (A) NAME/KEY: Modified-site
        (B) LOCATION: 33
        (D) OTHER INFORMATION: /note= "Xaa at position 33 is Pro,
                Leu, Gln, Ala, Thr, or Glu"

(ix) FEATURE:
        (A) NAME/KEY: Modified-site
        (B) LOCATION: 34
        (D) OTHER INFORMATION: /note= "Xaa at position 34 is Leu,
                Val, Gly, Ser, Lys, Glu, Gln, Thr, Arg, Ala, Phe,
                Ile, or Met"

(ix) FEATURE:
        (A) NAME/KEY: Modified-site
        (B) LOCATION: 35
        (D) OTHER INFORMATION: /note= "Xaa at position 35 is Leu,
                Ala, Gly, Asn, Pro, Gln, or Val"

(ix) FEATURE:
        (A) NAME/KEY: Modified-site
        (B) LOCATION: 36
```

(D) OTHER INFORMATION: /note= "Xaa at position 36 is Asp, Leu, or Val"

(ix) FEATURE:
    (A) NAME/KEY: Modified-site
    (B) LOCATION: 37
    (D) OTHER INFORMATION: /note= "Xaa at position 37 is Phe, Ser, Pro, Trp, or Ile"

(ix) FEATURE:
    (A) NAME/KEY: Modified-site
    (B) LOCATION: 38
    (D) OTHER INFORMATION: /note= "Xaa at position 38 is Asn, or Ala"

(ix) FEATURE:
    (A) NAME/KEY: Modified-site
    (B) LOCATION: 40
    (D) OTHER INFORMATION: /note= "Xaa at position 40 is Leu, Trp, or Arg"

(ix) FEATURE:
    (A) NAME/KEY: Modified-site
    (B) LOCATION: 41
    (D) OTHER INFORMATION: /note= "Xaa at position 41 is Asn, Cys, Arg, Leu, His, Met, or Pro"

(ix) FEATURE:
    (A) NAME/KEY: Modified-site
    (B) LOCATION: 42
    (D) OTHER INFORMATION: /note= "Xaa at position 42 is Gly, Asp, Ser, Cys, Asn, Lys, Thr, Leu, Val, Glu, Phe, Tyr, Ile, Met, or Ala"

(ix) FEATURE:
    (A) NAME/KEY: Modified-site
    (B) LOCATION: 43
    (D) OTHER INFORMATION: /note= "Xaa at position 43 is Glu, Asn, Tyr, Leu, Phe, Asp, Ala, Cys, Gln, Arg, Thr, Gly, or Ser"

(ix) FEATURE:
    (A) NAME/KEY: Modified-site
    (B) LOCATION: 44
    (D) OTHER INFORMATION: /note= "Xaa at position 44 is Asp, Ser, Leu, Arg, Lys, Thr, Met, Trp, Glu, Asn, Gln, Ala, or Pro"

(ix) FEATURE:
    (A) NAME/KEY: Modified-site
    (B) LOCATION: 45
    (D) OTHER INFORMATION: /note= "Xaa at position 45 is Gln, Pro, Phe, Val, Met, Leu, Thr, Lys, Trp, Asp, Asn, Arg, Ser, Ala, Ile, Glu, or His"

(ix) FEATURE:
    (A) NAME/KEY: Modified-site
    (B) LOCATION: 46
    (D) OTHER INFORMATION: /note= "Xaa at position 46 is Asp, Phe, Ser, Thr, Cys, Glu, Asn, Gln, Lys, His, Ala, Tyr, Ile, Val, or Gly"

(ix) FEATURE:
    (A) NAME/KEY: Modified-site
    (B) LOCATION: 47
    (D) OTHER INFORMATION: /note= "Xaa at position 47 is Ile, Gly, Val, Ser, Arg, Pro, or His"

(ix) FEATURE:
    (A) NAME/KEY: Modified-site
    (B) LOCATION: 48
    (D) OTHER INFORMATION: /note= "Xaa at position 48 is Leu, Ser, Cys, Arg, Ile, His, Phe, Glu, Lys, Thr, Ala, Met, Val, or Asn"

(ix) FEATURE:
    (A) NAME/KEY: Modified-site
    (B) LOCATION: 49
    (D) OTHER INFORMATION: /note= "Xaa at position 49 is Met,

```
                Arg, Ala, Gly, Pro, Asn, His, or Asp"

(ix) FEATURE:
    (A) NAME/KEY: Modified-site
    (B) LOCATION: 50
    (D) OTHER INFORMATION: /note= "Xaa at position 50 is Glu,
        Leu, Thr, Asp, Tyr, Lys, Asn, Ser, Ala, Ile, Val, His,
        Phe, Met, or Gln"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 52
    (D) OTHER INFORMATION: /note= "Xaa at position 52 is Asn,
        His, Arg, Leu, Gly, Ser, or Thr"

(ix) FEATURE:
    (A) NAME/KEY: Modified-site
    (B) LOCATION: 53
    (D) OTHER INFORMATION: /note= "Xaa at position 53 is
        Leu, Thr, Ala, Gly, Glu, Pro, Lys, Ser, or Met"

(ix) FEATURE:
    (A) NAME/KEY: Modified-site
    (B) LOCATION: 54
    (D) OTHER INFORMATION: /note= "Xaa at position 54 is Arg,
        Asp, Ile, Ser, Val, Thr, Gln, Asn, Lys, His, Ala,
        or Leu"

(ix) FEATURE:
    (A) NAME/KEY: Modified-site
    (B) LOCATION: 55
    (D) OTHER INFORMATION: /note= "Xaa at position 55 is Arg,
        Thr, Val, Ser, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Glu, Arg, His, Thr, Ala, Tyr,
        Phe, Leu, Val, or Lys"

(ix) FEATURE:
    (A) NAME/KEY: Modified-site
    (B) LOCATION: 57
    (D) OTHER INFORMATION: /note= "Xaa at position 57 is Asn
        or Gly"

(ix) FEATURE:
    (A) NAME/KEY: Modified-site
    (B) LOCATION: 58
    (D) OTHER INFORMATION: /note= "Xaa at position 58 is Leu,
        Ser, Asp, Arg, Gln, Val, or Cys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, Pro, or Arg"

(ix) FEATURE:
    (A) NAME/KEY: Modified-site
    (B) LOCATION: 60
    (D) OTHER INFORMATION: /note= "Xaa at position 60 is Ala,
        Ser, Pro, Tyr, Asn, or Thr"

(ix) FEATURE:
    (A) NAME/KEY: Modified-site
    (B) LOCATION: 61
    (D) OTHER INFORMATION: /note= "Xaa at position 61 is Phe,
        Asn, Glu, Pro, Lys, Arg, or Ser"

(ix) FEATURE:
    (A) NAME/KEY: Modified-site
```

```
          (B) LOCATION: 62
          (D) OTHER INFORMATION: /note= "Xaa at position 62 is Asn,
              His, Val, Arg, Pro, Thr, Asp, or Ile"

(ix) FEATURE:
          (A) NAME/KEY: Modified-site
          (B) LOCATION: 63
          (D) OTHER INFORMATION: /note= "Xaa at position 63 is Arg,
              Tyr, Trp, Lys, Ser, His, Pro, or Val"

(ix) FEATURE:
          (A) NAME/KEY: Modified-site
          (B) LOCATION: 64
          (D) OTHER INFORMATION: /note= "Xaa at position 64 is Ala,
              Asn, Pro, Ser, or Lys"

(ix) FEATURE:
          (A) NAME/KEY: Modified-site
          (B) LOCATION: 65
          (D) OTHER INFORMATION: /note= "Xaa at position 65 is Val,
              Thr, Pro, His, Leu, Phe, or Ser"

(ix) FEATURE:
          (A) NAME/KEY: Modified-site
          (B) LOCATION: 66
          (D) OTHER INFORMATION: /note= "Xaa at position 66 is Lys,
              Ile, Arg, Val, Asn, Glu, or Ser"

(ix) FEATURE:
          (A) NAME/KEY: Modified-site
          (B) LOCATION: 67
          (D) OTHER INFORMATION: /note= "Xaa at position 67 is Ser,
              Ala, Phe, Val, Gly, Asn, Ile, Pro, or His"

(ix) FEATURE:
          (A) NAME/KEY: Modified-site
          (B) LOCATION: 68
          (D) OTHER INFORMATION: /note= "Xaa at position 68 is Leu,
              Val, Trp, Ser, Ile, Phe, Thr, or His"

(ix) FEATURE:
          (A) NAME/KEY: Modified-site
          (B) LOCATION: 69
          (D) OTHER INFORMATION: /note= "Xaa at position 69 is Gln,
              Ala, Pro, Thr, Glu, Arg, Trp, Gly, or Leu"

(ix) FEATURE:
          (A) NAME/KEY: Modified-site
          (B) LOCATION: 70
          (D) OTHER INFORMATION: /note= "Xaa at position 70 is Asn,
              Leu, Val, Trp, Pro, or Ala"

(ix) FEATURE:
          (A) NAME/KEY: Modified-site
          (B) LOCATION: 71
          (D) OTHER INFORMATION: /note= "Xaa at position 71 is
              Ala, Met, Leu, Pro, Arg, Glu, Thr, Gln, Trp,
              or Asn"

(ix) FEATURE:
          (A) NAME/KEY: Modified-site
          (B) LOCATION: 72
          (D) OTHER INFORMATION: /note= "Xaa at position 72 is Ser,
              Glu, Met, Ala, His, Asn, Arg, or Asp"

(ix) FEATURE:
          (A) NAME/KEY: Modified-site
          (B) LOCATION: 73
          (D) OTHER INFORMATION: /note= "Xaa at position 73 is Ala,
              Glu, Asp, Leu, Ser, Gly, Thr, or Arg"

(ix) FEATURE:
          (A) NAME/KEY: Modified-site
          (B) LOCATION: 74
          (D) OTHER INFORMATION: /note= "Xaa at position 74 is Ile,
              Met, Thr, Pro, Arg, Gly, or Ala"

(ix) FEATURE:
          (A) NAME/KEY: Modified-site
```

```
        (B) LOCATION: 75
        (D) OTHER INFORMATION: /note= "Xaa at position 75 is
            Glu, Lys, Gly, Asp, Pro, Trp, Arg, Ser, Gln,
            or Leu"

(ix) FEATURE:
        (A) NAME/KEY: Modified-site
        (B) LOCATION: 76
        (D) OTHER INFORMATION: /note= "Xaa at position 76 is Ser,
            Val, Ala, Asn, Trp, Glu, Pro, Gly, or Asp"

(ix) FEATURE:
        (A) NAME/KEY: Modified-site
        (B) LOCATION: 77
        (D) OTHER INFORMATION: /note= "Xaa at position 77 is Ile,
            Ser, Arg, Thr, or Leu"

(ix) FEATURE:
        (A) NAME/KEY: Modified-site
        (B) LOCATION: 78
        (D) OTHER INFORMATION: /note= "Xaa at position 78 is Leu,
            Ala, Ser, Glu, Phe, Gly, or Arg"

(ix) FEATURE:
        (A) NAME/KEY: Modified-site
        (B) LOCATION: 79
        (D) OTHER INFORMATION: /note= "Xaa at position 79 is Lys, Thr,
            Asn, Met, Arg, Ile, Gly, or Asp"

(ix) FEATURE:
        (A) NAME/KEY: Modified-site
        (B) LOCATION: 80
        (D) OTHER INFORMATION: /note= "Xaa at position 80 is Asn,
            Trp, Val, Gly, Thr, Leu, Glu, or Arg"

(ix) FEATURE:
        (A) NAME/KEY: Modified-site
        (B) LOCATION: 81
        (D) OTHER INFORMATION: /note= "Xaa at position 81 is Leu,
            Gln, Gly, Ala, Trp, Arg, Val, or Lys"

(ix) FEATURE:
        (A) NAME/KEY: Modified-site
        (B) LOCATION: 82
        (D) OTHER INFORMATION: /note= "Xaa at position 82 is Leu,
            Gln, Lys, Trp, Arg, Asp, Glu, Asn, His, Thr, Ser, Ala,
            Tyr, Phe, Ile, Met, or Val"

(ix) FEATURE:
        (A) NAME/KEY: Modified-site
        (B) LOCATION: 83
        (D) OTHER INFORMATION: /note= "Xaa at position 83 is Pro,
            Ala, Thr, Trp, Arg, or Met"

(ix) FEATURE:
        (A) NAME/KEY: Modified-site
        (B) LOCATION: 84
        (D) OTHER INFORMATION: /note= "Xaa at position 84 is Cys,
            Glu, Gly, Arg, Met, or Val"

(ix) FEATURE:
        (A) NAME/KEY: Modified-site
        (B) LOCATION: 85
        (D) OTHER INFORMATION: /note= "Xaa at position 85 is Leu,
            Asn, Val, or Gln"

(ix) FEATURE:
        (A) NAME/KEY: Modified-site
        (B) LOCATION: 86
        (D) OTHER INFORMATION: /note= "Xaa at position 86 is Pro,
            Cys, Arg, Ala, or Lys"

(ix) FEATURE:
        (A) NAME/KEY: Modified-site
        (B) LOCATION: 87
        (D) OTHER INFORMATION: /note= "Xaa at position 87 is Leu,
            Ser, Trp, or Gly"

(ix) FEATURE:
```

```
          (A) NAME/KEY: Modified-site
          (B) LOCATION: 88
          (D) OTHER INFORMATION: /note= "Xaa at position 88 is Ala,
              Lys, Arg, Val, or Trp"

(ix) FEATURE:
          (A) NAME/KEY: Modified-site
          (B) LOCATION: 89
          (D) OTHER INFORMATION: /note= "Xaa at position 89 is Thr,
              Asp, Cys, Leu, Val, Glu, His, Asn, or Ser"

(ix) FEATURE:
          (A) NAME/KEY: Modified-site
          (B) LOCATION: 90
          (D) OTHER INFORMATION: /note= "Xaa at position 90 is Ala,
              Pro, Ser, Thr, Gly, Asp, Ile, or Met"

(ix) FEATURE:
          (A) NAME/KEY: Modified-site
          (B) LOCATION: 91
          (D) OTHER INFORMATION: /note= "Xaa at position 91 is Ala,
              Pro, Ser, Thr, Phe, Leu, Asp, or His"

(ix) FEATURE:
          (A) NAME/KEY: Modified-site
          (B) LOCATION: 92
          (D) OTHER INFORMATION: /note= "Xaa at position 92 is Pro,
              Phe, Arg, Ser, Lys, His, Ala, Gly, Ile, or Leu"

(ix) FEATURE:
          (A) NAME/KEY: Modified-site
          (B) LOCATION: 93
          (D) OTHER INFORMATION: /note= "Xaa at position 93 is Thr,
              Asp, Ser, Asn, Pro, Ala, Leu, or Arg"

(ix) FEATURE:
          (A) NAME/KEY: Modified-site
          (B) LOCATION: 94
          (D) OTHER INFORMATION: /note= "Xaa at position 94 is Arg,
              Ile, Ser, Glu, Leu, Val, Gln, Lys, His, Ala, or Pro"

(ix) FEATURE:
          (A) NAME/KEY: Modified-site
          (B) LOCATION: 95
          (D) OTHER INFORMATION: /note= "Xaa at position 95 is His,
              Gln, Pro, Arg, Val, Leu, Gly, Thr, Asn, Lys, Ser, Ala,
              Trp, Phe, Ile, or Tyr"

(ix) FEATURE:
          (A) NAME/KEY: Modified-site
          (B) LOCATION: 96
          (D) OTHER INFORMATION: /note= "Xaa at position 96 is Pro,
              Lys, Tyr, Gly, Ile, or Thr"

(ix) FEATURE:
          (A) NAME/KEY: Modified-site
          (B) LOCATION: 97
          (D) OTHER INFORMATION: /note= "Xaa at position 97 is Ile,
              Val, Lys, Ala, or Asn"

(ix) FEATURE:
          (A) NAME/KEY: Modified-site
          (B) LOCATION: 98
          (D) OTHER INFORMATION: /note= "Xaa at position 98 is His,
              Ile, Asn, Leu, Asp, Ala, Thr, Glu, Gln, Ser, Phe, Met,
              Val, Lys, Arg, Tyr, or Pro"

(ix) FEATURE:
          (A) NAME/KEY: Modified-site
          (B) LOCATION: 99
          (D) OTHER INFORMATION: /note= "Xaa at position 99 is Ile,
              Leu, Arg, Asp, Val, Pro, Gln, Gly, Ser, Phe,
              or His"

(ix) FEATURE:
          (A) NAME/KEY: Modified-site
          (B) LOCATION: 100
          (D) OTHER INFORMATION: /note= "Xaa at position 100 is
              Lys, Tyr, Leu, His, Arg, Ile, Ser, Gln, or Pro"
```

```
(ix) FEATURE:
     (A) NAME/KEY: Modified-site
     (B) LOCATION: 101
     (D) OTHER INFORMATION: /note= "Xaa at position 101 is
         Asp, Pro, Met, Lys, His, Thr, Val, Tyr, Glu, Asn, Ser,
         Ala, Gly, Ile, Leu, or Gln"

(ix) FEATURE:
     (A) NAME/KEY: Modified-site
     (B) LOCATION: 102
     (D) OTHER INFORMATION: /note= "Xaa at position 102 is Gly,
         Leu, Glu, Lys, Ser, Tyr, or Pro"

(ix) FEATURE:
     (A) NAME/KEY: Modified-site
     (B) LOCATION: 103
     (D) OTHER INFORMATION: /note= "Xaa at position 103 is Asp,
         or Ser"

(ix) FEATURE:
     (A) NAME/KEY: Modified-site
     (B) LOCATION: 104
     (D) OTHER INFORMATION: /note= "Xaa at position 104 is
         Trp, Val, Cys, Tyr, Thr, Met, Pro, Leu, Gln, Lys, Ala,
         Phe, or Gly"

(ix) FEATURE:
     (A) NAME/KEY: Modified-site
     (B) LOCATION: 105
     (D) OTHER INFORMATION: /note= "Xaa at position 105 is
         Asn, Pro, Ala, Phe, Ser, Trp, Gln, Tyr, Leu, Lys, Ile,
         Asp, or His"

(ix) FEATURE:
     (A) NAME/KEY: Modified-site
     (B) LOCATION: 106
     (D) OTHER INFORMATION: /note= "Xaa at position 106 is Glu,
         Ser, Ala, Lys, Thr, Ile, Gly, or Pro"

(ix) FEATURE:
     (A) NAME/KEY: Modified-site
     (B) LOCATION: 108
     (D) OTHER INFORMATION: /note= "Xaa at position 108 is Arg,
         Lys, Asp, Leu, Thr, Ile, Gln, His, Ser, Ala, or Pro"

(ix) FEATURE:
     (A) NAME/KEY: Modified-site
     (B) LOCATION: 109
     (D) OTHER INFORMATION: /note= "Xaa at position 109 is Arg,
         Thr, Pro, Glu, Tyr, Leu, Ser, or Gly"

(ix) FEATURE:
     (A) NAME/KEY: Modified-site
     (B) LOCATION: 110
     (D) OTHER INFORMATION: /note= "Xaa at position 110 is Lys,
         Ala, Asn, Thr, Leu, Arg, Gln, His, Glu, Ser, Ala,
         or Trp"

(ix) FEATURE:
     (A) NAME/KEY: Modified-site
     (B) LOCATION: 111
     (D) OTHER INFORMATION: /note= "Xaa at position 111 is Leu,
         Ile, Arg, Asp, or Met"

(ix) FEATURE:
     (A) NAME/KEY: Modified-site
     (B) LOCATION: 112
     (D) OTHER INFORMATION: /note= "Xaa at position 112 is Thr,
         Val, Gln, Tyr, Glu, His, Ser, or Phe"

(ix) FEATURE:
     (A) NAME/KEY: Modified-site
     (B) LOCATION: 113
     (D) OTHER INFORMATION: /note= "Xaa at position 113 is Phe,
         Ser, Cys, His, Gly, Trp, Tyr, Asp, Lys, Leu, Ile, Val,
         or Asn"

(ix) FEATURE:
```

(A) NAME/KEY: Modified-site
         (B) LOCATION: 114
         (D) OTHER INFORMATION: /note= "Xaa at position 114 is Tyr,
             Cys, His, Ser, Trp, Arg, or Leu"

(ix) FEATURE:
         (A) NAME/KEY: Modified-site
         (B) LOCATION: 115
         (D) OTHER INFORMATION: /note= "Xaa at position 115 is
             Leu, Asn, Val, Pro, Arg, Ala, His, Thr, Trp, or
             Met"

(ix) FEATURE:
         (A) NAME/KEY: Modified-site
         (B) LOCATION: 116
         (D) OTHER INFORMATION: /note= "Xaa at position 116 is Lys,
             Leu, Pro, Thr, Met, Asp, Val, Glu, Arg, Trp, Ser,
             Asn, His, Ala, Tyr, Phe, Gln, or Ile"

(ix) FEATURE:
         (A) NAME/KEY: Modified-site
         (B) LOCATION: 117
         (D) OTHER INFORMATION: /note= "Xaa at position 117 is Thr,
             Ser, Asn, Ile, Trp, Lys, or Pro"

(ix) FEATURE:
         (A) NAME/KEY: Modified-site
         (B) LOCATION: 118
         (D) OTHER INFORMATION: /note= "Xaa at position 118 is Leu,
             Ser, Pro, Ala, Glu, Cys, Asp, or Tyr"

(ix) FEATURE:
         (A) NAME/KEY: Modified-site
         (B) LOCATION: 119
         (D) OTHER INFORMATION: /note= "Xaa at position 119 is Glu,
             Ser, Lys, Pro, Leu, Thr, Tyr, or Arg"

(ix) FEATURE:
         (A) NAME/KEY: Modified-site
         (B) LOCATION: 120
         (D) OTHER INFORMATION: /note= "Xaa at position 120 is Asn,
             Ala, Pro, Leu, His, Val, or Gln"

(ix) FEATURE:
         (A) NAME/KEY: Modified-site
         (B) LOCATION: 121
         (D) OTHER INFORMATION: /note= "Xaa at position 121 is Ala,
             Ser, Ile, Asn, Pro, Lys, Asp, or Gly"

(ix) FEATURE:
         (A) NAME/KEY: Modified-site
         (B) LOCATION: 122
         (D) OTHER INFORMATION: /note= "Xaa at position 122 is
             Gln, Ser, Met, Trp, Arg, Phe, Pro, His, Ile, Tyr,
             or  Cys"

(ix) FEATURE:
         (A) NAME/KEY: Modified-site
         (B) LOCATION: 123
         (D) OTHER INFORMATION: /note= "Xaa at position 123 is Ala,
             Met, Glu, His, Ser, Pro, Tyr, or Leu"

(xi) SEQUENCE DESCRIPTION: SEQ ID NO:1:

Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Asn Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

```
Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Phe Xaa Xaa Xaa Xaa Xaa
        100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
    130
```

(2) INFORMATION FOR SEQ ID NO:2:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, Met, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 19
        (D) OTHER INFORMATION: /note= "Xaa at position 19 is Met
            or Ile"

(ix) FEATURE:
        (A) NAME/KEY: Modified-site
        (B) LOCATION: 21
        (D) OTHER INFORMATION: /note="Xaa at position 21 is Asp
            or Glu"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 24
        (D) OTHER INFORMATION: /note= "Xaa at position 24 is Ile,
            Val, or Leu"

(ix) FEATURE:
        (A) NAME/KEY: Modified-site
        (B) LOCATION: 25
        (D) OTHER INFORMATION: /note= "Xaa at position 25 is Thr,
            His, Gln, or Ala"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29

(D) OTHER INFORMATION: /note= "Xaa at position 29 is Gln,
                Asn, or Val"

(ix) FEATURE:
            (A) NAME/KEY: Modified-site
            (B) LOCATION: 30
            (D) OTHER INFORMATION: /note= "Xaa at position 30 is Pro,
                Gly, or Gln"

(ix) FEATURE:
            (A) NAME/KEY: Modified-site
            (B) LOCATION: 31
            (D) OTHER INFORMATION: /note= "Xaa at position 31 is Pro,
                Asp, Gly, or Gln"

(ix) FEATURE:
            (A) NAME/KEY: Modified-site
            (B) LOCATION: 32
            (D) OTHER INFORMATION: /note= "Xaa at position 32 is Leu,
                Arg, Gln, Asn, Gly, Ala, or Glu"

(ix) FEATURE:
            (A) NAME/KEY: Modified-site
            (B) LOCATION: 33
            (D) OTHER INFORMATION: /note= "Xaa at position 33 is Pro
                or Glu"

(ix) FEATURE:
            (A) NAME/KEY: Modified-site
            (B) LOCATION: 34
            (D) OTHER INFORMATION: /note= "Xaa at position 34 is Leu,
                Val, Gly, Ser, Lys, Ala, Arg, Gln, Glu, Ile, Phe,
                Thr, or Met"

(ix) FEATURE:
            (A) NAME/KEY: Modified-site
            (B) LOCATION: 35
            (D) OTHER INFORMATION: /note= "Xaa at position 35 is Leu,
                Ala, Asn, Pro, Gln, or Val"

(ix) FEATURE:
            (A) NAME/KEY: Modified-site
            (B) LOCATION: 37
            (D) OTHER INFORMATION: /note= "Xaa at position 37 is Phe,
                Ser, Pro, or Trp"

(ix) FEATURE:
            (A) NAME/KEY: Modified-site
            (B) LOCATION: 38
            (D) OTHER INFORMATION: /note="Xaa at position 38 is Asn
                or Ala"

(ix) FEATURE:
            (A) NAME/KEY: Modified-site
            (B) LOCATION: 42
            (D) OTHER INFORMATION: /note= "Xaa at position 42 is Gly,
                Asp, Ser, Cys, Ala, Asn, Ile, Leu, Met, Tyr,
                or Arg"

(ix) FEATURE:
            (A) NAME/KEY: Modified-site
            (B) LOCATION: 44
            (D) OTHER INFORMATION: /note="Xaa at position 44 is Asp
                or Glu"

(ix) FEATURE:
            (A) NAME/KEY: Modified-site
            (B) LOCATION: 45
            (D) OTHER INFORMATION: /note= "Xaa at position 45 is Gln,
                Val, Met, Leu, Thr, Ala, Asn, Glu, Ser, or Lys"

(ix) FEATURE:
            (A) NAME/KEY: Modified-site
            (B) LOCATION: 46
            (D) OTHER INFORMATION: /note= "Xaa at position 46 is Asp,
                Phe, Ser, Thr, Ala, Asn, Gln, Glu, His, Ile,
                Lys, Tyr, Val, or Cys"

(ix) FEATURE:

(A) NAME/KEY: Modified-site
            (B) LOCATION: 50
            (D) OTHER INFORMATION: /note= "Xaa at position 50 is Glu,
                Ala, Asn, Ser, or Asp"

(ix) FEATURE:
            (A) NAME/KEY: Modified-site
            (B) LOCATION: 51
            (D) OTHER INFORMATION: /note= "Xaa at position 51 is Asn,
                Arg, Met, Pro, Ser, Thr, or His"

(ix) FEATURE:
            (A) NAME/KEY: Modified-site
            (B) LOCATION: 54
            (D) OTHER INFORMATION: /note="Xaa at position 54 is Arg
                or Ala"

(ix) FEATURE:
            (A) NAME/KEY: Modified-site
            (B) LOCATION: 55
            (D) OTHER INFORMATION: /note= "Xaa at position 55 is Arg,
                Thr, Val, Leu, or Gly"

(ix) FEATURE:
            (A) NAME/KEY: Modified-site
            (B) LOCATION: 56
            (D) OTHER INFORMATION: /note= "Xaa at position 56 is Pro,
                Gly, Ser, Gln, Ala, Arg, Asn, Glu, Leu, Thr, Val,
                or Lys"

(ix) FEATURE:
            (A) NAME/KEY: Modified-site
            (B) LOCATION: 60
            (D) OTHER INFORMATION: /note= "Xaa at position 60 is Ala
                or Ser"

(ix) FEATURE:
            (A) NAME/KEY: Modified-site
            (B) LOCATION: 62
            (D) OTHER INFORMATION: /note= "Xaa at position 62 is Asn,
                Pro, Thr, or Ile"

(ix) FEATURE:
            (A) NAME/KEY: Modified-site
            (B) LOCATION: 63
            (D) OTHER INFORMATION: /note= "Xaa at position 63 is Arg
                or Lys"

(ix) FEATURE:
            (A) NAME/KEY: Modified-site
            (B) LOCATION: 64
            (D) OTHER INFORMATION: /note= "Xaa at position 64 is Ala
                or Asn"

(ix) FEATURE:
            (A) NAME/KEY: Modified-site
            (B) LOCATION: 65
            (D) OTHER INFORMATION: /note= "Xaa at position 65 is Val
                or Thr"

(ix) FEATURE:
            (A) NAME/KEY: Modified-site
            (B) LOCATION: 66
            (D) OTHER INFORMATION: /note= "Xaa at position 66 is Lys
                or Arg"

(ix) FEATURE:
            (A) NAME/KEY: Modified-site
            (B) LOCATION: 67
            (D) OTHER INFORMATION: /note= "Xaa at position 67 is Ser
                Phe or His"

(ix) FEATURE:
            (A) NAME/KEY: Modified-site
            (B) LOCATION: 68
            (D) OTHER INFORMATION: /note= "Xaa at position 68 is Leu,
                Ile, Phe, or His"

(ix) FEATURE:

```
           (A) NAME/KEY: Modified-site
           (B) LOCATION: 69
           (D) OTHER INFORMATION: /note= "Xaa at position 69 is Gln,
               Ala, Pro, Thr, Glu, Arg, or Gly"

(ix) FEATURE:
           (A) NAME/KEY: Modified-site
           (B) LOCATION: 71
           (D) OTHER INFORMATION: /note= "Xaa at position 71 is Ala,
               Pro, or Arg"

(ix) FEATURE:
           (A) NAME/KEY: Modified-site
           (B) LOCATION: 72
           (D) OTHER INFORMATION: /note= "Xaa at position 72 is Ser,
               Glu, Arg, or Asp"

(ix) FEATURE:
           (A) NAME/KEY: Modified-site
           (B) LOCATION: 73
           (D) OTHER INFORMATION: /note= "Xaa at position 73 is Ala
               or Leu"

(ix) FEATURE:
           (A) NAME/KEY: Modified-site
           (B) LOCATION: 76
           (D) OTHER INFORMATION: /note= "Xaa at position 76 is Ser,
               Val, Ala, Asn, Glu, Pro, or Gly"

(ix) FEATURE:
           (A) NAME/KEY: Modified-site
           (B) LOCATION: 77
           (D) OTHER INFORMATION: /note= "Xaa at position 77 is Ile
               or Leu"

(ix) FEATURE:
           (A) NAME/KEY: Modified-site
           (B) LOCATION: 79
           (D) OTHER INFORMATION: /note= "Xaa at position 79 is
               Lys, Thr, Gly, Asn, Met, Arg, Ile, Gly, or Asp"

(ix) FEATURE:
           (A) NAME/KEY: Modified-site
           (B) LOCATION: 80
           (D) OTHER INFORMATION: /note= "Xaa at position 80 is Asn,
               Gly, Glu, or Arg"

(ix) FEATURE:
           (A) NAME/KEY: Modified-site
           (B) LOCATION: 82
           (D) OTHER INFORMATION: /note= "Xaa at position 82 is Leu,
               Gln, Trp, Arg, Asp, Ala, Asn, Glu, His, Ile,
               Met, Phe, Ser, Thr, Tyr, or Val"

(ix) FEATURE:
           (A) NAME/KEY: Modified-site
           (B) LOCATION: 83
           (D) OTHER INFORMATION: /note= "Xaa at position 83 is Pro
               or Thr"

(ix) FEATURE:
           (A) NAME/KEY: Modified-site
           (B) LOCATION: 85
           (D) OTHER INFORMATION: /note= "Xaa at position 85 is Leu
               or Val"

(ix) FEATURE:
           (A) NAME/KEY: Modified-site
           (B) LOCATION: 87
           (D) OTHER INFORMATION: /note= "Xaa at position 87 is Leu
               or Ser"

(ix) FEATURE:
           (A) NAME/KEY: Modified-site
           (B) LOCATION: 88
           (D) OTHER INFORMATION: /note= "Xaa at position 88 is Ala
               or Trp"

(ix) FEATURE:
```

-continued

```
          (A) NAME/KEY: Modified-site
          (B) LOCATION: 91
          (D) OTHER INFORMATION: /note= "Xaa at position 91 is Ala
              or Pro"

(ix) FEATURE:
          (A) NAME/KEY: Modified-site
          (B) LOCATION: 93
          (D) OTHER INFORMATION: /note= "Xaa at position 93 is Thr,
              Asp, Ser, Pro, Ala, Leu, or Arg"

(ix) FEATURE:
          (A) NAME/KEY: Modified-site
          (B) LOCATION: 95
          (D) OTHER INFORMATION: /note= "Xaa at position 95 is His,
              Pro, Arg, Val, Leu, Gly, Asn, Phe, Ser, or Thr"

(ix) FEATURE:
          (A) NAME/KEY: Modified-site
          (B) LOCATION: 96
          (D) OTHER INFORMATION: /note= "Xaa at position 96 is Pro
              or Tyr"

(ix) FEATURE:
          (A) NAME/KEY: Modified-site
          (B) LOCATION: 97
          (D) OTHER INFORMATION: /note= "Xaa at position 97 is Ile
              or Val"

(ix) FEATURE:
          (A) NAME/KEY: Modified-site
          (B) LOCATION: 98
          (D) OTHER INFORMATION: /note= "Xaa at position 98 is His,
              Ile, Asn, Leu, Ala, Thr, Arg, Gln, Lys,
              Met, Ser, Tyr, Val, or Pro"

(ix) FEATURE:
          (A) NAME/KEY: Modified-site
          (B) LOCATION: 99
          (D) OTHER INFORMATION: /note= "Xaa at position 99 is Ile,
              Leu, or Val"

(ix) FEATURE:
          (A) NAME/KEY: Modified-site
          (B) LOCATION: 100
          (D) OTHER INFORMATION: /note= "Xaa at position 100 is Lys,
              Arg, Ile, Gln, Pro, or Ser"

(ix) FEATURE:
          (A) NAME/KEY: Modified-site
          (B) LOCATION: 101
          (D) OTHER INFORMATION: /note= "Xaa at position 101 is Asp,
              Pro, Met, Lys, Thr, His, Asn, Ile, Leu, or Tyr"

(ix) FEATURE:
          (A) NAME/KEY: Modified-site
          (B) LOCATION: 104
          (D) OTHER INFORMATION: /note= "Xaa at position 104 is Trp
              or Leu"

(ix) FEATURE:
          (A) NAME/KEY: Modified-site
          (B) LOCATION: 105
          (D) OTHER INFORMATION: /note= "Xaa at position 105 is
              Asn, Pro, Ala, Ser, Trp, Gln, Tyr, Leu, Lys, Ile,
              Asp, or His"

(ix) FEATURE:
          (A) NAME/KEY: Modified-site
          (B) LOCATION: 106
          (D) OTHER INFORMATION: /note= "Xaa at position 106 is Glu
              or Gly"

(ix) FEATURE:
          (A) NAME/KEY: Modified-site
          (B) LOCATION: 108
          (D) OTHER INFORMATION: /note="Xaa at position 108 is Arg,
              Ala, or Ser"
```

-continued

```
    (ix) FEATURE:
         (A) NAME/KEY: Modified-site
         (B) LOCATION: 109
         (D) OTHER INFORMATION: /note= "Xaa at position 109 is Arg,
             Thr, Glu, Leu, or Ser"

(ix) FEATURE:
         (A) NAME/KEY: Modified-site
         (B) LOCATION: 112
         (D) OTHER INFORMATION: /note= "Xaa at position 112 is Thr,
             Val, or Gln"

(ix) FEATURE:
         (A) NAME/KEY: Modified-site
         (B) LOCATION: 114
         (D) OTHER INFORMATION: /note= "Xaa at position 114 is Tyr
             or Trp"

(ix) FEATURE:
         (A) NAME/KEY: Modified-site
         (B) LOCATION: 115
         (D) OTHER INFORMATION: /note= "Xaa at position 115 is Leu
             or Ala"

(ix) FEATURE:
         (A) NAME/KEY: Modified-site
         (B) LOCATION: 116
         (D) OTHER INFORMATION: /note= "Xaa at position 116 is Lys,
             Thr, Val, Trp, Ser, Ala, His, Met, Phe, Tyr, or Ile"

(ix) FEATURE:
         (A) NAME/KEY: Modified-site
         (B) LOCATION: 117
         (D) OTHER INFORMATION: /note= "Xaa at position 117 is Thr
             or Ser"

(ix) FEATURE:
         (A) NAME/KEY: Modified-site
         (B) LOCATION: 120
         (D) OTHER INFORMATION: /note= "Xaa at position 120 is Asn,
             Pro, Leu, His, Val, or Gln"

(ix) FEATURE:
         (A) NAME/KEY: Modified-site
         (B) LOCATION: 121
         (D) OTHER INFORMATION: /note= "Xaa at position 121 is Ala,
             Ser, Ile, Asn, Pro, Asp, or Gly"

(ix) FEATURE:
         (A) NAME/KEY: Modified-site
         (B) LOCATION: 122
         (D) OTHER INFORMATION: /note= "Xaa at position 122 is
             Gln, Ser, Met, Trp, Arg, Phe, Pro, His, Ile, Tyr,
             or Cys"

(ix) FEATURE:
         (A) NAME/KEY: Modified-site
         (B) LOCATION: 123
         (D) OTHER INFORMATION: /note= "Xaa at position 123 is Ala,
             Met, Glu, His, Ser, Pro, Tyr, or Leu"

(xi) SEQUENCE DESCRIPTION: SEQ ID NO:2:

Ala Pro Met Thr Gln Thr Thr Ser Leu Lys Thr Ser Trp Val Asn Cys
1               5                  10                  15

Xaa Xaa Xaa Ile Xaa Glu Xaa Xaa Xaa Xaa Leu Lys Xaa Xaa Xaa Xaa
            20                  25                  30

Xaa Xaa Xaa Asp Xaa Xaa Asn Leu Asn Xaa Glu Xaa Xaa Xaa Ile Leu
        35                  40                  45

Met Xaa Xaa Asn Leu Xaa Xaa Xaa Asn Leu Glu Xaa Phe Xaa Xaa Xaa
    50                  55                  60

Xaa Xaa Xaa Xaa Xaa Asn Xaa Xaa Xaa Ile Glu Xaa Xaa Leu Xaa Xaa
65                  70                  75                  80

Leu Xaa Xaa Cys Xaa Pro Xaa Xaa Thr Ala Xaa Pro Xaa Arg Xaa Xaa
```

```
                    85                  90                  95
Xaa Xaa Xaa Xaa Xaa Gly Asp Xaa Xaa Xaa Phe Xaa Xaa Lys Leu Xaa
                100                 105                 110

Phe Xaa Xaa Xaa Xaa Leu Glu Xaa Xaa Xaa Xaa Gln Gln Thr Thr Leu
            115                 120                 125

Ser Leu Ala Ile Phe
    130
```

(2) INFORMATION FOR SEQ ID NO:3:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 25
        (D) OTHER INFORMATION: /note= "Xaa at position 25 is Thr,
            His, or Gln"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note="Xaa at position 29 is Gln
            or Asn"

(ix) FEATURE:
        (A) NAME/KEY: Modified-site
        (B) LOCATION: 30
        (D) OTHER INFORMATION: /note= "Xaa at position 30 is Pro
            or Gly"

(ix) FEATURE:
        (A) NAME/KEY: Modified-site
        (B) LOCATION: 32
        (D) OTHER INFORMATION: /note= "Xaa at position 32 is Leu,
            Arg, Asn, or Ala"

(ix) FEATURE:
        (A) NAME/KEY: Modified-site
        (B) LOCATION: 34
        (D) OTHER INFORMATION: /note= "Xaa at position 34 is Leu,

```
            Val, Ser, Ala, Arg, Gln, Glu, Ile, Phe, Thr, or Met"

(ix) FEATURE:
     (A) NAME/KEY: Modified-site
     (B) LOCATION: 35
     (D) OTHER INFORMATION: /note= "Xaa at position 35 is Leu,
         Ala, Asn, or Pro"

(ix) FEATURE:
     (A) NAME/KEY: Modified-site
     (B) LOCATION: 38
     (D) OTHER INFORMATION: /note= "Xaa at position 38 is Asn
         or Ala"

(ix) FEATURE:
     (A) NAME/KEY: Modified-site
     (B) LOCATION: 42
     (D) OTHER INFORMATION: /note= "Xaa at position 42 is Gly,
         Asp, Ser, Ala, Asn, Ile, Leu, Met, Tyr, or Arg"

(ix) FEATURE:
     (A) NAME/KEY: Modified-site
     (B) LOCATION: 45
     (D) OTHER INFORMATION: /note= "Xaa at position 45 is Gln,
         Val, Met, Leu, Ala, Asn, Glu, or Lys"

(ix) FEATURE:
     (A) NAME/KEY: Modified-site
     (B) LOCATION: 46
     (D) OTHER INFORMATION: /note= "Xaa at position 46 is Asp,
         Phe, Ser, Gln, Glu, His, Val, or Thr"

(ix) FEATURE:
     (A) NAME/KEY: Modified-site
     (B) LOCATION: 50
     (D) OTHER INFORMATION: /note= "Xaa at position 50 is Glu,
         Asn, Ser, or Asp"

(ix) FEATURE:
     (A) NAME/KEY: Modified-site
     (B) LOCATION: 51
     (D) OTHER INFORMATION: /note= "Xaa at position 51 is Asn,
         Arg, Pro, Thr, or His"

(ix) FEATURE:
     (A) NAME/KEY: Modified-site
     (B) LOCATION: 55
     (D) OTHER INFORMATION: /note= "Xaa at position 55 is Arg,
         Leu, or Gly"

(ix) FEATURE:
     (A) NAME/KEY: Modified-site
     (B) LOCATION: 56
     (D) OTHER INFORMATION: /note= "Xaa at position 56 is Pro,
         Gly, Ser, Ala, Asn, Val, Leu, or Gln"

(ix) FEATURE:
     (A) NAME/KEY: Modified-site
     (B) LOCATION: 62
     (D) OTHER INFORMATION: /note= "Xaa at position 62 is Asn,
         Pro, or Thr"

(ix) FEATURE:
     (A) NAME/KEY: Modified-site
     (B) LOCATION: 64
     (D) OTHER INFORMATION: /note= "Xaa at position 64 is Ala
         or Asn"

(ix) FEATURE:
     (A) NAME/KEY: Modified-site
     (B) LOCATION: 65
     (D) OTHER INFORMATION: /note= "Xaa at position 65 is Val
         or Thr"

(ix) FEATURE:
     (A) NAME/KEY: Modified-site
     (B) LOCATION: 67
     (D) OTHER INFORMATION: /note= "Xaa at position 67 is Ser
         or Phe"
```

-continued

```
(ix) FEATURE:
     (A) NAME/KEY: Modified-site
     (B) LOCATION: 68
     (D) OTHER INFORMATION: /note= "Xaa at position 68 is Leu
         or Phe"

(ix) FEATURE:
     (A) NAME/KEY: Modified-site
     (B) LOCATION: 69
     (D) OTHER INFORMATION: /note= "Xaa at position 69 is Gln,
         Ala, Glu, or Arg"

(ix) FEATURE:
     (A) NAME/KEY: Modified-site
     (B) LOCATION: 76
     (D) OTHER INFORMATION: /note= "Xaa at position 76 is Ser,
         Val, Asn, Pro, or Gly"

(ix) FEATURE:
     (A) NAME/KEY: Modified-site
     (B) LOCATION: 77
     (D) OTHER INFORMATION: /note= "Xaa at position 77 is Ile
         or Leu"

(ix) FEATURE:
     (A) NAME/KEY: Modified-site
     (B) LOCATION: 79
     (D) OTHER INFORMATION: /note= "Xaa at position 79 is Lys,
         Asn, Met, Arg, Ile, or Gly"

(ix) FEATURE:
     (A) NAME/KEY: Modified-site
     (B) LOCATION: 80
     (D) OTHER INFORMATION: /note= "Xaa at position 80 is Asn,
         Gly, Glu, or Arg"

(ix) FEATURE:
     (A) NAME/KEY: Modified-site
     (B) LOCATION: 82
     (D) OTHER INFORMATION: /note= "Xaa at position 82 is Leu,
         Gln, Trp, Arg, Asp, Asn, Glu, His, Met, Phe, Ser,
         Thr, Tyr, or Val"

(ix) FEATURE:
     (A) NAME/KEY: Modified-site
     (B) LOCATION: 87
     (D) OTHER INFORMATION: /note= "Xaa at position 87 is Leu
         or Ser"

(ix) FEATURE:
     (A) NAME/KEY: Modified-site
     (B) LOCATION: 88
     (D) OTHER INFORMATION: /note= "Xaa at position 88 is Ala
         or Trp"

(ix) FEATURE:
     (A) NAME/KEY: Modified-site
     (B) LOCATION: 91
     (D) OTHER INFORMATION: /note= "Xaa at position 91 is Ala
         or Pro"

(ix) FEATURE:
     (A) NAME/KEY: Modified-site
     (B) LOCATION: 93
     (D) OTHER INFORMATION: /note= "Xaa at position 93 is Thr,
         Asp, or Ala"

(ix) FEATURE:
     (A) NAME/KEY: Modified-site
     (B) LOCATION: 95
     (D) OTHER INFORMATION: /note= "Xaa at position 95 is His,
         Pro, Arg, Val, Gly, Asn, Ser, or Thr"

(ix) FEATURE:
     (A) NAME/KEY: Modified-site
     (B) LOCATION: 98
     (D) OTHER INFORMATION: /note= "Xaa at position 98 is His,
         Ile, Asn, Ala, Thr, Gln, Glu, Lys, Met, Ser, Tyr,
```

Val, or Leu"

(ix) FEATURE:
    (A) NAME/KEY: Modified-site
    (B) LOCATION: 99
    (D) OTHER INFORMATION: /note= "Xaa at position 99 is Ile
        or Leu"

(ix) FEATURE:
    (A) NAME/KEY: Modified-site
    (B) LOCATION: 100
    (D) OTHER INFORMATION: /note= "Xaa at position 100 is Lys
        or Arg"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, Thr, His, Asn, Ile, Leu, or Tyr"

(ix) FEATURE:
    (A) NAME/KEY: Modified-site
    (B) LOCATION: 105
    (D) OTHER INFORMATION: /note= "Xaa at position 105 is Asn,
        Pro, Ser, Ile, or Asp"

(ix) FEATURE:
    (A) NAME/KEY: Modified-site
    (B) LOCATION: 108
    (D) OTHER INFORMATION: /note= "Xaa at position 108 is Arg,
        Ala, or Ser"

(ix) FEATURE:
    (A) NAME/KEY: Modified-site
    (B) LOCATION: 109
    (D) OTHER INFORMATION: /note= "Xaa at position 109 is Arg,
        Thr, Glu, Leu, or Ser"

(ix) FEATURE:
    (A) NAME/KEY: Modified-site
    (B) LOCATION: 112
    (D) OTHER INFORMATION: /note= "Xaa at position 112 is Thr
        or Gln"

(ix) FEATURE:
    (A) NAME/KEY: Modified-site
    (B) LOCATION: 116
    (D) OTHER INFORMATION: /note= "Xaa at position 116 is Lys,
        Val, Trp, Ala, His, Phe, Tyr, or Ile"

(ix) FEATURE:
    (A) NAME/KEY: Modified-site
    (B) LOCATION: 117
    (D) OTHER INFORMATION: /note= "Xaa at position 117 is Thr
        or Ser"

(ix) FEATURE:
    (A) NAME/KEY: Modified-site
    (B) LOCATION: 120
    (D) OTHER INFORMATION: /note= "Xaa at position 120 is Asn,
        Pro, Leu, His, Val, or Gln"

(ix) FEATURE:
    (A) NAME/KEY: Modified-site
    (B) LOCATION: 121
    (D) OTHER INFORMATION: /note= "Xaa at position 121 is Ala,
        Ser, Ile, Pro, or Asp"

(ix) FEATURE:
    (A) NAME/KEY: Modified-site
    (B) LOCATION: 122
    (D) OTHER INFORMATION: /note= "Xaa at position 122 is Gln,
        Met, Trp, Phe, Pro, His, Ile, or Tyr"

(ix) FEATURE:
    (A) NAME/KEY: Modified-site
    (B) LOCATION: 123
    (D) OTHER INFORMATION: /note= "Xaa at position 123 is Ala,
        Met, Glu, Ser, or Leu"

(xi) SEQUENCE DESCRIPTION: SEQ ID NO:3:

Ala Pro Met Thr Gln Thr Thr Ser Leu Lys Thr Ser Trp Val Asn Cys
1               5                   10                  15

Xaa Xaa Met Ile Asp Glu Xaa Ile Xaa Xaa Leu Lys Xaa Xaa Pro Xaa
            20                  25                  30

Pro Xaa Xaa Asp Phe Xaa Asn Leu Asn Xaa Glu Asp Xaa Xaa Ile Leu
        35                  40                  45

Met Xaa Xaa Asn Leu Arg Xaa Xaa Asn Leu Glu Ala Phe Xaa Arg Xaa
    50                  55                  60

Xaa Lys Xaa Xaa Xaa Asn Ala Ser Ala Ile Glu Xaa Xaa Leu Xaa Xaa
65                  70                  75                  80

Leu Xaa Pro Cys Leu Pro Xaa Xaa Thr Ala Xaa Pro Xaa Arg Xaa Pro
            85                  90                  95

Ile Xaa Xaa Xaa Xaa Gly Asp Trp Xaa Glu Phe Xaa Xaa Lys Leu Xaa
            100                 105                 110

Phe Tyr Leu Xaa Xaa Leu Glu Xaa Xaa Xaa Xaa Gln Gln Thr Thr Leu
        115                 120                 125

Ser Leu Ala Ile Phe
    130

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

(ix) FEATURE:
        (A) NAME/KEY: Modified-site
        (B) LOCATION: 6
        (D) OTHER INFORMATION: /note= "Xaa at position 6 is Ile,
            Cys, Gln, Glu, Arg, Pro, or Ala"

(ix) FEATURE:
        (A) NAME/KEY: Modified-site
        (B) LOCATION: 7
        (D) OTHER INFORMATION: /note= "Xaa at position 7 is Asp,
            Phe, Lys, Arg, Ala, Gly, Glu, Gln, Asn, Thr, Ser,
            or Val"

(ix) FEATURE:
        (A) NAME/KEY: Modified-site (B) LOCATION: 8
        (D) OTHER INFORMATION: /note= "Xaa at position 8 is Glu,
            Trp, Pro, Ser, Ala, His, Asp, Asn, Gln, Leu, Val,
            or Gly"

(ix) FEATURE:
        (A) NAME/KEY: Modified-site
        (B) LOCATION: 9
        (D) OTHER INFORMATION: /note= "Xaa at position 9 is
            Ile, Val, Ala, Leu, Gly, Trp, Lys, Phe, Leu, Ser
            or Arg"

(ix) FEATURE:
        (A) NAME/KEY: Modified-site
        (B) LOCATION: 10
        (D) OTHER INFORMATION: /note= "Xaa at position 10 is Ile,
            Gly, Val, Arg, Ser, Phe, or Leu"

(ix) FEATURE:
        (A) NAME/KEY: Modified-site
        (B) LOCATION: 11
        (D) OTHER INFORMATION: /note= "Xaa at position 11 is Thr,
            His, Gly, Gln, Arg, Pro, or Ala"

(ix) FEATURE:
        (A) NAME/KEY: Modified-site
        (B) LOCATION: 12
        (D) OTHER INFORMATION: /note= "Xaa at position 12 is His,
            Thr, Phe, Gly, Arg, Ala, or Trp"

(ix) FEATURE:
        (A) NAME/KEY: Modified-site
        (B) LOCATION: 13
        (D) OTHER INFORMATION: /note= "Xaa at position 13 is Leu,
            Gly, Arg, Thr, Ser, or Ala"

(ix) FEATURE:
        (A) NAME/KEY: Modified-site
        (B) LOCATION: 14
        (D) OTHER INFORMATION: /note= "Xaa at position 14 is Lys,
            Arg, Leu, Gln, Gly, Pro, Val, or Trp"

(ix) FEATURE:
        (A) NAME/KEY: Modified-site
        (B) LOCATION: 15
        (D) OTHER INFORMATION: /note= "Xaa at position 15 is Gln,
            Asn, Leu, Pro, Arg, or Val"

(ix) FEATURE:
        (A) NAME/KEY: Modified-site
        (B) LOCATION: 16
        (D) OTHER INFORMATION: /note= "Xaa at position 16 is Pro,
            His, Thr, Gly, Asp, Gln, Ser, Leu, or Lys"

(ix) FEATURE:
        (A) NAME/KEY: Modified-site
        (B) LOCATION: 17
        (D) OTHER INFORMATION: /note= "Xaa at position 17 is Pro,
            Asp, Gly, Ala, Arg, Leu, or Gln"

(ix) FEATURE:
        (A) NAME/KEY: Modified-site
        (B) LOCATION: 18
        (D) OTHER INFORMATION: /note= "Xaa at position 18 is Leu,
            Val, Arg, Gln, Asn, Gly, Ala, or Glu"

(ix) FEATURE:
        (A) NAME/KEY: Modified-site
        (B) LOCATION: 19
        (D) OTHER INFORMATION: /note= "Xaa at position 19 is Pro,
            Leu, Gln, Ala, Thr, or Glu"

(ix) FEATURE:
        (A) NAME/KEY: Modified-site
        (B) LOCATION: 20
        (D) OTHER INFORMATION: /note= "Xaa at position 20 is Leu,
            Val, Gly, Ser, Lys, Glu, Gln, Thr, Arg, Ala, Phe,
            Ile, or Met"

```
(ix) FEATURE:
    (A) NAME/KEY: Modified-site
    (B) LOCATION: 21
    (D) OTHER INFORMATION: /note= "Xaa at position 21 is Leu,
        Ala, Gly, Asn, Pro, Gln, or Val"

(ix) FEATURE:
    (A) NAME/KEY: Modified-site
    (B) LOCATION: 22
    (D) OTHER INFORMATION: /note= "Xaa at position 22 is Asp,
        Leu, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, Trp, or Ile"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 26
    (D) OTHER INFORMATION: /note= "Xaa at position 26 is Leu,
        Trp, or Arg"

(ix) FEATURE:
    (A) NAME/KEY: Modified-site
    (B) LOCATION: 27
    (D) OTHER INFORMATION: /note= "Xaa at position 27 is Asn,
        Cys, Arg, Leu, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Lys, Asn, Thr, Leu, Val, Glu,
        Phe, Tyr, Ile, or Met"

(ix) FEATURE:
    (A) NAME/KEY: Modified-site
    (B) LOCATION: 29
    (D) OTHER INFORMATION: /note= "Xaa at position 29 is Glu,
        Asn, Tyr, Leu, Phe, Asp, Ala, Cys, Gln, Arg, Thr,
        Gly, or Ser"

(ix) FEATURE:
    (A) NAME/KEY: Modified-site
    (B) LOCATION: 30
    (D) OTHER INFORMATION: /note= "Xaa at position 30 is Asp,
        Ser, Leu, Arg, Lys, Thr, Met, Trp, Glu, Asn, Gln,
        Ala, or Pro"

(ix) FEATURE:
    (A) NAME/KEY: Modified-site
    (B) LOCATION: 31
    (D) OTHER INFORMATION: /note= "Xaa at position 31 is Gln,
        Pro, Phe, Val, Met, Leu, Thr, Lys, Asp, Asn, Arg,
        Ser, Ala, Ile, Glu, His, or Trp"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Cys, Glu, Asn, Gln, Lys, His, Ala,
        Tyr, Ile, Val, or Gly"

(ix) FEATURE:
    (A) NAME/KEY: Modified-site
    (B) LOCATION: 33
    (D) OTHER INFORMATION: /note= "Xaa at position 33 is Ile,
        Gly, Val, Ser, Arg, Pro, or His"

(ix) FEATURE:
    (A) NAME/KEY: Modified-site
```

```
        (B) LOCATION: 34
        (D) OTHER INFORMATION: /note= "Xaa at position 34 is Leu,
            Ser, Cys, Arg, Ile, His, Phe, Glu, Lys, Thr, Ala,
            Met, Val, or Asn"

(ix) FEATURE:
        (A) NAME/KEY: Modified-site
        (B) LOCATION: 35
        (D) OTHER INFORMATION: /note= "Xaa at position 35 is Met,
            Arg, Ala, Gly, Pro, Asn, His, or Asp"

(ix) FEATURE:
        (A) NAME/KEY: Modified-site
        (B) LOCATION: 36
        (D) OTHER INFORMATION: /note= "Xaa at position 36 is Glu,
            Leu, Thr, Asp, Tyr, Lys, Asn, Ser, Ala, Ile, Val,
            His, Phe, Met, or Gln"

(ix) FEATURE:
        (A) NAME/KEY: Modified-site
        (B) LOCATION: 37
        (D) OTHER INFORMATION: /note= "Xaa at position 37 is Asn,
            Arg, Met, Pro, Ser, Thr, or His"

(ix) FEATURE:
        (A) NAME/KEY: Modified-site
        (B) LOCATION: 38
        (D) OTHER INFORMATION: /note= "Xaa at position 38 is Asn,
            His, Arg, Leu, Gly, Ser, or Thr"

(ix) FEATURE:
        (A) NAME/KEY: Modified-site
        (B) LOCATION: 39
        (D) OTHER INFORMATION: /note= "Xaa at position 39 is
            Leu, Thr, Ala, Gly, Glu, Pro, Lys, Ser, or Met"

(ix) FEATURE:
        (A) NAME/KEY: Modified-site
        (B) LOCATION: 40
        (D) OTHER INFORMATION: /note= "Xaa at position 40 is Arg,
            Asp, Ile, Ser, Val, Thr, Gln, Asn, Lys, His,
            Ala, or Leu"

(ix) FEATURE:
        (A) NAME/KEY: Modified-site
        (B) LOCATION: 41
        (D) OTHER INFORMATION: /note= "Xaa at position 41 is Arg,
            Thr, Val, Ser, Leu, or Gly"

(ix) FEATURE:
        (A) NAME/KEY: Modified-site
        (B) LOCATION: 42
        (D) OTHER INFORMATION: /note= "Xaa at position 42 is Pro,
            Gly, Cys, Ser, Gln, Glu, Arg, His, Thr, Ala, Tyr,
            Phe, Leu, Val, or Lys"

(ix) FEATURE:
        (A) NAME/KEY: Modified-site
        (B) LOCATION: 43
        (D) OTHER INFORMATION: /note= "Xaa at position 43 is Asn
            or Gly"

(ix) FEATURE:
        (A) NAME/KEY: Modified-site
        (B) LOCATION: 44
        (D) OTHER INFORMATION: /note= "Xaa at position 44 is Leu,
            Ser, Asp, Arg, Gln, Val, or Cys"

(ix) FEATURE:
        (A) NAME/KEY: Modified-site
        (B) LOCATION: 45
        (D) OTHER INFORMATION: /note= "Xaa at position 45 is Glu,
            Tyr, His, Leu, Pro, or Arg"

(ix) FEATURE:
        (A) NAME/KEY: Modified-site
        (B) LOCATION: 46
        (D) OTHER INFORMATION: /note= "Xaa at position 46 is Ala,
            Ser, Pro, Tyr, Asn, or Thr"
```

```
(ix) FEATURE:
    (A) NAME/KEY: Modified-site
    (B) LOCATION: 47
    (D) OTHER INFORMATION: /note= "Xaa at position 47 is Phe,
        Asn, Glu, Pro, Lys, Arg, or Ser"

(ix) FEATURE:
    (A) NAME/KEY: Modified-site
    (B) LOCATION: 48
    (D) OTHER INFORMATION: /note= "Xaa at position 48 is Asn,
        His, Val, Arg, Pro, Thr, Asp, or Ile"

(ix) FEATURE:
    (A) NAME/KEY: Modified-site
    (B) LOCATION: 49
    (D) OTHER INFORMATION: /note= "Xaa at position 49 is Arg,
        Tyr, Trp, Lys, Ser, His, Pro, or Val"

(ix) FEATURE:
    (A) NAME/KEY: Modified-site
    (B) LOCATION: 50
    (D) OTHER INFORMATION: /note= "Xaa at position 50 is Ala,
        Asn, Pro, Ser, or Lys"

(ix) FEATURE:
    (A) NAME/KEY: Modified-site
    (B) LOCATION: 51
    (D) OTHER INFORMATION: /note= "Xaa at position 51 is Val,
        Thr, Pro, His, Leu, Phe, or Ser"

(ix) FEATURE:
    (A) NAME/KEY: Modified-site
    (B) LOCATION: 52
    (D) OTHER INFORMATION: /note= "Xaa at position 52 is Lys,
        Ile, Arg, Val, Asn, Glu, or Ser"

(ix) FEATURE:
    (A) NAME/KEY: Modified-site
    (B) LOCATION: 53
    (D) OTHER INFORMATION: /note= "Xaa at position 53 is Ser,
        Ala, Phe, Val, Gly, Asn, Ile, Pro, or His"

(ix) FEATURE:
    (A) NAME/KEY: Modified-site
    (B) LOCATION: 54
    (D) OTHER INFORMATION: /note= "Xaa at position 54 is Leu,
        Val, Trp, Ser, Ile, Phe, Thr, or His"

(ix) FEATURE:
    (A) NAME/KEY: Modified-site
    (B) LOCATION: 55
    (D) OTHER INFORMATION: /note= "Xaa at position 55 is Gln,
        Ala, Pro, Thr, Glu, Arg, Trp, Gly, or Leu"

(ix) FEATURE:
    (A) NAME/KEY: Modified-site
    (B) LOCATION: 56
    (D) OTHER INFORMATION: /note= "Xaa at position 56 is Asn,
        Leu, Val, Trp, Pro, or Ala"

(ix) FEATURE:
    (A) NAME/KEY: Modified-site
    (B) LOCATION: 57
    (D) OTHER INFORMATION: /note= "Xaa at position 57 is Ala,
        Met, Leu, Pro, Arg, Glu, Thr, Gln, Trp, or Asn"

(ix) FEATURE:
    (A) NAME/KEY: Modified-site
    (B) LOCATION: 58
    (D) OTHER INFORMATION: /note= "Xaa at position 58 is Ser,
        Glu, Met, Ala, His, Asn, Arg, or Asp"

(ix) FEATURE:
    (A) NAME/KEY: Modified-site
    (B) LOCATION: 59
    (D) OTHER INFORMATION: /note= "Xaa at position 59 is Ala,
        Glu, Asp, Leu, Ser, Gly, Thr, or Arg"
```

```
    (ix) FEATURE:
         (A) NAME/KEY: Modified-site
         (B) LOCATION: 60
         (D) OTHER INFORMATION: /note= "Xaa at position 60 is Ile,
             Met, Thr, Pro, Arg, Gly, Ala"

(ix) FEATURE:
         (A) NAME/KEY: Modified-site
         (B) LOCATION: 61
         (D) OTHER INFORMATION: /note= "Xaa at position 61 is
             Glu, Lys, Gly, Asp, Pro, Trp, Arg, Ser, Gln,
             or Leu"

(ix) FEATURE:
         (A) NAME/KEY: Modified-site
         (B) LOCATION: 62
         (D) OTHER INFORMATION: /note= "Xaa at position 62 is Ser,
             Val, Ala, Asn, Trp, Glu, Pro, Gly, or Asp"

(ix) FEATURE:
         (A) NAME/KEY: Modified-site
         (B) LOCATION: 63
         (D) OTHER INFORMATION: /note= "Xaa at position 63 is Ile,
             Ser, Arg, Thr, or Leu"

(ix) FEATURE:
         (A) NAME/KEY: Modified-site
         (B) LOCATION: 64
         (D) OTHER INFORMATION: /note= "Xaa at position 64 is Leu,
             Ala, Ser, Glu, Phe, Gly, or Arg"

(ix) FEATURE:
         (A) NAME/KEY: Modified-site
         (B) LOCATION: 65
         (D) OTHER INFORMATION: /note= "Xaa at position 65 is Lys,
             Thr, Gly, Asn, Met, Arg, Ile, or Asp"

(ix) FEATURE:
         (A) NAME/KEY: Modified-site
         (B) LOCATION: 66
         (D) OTHER INFORMATION: /note= "Xaa at position 66 is Asn,
             Trp, Val, Gly, Thr, Leu, Glu, or Arg"

(ix) FEATURE:
         (A) NAME/KEY: Modified-site
         (B) LOCATION: 67
         (D) OTHER INFORMATION: /note= "Xaa at position 67 is Leu,
             Gln, Gly, Ala, Trp, Arg, Val, or Lys"

(ix) FEATURE:
         (A) NAME/KEY: Modified-site
         (B) LOCATION: 68
         (D) OTHER INFORMATION: /note= "Xaa at position 68 is Leu,
             Gln, Lys, Trp, Arg, Asp, Glu, Asn, His, Thr, Ser, Ala,
             Tyr, Phe, Ile, Met, or Val"

(ix) FEATURE:
         (A) NAME/KEY: Modified-site
         (B) LOCATION: 69
         (D) OTHER INFORMATION: /note= "Xaa at position 69 is Pro,
             Ala, Thr, Trp, Arg, or Met"

(ix) FEATURE:
         (A) NAME/KEY: Modified-site
         (B) LOCATION: 70
         (D) OTHER INFORMATION: /note= "Xaa at position 70 is Cys,
             Glu, Gly, Arg, Met, or Val"

(ix) FEATURE:
         (A) NAME/KEY: Modified-site
         (B) LOCATION: 71
         (D) OTHER INFORMATION: /note= "Xaa at position 71 is Leu,
             Asn, Val, or Gln"

(ix) FEATURE:
         (A) NAME/KEY: Modified-site
         (B) LOCATION: 72
         (D) OTHER INFORMATION: /note= "Xaa at position 72 is Pro,
             Cys, Arg, Ala, or Lys"
```

```
(ix) FEATURE:
    (A) NAME/KEY: Modified-site
    (B) LOCATION: 73
    (D) OTHER INFORMATION: /note= "Xaa at position 73 is Leu,
        Ser, Trp, or Gly"

(ix) FEATURE:
    (A) NAME/KEY: Modified-site
    (B) LOCATION: 74
    (D) OTHER INFORMATION: /note= "Xaa at position 74 is Ala,
        Lys, Arg, Val, or Trp"

(ix) FEATURE:
    (A) NAME/KEY: Modified-site
    (B) LOCATION: 75
    (D) OTHER INFORMATION: /note= "Xaa at position 75 is Thr,
        Asp, Cys, Leu, Val, Glu, His, Asn, or Ser"

(ix) FEATURE:
    (A) NAME/KEY: Modified-site
    (B) LOCATION: 76
    (D) OTHER INFORMATION: /note= "Xaa at position 76 is Ala,
        Pro, Ser, Thr, Gly, Asp, Ile, or Met"

(ix) FEATURE:
    (A) NAME/KEY: Modified-site
    (B) LOCATION: 77
    (D) OTHER INFORMATION: /note= "Xaa at position 77 is Ala,
        Pro, Ser, Thr, Phe, Leu, Asp, or His"

(ix) FEATURE:
    (A) NAME/KEY: Modified-site
    (B) LOCATION: 78
    (D) OTHER INFORMATION: /note= "Xaa at position 78 is Pro,
        Phe, Arg, Ser, Lys, His, Ala, Gly, Ile, or Leu"

(ix) FEATURE:
    (A) NAME/KEY: Modified-site
    (B) LOCATION: 79
    (D) OTHER INFORMATION: /note= "Xaa at position 79 is Thr,
        Asp, Ser, Asn, Pro, Ala, Leu, or Arg"

(ix) FEATURE:
    (A) NAME/KEY: Modified-site
    (B) LOCATION: 80
    (D) OTHER INFORMATION: /note= "Xaa at position 80 is Arg,
        Ile, Ser, Glu, Leu, Val, Gln, Lys, His, Ala, or Pro"

(ix) FEATURE:
    (A) NAME/KEY: Modified-site
    (B) LOCATION: 81
    (D) OTHER INFORMATION: /note= "Xaa at position 81 is His,
        Gln, Pro, Arg, Val, Leu, Gly, Thr, Asn, Lys, Ser,
        Ala, Trp, Phe, Ile, or Tyr"

(ix) FEATURE:
    (A) NAME/KEY: Modified-site
    (B) LOCATION: 82
    (D) OTHER INFORMATION: /note= "Xaa at position 82 is Pro,
        Lys, Tyr, Gly, Ile, or Thr"

(ix) FEATURE:
    (A) NAME/KEY: Modified-site
    (B) LOCATION: 83
    (D) OTHER INFORMATION: /note= "Xaa at position 83 is Ile,
        Val, Lys, Ala, or Asn"

(ix) FEATURE:
    (A) NAME/KEY: Modified-site
    (B) LOCATION: 84
    (D) OTHER INFORMATION: /note= "Xaa at position 84 is His,
        Ile, Asn, Leu, Asp, Ala, Thr, Glu, Gln, Ser,
        Phe, Met, Val, Lys, Arg, Tyr, or Pro"

(ix) FEATURE:
    (A) NAME/KEY: Modified-site
    (B) LOCATION: 85
    (D) OTHER INFORMATION: /note= "Xaa at position 85 is
```

Ile, Leu, Arg, Asp, Val, Pro, Gln, Gly, Ser,
                Phe, or His"

(ix) FEATURE:
        (A) NAME/KEY: Modified-site
        (B) LOCATION: 86
        (D) OTHER INFORMATION: /note= "Xaa at position 86 is
                Lys, Tyr, Leu, His, Arg, Ile, Ser, Gln, or Pro"

(ix) FEATURE:
        (A) NAME/KEY: Modified-site
        (B) LOCATION: 87
        (D) OTHER INFORMATION: /note= "Xaa at position 87 is
                Asp, Pro, Met, Lys, His, Thr, Val, Tyr, Glu, Asn,
                Ser, Ala, Gly, Ile, Leu, or Gln"

(ix) FEATURE:
        (A) NAME/KEY: Modified-site
        (B) LOCATION: 88
        (D) OTHER INFORMATION: /note= "Xaa at position 88 Gly,
                Leu, Glu, Lys, Ser, Tyr, or Pro"

(ix) FEATURE:
        (A) NAME/KEY: Modified-site
        (B) LOCATION: 89
        (D) OTHER INFORMATION: /note= "Xaa at position 89 is Asp
                or Ser"

(ix) FEATURE:
        (A) NAME/KEY: Modified-site
        (B) LOCATION: 90
        (D) OTHER INFORMATION: /note= "Xaa at position 90 is
                Trp, Val, Cys, Tyr, Thr, Met, Pro, Leu, Gln, Lys,
                Ala, Phe, or Gly"

(ix) FEATURE:
        (A) NAME/KEY: Modified-site
        (B) LOCATION: 91
        (D) OTHER INFORMATION: /note= "Xaa at position 91 is
                Asn, Pro, Ala, Phe, Ser, Trp, Gln, Tyr, Leu, Lys,
                Ile, Asp, or His"

(ix) FEATURE:
        (A) NAME/KEY: Modified-site
        (B) LOCATION: 92
        (D) OTHER INFORMATION: /note= "Xaa at position 92 is Glu,
                Ser, Ala, Lys, Thr, Ile, Gly, or Pro"

(ix) FEATURE:
        (A) NAME/KEY: Modified-site
        (B) LOCATION: 94
        (D) OTHER INFORMATION: /note= "Xaa at position 94 is Arg,
                Lys, Asp, Leu, Thr, Ile, Gln, His, Ser, Ala, or Pro"

(ix) FEATURE:
        (A) NAME/KEY: Modified-site
        (B) LOCATION: 95
        (D) OTHER INFORMATION: /note= "Xaa at position 95 is Arg,
                Thr, Pro, Glu, Tyr, Leu, Ser, or Gly"

(ix) FEATURE:
        (A) NAME/KEY: Modified-site
        (B) LOCATION: 96
        (D) OTHER INFORMATION: /note= "Xaa at position 96 is Lys,
                Asn, Thr, Leu, Gln, Arg, His, Glu, Ser, Ala,
                or Trp"

(ix) FEATURE:
        (A) NAME/KEY: Modified-site
        (B) LOCATION: 97
        (D) OTHER INFORMATION: /note= "Xaa at position 97 is Leu,
                Ile, Arg, Asp, or Met"

(ix) FEATURE:
        (A) NAME/KEY: Modified-site
        (B) LOCATION: 98
        (D) OTHER INFORMATION: /note= "Xaa at position 98 is Thr,
                Val, Gln, Tyr, Glu, His, Ser, or Phe"

(ix) FEATURE:
   (A) NAME/KEY: Modified-site
   (B) LOCATION: 99
   (D) OTHER INFORMATION: /note= "Xaa at position 99 is Phe,
       Ser, Cys, His, Gly, Trp, Tyr, Asp, Lys, Leu, Ile,
       Val, or Asn"

(ix) FEATURE:
   (A) NAME/KEY: Modified-site
   (B) LOCATION: 100
   (D) OTHER INFORMATION: /note= "Xaa at position 100 is Tyr,
       Cys, His, Ser, Trp, Arg, or Leu"

(ix) FEATURE:
   (A) NAME/KEY: Modified-site
   (B) LOCATION: 101
   (D) OTHER INFORMATION: /note= "Xaa at position 101 is Leu,
       Asn, Val, Pro, Arg, Ala, His, Thr, Trp, or Met"

(ix) FEATURE:
   (A) NAME/KEY: Modified-site
   (B) LOCATION: 102
   (D) OTHER INFORMATION: /note= "Xaa at position 102 is
       Lys, Leu, Pro, Thr, Met, Asp, Val, Glu, Arg, Trp,
       Ser, Asn, His, Ala, Tyr, Phe, Gln, or Ile"

(ix) FEATURE:
   (A) NAME/KEY: Modified-site
   (B) LOCATION: 103
   (D) OTHER INFORMATION: /note= "Xaa at position 103 is Thr,
       Ser, Asn, Ile, Trp, Lys, or Pro"

(ix) FEATURE:
   (A) NAME/KEY: Modified-site
   (B) LOCATION: 104
   (D) OTHER INFORMATION: /note= "Xaa at position 104 is Leu,
       Ser, Pro, Ala, Glu, Cys, Asp, or Tyr"

(ix) FEATURE:
   (A) NAME/KEY: Modified-site
   (B) LOCATION: 105
   (D) OTHER INFORMATION: /note= "Xaa at position 105 is Glu,
       Ser, Lys, Pro, Leu, Thr, Tyr, or Arg"

(ix) FEATURE:
   (A) NAME/KEY: Modified-site
   (B) LOCATION: 106
   (D) OTHER INFORMATION: /note= "Xaa at position 106 is Asn,
       Ala, Pro, Leu, His, Val or Gln"

(ix) FEATURE:
   (A) NAME/KEY: Modified-site
   (B) LOCATION: 107
   (D) OTHER INFORMATION: /note= "Xaa at position 107 is Ala,
       Ser, Ile, Asn, Pro, Lys, Asp, or Gly"

(ix) FEATURE:
   (A) NAME/KEY: Modified-site
   (B) LOCATION: 108
   (D) OTHER INFORMATION: /note= "Xaa at position 108 is
       Gln, Ser, Met, Trp, Arg, Phe, Pro, His, Ile, Tyr,
       or Cys"

(ix) FEATURE:
   (A) NAME/KEY: Modified-site
   (B) LOCATION: 109
   (D) OTHER INFORMATION: /note= "Xaa at position 109 is Ala,
       Met, Glu, His, Ser, Pro, Tyr, or Leu"

(xi) SEQUENCE DESCRIPTION: SEQ ID NO:4:

Asn Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Asn Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Phe Xaa Xaa Xaa
            85                  90                  95

Xaa Xaa Xaa Xaa Xaa Xaa Xaa Xaa Xaa Xaa Xaa Xaa Gln Gln
            100                 105                 110

(2) INFORMATION FOR SEQ ID NO:5:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, Met, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 5
        (D) OTHER INFORMATION: /note= "Xaa at position 5 is Met
            or Ile"

(ix) FEATURE:
        (A) NAME/KEY: Modified-site
        (B) LOCATION: 7
        (C) OTHER INFORMATION: /note= "Xaa at position 7 is Asp or
            Glu"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 10
        (D) OTHER INFORMATION: /note= "Xaa at position 10 is Ile,
            Val, or Leu"

(ix) FEATURE:
        (A) NAME/KEY: Modified-site
        (B) LOCATION: 11
        (D) OTHER INFORMATION: /note= "Xaa at position 11 is Thr,
            His, Gln, or Ala"

(ix) FEATURE:
        (A) NAME/KEY: Modified-site
        (B) LOCATION: 12
        (D) OTHER INFORMATION: /note= "Xaa at position 12 is His
            or Ala"

(ix) FEATURE:
        (A) NAME/KEY: Modified-site

```
            (B) LOCATION: 15
            (D) OTHER INFORMATION: /note= "Xaa at position 15 is Gln,
                Asn, or Val"

(ix) FEATURE:
            (A) NAME/KEY: Modified-site
            (B) LOCATION: 16
            (D) OTHER INFORMATION: /note= "Xaa at position 16 is Pro,
                Gly, or Gln"

(ix) FEATURE:
            (A) NAME/KEY: Modified-site
            (B) LOCATION: 17
            (D) OTHER INFORMATION: /note= "Xaa at position 17 is Pro,
                Asp, Gly, or Gln"

(ix) FEATURE:
            (A) NAME/KEY: Modified-site
            (B) LOCATION: 18
            (D) OTHER INFORMATION: /note= "Xaa at position 18 is Leu,
                Arg, Gln, Asn, Gly, Ala, or Glu"

(ix) FEATURE:
            (A) NAME/KEY: Modified-site
            (B) LOCATION: 19
            (D) OTHER INFORMATION: /note= "Xaa at position 19 is Pro
                or Glu"

(ix) FEATURE:
            (A) NAME/KEY: Modified-site
            (B) LOCATION: 20
            (D) OTHER INFORMATION: /note= "Xaa at position 20 is Leu,
                Val, Gly, Ser, Lys, Ala, Arg, Gln, Glu, Ile, Phe,
                Thr, or Met"

(ix) FEATURE:
            (A) NAME/KEY: Modified-site
            (B) LOCATION: 21
            (D) OTHER INFORMATION: /note= "Xaa at position 21 is Leu,
                Ala, Asn, Pro, Gln, or Val"

(ix) FEATURE:
            (A) NAME/KEY: Modified-site
            (B) LOCATION: 23
            (D) OTHER INFORMATION: /note= "Xaa at position 23 is Phe,
                Ser, Pro, or Trp"

(ix) FEATURE:
            (A) NAME/KEY: Modified-site
            (B) LOCATION: 24
            (D) OTHER INFORMATION: /note= "Xaa at position 24 is Asn
                or Ala"

(ix) FEATURE:
            (A) NAME/KEY: Modified-site
            (B) LOCATION: 28
            (D) OTHER INFORMATION: /note= "Xaa at position 28 is Gly,
                Asp, Ser, Cys, Ala, Asn, Ile, Leu, Met, Tyr, or Arg"

(ix) FEATURE:
            (A) NAME/KEY: Modified-site
            (B) LOCATION: 30
            (D) OTHER INFORMATION: /note= "Xaa at position 30 is Asp
                or Glu"

(ix) FEATURE:
            (A) NAME/KEY: Modified-site
            (B) LOCATION: 31
            (D) OTHER INFORMATION: /note= "Xaa at position 31 is Gln,
                Val, Met, Leu, Thr, Ala, Asn, Glu, Ser, or Lys"

(ix) FEATURE:
            (A) NAME/KEY: Modified-site
            (B) LOCATION: 32
            (D) OTHER INFORMATION: /note= "Xaa at position 32 is Asp,
                Phe, Ser, Thr, Ala, Asn, Gln, Glu, His, Ile, Lys,
                Tyr, Val, or Cys"

(ix) FEATURE:
```

(A) NAME/KEY: Modified-site
        (B) LOCATION: 36
        (D) OTHER INFORMATION: /note= "Xaa at position 36 is Glu,
            Ala, Asn, Ser, or Asp"

(ix) FEATURE:
        (A) NAME/KEY: Modified-site
        (B) LOCATION: 37
        (D) OTHER INFORMATION: /note= "Xaa at position 37 is Asn,
            Arg, Met, Pro, Ser, Thr, or His"

(ix) FEATURE:
        (A) NAME/KEY: Modified-site
        (B) LOCATION: 40
        (D) OTHER INFORMATION: /note= "Xaa at position 40 is Arg
            or Ala"

(ix) FEATURE:
        (A) NAME/KEY: Modified-site
        (B) LOCATION: 41
        (D) OTHER INFORMATION: /note= "Xaa at position 41 is Arg,
            Thr, Val, Leu, or Gly"

(ix) FEATURE:
        (A) NAME/KEY: Modified-site
        (B) LOCATION: 42
        (D) OTHER INFORMATION: /note= "Xaa at position 42 is Pro,
            Gly, Ser, Gln, Ala, Arg, Asn, Glu, Leu, Thr, Val,
            or Lys"

(ix) FEATURE:
        (A) NAME/KEY: Modified-site
        (B) LOCATION: 46
        (D) OTHER INFORMATION: /note= "Xaa at position 46 is Ala
            or Ser"

(ix) FEATURE:
        (A) NAME/KEY: Modified-site
        (B) LOCATION: 48
        (D) OTHER INFORMATION: /note= "Xaa at position 48 is Asn,
            Pro, Thr, or Ile"

(ix) FEATURE:
        (A) NAME/KEY: Modified-site
        (B) LOCATION: 49
        (D) OTHER INFORMATION: /note= "Xaa at position 49 is Arg
            or Lys"

(ix) FEATURE:
        (A) NAME/KEY: Modified-site
        (B) LOCATION: 50
        (D) OTHER INFORMATION: /note= "Xaa at position 50 is Ala
            or Asn"

(ix) FEATURE:
        (A) NAME/KEY: Modified-site
        (B) LOCATION: 51
        (D) OTHER INFORMATION: /note= "Xaa at position 51 is Val
            or Thr"

(ix) FEATURE:
        (A) NAME/KEY: Modified-site
        (B) LOCATION: 52
        (D) OTHER INFORMATION: /note= "Xaa at position 52 is Lys
            or Arg"

(ix) FEATURE:
        (A) NAME/KEY: Modified-site
        (B) LOCATION: 53
        (D) OTHER INFORMATION: /note= "Xaa at position 53 is Ser,
            Phe, or His"

(ix) FEATURE:
        (A) NAME/KEY: Modified-site
        (B) LOCATION: 54
        (D) OTHER INFORMATION: /note= "Xaa at position 54 is Leu,
            Ile, Phe, or His"

(ix) FEATURE:

-continued

```
           (A) NAME/KEY: Modified-site
           (B) LOCATION: 55
           (D) OTHER INFORMATION: /note= "Xaa at position 55 is Gln,
               Ala, Pro, Thr, Glu, Arg, or Gly"

(ix) FEATURE:
           (A) NAME/KEY: Modified-site
           (B) LOCATION: 57
           (D) OTHER INFORMATION: /note= "Xaa at position 57 is Ala,
               Pro, or Arg"

(ix) FEATURE:
           (A) NAME/KEY: Modified-site
           (B) LOCATION: 58
           (D) OTHER INFORMATION: /note= "Xaa at position 58 is Ser,
               Glu, Arg, or Asp"

(ix) FEATURE:
           (A) NAME/KEY: Modified-site
           (B) LOCATION: 59
           (D) OTHER INFORMATION: /note= "Xaa at position 59 is Ala
               or Leu"

(ix) FEATURE:
           (A) NAME/KEY: Modified-site
           (B) LOCATION: 62
           (D) OTHER INFORMATION: /note= "Xaa at position 62 is Ser,
               Val, Ala, Asn, Glu, Pro, or Gly"

(ix) FEATURE:
           (A) NAME/KEY: Modified-site
           (B) LOCATION: 63
           (D) OTHER INFORMATION: /note= "Xaa at position 63 is Ile
               or Leu"

(ix) FEATURE:
           (A) NAME/KEY: Modified-site
           (B) LOCATION: 65
           (D) OTHER INFORMATION: /note= "Xaa at position 65 is Lys,
               Thr, Gly, Asn, Met, Arg, Ile, Gly, or Asp"

(ix) FEATURE:
           (A) NAME/KEY: Modified-site
           (B) LOCATION: 66
           (D) OTHER INFORMATION: /note= "Xaa at position 66 is Asn,
               Gly, Glu, or Arg"

(ix) FEATURE:
           (A) NAME/KEY: Modified-site
           (B) LOCATION: 68
           (D) OTHER INFORMATION: /note= "Xaa at position 68 is Leu,
               Gln, Trp, Arg, Asp, Ala, Asn, Glu, His, Ile, Met,
               Phe, Ser, Thr, Tyr, or Val"

(ix) FEATURE:
           (A) NAME/KEY: Modified-site
           (B) LOCATION: 69
           (D) OTHER INFORMATION: /note= "Xaa at position 69 is Pro
               or Thr"

(ix) FEATURE:
           (A) NAME/KEY: Modified-site
           (B) LOCATION: 71
           (D) OTHER INFORMATION: /note= "Xaa at position 71 is Leu
               or Val"

(ix) FEATURE:
           (A) NAME/KEY: Modified-site
           (B) LOCATION: 73
           (D) OTHER INFORMATION: /note= "Xaa at position 73 is Leu
               or Ser"

(ix) FEATURE:
           (A) NAME/KEY: Modified-site
           (B) LOCATION: 74
           (D) OTHER INFORMATION: /note= "Xaa at position 74 is Ala
               or Trp"

(ix) FEATURE:
```

```
            (A) NAME/KEY: Modified-site
            (B) LOCATION: 77
            (D) OTHER INFORMATION: /note= "Xaa at position 77 is Ala
                or Pro"

(ix) FEATURE:
            (A) NAME/KEY: Modified-site
            (B) LOCATION: 79
            (D) OTHER INFORMATION: /note= "Xaa at position 79 is Thr,
                Asp, Ser, Pro, Ala, Leu, or Arg"

(ix) FEATURE:
            (A) NAME/KEY: Modified-site
            (B) LOCATION: 81
            (D) OTHER INFORMATION: /note= "Xaa at position 81 is His,
                Pro, Arg, Val, Leu, Gly, Asn, Phe, Ser, or Thr"

(ix) FEATURE:
            (A) NAME/KEY: Modified-site
            (B) LOCATION: 82
            (D) OTHER INFORMATION: /note= "Xaa at position 82 is Pro
                or Tyr"

(ix) FEATURE:
            (A) NAME/KEY: Modified-site
            (B) LOCATION: 83
            (D) OTHER INFORMATION: /note= "Xaa at position 83 is Ile
                or Val"

(ix) FEATURE:
            (A) NAME/KEY: Modified-site
            (B) LOCATION: 84
            (D) OTHER INFORMATION: /note= "Xaa at position 84 is His,
                Ile, Asn, Leu, Ala, Thr, Arg, Gln, Lys,
                Met, Ser, Tyr, Val, or Pro"

(ix) FEATURE:
            (A) NAME/KEY: Modified-site
            (B) LOCATION: 85
            (D) OTHER INFORMATION: /note= "Xaa at position 85 is Ile,
                Leu, or Val"

(ix) FEATURE:
            (A) NAME/KEY: Modified-site
            (B) LOCATION: 86
            (D) OTHER INFORMATION: /note= "Xaa at position 86 is Lys,
                Arg, Ile, Gln, Pro, or Ser"

(ix) FEATURE:
            (A) NAME/KEY: Modified-site
            (B) LOCATION: 87
            (D) OTHER INFORMATION: /note= "Xaa at position 87 is Asp,
                Pro, Met, Lys, His, Thr, Asn, Ile, Leu, or Tyr"

(ix) FEATURE:
            (A) NAME/KEY: Modified-site
            (B) LOCATION: 90
            (D) OTHER INFORMATION: /note= "Xaa at position 90 is Trp
                or Leu"

(ix) FEATURE:
            (A) NAME/KEY: Modified-site
            (B) LOCATION: 91
            (D) OTHER INFORMATION: /note="Xaa at position 91 is Asn,
                Pro, Ala, Ser, Trp, Gln, Tyr, Leu, Lys, Ile, Asp,
                or His"

(ix) FEATURE:
            (A) NAME/KEY: Modified-site
            (B) LOCATION: 92
            (D) OTHER INFORMATION: /note= "Xaa at position 92 is Glu
                or Gly"

(ix) FEATURE:
            (A) NAME/KEY: Modified-site
            (B) LOCATION: 94
            (C) OTHER INFORMATION: /note= "Xaa at position 94 is Arg,
                Ala, or Ser"
```

```
    (ix) FEATURE:
          (A) NAME/KEY: Modified-site
          (B) LOCATION: 95
          (D) OTHER INFORMATION: /note= "Xaa at position 95 is Arg,
              Thr, Glu, Leu, or Ser"

(ix) FEATURE:
          (A) NAME/KEY: Modified-site
          (B) LOCATION: 98
          (D) OTHER INFORMATION: /note= "Xaa at position 98 is Thr,
              Val, or Gln"

(ix) FEATURE:
          (A) NAME/KEY: Modified-site
          (B) LOCATION: 100
          (D) OTHER INFORMATION: /note= "Xaa at position 100 is Tyr
              or Trp"

(ix) FEATURE:
          (A) NAME/KEY: Modified-site
          (B) LOCATION: 101
          (D) OTHER INFORMATION: /note= "Xaa at position 101 is Leu
              or Ala"

(ix) FEATURE:
          (A) NAME/KEY: Modified-site
          (B) LOCATION: 102
          (D) OTHER INFORMATION: /note= "Xaa at position 102 is Lys,
              Thr, Val, Trp, Ser, Ala, His, Met, Phe, Tyr, or Ile"

(ix) FEATURE:
          (A) NAME/KEY: Modified-site
          (B) LOCATION: 103
          (D) OTHER INFORMATION: /note= "Xaa at position 103 is Thr
              or Ser"

(ix) FEATURE:
          (A) NAME/KEY: Modified-site
          (B) LOCATION: 106
          (D) OTHER INFORMATION: /note= "Xaa at position 106 is Asn,
              Pro, Leu, His, Val, or Gln"

(ix) FEATURE:
          (A) NAME/KEY: Modified-site
          (B) LOCATION: 107
          (D) OTHER INFORMATION: /note= "Xaa at position 107 is Ala,
              Ser, Ile, Asn, Pro, Asp, or Gly"

(ix) FEATURE:
          (A) NAME/KEY: Modified-site
          (B) LOCATION: 108
          (D) OTHER INFORMATION: /note= "Xaa at position 108 is Gln,
              Ser, Met, Trp, Arg, Phe, Pro, His, Ile, Tyr, or Cys"

(ix) FEATURE:
          (A) NAME/KEY: Modified-site
          (B) LOCATION: 109
          (D) OTHER INFORMATION: /note= "Xaa at position 109 is Ala,
              Met, Glu, His, Ser, Pro, Tyr, or Leu"

(xi) SEQUENCE DESCRIPTION: SEQ ID NO:5:

Asn Cys Xaa Xaa Xaa Ile Xaa Glu Xaa Xaa Xaa Xaa Leu Lys Xaa Xaa
1               5                   10                  15

Xaa Xaa Xaa Xaa Xaa Asp Xaa Xaa Asn Leu Asn Xaa Glu Xaa Xaa Xaa
                20                  25                  30

Ile Leu Met Xaa Xaa Asn Leu Xaa Xaa Xaa Asn Leu Glu Xaa Phe Xaa
            35                  40                  45

Xaa Xaa Xaa Xaa Xaa Xaa Xaa Asn Xaa Xaa Xaa Ile Glu Xaa Xaa Leu
        50                  55                  60

Xaa Xaa Leu Xaa Xaa Cys Xaa Pro Xaa Xaa Thr Ala Xaa Pro Xaa Arg
65                  70                  75                  80

Xaa Xaa Xaa Xaa Xaa Xaa Xaa Gly Asp Xaa Xaa Xaa Phe Xaa Xaa Lys
                85                  90                  95
```

```
Leu Xaa Phe Xaa Xaa Xaa Xaa Leu Glu Xaa Xaa Xaa Xaa Gln Gln
         100                 105                 110
```

(2) INFORMATION FOR SEQ ID NO:6:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 11
        (D) OTHER INFORMATION: /note= "Xaa at position 11 is Thr,
            His, or Gln"

(ix) FEATURE:
        (A) NAME/KEY: Modified-site
        (B) LOCATION: 12
        (D) OTHER INFORMATION: /note= "Xaa at position 12 is His
            or Ala"

(ix) FEATURE:
        (A) NAME/KEY: Modified-site
        (B) LOCATION: 15
        (D) OTHER INFORMATION: /note= "Xaa at position 15 is Gln
            or Asn"

(ix) FEATURE:
        (A) NAME/KEY: Modified-site
        (B) LOCATION: 16
        (D) OTHER INFORMATION: /note= "Xaa at position 16 is Pro
            or Gly"

(ix) FEATURE:
        (A) NAME/KEY: Modified-site
        (B) LOCATION: 18
        (D) OTHER INFORMATION: /note= "Xaa at position 18 is Leu,
            Arg, Asn, or Ala"

(ix) FEATURE:
        (A) NAME/KEY: Modified-site
        (B) LOCATION: 20
        (D) OTHER INFORMATION: /note= "Xaa at position 20 is Leu,
            Val, Ser, Ala, Arg, Gln, Glu, Ile, Phe, Thr, or Met"

(ix) FEATURE:
        (A) NAME/KEY: Modified-site
        (B) LOCATION: 21
        (D) OTHER INFORMATION: /note= "Xaa at position 21 is Leu,
            Ala, Asn, or Pro"

-continued

```
(ix) FEATURE:
     (A) NAME/KEY: Modified-site
     (B) LOCATION: 24
     (D) OTHER INFORMATION: /note= "Xaa at position 24 is Asn
         or Ala"

(ix) FEATURE:
     (A) NAME/KEY: Modified-site
     (B) LOCATION: 28
     (D) OTHER INFORMATION: /note= "Xaa at position 28 is Gly,
         Asp, Ser, Ala, Asn, Ile, Leu, Met, Tyr, or Arg"

(ix) FEATURE:
     (A) NAME/KEY: Modified-site
     (B) LOCATION: 31
     (D) OTHER INFORMATION: /note= "Xaa at position 31 is Gln,
         Val, Met, Leu, Ala, Asn, Glu, or Lys"

(ix) FEATURE:
     (A) NAME/KEY: Modified-site
     (B) LOCATION: 32
     (D) OTHER INFORMATION: /note= "Xaa at position 32 is Asp,
         Phe, Ser, Ala, Gln, Glu, His, Val, or Thr"

(ix) FEATURE:
     (A) NAME/KEY: Modified-site
     (B) LOCATION: 36
     (D) OTHER INFORMATION: /note= "Xaa at position 36 is Glu,
         Asn, Ser, or Asp"

(ix) FEATURE:
     (A) NAME/KEY: Modified-site
     (B) LOCATION: 37
     (D) OTHER INFORMATION: /note= "Xaa at position 37 is Asn,
         Arg, Pro, Thr, or His"

(ix) FEATURE:
     (A) NAME/KEY: Modified-site
     (B) LOCATION: 41
     (D) OTHER INFORMATION: /note= "Xaa at position 41 is Arg,
         Leu, or Gly"

(ix) FEATURE:
     (A) NAME/KEY: Modified-site
     (B) LOCATION: 42
     (D) OTHER INFORMATION: /note= "Xaa at position 42 is Pro,
         Gly, Ser, Ala, Asn, Val, Leu, or Gln"

(ix) FEATURE:
     (A) NAME/KEY: Modified-site
     (B) LOCATION: 48
     (D) OTHER INFORMATION: /note= "Xaa at position 48 is Asn,
         Pro, or Thr"

(ix) FEATURE:
     (A) NAME/KEY: Modified-site
     (B) LOCATION: 50
     (D) OTHER INFORMATION: /note= "Xaa at position 50 is Ala
         or Asn"

(ix) FEATURE:
     (A) NAME/KEY: Modified-site
     (B) LOCATION: 51
     (D) OTHER INFORMATION: /note= "Xaa at position 51 is Val
         or Thr"

(ix) FEATURE:
     (A) NAME/KEY: Modified-site
     (B) LOCATION: 53
     (D) OTHER INFORMATION: /note= "Xaa at position 53 is Ser
         or Phe"

(ix) FEATURE:
     (A) NAME/KEY: Modified-site
     (B) LOCATION: 54
     (D) OTHER INFORMATION: /note= "Xaa at position 54 is Leu
         or Phe"
```

```
(ix) FEATURE:
      (A) NAME/KEY: Modified-site
      (B) LOCATION: 55
      (D) OTHER INFORMATION: /note= "Xaa at position 55 is Gln,
          Ala, Glu, or Arg"

(ix) FEATURE:
      (A) NAME/KEY: Modified-site
      (B) LOCATION: 62
      (D) OTHER INFORMATION: /note= "Xaa at position 62 is Ser,
          Val, Asn, Pro, or Gly"

(ix) FEATURE:
      (A) NAME/KEY: Modified-site
      (B) LOCATION: 63
      (D) OTHER INFORMATION: /note= "Xaa at position 63 is Ile
          or Leu"

(ix) FEATURE:
      (A) NAME/KEY: Modified-site
      (B) LOCATION: 65
      (D) OTHER INFORMATION: /note= "Xaa at position 65 is Lys,
          Asn, Met, Arg, Ile, or Gly"

(ix) FEATURE:
      (A) NAME/KEY: Modified-site
      (B) LOCATION: 66
      (D) OTHER INFORMATION: /note= "Xaa at position 66 is Asn,
          Gly, Glu, or Arg"

(ix) FEATURE:
      (A) NAME/KEY: Modified-site
      (B) LOCATION: 68
      (D) OTHER INFORMATION: /note= "Xaa at position 68 is Leu,
          Gln, Trp, Arg, Asp, Asn, Glu, His, Met, Phe, Ser,
          Thr, Tyr, or Val"

(ix) FEATURE:
      (A) NAME/KEY: Modified-site
      (B) LOCATION: 73
      (D) OTHER INFORMATION: /note= "Xaa at position 73 is Leu
          or Ser"

(ix) FEATURE:
      (A) NAME/KEY: Modified-site
      (B) LOCATION: 74
      (D) OTHER INFORMATION: /note= "Xaa at position 74 is Ala
          or Trp"

(ix) FEATURE:
      (A) NAME/KEY: Modified-site
      (B) LOCATION: 77
      (D) OTHER INFORMATION: /note= "Xaa at position 77 is Ala
          or Pro"

(ix) FEATURE:
      (A) NAME/KEY: Modified-site
      (B) LOCATION: 79
      (D) OTHER INFORMATION: /note= "Xaa at position 79 is Thr,
          Asp, or Ala"

(ix) FEATURE:
      (A) NAME/KEY: Modified-site
      (B) LOCATION: 81
      (D) OTHER INFORMATION: /note= "Xaa at position 81 is His,
          Pro, Arg, Val, Gly, Asn, Ser, or Thr"

(ix) FEATURE:
      (A) NAME/KEY: Modified-site
      (B) LOCATION: 84
      (D) OTHER INFORMATION: /note= "Xaa at position 84 is His,
          Ile, Asn, Leu, Ala, Thr, Arg, Gln, Glu, Lys, Met,
          Ser, Tyr, Val, or Leu"

(ix) FEATURE:
      (A) NAME/KEY: Modified-site
      (B) LOCATION: 85
      (D) OTHER INFORMATION: /note= "Xaa at position 85 is Ile
          or Leu"
```

(ix) FEATURE:
      (A) NAME/KEY: Modified-site
      (B) LOCATION: 86
      (D) OTHER INFORMATION: /note= "Xaa at position 86 is Lys
          or Arg"

(ix) FEATURE:
      (A) NAME/KEY: Modified-site
      (B) LOCATION: 87
      (D) OTHER INFORMATION: /note= "Xaa at position 87 is Asp,
          Pro, Met, Lys, His, Pro, Asn, Ile, Leu, or Tyr"

(ix) FEATURE:
      (A) NAME/KEY: Modified-site
      (B) LOCATION: 91
      (D) OTHER INFORMATION: /note= "Xaa at position 91 is Asn,
          Pro, Ser, Ile, or Asp"

(ix) FEATURE:
      (A) NAME/KEY: Modified-site
      (B) LOCATION: 94
      (D) OTHER INFORMATION: /note="Xaa at position 94 is Arg,
          Ala, or Ser"

(ix) FEATURE:
      (A) NAME/KEY: Modified-site
      (B) LOCATION: 95
      (D) OTHER INFORMATION: /note= "Xaa at position 95 is Arg,
          Thr, Glu, Leu, or Ser"

(ix) FEATURE:
      (A) NAME/KEY: Modified-site
      (B) LOCATION: 98
      (D) OTHER INFORMATION: /note= "Xaa at position 98 is Thr
          or Gln"

(ix) FEATURE:
      (A) NAME/KEY: Modified-site
      (B) LOCATION: 102
      (D) OTHER INFORMATION: /note= "Xaa at position 102 is Lys,
          Val, Trp, or Ile"

(ix) FEATURE:
      (A) NAME/KEY: Modified-site
      (B) LOCATION: 103
      (D) OTHER INFORMATION: /note= "Xaa at position 103 is Thr,
          Ala, His, Phe, Tyr, or Ser"

(ix) FEATURE:
      (A) NAME/KEY: Modified-site
      (B) LOCATION: 106
      (D) OTHER INFORMATION: /note= "Xaa at position 106 is Asn,
          Pro, Leu, His, Val, or Gln"

(ix) FEATURE:
      (A) NAME/KEY: Modified-site
      (B) LOCATION: 107
      (D) OTHER INFORMATION: /note= "Xaa at position 107 is Ala,
          Ser, Ile, Pro, or Asp"

(ix) FEATURE:
      (A) NAME/KEY: Modified-site
      (B) LOCATION: 108
      (D) OTHER INFORMATION: /note= "Xaa at position 108 is Gln,
          Met, Trp, Phe, Pro, His, Ile, or Tyr"

(ix) FEATURE:
      (A) NAME/KEY: Modified-site
      (B) LOCATION: 109
      (D) OTHER INFORMATION: /note= "Xaa at position 109 is Ala,
          Met, Glu, Ser, or Leu"

(xi) SEQUENCE DESCRIPTION: SEQ ID NO:6:

Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa

```
                    20                  25                  30
Ile Leu Met Xaa Xaa Asn Leu Arg Xaa Xaa Asn Leu Glu Ala Phe Xaa
                35                  40                  45
Arg Xaa Xaa Lys Xaa Xaa Xaa Asn Ala Ser Ala Ile Glu Xaa Xaa Leu
 50                  55                  60
Xaa Xaa Leu Xaa Pro Cys Leu Pro Xaa Xaa Thr Ala Xaa Pro Xaa Arg
 65                  70                  75                  80
Xaa Pro Ile Xaa Xaa Xaa Xaa Gly Asp Trp Xaa Glu Phe Xaa Xaa Lys
                85                  90                  95
Leu Xaa Phe Tyr Leu Xaa Xaa Leu Glu Xaa Xaa Xaa Xaa Gln Gln
                100                 105                 110
```

(2) INFORMATION FOR SEQ ID NO:7:

(i) SEQUENCE CHARACTERISTICS:
      (A) LENGTH: 133 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /note= "Met- may or may not precede
         the amino acid in position 1"

(ix) FEATURE:
      (A) NAME/KEY: Modified-site
      (B) LOCATION: 18
      (D) OTHER INFORMATION: /note= "Xaa at position 18 is Asn
         or Ile"

(ix) FEATURE:
      (A) NAME/KEY: Modified-site
      (B) LOCATION: 19
      (D) OTHER INFORMATION: /note= "Xaa at position 19 is Met,
         Ala, or Ile"

(ix) FEATURE:
      (A) NAME/KEY: Modified-site
      (B) LOCATION: 20
      (D) OTHER INFORMATION: /note= "Xaa at position 20 is Ile,
         Pro, or Leu"

(ix) FEATURE:
      (A) NAME/KEY: Modified-site
      (B) LOCATION: 23
      (D) OTHER INFORMATION: /note= "Xaa at position 23 is Ile,
         Ala, or Leu"

(ix) FEATURE:
      (A) NAME/KEY: Modified-site
      (B) LOCATION: 25
      (D) OTHER INFORMATION: /note= "Xaa at position 25 is Thr
         or His"

(ix) FEATURE:
      (A) NAME/KEY: Modified-site
      (B) LOCATION: 29
      (D) OTHER INFORMATION: /note= "Xaa at position 29 is Gln,
         Arg, Val, or Ile"

(ix) FEATURE:
      (A) NAME/KEY: Modified-site
      (B) LOCATION: 32
      (D) OTHER INFORMATION: /note= "Xaa at position 32 is Leu,
         Ala, Asn, or Arg"

(ix) FEATURE:
      (A) NAME/KEY: Modified-site
      (B) LOCATION: 34
      (D) OTHER INFORMATION: /note= "Xaa at position 34 is Leu or Ser"

(ix) FEATURE:
    (A) NAME/KEY: Modified-site
    (B) LOCATION: 37
    (D) OTHER INFORMATION: /note= "Xaa at position 37 is Phe,
        Pro, or Ser"

(ix) FEATURE:
    (A) NAME/KEY: Modified-site
    (B) LOCATION:; 38
    (D) OTHER INFORMATION: /note= "Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Ala, Ser, Asp, or Asn"

(ix) FEATURE:
    (A) NAME/KEY: Modified-site
    (B) LOCATION: 45
    (D) OTHER INFORMATION: /note= "Xaa at position 45 is Gln,
        Val, or Met"

(ix) FEATURE:
    (A) NAME/KEY: Modified-site
    (B) LOCATION: 46
    (D) OTHER INFORMATION: /note= "Xaa at position 46 is Asp
        or Ser"

(ix) FEATURE:
    (A) NAME/KEY: Modified-site
    (B) LOCATION: 49
    (D) OTHER INFORMATION: /note= "Xaa at position 49 is Met,
        Ile, Leu, or Asp"

(ix) FEATURE:
    (A) NAME/KEY: Modified-site
    (B) LOCATION: 50
    (D) OTHER INFORMATION: /note= "Xaa at position 50 is Glu
        or Asp"

(ix) FEATURE:
    (A) NAME/KEY: Modified-site
    (B) LOCATION: 51
    (D) OTHER INFORMATION: /note= "Xaa at position 51 is Asn,
        Arg, or Ser"

(ix) FEATURE:
    (A) NAME/KEY: Modified-site
    (B) LOCATION: 55
    (D) OTHER INFORMATION: /note= "Xaa at position 55 is Arg,
        Leu, or Thr"

(ix) FEATURE:
    (A) NAME/KEY: Modified-site
    (B) LOCATION: 56
    (D) OTHER INFORMATION: /note= "Xaa at position 56 is Pro
        or Ser"

(ix) FEATURE:
    (A) NAME/KEY: Modified-site
    (B) LOCATION: 59
    (D) OTHER INFORMATION: /note= "Xaa at position 59 is Glu
        or Leu"

(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn
        Val, or Pro"

(ix) FEATURE:
      (A) NAME/KEY: Modified-site
      (B) LOCATION: 63
      (D) OTHER INFORMATION: /note= "Xaa at position 63 is Arg
          or His"

(ix) FEATURE:
      (A) NAME/KEY: Modified-site
      (B) LOCATION: 65
      (D) OTHER INFORMATION: /note= "Xaa at position 65 is Val
          or Ser"

(ix) FEATURE:
      (A) NAME/KEY: Modified-site
      (B) LOCATION: 67
      (D) OTHER INFORMATION: /note= "Xaa at position 67 is Ser,
          Asn, His, or Gln"

(ix) FEATURE:
      (A) NAME/KEY: Modified-site
      (B) LOCATION: 69
      (D) OTHER INFORMATION: /note= "Xaa at position 69 is Gln
          or Glu"

(ix) FEATURE:
      (A) NAME/KEY: Modified-site
      (B) LOCATION: 73
      (D) OTHER INFORMATION: /note= "Xaa at position 73 is Ala
          or Gly"

(ix) FEATURE:
      (A) NAME/KEY: Modified-site
      (B) LOCATION: 76
      (D) OTHER INFORMATION: /note= "Xaa at position 76 is Ser,
          Ala, or Pro"

(ix) FEATURE:
      (A) NAME/KEY: Modified-site
      (B) LOCATION: 79
      (D) OTHER INFORMATION: /note= "Xaa at position 79 is Lys,
          Arg, or Ser"

(ix) FEATURE:
      (A) NAME/KEY: Modified-site
      (B) LOCATION: 82
      (D) OTHER INFORMATION: /note= "Xaa at position 82 is Leu,
          Glu, Val, or Trp"

(ix) FEATURE:
      (A) NAME/KEY: Modified-site
      (B) LOCATION: 85
      (D) OTHER INFORMATION: /note= "Xaa at position 85 is Leu
          or Val"

(ix) FEATURE:
      (A) NAME/KEY: Modified-site
      (B) LOCATION: 87
      (D) OTHER INFORMATION: /note= "Xaa at position 87 is Leu,
          Ser, or Tyr"

(ix) FEATURE:
      (A) NAME/KEY: Modified-site
      (B) LOCATION: 88
      (D) OTHER INFORMATION: /note= "Xaa at position 88 is Ala
          or Trp"

(ix) FEATURE:
      (A) NAME/KEY: Modified-site
      (B) LOCATION: 91
      (D) OTHER INFORMATION: /note= "Xaa at position 91 is Ala
          or Pro"

(ix) FEATURE:
      (A) NAME/KEY: Modified-site
      (B) LOCATION: 93
      (D) OTHER INFORMATION: /note= "Xaa at position 93 is Pro
          or Ser"

(ix) FEATURE:
           (A) NAME/KEY: Modified-site
           (B) LOCATION: 95
           (D) OTHER INFORMATION: /note= "Xaa at position 95 is His
                 or Thr"

(ix) FEATURE:
           (A) NAME/KEY: Modified-site
           (B) LOCATION: 98
           (D) OTHER INFORMATION: /note= "Xaa at position 98 is His,
                 Ile, or Thr"

(ix) FEATURE:
           (A) NAME/KEY: Modified-site
           (B) LOCATION: 100
           (D) OTHER INFORMATION: /note= "Xaa at position 100 is Lys
                 or Arg"

(ix) FEATURE:
           (A) NAME/KEY: Modified-site
           (B) LOCATION: 101
           (D) OTHER INFORMATION: /note= "Xaa at position 101 is Asp,
                 Ala, or Met"

(ix) FEATURE:
           (A) NAME/KEY: Modified-site
           (B) LOCATION: 105
           (D) OTHER INFORMATION: /note= "Xaa at position 105 is Asn
                 or Glu"

(ix) FEATURE:
           (A) NAME/KEY: Modified-site
           (B) LOCATION: 109
           (D) OTHER INFORMATION: /note= "Xaa at position 109 is Arg,
                 Glu, or Leu"

(ix) FEATURE:
           (A) NAME/KEY: Modified-site
           (B) LOCATION: 112
           (D) OTHER INFORMATION: /note= "Xaa at position 112 is Thr
                 or Gln"

(ix) FEATURE:
           (A) NAME/KEY: Modified-site
           (B) LOCATION: 116
           (D) OTHER INFORMATION: /note= "Xaa at position 116 is Lys,
                 Val, Trp, or Ser"

(ix) FEATURE:
           (A) NAME/KEY: Modified-site
           (B) LOCATION: 117
           (D) OTHER INFORMATION: /note= "Xaa at position 117 is Thr
                 or Ser"

(ix) FEATURE:
           (A) NAME/KEY: Modified-site
           (B) LOCATION: 120
           (D) OTHER INFORMATION: /note= "Xaa at position 120 is Asn,
                 Gln, or His"

(ix) FEATURE:
           (A) NAME/KEY: Modified-site
           (B) LOCATION: 123
           (D) OTHER INFORMATION: /note= "Xaa at position 123 is Ala
                 or Glu"

(xi) SEQUENCE DESCRIPTION: SEQ ID NO:7:

Ala Pro Met Thr Gln Thr Thr Ser Leu Lys Thr Ser Trp Val Asn Cys
1               5                   10                  15

Ser Xaa Xaa Xaa Asp Glu Xaa Ile Xaa His Leu Lys Xaa Pro Pro Xaa
            20                  25                  30

Pro Xaa Leu Asp Xaa Xaa Asn Leu Asn Xaa Glu Asp Xaa Xaa Ile Leu
        35                  40                  45

Xaa Xaa Xaa Asn Leu Arg Xaa Xaa Asn Leu Xaa Xaa Phe Xaa Xaa Ala
50                  55                  60

```
Xaa Lys Xaa Leu Xaa Asn Ala Ser Xaa Ile Glu Xaa Ile Leu Xaa Asn
 65                  70                  75                  80

Leu Xaa Pro Cys Xaa Pro Xaa Xaa Thr Ala Xaa Pro Xaa Arg Xaa Pro
             85                  90                  95

Ile Xaa Ile Xaa Xaa Gly Asp Trp Xaa Glu Phe Arg Xaa Lys Leu Xaa
        100                 105                 110

Phe Tyr Leu Xaa Xaa Leu Glu Xaa Ala Gln Xaa Gln Gln Thr Thr Leu
            115                 120                 125

Ser Leu Ala Ile Phe
    130
```

(2) INFORMATION FOR SEQ ID NO:8:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala may or may
            not precede the amino acid in position 1"

(ix) FEATURE:
        (A) NAME/KEY: Modified-site
        (B) LOCATION: 4
        (D) OTHER INFORMATION: /note= "Xaa at position 4 is Asn or
            Ile"

(ix) FEATURE:
        (A) NAME/KEY: Modified-site
        (B) LOCATION: 5
        (D) OTHER INFORMATION: /note= "Xaa at position 5 is Met,
            Ala, or Ile"

(ix) FEATURE:
        (A) NAME/KEY: Modified-site
        (B) LOCATION: 6
        (D) OTHER INFORMATION: /note= "Xaa at position 6 is Ile,
            Pro, or Leu"

(ix) FEATURE:
        (A) NAME/KEY: Modified-site
        (B) LOCATION: 9
        (D) OTHER INFORMATION: /note= "Xaa at position 9 is Ile,
            Ala, or Leu"

(ix) FEATURE:
        (A) NAME/KEY: Modified-site
        (B) LOCATION: 11
        (D) OTHER INFORMATION: /note= "Xaa at position 11 is Thr
            or His"

(ix) FEATURE:
        (A) NAME/KEY: Modified-site
        (B) LOCATION: 15
        (D) OTHER INFORMATION: /note= "Xaa at position 15 is Gln,
            Arg, Val, or Ile"

(ix) FEATURE:
        (A) NAME/KEY: Modified-site
        (B) LOCATION: 18
        (D) OTHER INFORMATION: /note= "Xaa at position 18 is Leu,
            Ala, Asn, or Arg"

(ix) FEATURE:
        (A) NAME/KEY: Modified-site
        (B) LOCATION: 20
        (D) OTHER INFORMATION: /note= "Xaa at position 20 is Leu
            or Ser"

-continued

```
(ix) FEATURE:
     (A) NAME/KEY: Modified-site
     (B) LOCATION: 23
     (D) OTHER INFORMATION: /note= "Xaa at position 23 is Phe,
         Pro, or Ser"

(ix) FEATURE:
     (A) NAME/KEY: Modified-site
     (B) LOCATION: 24
     (D) OTHER INFORMATION: /note= "Xaa at position 24 is Asn
         or Ala"

(ix) FEATURE:
     (A) NAME/KEY: Modified-site
     (B) LOCATION: 28
     (D) OTHER INFORMATION: /note= "Xaa at position 28 is Gly,
         Ala, Ser, Asp, or Asn"

(ix) FEATURE:
     (A) NAME/KEY: Modified-site
     (B) LOCATION: 31
     (D) OTHER INFORMATION: /note= "Xaa at position 31 is Gln,
         Val, or Met"

(ix) FEATURE:
     (A) NAME/KEY: Modified-site
     (B) LOCATION: 32
     (D) OTHER INFORMATION: /note= "Xaa at position 32 is Asp
         or Ser"

(ix) FEATURE:
     (A) NAME/KEY: Modified-site
     (B) LOCATION: 35
     (D) OTHER INFORMATION: /note= "Xaa at position 35 is Met,
         Ile, or Asp"

(ix) FEATURE:
     (A) NAME/KEY: Modified-site
     (B) LOCATION: 36
     (D) OTHER INFORMATION: /note= "Xaa at position 36 is Glu
         or Asp"

(ix) FEATURE:
     (A) NAME/KEY: Modified-site
     (B) LOCATION: 37
     (D) OTHER INFORMATION: /note= "Xaa at position 37 is Asn,
         Arg, or Ser"

(ix) FEATURE:
     (A) NAME/KEY: Modified-site
     (B) LOCATION: 41
     (D) OTHER INFORMATION: /note= "Xaa at position 41 is Arg,
         Leu, or Thr"

(ix) FEATURE:
     (A) NAME/KEY: Modified-site
     (B) LOCATION: 42
     (D) OTHER INFORMATION: /note= "Xaa at position 42 is Pro
         or Ser"

(ix) FEATURE:
     (A) NAME/KEY: Modified-site
     (B) LOCATION: 45
     (D) OTHER INFORMATION: /note= "Xaa at position 45 is Glu
         or Leu"

(ix) FEATURE:
     (A) NAME/KEY: Modified-site
     (B) LOCATION: 46
     (D) OTHER INFORMATION: /note= "Xaa at position 46 is Ala
         or Ser"

(ix) FEATURE:
     (A) NAME/KEY: Modified-site
     (B) LOCATION: 48
     (D) OTHER INFORMATION: /note= "Xaa at position 48 is Asn,
         Val, or Pro"
```

-continued

```
(ix) FEATURE:
    (A) NAME/KEY: Modified-site
    (B) LOCATION: 49
    (D) OTHER INFORMATION: /note= "Xaa at position 49 is Arg
        or His"

(ix) FEATURE:
    (A) NAME/KEY: Modified-site
    (B) LOCATION: 51
    (D) OTHER INFORMATION: /note= "Xaa at position 51 is Val
        or Ser"

(ix) FEATURE:
    (A) NAME/KEY: Modified-site
    (B) LOCATION: 53
    (D) OTHER INFORMATION: /note= "Xaa at position 53 is Ser,
        Asn, His, or Gln"

(ix) FEATURE:
    (A) NAME/KEY: Modified-site
    (B) LOCATION: 55
    (D) OTHER INFORMATION: /note= "Xaa at position 55 is Gln
        or Glu"

(ix) FEATURE:
    (A) NAME/KEY: Modified-site
    (B) LOCATION: 59
    (D) OTHER INFORMATION: /note= "Xaa at position 59 is Ala
        or Gly"

(ix) FEATURE:
    (A) NAME/KEY: Modified-site
    (B) LOCATION: 62
    (D) OTHER INFORMATION: /note= "Xaa at position 62 is Ser,
        Ala, or Pro"

(ix) FEATURE:
    (A) NAME/KEY: Modified-site
    (B) LOCATION: 65
    (D) OTHER INFORMATION: /note= "Xaa at position 65 is Lys,
        Arg, or Ser"

(ix) FEATURE:
    (A) NAME/KEY: Modified-site
    (B) LOCATION: 67
    (D) OTHER INFORMATION: /note= "Xaa at position 67 is Leu,
        Glu, or Val"

(ix) FEATURE:
    (A) NAME/KEY: Modified-site
    (B) LOCATION: 68
    (D) OTHER INFORMATION: /note= "Xaa at position 68 is Leu,
        Glu, Val, or Trp"

(ix) FEATURE:
    (A) NAME/KEY: Modified-site
    (B) LOCATION: 71
    (D) OTHER INFORMATION: /note= "Xaa at position 71 is Leu
        or Val"

(ix) FEATURE:
    (A) NAME/KEY: Modified-site
    (B) LOCATION: 73
    (D) OTHER INFORMATION: /note= "Xaa at position 73 is Leu,
        Ser, or Tyr"

(ix) FEATURE:
    (A) NAME/KEY: Modified-site
    (B) LOCATION: 74
    (D) OTHER INFORMATION: /note= "Xaa at position 74 is Ala
        or Trp"

(ix) FEATURE:
    (A) NAME/KEY: Modified-site
    (B) LOCATION: 77
    (D) OTHER INFORMATION: /note= "Xaa at position 77 is Ala
        or Pro"

(ix) FEATURE:
```

```
          (A) NAME/KEY: Modified-site
          (B) LOCATION: 79
          (D) OTHER INFORMATION: /note= "Xaa at position 79 is Pro
              or Ser"

(ix) FEATURE:
          (A) NAME/KEY: Modified-site
          (B) LOCATION: 81
          (D) OTHER INFORMATION: /note= "Xaa at position 81 is His
              or Thr"

(ix) FEATURE:
          (A) NAME/KEY: Modified-site
          (B) LOCATION: 84
          (D) OTHER INFORMATION: /note= "Xaa at position 84 is His,
              Ile, or Thr"

(ix) FEATURE:
          (A) NAME/KEY: Modified-site
          (B) LOCATION: 86
          (D) OTHER INFORMATION: /note= "Xaa at position 86 is Lys
              or Arg"

(ix) FEATURE:
          (A) NAME/KEY: Modified-site
          (B) LOCATION: 87
          (D) OTHER INFORMATION: /note= "Xaa at position 87 is Asp,
              Ala, or Met"

(ix) FEATURE:
          (A) NAME/KEY: Modified-site
          (B) LOCATION: 91
          (D) OTHER INFORMATION: /note= "Xaa at position 91 is Asn
              or Glu"

(ix) FEATURE:
          (A) NAME/KEY: Modified-site
          (B) LOCATION: 95
          (D) OTHER INFORMATION: /note= "Xaa at position 95 is Arg,
              Glu, or Leu"

(ix) FEATURE:
          (A) NAME/KEY: Modified-site
          (B) LOCATION: 98
          (D) OTHER INFORMATION: /note= "Xaa at position 98 is Thr
              or Gln"

(ix) FEATURE:
          (A) NAME/KEY: Modified-site
          (B) LOCATION: 102
          (D) OTHER INFORMATION: /note= "Xaa at position 102 is Lys,
              Val, Trp, or Ser"

(ix) FEATURE:
          (A) NAME/KEY: Modified-site
          (B) LOCATION: 103
          (D) OTHER INFORMATION: /note= "Xaa at position 103 is Thr
              or Ser"

(ix) FEATURE:
          (A) NAME/KEY: Modified-site
          (B) LOCATION: 106
          (D) OTHER INFORMATION: /note= "Xaa at position 106 is Asn,
              Gln, or His"

(ix) FEATURE:
          (A) NAME/KEY: Modified-site
          (B) LOCATION: 109
          (D) OTHER INFORMATION: /note= "Xaa at position 109 is Ala
              or Glu"

(xi) SEQUENCE DESCRIPTION: SEQ ID NO:8:

Asn Cys Ser Xaa Xaa Xaa Asp Glu Xaa Ile Xaa His Leu Lys Xaa Pro
 1               5                  10                  15

Pro Xaa Pro Xaa Leu Asp Xaa Xaa Asn Leu Asn Xaa Glu Asp Xaa Xaa
             20                  25                  30
```

```
Ile Leu Xaa Xaa Xaa Asn Leu Arg Xaa Xaa Asn Leu Xaa Xaa Phe Xaa
            35                  40                  45

Xaa Ala Xaa Lys Xaa Leu Xaa Asn Ala Ser Xaa Ile Glu Xaa Ile Leu
        50                  55                  60

Xaa Asn Xaa Xaa Pro Cys Xaa Pro Xaa Xaa Thr Ala Xaa Pro Xaa Arg
65                  70                  75                  80

Xaa Pro Ile Xaa Ile Xaa Xaa Gly Asp Trp Xaa Glu Phe Arg Xaa Lys
                85                  90                  95

Leu Xaa Phe Tyr Leu Xaa Xaa Leu Glu Xaa Ala Gln Xaa Gln Gln
            100                 105                 110

(2) INFORMATION FOR SEQ ID NO:9:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:9:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
                20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
            100                 105                 110

(2) INFORMATION FOR SEQ ID NO:10:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:10:

Asn Cys Ser Ile Met Ile Asp Glu Ile Ile His His Leu Lys Arg Pro
1               5                   10                  15

Pro Asn Pro Leu Leu Asp Pro Asn Asn Leu Asn Ser Glu Asp Met Asp
                20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
```

(2) INFORMATION FOR SEQ ID NO:11:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:11:

```
Asn Cys Ser Ile Met Ile Asp Glu Ile Ile His His Leu Lys Val Pro
 1               5                  10                  15

Pro Ala Pro Leu Leu Asp Ser Asn Asn Leu Asn Ser Glu Asp Met Asp
            20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:12:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:12:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
            20                  25                  30

Ile Leu Met Glu Arg Asn Leu Arg Leu Pro Asn Leu Leu Ala Phe Val
                35                  40                  45

Arg Ala Val Lys Asn Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:13:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:13:

```
Asn Cys Ser Asn Met Ile Asp Glu Ile Ile Thr His Leu Lys Gln Pro
  1               5                   10                  15

Pro Leu Pro Leu Leu Asp Phe Asn Asn Leu Asn Gly Glu Asp Gln Asp
             20                  25                  30

Ile Leu Met Glu Arg Asn Leu Arg Leu Pro Asn Leu Glu Ser Phe Val
             35                  40                  45

Arg Ala Val Lys Asn Leu Glu Asn Ala Ser Ala Ile Glu Ser Ile Leu
         50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110
```

(2) INFORMATION FOR SEQ ID NO:14:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:14:

```
Asn Cys Ser Asn Met Ile Asp Glu Ile Ile Thr His Leu Lys Gln Pro
  1               5                   10                  15

Pro Leu Pro Leu Leu Asp Phe Asn Asn Leu Asn Gly Glu Asp Gln Asp
             20                  25                  30

Ile Leu Met Glu Arg Asn Leu Arg Thr Pro Asn Leu Leu Ala Phe Val
             35                  40                  45

Arg Ala Val Lys His Leu Glu Asn Ala Ser Ala Ile Glu Ser Ile Leu
         50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110
```

(2) INFORMATION FOR SEQ ID NO:15:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:15:

```
Asn Cys Ser Asn Met Ile Asp Glu Ile Ile Thr His Leu Lys Gln Pro
  1               5                   10                  15

Pro Leu Pro Leu Leu Asp Phe Asn Asn Leu Asn Gly Glu Asp Gln Asp
             20                  25                  30

Ile Leu Met Glu Asn Asn Leu Arg Arg Pro Asn Leu Glu Ala Phe Asn
             35                  40                  45

Arg Ala Val Lys Ser Leu Gln Asn Ala Ser Gly Ile Glu Ala Ile Leu
         50                  55                  60
```

```
Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Arg Lys
                     85                  90                  95

Leu Thr Phe Tyr Leu Lys Thr Leu Glu Asn Ala Gln Ala Gln Gln
                100                 105                 110
```

(2) INFORMATION FOR SEQ ID NO:16:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:16:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
             35                  40                  45

Arg Ala Val Lys Ser Leu Gln Asn Ala Ser Gly Ile Glu Ala Ile Leu
 50                  55                  60

Arg Asn Leu Val Pro Cys Leu Pro Ser Ala Thr Ala Ala Pro Ser Arg
 65                  70                  75                  80

His Pro Ile Thr Ile Lys Ala Gly Asp Trp Gln Glu Phe Arg Arg Lys
                     85                  90                  95

Leu Thr Phe Tyr Leu Lys Thr Leu Glu Asn Ala Gln Ala Gln Gln
                100                 105                 110
```

(2) INFORMATION FOR SEQ ID NO:17:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:17:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
             35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Glu Lys
                     85                  90                  95

Leu Thr Phe Tyr Leu Val Thr Leu Glu Gln Ala Gln Glu Gln Gln
                100                 105                 110
```

(2) INFORMATION FOR SEQ ID NO:18:

(i) SEQUENCE CHARACTERISTICS:

(A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:18:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Glu Lys
                85                  90                  95

Leu Thr Phe Tyr Leu Val Ser Leu Glu His Ala Gln Glu Gln Gln
            100                 105                 110

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:19:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Gly Ile Glu Ala Ile Leu
    50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
            100                 105                 110

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:20:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

```
Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
 50                  55                  60

Arg Asn Leu Val Pro Cys Leu Pro Ser Ala Thr Ala Ala Pro Ser Arg
 65                  70                  75                  80

His Pro Ile Thr Ile Lys Ala Gly Asp Trp Gln Glu Phe Arg Glu Lys
                 85                  90                  95

Leu Thr Phe Tyr Leu Val Thr Leu Glu Gln Ala Gln Glu Gln Gln
                100                 105                 110

(2) INFORMATION FOR SEQ ID NO:21:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:21:

Asn Cys Ser Asn Met Ile Asp Glu Ile Ile Thr His Leu Lys Gln Pro
 1                5                   10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
 50                  55                  60

Arg Asn Leu Val Pro Cys Leu Pro Ser Ala Thr Ala Ala Pro Ser Arg
 65                  70                  75                  80

His Pro Ile Thr Ile Lys Ala Gly Asp Trp Gln Glu Phe Arg Glu Lys
                 85                  90                  95

Leu Thr Phe Tyr Leu Val Ser Leu Glu His Ala Gln Glu Gln Gln
                100                 105                 110

(2) INFORMATION FOR SEQ ID NO:22:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:22:

Asn Cys Ser Ile Met Ile Asp Glu Ile Ile His His Leu Lys Arg Pro
 1                5                   10                  15

Pro Ala Pro Leu Leu Asp Pro Asn Asn Leu Asn Ala Glu Asp Val Asp
                 20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95
```

```
Leu Thr Phe Tyr Leu Lys Thr Leu Glu Asn Ala Gln Ala Gln Gln
            100                 105                 110
```

(2) INFORMATION FOR SEQ ID NO:23:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:23:

```
Asn Cys Ser Ile Met Ile Asp Glu Ile Ile His His Leu Lys Arg Pro
1                5                  10                 15

Pro Asn Pro Leu Leu Asp Pro Asn Asn Leu Asn Ser Glu Asp Met Asp
                20                 25                 30

Ile Leu Met Glu Arg Asn Leu Arg Thr Pro Asn Leu Leu Ala Phe Val
            35                 40                 45

Arg Ala Val Lys His Leu Glu Asn Ala Ser Ala Ile Glu Ser Ile Leu
        50                 55                 60

Lys Asn Leu Leu Pro Cys Leu Pro Leu Ala Thr Ala Ala Pro Thr Arg
65                 70                 75                 80

His Pro Ile His Ile Lys Asp Gly Asp Trp Asn Glu Phe Arg Arg Lys
                85                 90                 95

Leu Thr Phe Tyr Leu Lys Thr Leu Glu Asn Ala Gln Ala Gln Gln
            100                 105                 110
```

(2) INFORMATION FOR SEQ ID NO:24:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:24:

```
Asn Cys Ser Ile Met Ile Asp Glu Ile Ile His His Leu Lys Val Pro
1                5                  10                 15

Pro Ala Pro Leu Leu Asp Ser Asn Asn Leu Asn Ser Glu Asp Met Asp
                20                 25                 30

Ile Leu Met Glu Arg Asn Leu Arg Leu Pro Asn Leu Leu Ala Phe Val
            35                 40                 45

Arg Ala Val Lys Asn Leu Glu Asn Ala Ser Ala Ile Glu Ser Ile Leu
        50                 55                 60

Lys Asn Leu Leu Pro Cys Leu Pro Leu Ala Thr Ala Ala Pro Thr Arg
65                 70                 75                 80

His Pro Ile His Ile Lys Asp Gly Asp Trp Asn Glu Phe Arg Arg Lys
                85                 90                 95

Leu Thr Phe Tyr Leu Lys Thr Leu Glu Asn Ala Gln Ala Gln Gln
            100                 105                 110
```

(2) INFORMATION FOR SEQ ID NO:25:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:25:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:26:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:26:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Gln Gln Ala Gln Glu Gln
                100                 105                 110

Gln (2) INFORMATION FOR SEQ ID NO:27:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:27:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala

```
                35                  40                  45
Phe Asn Arg Ala Val Lys Ser Leu Gln Asn Ala Ser Gly Ile Glu Ala
 50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:28:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:28:

```
Met Ala Asn Cys Ser Ile Met Ile Asp Glu Ile Ile His His Leu Lys
 1                   5                  10                  15

Arg Pro Pro Ala Pro Leu Leu Asp Pro Asn Asn Leu Asn Ala Glu Asp
                 20                  25                  30

Val Asp Ile Leu Met Glu Arg Asn Leu Arg Leu Pro Asn Leu Glu Ser
                 35                  40                  45

Phe Val Arg Ala Val Lys Asn Leu Glu Asn Ala Ser Ala Ile Glu Ser
 50                  55                  60

Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                 85                  90                  95

Arg Lys Leu Thr Phe Tyr Leu Lys Thr Leu Glu Asn Ala Gln Ala Gln
                100                 105                 110

Gln
```

(2) INFORMATION FOR SEQ ID NO:29:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:29:

```
Met Ala Asn Cys Ser Ile Met Ile Asp Glu Ile Ile His His Leu Lys
 1                   5                  10                  15

Arg Pro Pro Asn Pro Leu Leu Asp Pro Asn Asn Leu Asn Ser Glu Asp
                 20                  25                  30

Met Asp Ile Leu Met Glu Arg Asn Leu Arg Thr Pro Asn Leu Leu Ala
                 35                  40                  45

Phe Val Arg Ala Val Lys His Leu Glu Asn Ala Ser Ala Ile Glu Ser
 50                  55                  60

Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
```

```
                    85                  90                  95
Arg Lys Leu Thr Phe Tyr Leu Lys Thr Leu Glu Asn Ala Gln Ala Gln
                100                 105                 110
Gln (2) INFORMATION FOR SEQ ID NO:30:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:30:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Ala Ile Glu Ser
        50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110

Gln (2) INFORMATION FOR SEQ ID NO:31:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:31:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:32:
```

(i) SEQUENCE CHARACTERISTICS:
    (A) LENGTH: 113 amino acids
    (B) TYPE: amino acid
    (D) TOPOLOGY: linear (ii) MOLECULE TYPE: peptide (xi) SEQUENCE DESCRIPTION: SEQ ID NO:32:

```
Met Ala Asn Cys Ser Ile Met Ile Asp Glu Ile Ile His His Leu Lys
1               5                   10                  15
Arg Pro Pro Asn Pro Leu Leu Asp Pro Asn Asn Leu Asn Ser Glu Asp
                20                  25                  30
Met Asp Ile Leu Met Glu Arg Asn Leu Arg Thr Pro Asn Leu Leu Ala
            35                  40                  45
Phe Val Arg Ala Val Lys His Leu Glu Asn Ala Ser Gly Ile Glu Ala
        50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:33:

(i) SEQUENCE CHARACTERISTICS:
    (A) LENGTH: 113 amino acids
    (B) TYPE: amino acid
    (D) TOPOLOGY: linear (ii) MOLECULE TYPE: peptide (xi) SEQUENCE DESCRIPTION: SEQ ID NO:33:

```
Met Ala Asn Cys Ser Ile Met Ile Asp Glu Ile Ile His His Leu Lys
1               5                   10                  15
Val Pro Pro Ala Pro Leu Leu Asp Ser Asn Asn Leu Asn Ser Glu Asp
                20                  25                  30
Met Asp Ile Leu Met Glu Arg Asn Leu Arg Leu Pro Asn Leu Leu Ala
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:34:

(i) SEQUENCE CHARACTERISTICS:
    (A) LENGTH: 113 amino acids
    (B) TYPE: amino acid
    (D) TOPOLOGY: linear (ii) MOLECULE TYPE: peptide (xi) SEQUENCE DESCRIPTION: SEQ ID NO:34:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:35:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:35:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:36:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:36:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45
```

```
Phe Val Arg Ala Val Lys His Leu Glu Asn Ala Ser Gly Ile Glu Ala
         50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:37:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:37:

```
Met Ala Asn Cys Ser Ile Met Ile Asp Glu Ile Ile His His Leu Lys
 1               5                  10                  15

Val Pro Ala Pro Leu Leu Asp Ser Asn Asn Leu Asn Ser Glu Asp
                 20                  25                  30

Met Asp Ile Leu Met Glu Arg Asn Leu Arg Leu Pro Asn Leu Leu Ala
                 35                  40                  45

Phe Val Arg Ala Val Lys Asn Leu Glu Asn Ala Ser Gly Ile Glu Ala
         50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:38:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:38:

```
Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
                 20                  25                  30

Met Asp Ile Leu Met Glu Arg Asn Leu Arg Thr Pro Asn Leu Leu Ala
                 35                  40                  45

Phe Val Arg Ala Val Lys His Leu Glu Asn Ala Ser Gly Ile Glu Ala
         50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95
```

Glu Lys Leu Thr Phe Tyr Leu Val Thr Leu Glu Gln Ala Gln Glu Gln
                100                 105                 110

Gln (2) INFORMATION FOR SEQ ID NO:39:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:39:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
                100                 105                 110

Gln (2) INFORMATION FOR SEQ ID NO:40:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:40:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Ser Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:41:

(i) SEQUENCE CHARACTERISTICS:
    (A) LENGTH: 113 amino acids
    (B) TYPE: amino acid
    (D) TOPOLOGY: linear (ii) MOLECULE TYPE: peptide (xi) SEQUENCE DESCRIPTION: SEQ ID NO:41:

```
Met Ala Asn Cys Ser Ile Met Ile Asp Glu Ala Ile His His Leu Lys
1               5                   10                  15
Arg Pro Pro Ala Pro Ser Leu Asp Pro Asn Asn Leu Asn Asp Glu Asp
                20                  25                  30
Met Ser Ile Leu Met Glu Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:42:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:42:

```
Met Ala Asn Cys Ser Ile Met Ile Asp Glu Ile Ile His His Leu Lys
1               5                   10                  15
Arg Pro Pro Ala Pro Leu Leu Asp Pro Asn Asn Leu Asn Asp Glu Asp
                20                  25                  30
Met Ser Ile Leu Met Glu Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:43:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:43:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:44:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:44:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:45:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:45:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Met Ser Ile Leu Met Glu Arg Asn Leu Arg Leu Pro Asn Leu Glu Ser
            35                  40                  45

```
Phe Val Arg Ala Val Lys Asn Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:46:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:46:

Met Ala Tyr Pro Glu Thr Asp Tyr Lys Asp Asp Asp Lys Asn Cys
  1               5                  10                  15

Ser Ile Met Ile Asp Glu Ile Ile His His Leu Lys Arg Pro Pro Ala
                 20                  25                  30

Pro Leu Leu Asp Pro Asn Asn Leu Asn Ala Glu Asp Val Asp Ile Leu
             35                  40                  45

Met Glu Arg Asn Leu Arg Leu Pro Asn Leu Glu Ser Phe Val Arg Ala
 50                  55                  60

Val Lys Asn Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                 85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
            115                 120                 125

(2) INFORMATION FOR SEQ ID NO:47:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:47:

Met Ala Tyr Pro Glu Thr Asp Tyr Lys Asp Asp Asp Lys Asn Cys
  1               5                  10                  15

Ser Ile Met Ile Asp Glu Ile Ile His His Leu Lys Arg Pro Pro Asn
                 20                  25                  30

Pro Leu Leu Asp Pro Asn Asn Leu Asn Ser Glu Asp Met Asp Ile Leu
             35                  40                  45

Met Glu Arg Asn Leu Arg Thr Pro Asn Leu Leu Ala Phe Val Arg Ala
 50                  55                  60

Val Lys His Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                 85                  90                  95
```

```
Ile Ile Ile Lys Ala Gly Asp Trp Gln Glu Phe Arg Glu Lys Leu Thr
            100                 105                 110

Phe Tyr Leu Val Thr Leu Glu Gln Ala Gln Glu Gln Gln
        115                 120                 125
```

(2) INFORMATION FOR SEQ ID NO:48:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:48:

```
Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
            20                  25                  30

Val Ser Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:49:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:49:

```
Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
            20                  25                  30

Leu Pro Leu Leu Asp Phe Asn Asn Leu Asn Gly Glu Asp Gln Asp Ile
        35                  40                  45

Leu Met Glu Asn Asn Leu Arg Arg Pro Asn Leu Glu Ala Phe Asn Arg
    50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
            100                 105                 110

Thr Phe Tyr Leu Lys Thr Leu Glu Asn Ala Gln Ala Gln Gln Thr Thr
        115                 120                 125

Leu Ser Leu Ala Ile Phe
```

130

(2) INFORMATION FOR SEQ ID NO:50:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:50:

```
Gly Gly Gly Ser Gly Gly Gly Ser Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35
```

(2) INFORMATION FOR SEQ ID NO:51:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:51:

```
Ile Ser Glu Pro Ser Gly Pro Ile Ser Thr Ile Asn Pro Ser Pro Pro
1               5                   10                  15

Ser Lys Glu Ser His Lys Ser Pro
            20
```

(2) INFORMATION FOR SEQ ID NO:52:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:52:

```
Ile Glu Gly Arg Ile Ser Glu Pro Ser Gly Pro Ile Ser Thr Ile Asn
1               5                   10                  15

Pro Ser Pro Pro Ser Lys Glu Ser His Lys Ser Pro
            20                  25
```

(2) INFORMATION FOR SEQ ID NO:53:

(i) SEQUENCE CHARACTERISTICS:
        (A) LENGTH: 906 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:53:

```
ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAATCGA GGGAAGGATT        360

TCCCCGGGTG GTGGTTCTGG CGGCGGCTCC AACATGGCTA CACCATTAGG CCCTGCCAGC        420

TCCCTGCCCC AGAGCTTCCT GCTCAAGTGC TTAGAGCAAG TGAGGAAGAT CCAGGGCGAT        480

GGCGCAGCGC TCCAGGAGAA GCTGTGTGCC ACCTACAAGC TGTGCCACCC CGAGGAGCTG        540

GTGCTGCTCG GACACTCTCT GGGCATCCCC TGGGCTCCCC TGAGCTCCTG CCCCAGCCAG        600

GCCCTGCAGC TGGCAGGCTG CTTGAGCCAA CTCCATAGCG GCCTTTTCCT CTACCAGGGG        660

CTCCTGCAGG CCCTGGAAGG GATATCCCCC GAGTTGGGTC CCACCTTGGA CACACTGCAG        720

CTGGACGTCG CCGACTTTGC CACCACCATC TAACTGGGAA TGGCCCCTGC CCTGCAGCCC        780

ACCCAGGGTG CCATGCCGGC CTTCGCCTCT GCTTTCCAGC GCCGGGCAGG AGGGGTCCTG        840

GTTGCTAGCC ATCTGCAGAG CTTCCTGGAG GTGTCGTACC GCGTTCTACG CCACCTTGCG        900

CAGCCC                                                                  906

(2) INFORMATION FOR SEQ ID NO:54:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54:

ATGGCTAACT GCTCTATAAT GATCGATGAA ATTATACATC ACTTAAAGAG ACCACCTAAC         60

CCTTTGCTGG ACCCGAACAA CCTCAATTCT GAAGACATGG ATATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAATCGA GGGAAGGATT        360

TCCCCGGGTG GTGGTTCTGG CGGCGGCTCC AACATGGCTA ACTGCTCTAT AATGATCGAT        420

GAAATTATAC ATCACTTAAA GAGACCACCT AACCCTTTGC TGGACCCGAA CAACCTCAAT        480

TCTGAAGACA TGGATATCCT GATGGAACGA AACCTTCGAA CTCCAAACCT GCTCGCATTC        540

GTAAGGGCTG TCAAGCACTT AGAAAATGCA TCAGGTATTG AGGCAATTCT TCGTAATCTC        600

CAACCATGTC TGCCCTCTGC CACGGCCGCA CCCTCTCGAC ATCCAATCAT CATCAAGGCA        660

GGTGACTGGC AAGAATTCCG GGAAAAACTG ACGTTCTATC TGGTTACCCT TGAGCAAGCG        720

CAGGAACAAC AG                                                           732

(2) INFORMATION FOR SEQ ID NO:55:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:55:

ATGGCTAACT GCTCTATAAT GATCGATGAA ATTATACATC ACTTAAAGAG ACCACCTAAC         60
```

```
CCTTTGCTGG ACCCGAACAA CCTCAATTCT GAAGACATGG ATATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAATCGA GGGAAGGATT        360

TCCCCGGGTG GTGGTTCTGG CGGCGGCTCC AACATGGCAC CGGCTCGTTC CCCGTCCCCG        420

TCTACCCAGC CGTGGGAACA CGTGAATGCC ATCCAGGAGG CCCGGCGTCT CCTGAACCTG        480

AGTAGAGACA CTGCTGCTGA GATGAATGAA ACAGTAGAAG TGATATCAGA AATGTTTGAC        540

CTCCAGGAGC CGACTTGCCT ACAGACCCGC CTGGAGCTGT ACAAGCAGGG CCTGCGGGGC        600

AGCCTCACCA AGCTCAAGGG CCCCTTGACC ATGATGGCCA GCCACTACAA GCAGCACTGC        660

CCTCCAACCC CGGAAACTTC CTGTGCAACC CAGATTATCA CCTTTGAAAG TTTCAAAGAG        720

AACCTGAAGG ACTTCCTGCT TGTCATCCCC TTTGACTGCT GGGAGCCAGT CCAGGAG           777

(2) INFORMATION FOR SEQ ID NO:56:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:56:

ATGGCTAACT GCTCTATAAT GATCGATGAA ATTATACATC ACTTAAAGAG ACCACCTAAC         60

CCTTTGCTGG ACCCGAACAA CCTCAATTCT GAAGACATGG ATATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAATCGA GGGAAGGATT        360

TCCCCGGGTG GTGGTTCTGG CGGCGGCTCC AACATGGCTA CACCATTGGG CCCTGCCAGC        420

TCCCTGCCCC AGAGCTTCCT GCTCAAGTCT TTAGAGCAAG TGAGGAAGAT CCAGGGCGAT        480

GGCGCAGCGC TCCAGGAGAA GCTGTGTGCC ACCTACAAGC TGTGCCACCC CGAGGAGCTG        540

GTGCTGCTCG GACACTCTCT GGGCATCCCC TGGGCTCCCC TGAGCTCCTG CCCCAGCCAG        600

GCCCTGCAGC TGGCAGGCTG CTTGAGCCAA CTCCATAGCG GCCTTTTCCT CTACCAGGGG        660

CTCCTGCAGG CCCTGGAAGG GATATCCCCC GAGTTGGGTC CCACCTTGGA CACACTGCAG        720

CTGGACGTCG CCGACTTTGC CACCACCATC TGGCAGCAGA TGGAAGAACT GGGAATGGCC        780

CCTGCCCTGC AGCCCACCCA GGGTGCCATG CCGGCCTTCG CCTCTGCTTT CCAGCGCCGG        840

GCAGGAGGGG TCCTGGTTGC TAGCCATCTG CAGAGCTTCC TGGAGGTGTC GTACCGCGTT        900

CTACGCCACC TTGCGCAGCC C                                                  921

(2) INFORMATION FOR SEQ ID NO:57:

(i) SEQUENCE CHARACTERISTICS:
        (A) LENGTH: 951 base pairs
        (B) TYPE: nucleic acid
        (C) STRANDEDNESS: double
        (D) TOPOLOGY: linear (ii) MOLECULE TYPE: DNA (genomic)
```

(xi) SEQUENCE DESCRIPTION: SEQ ID NO:57:

```
ATGGCTAACT GCTCTATAAT GATCGATGAA ATTATACATC ACTTAAAGAG ACCACCTAAC      60
CCTTTGCTGG ACCCGAACAA CCTCAATTCT GAAGACATGG ATATCCTGAT GGAACGAAAC     120
CTTCGAACTC CAAACCTGCT CGCATTCGTA AGGGCTGTCA AGCACTTAGA AAATGCATCA     180
GGTATTGAGG CAATTCTTCG TAATCTCCAA CCATGTCTGC CCTCTGCCAC GGCCGCACCC     240
TCTCGACATC AATCATCAT CAAGGCAGGT GACTGGCAAG AATTCCGGGA AAAACTGACG      300
TTCTATCTGG TTACCCTTGA GCAAGCGCAG GAACAACAGT ACGTAATCGA GGGAAGGATT     360
TCCCCGGGTG GTGGTTCTGG CGGCGGCTCC AACATGGCTC CAGTACCACC AGGTGAAGAT     420
TCCAAAGATG TGGCCGCCCC ACACAGACAG CCACTCACCT CTTCAGAACG AATTGACAAA     480
CAAATTCGGT ACATCCTCGA CGGGATATCA GCCCTGAGAA AGGAGACATG TAACAAGAGT     540
AACATGTGTG AAAGCAGCAA AGAGGCGCTA GCAGAAAACA ACCTGAACCT TCCAAAGATG     600
GCTGAAAAAG ATGGATGCTT CCAATCCGGA TTCAATGAGG AGACTTGCCT GGTGAAAATC     660
ATCACTGGTC TTTTGGAGTT TGAGGTATAC CTCGAGTACC TCCAGAACAG ATTTGAGAGT     720
AGTGAGGAAC AAGCCAGAGC TGTGCAGATG TCGACAAAAG TCCTGATCCA GTTCCTGCAG     780
AAAAAGGCAA AGAATCTAGA TGCAATAACC ACCCCTGACC CAACCACAAA TGCATCCCTG     840
CTGACGAAGC TGCAGGCACA GAACCAGTGG CTGCAGGACA TGACAACTCA TCTCATTCTG     900
CGCAGCTTTA AGGAGTTCCT GCAGTCCAGC CTGAGGGCTC TTCGGCAAAT G              951
```

(2) INFORMATION FOR SEQ ID NO:58:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:58:

```
ATGGCTAACT GCTCTATAAT GATCGATGAA ATTATACATC ACTTAAAGAG ACCACCTAAC      60
CCTTTGCTGG ACCCGAACAA CCTCAATTCT GAAGACATGG ATATCCTGAT GGAACGAAAC     120
CTTCGAACTC CAAACCTGCT CGCATTCGTA AGGGCTGTCA AGCACTTAGA AAATGCATCA     180
GGTATTGAGG CAATTCTTCG TAATCTCCAA CCATGTCTGC CCTCTGCCAC GGCCGCACCC     240
TCTCGACATC AATCATCAT CAAGGCAGGT GACTGGCAAG AATTCCGGGA AAAACTGACG      300
TTCTATCTGG TTACCCTTGA GCAAGCGCAG GAACAACAGT ACGTAATCGA GGGAAAGATT     360
TCCCCGGGTG GTGGTTCTGG CGGCGGCTCC AACATGGCTA ACTGCTCTAT AATGATCGAT     420
GAAATTATAC ATCACTTAAA GAGACCACCT AACCCTTTGC TGGACCCGAA CAACCTCAAT     480
TCTGAAGACA TGGATATCCT GATGGAACGA AACCTTCGAA CTCCAAACCT GCTCGCATTC     540
GTAAGGGCTG TCAAGCACTT AGAAAATGCA TCAGGTATTG AGGCAATTCT TCGTAATCTC     600
CAACCATGTC TGCCCTCTGC CACGGCCGCA CCCTCTCGAC ATCCAATCAT CATCAAGGCA     660
GGTGACTGGC AAGAATTCCG GGAAAAACTG ACGTTCTATC TGGTTACCCT TGAGCAAGCG     720
CAGGAACAAC AG                                                         732
```

(2) INFORMATION FOR SEQ ID NO:59:

(i) SEQUENCE CHARACTERISTICS:
        (A) LENGTH: 921 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:59:

```
ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAATCGA GGGAAAGATT     360

TCCCCGGGTG GTGGTTCTGG CGGCGGCTCC AACATGGCTA CACCATTGGG CCCTGCCAGC     420

TCCCTGCCCC AGAGCTTCCT GCTCAAGTCT TTAGAGCAAG TGAGGAAGAT CCAGGGCGAT     480

GGCGCAGCGC TCCAGGAGAA GCTGTGTGCC ACCTACAAGC TGTGCCACCC CGAGGAGCTG     540

GTGCTGCTCG ACACTCTCT GGGCATCCCC TGGGCTCCCC TGAGCTCCTG CCCCAGCCAG      600

GCCCTGCAGC TGGCAGGCTG CTTGAGCCAA CTCCATAGCG GCCTTTTCCT CTACCAGGGG     660

CTCCTGCAGG CCCTGGAAGG GATATCCCCC GAGTTGGGTC CCACCTTGGA CACACTGCAG     720

CTGGACGTCG CCGACTTTGC CACCACCATC TGGCAGCAGA TGGAAGAACT GGGAATGGCC     780

CCTGCCCTGC AGCCCACCCA GGGTGCCATG CCGGCCTTCG CCTCTGCTTT CCAGCGCCGG     840

GCAGGAGGGG TCCTGGTTGC TAGCCATCTG CAGAGCTTCC TGGAGGTGTC GTACCGCGTT     900

CTACGCCACC TTGCGCAGCC C                                               921
```

(2) INFORMATION FOR SEQ ID NO:60:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:60:

```
ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG GTGGTTCTGG CGGCGGCTCC AACATGGCTA CACCATTGGG CCCTGCCAGC     420

TCCCTGCCCC AGAGCTTCCT GCTCAAGTCT TTAGAGCAAG TGAGGAAGAT CCAGGGCGAT     480

GGCGCAGCGC TCCAGGAGAA GCTGTGTGCC ACCTACAAGC TGTGCCACCC CGAGGAGCTG     540

GTGCTGCTCG ACACTCTCT GGGCATCCCC TGGGCTCCCC TGAGCTCCTG CCCCAGCCAG      600

GCCCTGCAGC TGGCAGGCTG CTTGAGCCAA CTCCATAGCG GCCTTTTCCT CTACCAGGGG     660

CTCCTGCAGG CCCTGGAAGG GATATCCCCC GAGTTGGGTC CCACCTTGGA CACACTGCAG     720

CTGGACGTCG CCGACTTTGC CACCACCATC TGGCAGCAGA TGGAAGAACT GGGAATGGCC     780
```

| CCTGCCCTGC AGCCCACCCA GGGTGCCATG CCGGCCTTCG CCTCTGCTTT CCAGCGCCGG | 840 |
| GCAGGAGGGG TCCTGGTTGC TAGCCATCTG CAGAGCTTCC TGGAGGTGTC GTACCGCGTT | 900 |
| CTACGCCACC TTGCGCAGCC C | 921 |

(2) INFORMATION FOR SEQ ID NO:61:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:61:

| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG GTGGTTCTGG CGGCGGCTCC AACATGGCTA ACTGCTCTAT AATGATCGAT | 420 |
| GAAATTATAC ATCACTTAAA GAGACCACCT AACCCTTTGC TGGACCCGAA CAACCTCAAT | 480 |
| TCTGAAGACA TGGATATCCT GATGGAACGA AACCTTCGAA CTCCAAACCT GCTCGCATTC | 540 |
| GTAAGGGCTG TCAAGCACTT AGAAAATGCA TCAGGTATTG AGGCAATTCT TCGTAATCTC | 600 |
| CAACCATGTC TGCCCTCTGC CACGGCCGCA CCCTCTCGAC ATCCAATCAT CATCAAGGCA | 660 |
| GGTGACTGGC AAGAATTCCG GGAAAAACTG ACGTTCTATC TGGTTACCCT TGAGCAAGCG | 720 |
| CAGGAACAAC AG | 732 |

(2) INFORMATION FOR SEQ ID NO:62:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:62:

| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAATCGA GGGAAGGATT | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTAACTGC TCTATAATGA TCGATGAAAT TATACATCAC | 480 |
| TTAAAGAGAC CACCTAACCC TTTGCTGGAC CCGAACAACC TCAATTCTGA AGACATGGAT | 540 |
| ATCCTGATGG AACGAAACCT TCGAACTCCA AACCTGCTCG CATTCGTAAG GCTGTCAAG | 600 |
| CACTTAGAAA ATGCATCAGG TATTGAGGCA ATTCTTCGTA ATCTCCAACC ATGTCTGCCC | 660 |

```
TCTGCCACGG CCGCACCCTC TCGACATCCA ATCATCATCA AGGCAGGTGA CTGGCAAGAA      720

TTCCGGGAAA AACTGACGTT CTATCTGGTT ACCCTTGAGC AAGCGCAGGA ACAACAG        777
```

(2) INFORMATION FOR SEQ ID NO:63:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:63:

```
ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAAGATT      360

TCCCCGGGTG AACCGTCTGG TCCAATCTCT ACTATCAACC CGTCTCCTCC GTCTAAAGAA      420

TCTCATAAAT CTCCAAACAT GGCTAACTGC TCTATAATGA TCGATGAAAT TATACATCAC      480

TTAAAGAGAC CACCTAACCC TTTGCTGGAC CCGAACAACC TCAATTCTGA AGACATGGAT      540

ATCCTGATGG AACGAAACCT TCGAACTCCA AACCTGCTCG CATTCGTAAG GGCTGTCAAG      600

CACTTAGAAA ATGCATCAGG TATTGAGGCA ATTCTTCGTA ATCTCCAACC ATGTCTGCCC      660

TCTGCCACGG CCGCACCCTC TCGACATCCA ATCATCATCA AGGCAGGTGA CTGGCAAGAA      720

TTCCGGGAAA AACTGACGTT CTATCTGGTT ACCCTTGAGC AAGCGCAGGA ACAACAG        777
```

(2) INFORMATION FOR SEQ ID NO:64:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:64:

```
ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTAACTGC TCTATAATGA TCGATGAAAT TATACATCAC      480

TTAAAGAGAC CACCTAACCC TTTGCTGGAC CCGAACAACC TCAATTCTGA AGACATGGAT      540

ATCCTGATGG AACGAAACCT TCGAACTCCA AACCTGCTCG CATTCGTAAG GGCTGTCAAG      600

CACTTAGAAA ATGCATCAGG TATTGAGGCA ATTCTTCGTA ATCTCCAACC ATGTCTGCCC      660
```

| | | |
|---|---|---|
| TCTGCCACGG CCGCACCCTC TCGACATCCA ATCATCATCA AGGCAGGTGA CTGGCAAGAA | 720 | |
| TTCCGGGAAA AACTGACGTT CTATCTGGTT ACCCTTGAGC AAGCGCAGGA ACAACAG | 777 | |

(2) INFORMATION FOR SEQ ID NO:65:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:65:

| | |
|---|---|
| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAACTGACG | 300 |
| TTCTATCTGG TTACCCTTGA GCAAGCGCAG GAACAACAGT ACGTAATCGA GGGAAGGATT | 360 |
| TCCCCCGGGC CTCCTGTCAA TGCTGGCGGC GGCTCTGGTG GTGGTTCTGG TGGCGGCTCT | 420 |
| GAGGGTGGCG GCTCTGAGGG TGGCGGTTCT GAGGGTGGCG GCTCTGAGGG TGGCGGTTCC | 480 |
| GGTGGCGGCT CCGGTTCCGG TGATTTTGAT TATGAAAACA TGGCTACACC ATTGGGCCCT | 540 |
| GCCAGCTCCC TGCCCCAGAG CTTCCTGCTC AAGTCTTTAG AGCAAGTGAG GAAGATCCAG | 600 |
| GGCGATGGCA CAGCGCTCCA GGAGAAGCTG TGTGCCACCT ACAAGCTGTG CCACCCCGAG | 660 |
| GAGCTGGTGC TGCTCGGACA CTCTCTGGGC ATCCCCTGGG CTCCCCTGAG CTCCTGCCCC | 720 |
| AGCCAGGCCC TGCAGCTGGC AGGCTGCTTG AGCCAACTCC ATAGCGGCCT TTTCCTCTAC | 780 |
| CAGGGGCTCC TGCAGGCCCT GGAAGGGATA TCCCCCGAGT TGGGTCCCAC CTTGGACACA | 840 |
| CTGCAGCTGG ACGTCGCCGA CTTTGCCACC ACCATCTGGC AGCAGATGGA AGAACTGGGA | 900 |
| ATGGCCCCTG CCCTGCAGCC CACCCAGGGT GCCATGCCGG CCTTCGCCTC TGCTTTCCAG | 960 |
| CGCCGGGCAG GAGGGGTCCT GGTTGCTAGC CATCTGCAGA GCTTCCTGGA GGTGTCGTAC | 1020 |
| CGCGTTCTAC GCCACCTTGC GCAGCCC | 1047 |

(2) INFORMATION FOR SEQ ID NO:66:

(i) SEQUENCE CHARACTERISTICS:
        (A) LENGTH: 903 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:66:

| | |
|---|---|
| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAACTGACG | 300 |
| TTCTATCTGG TTACCCTTGA GCAAGCGCAG GAACAACAGT ACGTAATCGA GGGAAGGATT | 360 |
| TCCCCCGGGC CTCCTGTCAA TGCTGGCGGC GGCTCTGGTG GTGGTTCTGG TGGCGGCTCT | 420 |

```
GAGGGTGGCG GCTCTGAGGG TGGCGGTTCT GAGGGTGGCG GCTCTGAGGG TGGCGGTTCC      480

GGTGGCGGCT CCGGTTCCGG TGATTTTGAT TATGAAAACA TGGCACCGGC TCGTTCCCCG      540

TCCCCGTCTA CCCAGCCGTG GGAACACGTG AATGCCATCC AGGAGGCCCG GCGTCTCCTG      600

AACCTGAGTA GAGACACTGC TGCTGAGATG AATGAAACAG TAGAAGTGAT ATCAGAAATG      660

TTTGACCTCC AGGAGCCGAC TTGCCTACAG ACCCGCCTGG AGCTGTACAA GCAGGGCCTG      720

CGGGGCAGCC TCACCAAGCT CAAGGGCCCC TTGACCATGA TGGCCAGCCA CTACAAGCAG      780

CACTGCCCTC CAACCCCGGA AACTTCCTGT GCAACCCAGA TTATCACCTT TGAAAGTTTC      840

AAAGAGAACC TGAAGGACTT CCTGCTTGTC ATCCCCTTTG ACTGCTGGGA GCCAGTCCAG      900

GAG                                                                    903
```

(2) INFORMATION FOR SEQ ID NO:67:

(i) SEQUENCE CHARACTERISTICS:
        (A) LENGTH: 1017 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:67:

```
ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAGGATT      360

TCCCCCGGTG GCGGCGGCTC TGGTGGTGGT TCTGGTGGCG GCTCTGAGGG TGGCGGCTCT      420

GAGGGTGGCG GTTCTGAGGG TGGCGGCTCT GAGGGTGGCG GTTCCGGTGG CGGCTCCGGT      480

TCCGGTAACA TGGCTACACC ATTAGGCCCT GCCAGCTCCC TGCCCCAGAG CTTCCTGCTC      540

AAGTGCTTAG AGCAAGTGAG GAAGATCCAG GGCGATGGCG CAGCGCTCCA GGAGAAGCTG      600

TGTGCCACCT ACAAGCTGTG CCACCCCGAG GAGCTGGTGC TGCTCGGACA CTCTCTGGGC      660

ATCCCCTGGG CTCCCCTGAG CTCCTGCCCC AGCCAGGCCC TGCAGCTGGC AGGCTGCTTG      720

AGCCAACTCC ATAGCGGCCT TTTCCTCTAC CAGGGGCTCC TGCAGGCCCT GGAAGGGATA      780

TCCCCCGAGT TGGGTCCCAC CTTGGACACA CTGCAGCTGG ACGTCGCCGA CTTTGCCACC      840

ACCATCTGGC AGCAGATGGA AGAACTGGGA ATGGCCCCTG CCCTGCAGCC CACCCAGGGT      900

GCCATGCCGG CCTTCGCCTC TGCTTTCCAG CGCCGGGCAG GAGGGGTCCT GGTTGCTAGC      960

CATCTGCAGA GCTTCCTGGA GGTGTCGTAC CGCGTTCTAC GCCACCTTGC GCAGCCC       1017
```

(2) INFORMATION FOR SEQ ID NO:68:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:68:

-continued

| | |
|---|---|
| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAATCGA GGGAAGGATT | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTACACCA TTAGGCCCTG CCAGCTCCCT GCCCCAGAGC | 480 |
| TTCCTGCTCA AGTGCTTAGA GCAAGTGAGG AAGATCCAGG GCGATGGCGC AGCGCTCCAG | 540 |
| GAGAAGCTGT GTGCCACCTA CAAGCTGTGC CACCCCGAGG AGCTGGTGCT GCTCGGACAC | 600 |
| TCTCTGGGCA TCCCCTGGGC TCCCCTGAGC TCCTGCCCCA GCCAGGCCCT GCAGCTGGCA | 660 |
| GGCTGCTTGA GCCAACTCCA TAGCGGCCTT TTCCTCTACC AGGGGCTCCT GCAGGCCCTG | 720 |
| GAAGGGATAT CCCCCGAGTT GGGTCCCACC TTGGACACAC TGCAGCTGGA CGTCGCCGAC | 780 |
| TTTGCCACCA CCATCTGGCA GCAGATGGAA GAACTGGGAA TGGCCCCTGC CCTGCAGCCC | 840 |
| ACCCAGGGTG CCATGCCGGC CTTCGCCTCT GCTTTCCAGC GCCGGGCAGG AGGGGTCCTG | 900 |
| GTTGCTAGCC ATCTGCAGAG CTTCCTGGAG GTGTCGTACC GCGTTCTACG CCACCTTGCG | 960 |
| CAGCCC | 966 |

(2) INFORMATION FOR SEQ ID NO:69:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:69:

| | |
|---|---|
| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAATCGA GGGAAGGATT | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCACCGGCT CGTTCCCCGT CCCCGTCTAC CCAGCCGTGG | 480 |
| GAACACGTGA ATGCCATCCA GGAGGCCCGG CGTCTCCTGA ACCTGAGTAG AGACACTGCT | 540 |
| GCTGAGATGA ATGAAACAGT AGAAGTGATA TCAGAAATGT TTGACCTCCA GGAGCCGACT | 600 |
| TGCCTACAGA CCCGCCTGGA GCTGTACAAG CAGGGCCTGC GGGGCAGCCT CACCAAGCTC | 660 |
| AAGGGCCCCT TGACCATGAT GGCCAGCCAC TACAAGCAGC ACTGCCCTCC AACCCCGGAA | 720 |
| ACTTCCTGTG CAACCCAGAT TATCACCTTT GAAAGTTTCA AAGAGAACCT GAAGGACTTC | 780 |
| CTGCTTGTCA TCCCCTTTGA CTGCTGGGAG CCAGTCCAGG AG | 822 |

(2) INFORMATION FOR SEQ ID NO:70:

(i) SEQUENCE CHARACTERISTICS:

(A) LENGTH: 966 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:70:

ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAATCGA GGGAAAGATT    360

TCCCCGGGTG AACCGTCTGG TCCAATCTCT ACTATCAACC CGTCTCCTCC GTCTAAAGAA    420

TCTCATAAAT CTCCAAACAT GGCTACACCA TTAGGCCCTG CCAGCTCCCT GCCCCAGAGC    480

TTCCTGCTCA AGTGCTTAGA GCAAGTGAGG AAGATCCAGG GCGATGGCGC AGCGCTCCAG    540

GAGAAGCTGT GTGCCACCTA CAAGCTGTGC CACCCCGAGG AGCTGGTGCT GCTCGGACAC    600

TCTCTGGGCA TCCCCTGGGC TCCCCTGAGC TCCTGCCCCA GCCAGGCCCT GCAGCTGGCA    660

GGCTGCTTGA GCCAACTCCA TAGCGGCCTT TTCCTCTACC AGGGGCTCCT GCAGGCCCTG    720

GAAGGGATAT CCCCCGAGTT GGGTCCCACC TTGGACACAC TGCAGCTGGA CGTCGCCGAC    780

TTTGCCACCA CCATCTGGCA GCAGATGGAA GAACTGGGAA TGGCCCCTGC CCTGCAGCCC    840

ACCCAGGGTG CCATGCCGGC CTTCGCCTCT GCTTTCCAGC GCCGGGCAGG AGGGGTCCTG    900

GTTGCTAGCC ATCTGCAGAG CTTCCTGGAG GTGTCGTACC GCGTTCTACG CCACCTTGCG    960

CAGCCC                                                              966

(2) INFORMATION FOR SEQ ID NO:71:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:71:

ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAGAGGG CGGTGGAGGC    360

TCCCCGGGTG AACCGTCTGG TCCAATCTCT ACTATCAACC CGTCTCCTCC GTCTAAAGAA    420

TCTCATAAAT CTCCAAACAT GGCTACACCA TTAGGCCCTG CCAGCTCCCT GCCCCAGAGC    480

TTCCTGCTCA AGTGCTTAGA GCAAGTGAGG AAGATCCAGG GCGATGGCGC AGCGCTCCAG    540

GAGAAGCTGT GTGCCACCTA CAAGCTGTGC CACCCCGAGG AGCTGGTGCT GCTCGGACAC    600

TCTCTGGGCA TCCCCTGGGC TCCCCTGAGC TCCTGCCCCA GCCAGGCCCT GCAGCTGGCA    660

GGCTGCTTGA GCCAACTCCA TAGCGGCCTT TTCCTCTACC AGGGGCTCCT GCAGGCCCTG    720

```
GAAGGGATAT CCCCCGAGTT GGGTCCCACC TTGGACACAC TGCAGCTGGA CGTCGCCGAC      780

TTTGCCACCA CCATCTGGCA GCAGATGGAA GAACTGGGAA TGGCCCCTGC CCTGCAGCCC      840

ACCCAGGGTG CCATGCCGGC CTTCGCCTCT GCTTTCCAGC GCCGGGCAGG AGGGGTCCTG      900

GTTGCTAGCC ATCTGCAGAG CTTCCTGGAG GTGTCGTACC GCGTTCTACG CCACCTTGCG      960

CAGCCC                                                                 966

(2) INFORMATION FOR SEQ ID NO:72:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:72:

ATGGCTACAC CATTAGGCCC TGCCAGCTCC CTGCCCCAGA GCTTCCTGCT CAAGTGCTTA       60

GAGCAAGTGA GGAAGATCCA GGGCGATGGC GCAGCGCTCC AGGAGAAGCT GTGTGCCACC      120

TACAAGCTGT GCCACCCCGA GGAGCTGGTG CTGCTCGGAC ACTCTCTGGG CATCCCCTGG      180

GCTCCCCTGA GCTCCTGCCC CAGCCAGGCC CTGCAGCTGG CAGGCTGCTT GAGCCAACTC      240

CATAGCGGCC TTTTCCTCTA CCAGGGGCTC CTGCAGGCCC TGGAAGGGAT ATCCCCCGAG      300

TTGGGTCCCA CCTTGGACAC ACTGCAGCTG GACGTCGCCG ACTTTGCCAC CACCATCTGG      360

CAGCAGATGG AAGAACTGGG AATGGCCCCT GCCCTGCAGC CCACCCAGGG TGCCATGCCG      420

GCCTTCGCCT CTGCTTTCCA GCGCCGGGCA GGAGGGGTCC TGGTTGCTAG CCATCTGCAG      480

AGCTTCCTGG AGGTGTCGTA CCGCGTTCTA CGCCACCTTG CGCAGCCCTA CGTAATCGAG      540

GGAAGGATTT CCCCGGGTGG TGGTTCTGGC GGCGGCTCCA ACATGGCTAA CTGCTCTATA      600

ATGATCGATG AAATTATACA TCACTTAAAG AGACCACCTA ACCCTTTGCT GGACCCGAAC      660

AACCTCAATT CTGAAGACAT GGATATCCTG ATGGAACGAA ACCTTCGAAC TCCAAACCTG      720

CTCGCATTCG TAAGGGCTGT CAAGCACTTA GAAAATGCAT CAGGTATTGA GGCAATTCTT      780

CGTAATCTCC AACCATGTCT GCCCTCTGCC ACGGCCGCAC CCTCTCGACA TCCAATCATC      840

ATCAAGGCAG GTGACTGGCA AGAATTCCGG GAAAAACTGA CGTTCTATCT GGTTACCCTT      900

GAGCAAGCGC AGGAACAACA G                                               921

(2) INFORMATION FOR SEQ ID NO:73:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:73:

ATGGCTACAC CATTAGGCCC TGCCAGCTCC CTGCCCCAGA GCTTCCTGCT CAAGTGCTTA       60

GAGCAAGTGA GGAAGATCCA GGGCGATGGC GCAGCGCTCC AGGAGAAGCT GTGTGCCACC      120

TACAAGCTGT GCCACCCCGA GGAGCTGGTG CTGCTCGGAC ACTCTCTGGG CATCCCCTGG      180

GCTCCCCTGA GCTCCTGCCC CAGCCAGGCC CTGCAGCTGG CAGGCTGCTT GAGCCAACTC      240

CATAGCGGCC TTTTCCTCTA CCAGGGGCTC CTGCAGGCCC TGGAAGGGAT ATCCCCCGAG      300
```

-continued

| | |
|---|---|
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTA CGTAATCGAG | 540 |
| GGAAGGATTT CCCCGGGTGA ACCGTCTGGT CCAATCTCTA CTATCAACCC GTCTCCTCCG | 600 |
| TCTAAAGAAT CTCATAAATC TCCAAACATG GCTAACTGCT CTATAATGAT CGATGAAATT | 660 |
| ATACATCACT TAAAGAGACC ACCTAACCCT TTGCTGGACC CGAACAACCT CAATTCTGAA | 720 |
| GACATGGATA TCCTGATGGA ACGAAACCTT CGAACTCCAA ACCTGCTCGC ATTCGTAAGG | 780 |
| GCTGTCAAGC ACTTAGAAAA TGCATCAGGT ATTGAGGCAA TTCTTCGTAA TCTCCAACCA | 840 |
| TGTCTGCCCT CTGCCACGGC CGCACCCTCT CGACATCCAA TCATCATCAA GGCAGGTGAC | 900 |
| TGGCAAGAAT TCCGGGAAAA ACTGACGTTC TATCTGGTTA CCCTTGAGCA AGCGCAGGAA | 960 |
| CAACAG | 966 |

(2) INFORMATION FOR SEQ ID NO:74:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:74:

| | |
|---|---|
| ATGGCTACAC CATTAGGCCC TGCCAGCTCC CTGCCCCAGA GCTTCCTGCT CAAGTGCTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTA CGTAATCGAG | 540 |
| GGAAGGATTT CCCCCGGGCC TCCTGTCAAT GCTGGCGGCG GCTCTGGTGG TGGTTCTGGT | 600 |
| GGCGGCTCTG AGGGTGGCGG CTCTGAGGGT GGCGGTTCTG AGGGTGGCGG CTCTGAGGGT | 660 |
| GGCGGTTCCG GTGGCGGCTC CGGTTCCGGT GATTTTGATT ATGAAAACAT GGCTAACTGC | 720 |
| TCTATAATGA TCGATGAAAT TATACATCAC TTAAAGAGAC CACCTAACCC TTTGCTGGAC | 780 |
| CCGAACAACC TCAATTCTGA AGACATGGAT ATCCTGATGG AACGAAACCT TCGAACTCCA | 840 |
| AACCTGCTCG CATTCGTAAG GGCTGTCAAG CACTTAGAAA ATGCATCAGG TATTGAGGCA | 900 |
| ATTCTTCGTA ATCTCCAACC ATGTCTGCCC TCTGCCACGG CCGCACCCTC TCGACATCCA | 960 |
| ATCATCATCA AGGCAGGTGA CTGGCAAGAA TTCCGGGAAA AACTGACGTT CTATCTGGTT | 1020 |
| ACCCTTGAGC AAGCGCAGGA ACAACAG | 1047 |

(2) INFORMATION FOR SEQ ID NO:75:

(i) SEQUENCE CHARACTERISTICS:
        (A) LENGTH: 921 base pairs
        (B) TYPE: nucleic acid

```
        (C) STRANDEDNESS: double
        (D) TOPOLOGY: linear (ii) MOLECULE TYPE: DNA (genomic)

(xi) SEQUENCE DESCRIPTION: SEQ ID NO:75:

ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTA CGTAATCGAG     540

GGAAGGATTT CCCCGGGTGG TGGTTCTGGC GGCGGCTCCA ACATGGCTAA CTGCTCTATA     600

ATGATCGATG AAATTATACA TCACTTAAAG AGACCACCTG CACCTTTGCT GGACCCGAAC     660

AACCTCAATG ACGAAGACGT CTCTATCCTG ATGGAACGAA ACCTTCGACT TCCAAACCTG     720

GAGAGCTTCG TAAGGGCTGT CAAGAACTTA GAAAATGCAT CAGGTATTGA GGCAATTCTT     780

CGTAATCTCC AACCATGTCT GCCCTCTGCC ACGGCCGCAC CCTCTCGACA TCCAATCATC     840

ATCAAGGCAG GTGACTGGCA AGAATTCCGG GAAAAACTGA CGTTCTATCT GGTTACCCTT     900

GAGCAAGCGC AGGAACAACA G                                               921

(2) INFORMATION FOR SEQ ID NO:76:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:76:

ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTA CGTAATCGAG     540

GGAAGGATTT CCCCCGGGCC TCCTGTCAAT GCTGGCGGCG GCTCTGGTGG TGGTTCTGGT     600

GGCGGCTCTG AGGGTGGCGG CTCTGAGGGT GGCGGTTCTG AGGGTGGCGG CTCTGAGGGT     660

GGCGGTTCCG GTGGCGGCTC CGGTTCCGGT GATTTTGATT ATGAAAACAT GGCTAACTGC     720

TCTATAATGA TCGATGAAAT TATACATCAC TTAAAGAGAC CACCTGCACC TTTGCTGGAC     780

CCGAACAACC TCAATGACGA AGACGTCTCT ATCCTGATGG AACGAAACCT TCGACTTCCA     840
```

| AACCTGGAGA GCTTCGTAAG GGCTGTCAAG AACTTAGAAA ATGCATCAGG TATTGAGGCA | 900 |
| ATTCTTCGTA ATCTCCAACC ATGTCTGCCC TCTGCCACGG CCGCACCCTC TCGACATCCA | 960 |
| ATCATCATCA AGGCAGGTGA CTGGCAAGAA TTCCGGGAAA AACTGACGTT CTATCTGGTT | 1020 |
| ACCCTTGAGC AAGCGCAGGA ACAACAG | 1047 |

(2) INFORMATION FOR SEQ ID NO:77:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:77:

| ATGGCTACAC CATTAGGCCC TGCCAGCTCC CTGCCCCAGA GCTTCCTGCT CAAGTGCTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTA CGTAATCGAG | 540 |
| GGAAGGATTT CCCCGGGTGA ACCGTCTGGT CCAATCTCTA CTATCAACCC GTCTCCTCCG | 600 |
| TCTAAAGAAT CTCATAAATC TCCAAACATG GCTAACTGCT CTATAATGAT CGATGAAATT | 660 |
| ATACATCACT TAAAGAGACC ACCTGCACCT TTGCTGGACC CGAACAACCT CAATGACGAA | 720 |
| GACGTCTCTA TCCTGATGGA ACGAAACCTT CGACTTCCAA ACCTGGAGAG CTTCGTAAGG | 780 |
| GCTGTCAAGA ACTTAGAAAA TGCATCAGGT ATTGAGGCAA TTCTTCGTAA TCTCCAACCA | 840 |
| TGTCTGCCCT CTGCCACGGC CGCACCCTCT CGACATCCAA TCATCATCAA GGCAGGTGAC | 900 |
| TGGCAAGAAT TCCGGGAAAA ACTGACGTTC TATCTGGTTA CCCTTGAGCA AGCGCAGGAA | 960 |
| CAACAG | 966 |

(2) INFORMATION FOR SEQ ID NO:78:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:78:

| ATGGCTACAC CATTAGGCCC TGCCAGCTCC CTGCCCCAGA GCTTCCTGCT CAAGTGCTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |

```
TTGGGTCCCA CCTTGGACAC ACTGCAGCTG GACGTCGCCG ACTTTGCCAC CACCATCTGG      360

CAGCAGATGG AAGAACTGGG AATGGCCCCT GCCCTGCAGC CCACCCAGGG TGCCATGCCG      420

GCCTTCGCCT CTGCTTTCCA GCGCCGGGCA GGAGGGGTCC TGGTTGCTAG CCATCTGCAG      480

AGCTTCCTGG AGGTGTCGTA CCGCGTTCTA CGCCACCTTG CGCAGCCCTA CGTAGAGGGC      540

GGTGGAGGCT CCCCGGGTGG TGGTTCTGGC GGCGGCTCCA ACATGGCTAA CTGCTCTATA      600

ATGATCGATG AAATTATACA TCACTTAAAG AGACCACCTG CACCTTTGCT GGACCCGAAC      660

AACCTCAATG ACGAAGACGT CTCTATCCTG ATGGAACGAA ACCTTCGACT TCCAAACCTG      720

GAGAGCTTCG TAAGGGCTGT CAAGAACTTA GAAAATGCAT CAGGTATTGA GGCAATTCTT      780

CGTAATCTCC AACCATGTCT GCCCTCTGCC ACGGCCGCAC CCTCTCGACA TCCAATCATC      840

ATCAAGGCAG GTGACTGGCA AGAATTCCGG GAAAAACTGA CGTTCTATCT GGTTACCCTT      900

GAGCAAGCGC AGGAACAACA G                                                921
```

(2) INFORMATION FOR SEQ ID NO:79:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:79:

```
ATGGCTACAC CATTAGGCCC TGCCAGCTCC CTGCCCCAGA GCTTCCTGCT CAAGTGCTTA       60

GAGCAAGTGA GGAAGATCCA GGGCGATGGC GCAGCGCTCC AGGAGAAGCT GTGTGCCACC      120

TACAAGCTGT GCCACCCCGA GGAGCTGGTG CTGCTCGGAC ACTCTCTGGG CATCCCCTGG      180

GCTCCCCTGA GCTCCTGCCC CAGCCAGGCC CTGCAGCTGG CAGGCTGCTT GAGCCAACTC      240

CATAGCGGCC TTTTCCTCTA CCAGGGGCTC CTGCAGGCCC TGGAAGGGAT ATCCCCCGAG      300

TTGGGTCCCA CCTTGGACAC ACTGCAGCTG GACGTCGCCG ACTTTGCCAC CACCATCTGG      360

CAGCAGATGG AAGAACTGGG AATGGCCCCT GCCCTGCAGC CCACCCAGGG TGCCATGCCG      420

GCCTTCGCCT CTGCTTTCCA GCGCCGGGCA GGAGGGGTCC TGGTTGCTAG CCATCTGCAG      480

AGCTTCCTGG AGGTGTCGTA CCGCGTTCTA CGCCACCTTG CGCAGCCCTA CGTAGAGGGC      540

GGTGGAGGCT CCCCGGGTGA ACCGTCTGGT CCAATCTCTA CTATCAACCC GTCTCCTCCG      600

TCTAAAGAAT CTCATAAATC TCCAAACATG GCTAACTGCT CTATAATGAT CGATGAAATT      660

ATACATCACT TAAAGAGACC ACCTGCACCT TTGCTGGACC CGAACAACCT CAATGACGAA      720

GACGTCTCTA TCCTGATGGA ACGAAACCTT CGACTTCCAA ACCTGGAGAG CTTCGTAAGG      780

GCTGTCAAGA ACTTAGAAAA TGCATCAGGT ATTGAGGCAA TTCTTCGTAA TCTCCAACCA      840

TGTCTGCCCT CTGCCACGGC CGCACCCTCT CGACATCCAA TCATCATCAA GGCAGGTGAC      900

TGGCAAGAAT TCCGGGAAAA ACTGACGTTC TATCTGGTTA CCCTTGAGCA AGCGCAGGAA      960

CAACAG                                                                 966
```

(2) INFORMATION FOR SEQ ID NO:80:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:80:

```
ATGGCTACAC CATTGGGCCC TGCCAGCTCC CTGCCCCAGA GCTTCCTGCT CAAGTCTTTA      60
GAGCAAGTGA GGAAGATCCA GGGCGATGGC GCAGCGCTCC AGGAGAAGCT GTGTGCCACC     120
TACAAGCTGT GCCACCCCGA GGAGCTGGTG CTGCTCGGAC ACTCTCTGGG CATCCCCTGG     180
GCTCCCCTGA GCTCCTGCCC CAGCCAGGCC CTGCAGCTGG CAGGCTGCTT GAGCCAACTC     240
CATAGCGGCC TTTTCCTCTA CCAGGGGCTC CTGCAGGCCC TGGAAGGGAT ATCCCCCGAG     300
TTGGGTCCCA CCTTGGACAC ACTGCAGCTG GACGTCGCCG ACTTTGCCAC CACCATCTGG     360
CAGCAGATGG AAGAACTGGG AATGGCCCCT GCCCTGCAGC CCACCCAGGG TGCCATGCCG     420
GCCTTCGCCT CTGCTTTCCA GCGCCGGGCA GGAGGGGTCC TGGTTGCTAG CCATCTGCAG     480
AGCTTCCTGG AGGTGTCGTA CCGCGTTCTA CGCCACCTTG CGCAGCCCTA CGTAGAGGGC     540
GGTGGAGGCT CCCCGGGTGG TGGTTCTGGC GGCGGCTCCA ACATGGCTAA CTGCTCTATA     600
ATGATCGATG AAATTATACA TCACTTAAAG AGACCACCTG CACCTTTGCT GGACCCGAAC     660
AACCTCAATG ACGAAGACGT CTCTATCCTG ATGGAACGAA ACCTTCGACT TCCAAACCTG     720
GAGAGCTTCG TAAGGGCTGT CAAGAACTTA GAAAATGCAT CAGGTATTGA GGCAATTCTT     780
CGTAATCTCC AACCATGTCT GCCCTCTGCC ACGGCCGCAC CCTCTCGACA TCCAATCATC     840
ATCAAGGCAG GTGACTGGCA AGAATTCCGG GAAAAACTGA CGTTCTATCT GGTTACCCTT     900
GAGCAAGCGC AGGAACAACA G                                               921
```

(2) INFORMATION FOR SEQ ID NO:81:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:81:

```
ATGGCTACAC CATTGGGCCC TGCCAGCTCC CTGCCCCAGA GCTTCCTGCT CAAGTCTTTA      60
GAGCAAGTGA GGAAGATCCA GGGCGATGGC GCAGCGCTCC AGGAGAAGCT GTGTGCCACC     120
TACAAGCTGT GCCACCCCGA GGAGCTGGTG CTGCTCGGAC ACTCTCTGGG CATCCCCTGG     180
GCTCCCCTGA GCTCCTGCCC CAGCCAGGCC CTGCAGCTGG CAGGCTGCTT GAGCCAACTC     240
CATAGCGGCC TTTTCCTCTA CCAGGGGCTC CTGCAGGCCC TGGAAGGGAT ATCCCCCGAG     300
TTGGGTCCCA CCTTGGACAC ACTGCAGCTG GACGTCGCCG ACTTTGCCAC CACCATCTGG     360
CAGCAGATGG AAGAACTGGG AATGGCCCCT GCCCTGCAGC CCACCCAGGG TGCCATGCCG     420
GCCTTCGCCT CTGCTTTCCA GCGCCGGGCA GGAGGGGTCC TGGTTGCTAG CCATCTGCAG     480
AGCTTCCTGG AGGTGTCGTA CCGCGTTCTA CGCCACCTTG CGCAGCCCTA CGTAGAGGGC     540
GGTGGAGGCT CCCCGGGTGA ACCGTCTGGT CCAATCTCTA CTATCAACCC GTCTCCTCCG     600
TCTAAAGAAT CTCATAAATC TCCAAACATG GCTAACTGCT CTATAATGAT CGATGAAATT     660
ATACATCACT TAAAGAGACC ACCTGCACCT TTGCTGGACC CGAACAACCT CAATGACGAA     720
GACGTCTCTA TCCTGATGGA ACGAAACCTT CGACTTCCAA ACCTGGAGAG CTTCGTAAGG     780
GCTGTCAAGA ACTTAGAAAA TGCATCAGGT ATTGAGGCAA TTCTTCGTAA TCTCCAACCA     840
TGTCTGCCCT CTGCCACGGC CGCACCCTCT CGACATCCAA TCATCATCAA GGCAGGTGAC     900
TGGCAAGAAT TCCGGGAAAA ACTGACGTTC TATCTGGTTA CCCTTGAGCA AGCGCAGGAA     960
```

CAACAG 966

(2) INFORMATION FOR SEQ ID NO:82:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:82:

```
ATGGCTAACT GCTCTATAAT GATCGATGAA ATTATACATC ACTTAAAGAG ACCACCTGCA      60
CCTTTGCTGG ACCCGAACAA CCTCAATGAC GAAGACGTCT CTATCCTGAT GGAACGAAAC     120
CTTCGACTTC CAAACCTGGA GAGCTTCGTA AGGGCTGTCA AGAACTTAGA AAATGCATCA     180
GGTATTGAGG CAATTCTTCG TAATCTCCAA CCATGTCTGC CCTCTGCCAC GGCCGCACCC     240
TCTCGACATC CAATCATCAT CAAGGCAGGT GACTGGCAAG AATTCCGGGA AAAACTGACG     300
TTCTATCTGG TTACCCTTGA GCAAGCGCAG GAACAACAGT ACGTAATCGA GGGAAGGATT     360
TCCCCGGGTG AACCGTCTGG TCCAATCTCT ACTATCAACC CGTCTCCTCC GTCTAAAGAA     420
TCTCATAAAT CTCCAAACAT GGCTAACTGC TCTATAATGA TCGATGAAAT TATACATCAC     480
TTAAAGAGAC CACCTGCACC TTTGCTGGAC CCGAACAACC TCAATGACGA AGACGTCTCT     540
ATCCTGATGG AACGAAACCT TCGACTTCCA AACCTGGAGA GCTTCGTAAG GGCTGTCAAG     600
AACTTAGAAA ATGCATCAGG TATTGAGGCA ATTCTTCGTA ATCTCCAACC ATGTCTGCCC     660
TCTGCCACGG CCGCACCCTC TCGACATCCA ATCATCATCA AGGCAGGTGA CTGGCAAGAA     720
TTCCGGGAAA AACTGACGTT CTATCTGGTT ACCCTTGAGC AAGCGCAGGA ACAACAG       777
```

(2) INFORMATION FOR SEQ ID NO:83:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:83:

```
ATGGCTAACT GCTCTATAAT GATCGATGAA ATTATACATC ACTTAAAGAG ACCACCTGCA      60
CCTTTGCTGG ACCCGAACAA CCTCAATGAC GAAGACGTCT CTATCCTGAT GGAACGAAAC     120
CTTCGACTTC CAAACCTGGA GAGCTTCGTA AGGGCTGTCA AGAACTTAGA AAATGCATCA     180
GGTATTGAGG CAATTCTTCG TAATCTCCAA CCATGTCTGC CCTCTGCCAC GGCCGCACCC     240
TCTCGACATC CAATCATCAT CAAGGCAGGT GACTGGCAAG AATTCCGGGA AAAACTGACG     300
TTCTATCTGG TTACCCTTGA GCAAGCGCAG GAACAACAGT ACGTAATCGA GGGAAGGATT     360
TCCCCGGGTG AACCGTCTGG TCCAATCTCT ACTATCAACC CGTCTCCTCC GTCTAAAGAA     420
TCTCATAAAT CTCCAAACAT GGCTACACCA TTGGGCCCTG CCAGCTCCCT GCCCCAGAGC     480
TTCCTGCTCA AGTCTTTAGA GCAAGTGAGG AAGATCCAGG GCGATGGCGC AGCGCTCCAG     540
GAGAAGCTGT GTGCCACCTA CAAGCTGTGC CACCCCGAGG AGCTGGTGCT GCTCGGACAC     600
TCTCTGGGCA TCCCCTGGGC TCCCCTGAGC TCCTGCCCCA GCCAGGCCCT GCAGCTGGCA     660
GGCTGCTTGA GCCAACTCCA TAGCGGCCTT TTCCTCTACC AGGGGCTCCT GCAGGCCCTG     720
```

```
GAAGGGATAT CCCCCGAGTT GGGTCCCACC TTGGACACAC TGCAGCTGGA CGTCGCCGAC        780

TTTGCCACCA CCATCTGGCA GCAGATGGAA GAACTGGGAA TGGCCCCTGC CCTGCAGCCC        840

ACCCAGGGTG CCATGCCGGC CTTCGCCTCT GCTTTCCAGC GCCGGGCAGG AGGGGTCCTG        900

GTTGCTAGCC ATCTGCAGAG CTTCCTGGAG GTGTCGTACC GCGTTCTACG CCACCTTGCG        960

CAGCCCTGAT AAGGATCCGA ATTC                                              984

(2) INFORMATION FOR SEQ ID NO:84:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:84:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACGTCT CTATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAATCGA GGGAAGGATT        360

TCCCCGGGTG GTGGTTCTGG CGGCGGCTCC AACATGGCTA CACCATTAGG CCCTGCCAGC        420

TCCCTGCCCC AGAGCTTCCT GCTCAAGTGC TTAGAGCAAG TGAGGAAGAT CCAGGGCGAT        480

GGCGCAGCGC TCCAGGAGAA GCTGTGTGCC ACCTACAAGC TGTGCCACCC CGAGGAGCTG        540

GTGCTGCTCG ACACTCTCT GGGCATCCCC TGGGCTCCCC TGAGCTCCTG CCCCAGCCAG         600

GCCCTGCAGC TGGCAGGCTG CTTGAGCCAA CTCCATAGCG GCCTTTTCCT CTACCAGGGG        660

CTCCTGCAGG CCCTGGAAGG GATATCCCCC GAGTTGGGTC CCACCTTGGA CACACTGCAG        720

CTGGACGTCG CCGACTTTGC CACCACCATC TGGCAGCAGA TGGAAGAACT GGGAATGGCC        780

CCTGCCCTGC AGCCCACCCA GGGTGCCATG CCGGCCTTCG CCTCTGCTTT CCAGCGCCGG        840

GCAGGAGGGG TCCTGGTTGC TAGCCATCTG CAGAGCTTCC TGGAGGTGTC GTACCGCGTT        900

CTACGCCACC TTGCGCAGCC C                                                 921

(2) INFORMATION FOR SEQ ID NO:85:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:85:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACGTCT CTATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAGT ACGTAATCGA GGGAAGGATT        360
```

```
TCCCCGGGTG GTGGTTCTGG CGGCGGCTCC AACATGGCTA CACCATTGGG CCCTGCCAGC      420

TCCCTGCCCC AGAGCTTCCT GCTCAAGTCT TTAGAGCAAG TGAGGAAGAT CCAGGGCGAT      480

GGCGCAGCGC TCCAGGAGAA GCTGTGTGCC ACCTACAAGC TGTGCCACCC CGAGGAGCTG      540

GTGCTGCTCG GACACTCTCT GGGCATCCCC TGGGCTCCCC TGAGCTCCTG CCCCAGCCAG      600

GCCCTGCAGC TGGCAGGCTG CTTGAGCCAA CTCCATAGCG GCCTTTTCCT CTACCAGGGG      660

CTCCTGCAGG CCCTGGAAGG GATATCCCCC GAGTTGGGTC CCACCTTGGA CACACTGCAG      720

CTGGACGTCG CCGACTTTGC CACCACCATC TGGCAGCAGA TGGAAGAACT GGGAATGGCC      780

CCTGCCCTGC AGCCCACCCA GGGTGCCATG CCGGCCTTCG CCTCTGCTTT CCAGCGCCGG      840

GCAGGAGGGG TCCTGGTTGC TAGCCATCTG CAGAGCTTCC TGGAGGTGTC GTACCGCGTT      900

CTACGCCACC TTGCGCAGCC C                                                921

(2) INFORMATION FOR SEQ ID NO:86:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:86:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAGGATT      360

TCCCCGGGTG GTGGTTCTGG CGGCGGCTCC AACATGGCTA ACTGCTCTAT AATGATCGAT      420

GAAATTATAC ATCACTTAAA GAGACCACCT GCACCTTTGC TGGACCCGAA CAACCTCAAT      480

GACGAAGACG TCTCTATCCT GATGGAACGA AACCTTCGAC TTCCAAACCT GGAGAGCTTC      540

GTAAGGGCTG TCAAGAACTT AGAAAATGCA TCAGGTATTG AGGCAATTCT TCGTAATCTC      600

CAACCATGTC TGCCCTCTGC CACGGCCGCA CCCTCTCGAC ATCCAATCAT CATCAAGGCA      660

GGTGACTGGC AAGAATTCCG GGAAAAACTG ACGTTCTATC TGGTTACCCT TGAGCAAGCG      720

CAGGAACAAC AG                                                          732

(2) INFORMATION FOR SEQ ID NO:87:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:87:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGAACGAAAC      120

CTTCGACTTC CAAACCTGGA GAGCTTCGTA AGGGCTGTCA AGAACTTAGA AAATGCATCA      180
```

```
GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCTA CACCATTGGG CCCTGCCAGC      420

TCCCTGCCCC AGAGCTTCCT GCTCAAGTCT TTAGAGCAAG TGAGGAAGAT CCAGGGCGAT      480

GGCGCAGCGC TCCAGGAGAA GCTGTGTGCC ACCTACAAGC TGTGCCACCC CGAGGAGCTG      540

GTGCTGCTCG GACACTCTCT GGGCATCCCC TGGGCTCCCC TGAGCTCCTG CCCCAGCCAG      600

GCCCTGCAGC TGGCAGGCTG CTTGAGCCAA CTCCATAGCG GCCTTTTCCT CTACCAGGGG      660

CTCCTGCAGG CCCTGGAAGG GATATCCCCC GAGTTGGGTC CCACCTTGGA CACACTGCAG      720

CTGGACGTCG CCGACTTTGC CACCACCATC TGGCAGCAGA TGGAAGAACT GGGAATGGCC      780

CCTGCCCTGC AGCCCACCCA GGGTGCCATG CCGGCCTTCG CCTCTGCTTT CCAGCGCCGG      840

GCAGGAGGGG TCCTGGTTGC TAGCCATCTG CAGAGCTTCC TGGAGGTGTC GTACCGCGTT      900

CTACGCCACC TTGCGCAGCC C                                                921

(2) INFORMATION FOR SEQ ID NO:88:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:88:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCTA ACTGCTCTAT AATGATCGAT      420

GAAATTATAC ATCACTTAAA GAGACCACCT GCACCTTTGC TGGACCCGAA CAACCTCAAT      480

GACGAAGACG TCTCTATCCT GATGGAACGA AACCTTCGAC TTCCAAACCT GGAGAGCTTC      540

GTAAGGGCTG TCAAGAACTT AGAAAATGCA TCAGGTATTG AGGCAATTCT TCGTAATCTC      600

CAACCATGTC TGCCCTCTGC CACGGCCGCA CCCTCTCGAC ATCCAATCAT CATCAAGGCA      660

GGTGACTGGC AAGAATTCCG GGAAAAACTG ACGTTCTATC TGGTTACCCT TGAGCAAGCG      720

CAGGAACAAC AG                                                          732

(2) INFORMATION FOR SEQ ID NO:89:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:89:

ATGGCTAACT GCTCTATAAT GATCGATGAA ATTATACATC ACTTAAAGAG ACCACCTGCA       60
```

```
CCTTTGCTGG ACCCGAACAA CCTCAATGAC GAAGACGTCT CTATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTACACCA TTGGGCCCTG CCAGCTCCCT GCCCCAGAGC      480

TTCCTGCTCA AGTCTTTAGA GCAAGTGAGG AAGATCCAGG GCGATGGCGC AGCGCTCCAG      540

GAGAAGCTGT GTGCCACCTA CAAGCTGTGC CACCCCGAGG AGCTGGTGCT GCTCGGACAC      600

TCTCTGGGCA TCCCCTGGGC TCCCCTGAGC TCCTGCCCCA GCCAGGCCCT GCAGCTGGCA      660

GGCTGCTTGA GCCAACTCCA TAGCGGCCTT TTCCTCTACC AGGGGCTCCT GCAGGCCCTG      720

GAAGGGATAT CCCCCGAGTT GGGTCCCACC TTGGACACAC TGCAGCTGGA CGTCGCCGAC      780

TTTGCCACCA CCATCTGGCA GCAGATGGAA GAACTGGGAA TGGCCCCTGC CCTGCAGCCC      840

ACCCAGGGTG CCATGCCGGC CTTCGCCTCT GCTTTCCAGC GCCGGGCAGG AGGGGTCCTG      900

GTTGCTAGCC ATCTGCAGAG CTTCCTGGAG GTGTCGTACC GCGTTCTACG CCACCTTGCG      960

CAGCCC                                                                966

(2) INFORMATION FOR SEQ ID NO:90:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:90:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTAACTGC TCTATAATGA TCGATGAAAT TATACATCAC      480

TTAAAGAGAC CACCTGCACC TTTGCTGGAC CCGAACAACC TCAATGACGA AGACGTCTCT      540

ATCCTGATGG AACGAAACCT TCGACTTCCA AACCTGGAGA GCTTCGTAAG GCTGTCAAG      600

AACTTAGAAA ATGCATCAGG TATTGAGGCA ATTCTTCGTA ATCTCCAACC ATGTCTGCCC      660

TCTGCCACGG CCGCACCCTC TCGACATCCA ATCATCATCA AGGCAGGTGA CTGGCAAGAA      720

TTCCGGGAAA AACTGACGTT CTATCTGGTT ACCCTTGAGC AAGCGCAGGA ACAACAG        777

(2) INFORMATION FOR SEQ ID NO:91:

(i) SEQUENCE CHARACTERISTICS:
        (A) LENGTH: 41 base pairs
        (B) TYPE: nucleic acid
        (C) STRANDEDNESS: single
```

(D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:91:

AATTCCGGGA AAAACTGACG TTCTATCTGG TTACCCTTGA G          41

(2) INFORMATION FOR SEQ ID NO:92:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:92:

CTGCGCTTGC TCAAGGGTAA CCAGATAGAA CGTCAGTTTT TCCCGG         46

(2) INFORMATION FOR SEQ ID NO:93:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:93:

CAAGCGCAGG AACAACAGTA CGTAATCGAG GGAAGGATT             39

(2) INFORMATION FOR SEQ ID NO:94:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:94:

ACCCGGGGAA ATCCTTCCCT CGATTACGTA CTGTTGTTC             39

(2) INFORMATION FOR SEQ ID NO:95:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:95:

TCCCCGGGTG GTGGTTCTGG CGGCGGCTCC AACATGTAAG GTACCGCATG CAAGCTTAGA        60

TCT                                                                    63

(2) INFORMATION FOR SEQ ID NO:96:

(i) SEQUENCE CHARACTERISTICS:

```
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:96:

AGCTAGATCT AAGCTTGCAT GCGGTACCTT ACATGTTGGA GCCGCCGCCA GAACCACC          58

(2) INFORMATION FOR SEQ ID NO:97:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:97:

CCGGGTGAAC CGTCTGGTCC AATCTCTACT ATCAACCCGT CTCCTCCGTC TAAAGAATCT       60

CATAAATCTC CAAA                                                        74

(2) INFORMATION FOR SEQ ID NO:98:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:98:

CATGTTTGGA GATTTATGAG ATTCTTTAGA CGGAGGAGAC GGGTTGATAG TAGAGATTGG       60

ACCAGACGGT TCAC                                                        74

(2) INFORMATION FOR SEQ ID NO:99:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:99:

CTAGCCATCT GCAGAGCTTC CTGGAGGTGT CGTACCGCGT TCTACGCCAC CTTGCGCAGC       60

CCTACGTA                                                               68

(2) INFORMATION FOR SEQ ID NO:100:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:100:
```

AGCTTACGTA GGGCTGCGCA AGGTGGCGTA GAACGCGGTA CGACACCTCC AGGAAGCTCT        60

GCAGATGG        68

(2) INFORMATION FOR SEQ ID NO:101:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:101:

GTAATCGAGG GAAAGATTTC C        21

(2) INFORMATION FOR SEQ ID NO:102:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:102:

CCGGGGAAAT CTTTCCCTCG ATTAC        25

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:103:

GTAGAGGGCG GTGGAGGCTC C        21

(2) INFORMATION FOR SEQ ID NO:104:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:104:

CCGGGGAGCC TCCACCGCCC TCTAC        25

(2) INFORMATION FOR SEQ ID NO:105:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "sythetic DNA"

(xi) SEQUENCE DESCRIPTION: SEQ ID NO:105:

CATGGCACCA GCAAGATCAC CATCACCATC AACTCAACCT TGGGAACATG TGAATGCC         58

(2) INFORMATION FOR SEQ ID NO:106:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:106:

CATTCACATG TTCCCAAGGT TGAGTTGATG GTGATGGTGA TCTTGCTGGT GC               52

(2) INFORMATION FOR SEQ ID NO:107:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:107:

CTGCCAGCTC CCTGCCCCAG AGCTTCCTGC TCAAGTCTTT AGAGCAAGTG AGGAAGATCC      60

AGGGCG                                                                  66

(2) INFORMATION FOR SEQ ID NO:108:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:108:

CTGGATCTTC CTCACTTGCT CTAAAGACTT GAGCAGGAAG CTCTGGGGCA GGGAGCTGGC      60

AGGGCC                                                                  66

(2) INFORMATION FOR SEQ ID NO:109:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:109:

AGCTTACCTG CCATGGCTCC AGTACCACCA GGTGAAGATT CCAAAGAT                    48

(2) INFORMATION FOR SEQ ID NO:110:

(i) SEQUENCE CHARACTERISTICS:
        (A) LENGTH: 40 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:110:

TTGGAATCTT CACCTGGTGG TACTGGAGCC ATGGCAGGTA        40

(2) INFORMATION FOR SEQ ID NO:111:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:111:

AGCTTCCATG GCTACCCCCC TGGGCC        26

(2) INFORMATION FOR SEQ ID NO:112:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:112:

CAGGGGGTA GCCATGGA        18

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:113:

CATGGCTACA CCATTGGGCC        20

(2) INFORMATION FOR SEQ ID NO:114:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:114:

CAATGGTGTA GC        12

(2) INFORMATION FOR SEQ ID NO:115:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:115:

CATGGCTACA CCATTAGGAC                                               20

(2) INFORMATION FOR SEQ ID NO:116:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:116:

TAATGGTGTA GC                                                       12

(2) INFORMATION FOR SEQ ID NO:117:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:117:

CCTGTCAACC CGGGCGGCGG CTCTGGTGGT                                    30

(2) INFORMATION FOR SEQ ID NO:118:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:118:

TCATAATACA TGTTACCGGA ACGGAGCCGC C                                  31

(2) INFORMATION FOR SEQ ID NO:119:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:119:

ATCGTCTGAC CTCCCGGGAC CTCCTGTCAA TGCT                               34

(2) INFORMATION FOR SEQ ID NO:120:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA"

(xi) SEQUENCE DESCRIPTION: SEQ ID NO:120:

AGCGTTTGAC ATGTTTTCAT AATCAAAATC                           30

(2) INFORMATION FOR SEQ ID NO:121:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:121:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Ser Gly Gly
        115                 120                 125

Gly Ser Asn Met Ala Thr Pro Leu Gly Pro Ala Ser Ser Leu Pro Gln
130                 135                 140

Ser Phe Leu Leu Lys Cys Leu Glu Gln Val Arg Lys Ile Gln Gly Asp
145                 150                 155                 160

Gly Ala Ala Leu Gln Glu Lys Leu Cys Ala Thr Tyr Lys Leu Cys His
            165                 170                 175

Pro Glu Glu Leu Val Leu Leu Gly His Ser Leu Gly Ile Pro Trp Ala
            180                 185                 190

Pro Leu Ser Ser Cys Pro Ser Gln Ala Leu Gln Leu Ala Gly Cys Leu
        195                 200                 205

Ser Gln Leu His Ser Gly Leu Phe Leu Tyr Gln Gly Leu Leu Gln Ala
210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
            245                 250                 255

Leu Gly Met Ala Pro Ala Leu Gln Pro Thr Gln Gly Ala Met Pro Ala
        260                 265                 270

Phe Ala Ser Ala Phe Gln Arg Arg Ala Gly Gly Val Leu Val Ala Ser
    275                 280                 285

```
His Leu Gln Ser Phe Leu Glu Val Ser Tyr Arg Val Leu Arg His Leu
    290                 295                 300

Ala Gln Pro
305
```

(2) INFORMATION FOR SEQ ID NO:122:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:122:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
            115                 120                 125

Gly Ser Asn Met Ala Thr Pro Leu Gly Pro Ala Ser Ser Leu Pro Gln
130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190

Pro Leu Ser Ser Cys Pro Ser Gln Ala Leu Gln Leu Ala Gly Cys Leu
            195                 200                 205

Ser Gln Leu His Ser Gly Leu Phe Leu Tyr Gln Gly Leu Leu Gln Ala
        210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
                260                 265                 270

Phe Ala Ser Ala Phe Gln Arg Arg Ala Gly Gly Val Leu Val Ala Ser
            275                 280                 285

His Leu Gln Ser Phe Leu Glu Val Ser Tyr Arg Val Leu Arg His Leu
        290                 295                 300

Ala Gln Pro
305
```

(2) INFORMATION FOR SEQ ID NO:123:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:123:

```
Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Lys Ile Ser Pro Gly Gly Ser Gly Gly
        115                 120                 125

Gly Ser Asn Met Ala Thr Pro Leu Gly Pro Ala Ser Ser Leu Pro Gln
    130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
            180                 185                 190

Pro Leu Ser Ser Cys Pro Ser Gln Ala Leu Gln Leu Ala Gly Cys Leu
        195                 200                 205

Ser Gln Leu His Ser Gly Leu Phe Leu Tyr Gln Gly Leu Leu Gln Ala
    210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
            260                 265                 270

Phe Ala Ser Ala Phe Gln Arg Arg Ala Gly Gly Val Leu Val Ala Ser
        275                 280                 285

His Leu Gln Ser Phe Leu Glu Val Ser Tyr Arg Val Leu Arg His Leu
    290                 295                 300

Ala Gln Pro
305
```

(2) INFORMATION FOR SEQ ID NO:124:

(i) SEQUENCE CHARACTERISTICS:
        (A) LENGTH: 307 amino acids

```
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:124:

Met Ala Asn Cys Ser Ile Met Ile Asp Glu Ile Ile His His Leu Lys
1               5                  10                 15

Arg Pro Pro Asn Pro Leu Leu Asp Pro Asn Asn Leu Asn Ser Glu Asp
                20                  25                 30

Met Asp Ile Leu Met Glu Arg Asn Leu Arg Thr Pro Asn Leu Leu Ala
            35                  40                 45

Phe Val Arg Ala Val Lys His Leu Glu Asn Ala Ser Gly Ile Glu Ala
        50                  55                 60

Ile Leu Arg Asn Leu Gln Pro Cys Leu Pro Ser Ala Thr Ala Ala Pro
65                  70                  75                 80

Ser Arg His Pro Ile Ile Lys Ala Gly Asp Trp Gln Glu Phe Arg
                85                  90                  95

Glu Lys Leu Thr Phe Tyr Leu Val Thr Leu Gln Ala Gln Glu Gln
                100                 105                110

Gln Tyr Val Glu Gly Gly Gly Ser Pro Gly Gly Ser Gly Gly
        115                 120                 125

Gly Ser Asn Met Ala Thr Pro Leu Gly Pro Ala Ser Ser Leu Pro Gln
130                 135                 140

Ser Phe Leu Leu Lys Ser Leu Glu Gln Val Arg Lys Ile Gln Gly Asp
145                 150                 155                160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190

Pro Leu Ser Ser Cys Pro Ser Gln Ala Leu Gln Leu Ala Gly Cys Leu
                195                 200                 205

Ser Gln Leu His Ser Gly Leu Phe Leu Tyr Gln Gly Leu Leu Gln Ala
210                 215                 220

Leu Glu Gly Ile Ser Pro Glu Leu Gly Pro Thr Leu Asp Thr Leu Gln
225                 230                 235                240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
                260                 265                 270

Phe Ala Ser Ala Phe Gln Arg Arg Ala Gly Gly Val Leu Val Ala Ser
                275                 280                 285

His Leu Gln Ser Phe Leu Glu Val Ser Tyr Arg Val Leu Arg His Leu
                290                 295                 300

Ala Gln Pro
305

(2) INFORMATION FOR SEQ ID NO:125:

(i) SEQUENCE CHARACTERISTICS:
          (A) LENGTH: 244 amino acids
          (B) TYPE: amino acid
          (C) STRANDEDNESS:
          (D) TOPOLOGY: linear (ii) MOLECULE TYPE: protein
```

```
    (xi) SEQUENCE DESCRIPTION: SEQ ID NO:125:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
            115                 120                 125

Gly Ser Asn Met Ala Asn Cys Ser Ile Met Ile Asp Glu Ile Ile His
    130                 135                 140

His Leu Lys Arg Pro Pro Asn Pro Leu Leu Asp Pro Asn Asn Leu Asn
145                 150                 155                 160

Ser Glu Asp Met Asp Ile Leu Met Glu Arg Asn Leu Arg Thr Pro Asn
                165                 170                 175

Leu Leu Ala Phe Val Arg Ala Val Lys His Leu Glu Asn Ala Ser Gly
            180                 185                 190

Ile Glu Ala Ile Leu Arg Asn Leu Gln Pro Cys Leu Pro Ser Ala Thr
        195                 200                 205

Ala Ala Pro Ser Arg His Pro Ile Ile Ile Lys Ala Gly Asp Trp Gln
    210                 215                 220

Glu Phe Arg Glu Lys Leu Thr Phe Tyr Leu Val Thr Leu Glu Gln Ala
225                 230                 235                 240

Gln Glu Gln Gln (2) INFORMATION FOR SEQ ID NO:126:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:126:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95
```

```
Glu Lys Leu Thr Phe Tyr Leu Val Thr Leu Glu Gln Ala Gln Glu Gln
            100                 105                 110

Gln Tyr Val Ile Glu Gly Lys Ile Ser Pro Gly Gly Ser Gly Gly
            115                 120                 125

Gly Ser Asn Met Ala Asn Cys Ser Ile Met Ile Asp Glu Ile Ile His
            130                 135                 140

His Leu Lys Arg Pro Pro Asn Pro Leu Leu Asp Pro Asn Asn Leu Asn
145                 150                 155                 160

Ser Glu Asp Met Asp Ile Leu Met Glu Arg Asn Leu Arg Thr Pro Asn
                    165                 170                 175

Leu Leu Ala Phe Val Arg Ala Val Lys His Leu Glu Asn Ala Ser Gly
            180                 185                 190

Ile Glu Ala Ile Leu Arg Asn Leu Gln Pro Cys Leu Pro Ser Ala Thr
            195                 200                 205

Ala Ala Pro Ser Arg His Pro Ile Ile Ile Lys Ala Gly Asp Trp Gln
            210                 215                 220

Glu Phe Arg Glu Lys Leu Thr Phe Tyr Leu Val Thr Leu Glu Gln Ala
225                 230                 235                 240

Gln Glu Gln Gln
```

(2) INFORMATION FOR SEQ ID NO:127:

(i) SEQUENCE CHARACTERISTICS:
    (A) LENGTH: 244 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:127:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                    85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Gly Gly Ser Gly Gly
            115                 120                 125

Gly Ser Asn Met Ala Asn Cys Ser Ile Met Ile Asp Glu Ile Ile His
            130                 135                 140

His Leu Lys Arg Pro Pro Asn Pro Leu Leu Asp Pro Asn Asn Leu Asn
145                 150                 155                 160

Ser Glu Asp Met Asp Ile Leu Met Glu Arg Asn Leu Arg Thr Pro Asn
                    165                 170                 175

Leu Leu Ala Phe Val Arg Ala Val Lys His Leu Glu Asn Ala Ser Gly
            180                 185                 190
```

```
Ile Glu Ala Ile Leu Arg Asn Leu Gln Pro Cys Leu Pro Ser Ala Thr
        195                 200                 205

Ala Ala Pro Ser Arg His Pro Ile Ile Lys Ala Gly Asp Trp Gln
        210                 215                 220

Glu Phe Arg Glu Lys Leu Thr Phe Tyr Leu Val Thr Leu Glu Gln Ala
225                 230                 235                 240

Gln Glu Gln Gln
```

(2) INFORMATION FOR SEQ ID NO:128:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:128:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Glu Pro Ser Gly Pro
            115                 120                 125

Ile Ser Thr Ile Asn Pro Ser Pro Ser Lys Glu Ser His Lys Ser
    130                 135                 140

Pro Asn Met Ala Thr Pro Leu Gly Pro Ala Ser Ser Leu Pro Gln Ser
145                 150                 155                 160

Phe Leu Leu Lys Cys Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
            195                 200                 205

Leu Ser Ser Cys Pro Ser Gln Ala Leu Gln Leu Ala Gly Cys Leu Ser
    210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
            260                 265                 270

Gly Met Ala Pro Ala Leu Gln Pro Thr Gln Gly Ala Met Pro Ala Phe
        275                 280                 285

Ala Ser Ala Phe Gln Arg Arg Ala Gly Gly Val Leu Val Ala Ser His
```

```
        290                 295                 300

Leu Gln Ser Phe Leu Glu Val Ser Tyr Arg Val Leu Arg His Leu Ala
305                 310                 315                 320

Gln Pro
```

(2) INFORMATION FOR SEQ ID NO:129:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:129:

```
Met Ala Asn Cys Ser Ile Met Ile Asp Glu Ile Ile His His Leu Lys
1               5                  10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Lys Ile Ser Pro Gly Glu Pro Ser Gly Pro
            115                 120                 125

Ile Ser Thr Ile Asn Pro Ser Pro Pro Ser Lys Glu Ser His Lys Ser
130                 135                 140

Pro Asn Met Ala Thr Pro Leu Gly Pro Ala Ser Ser Leu Pro Gln Ser
145                 150                 155                 160

Phe Leu Leu Lys Cys Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
        195                 200                 205

Leu Ser Ser Cys Pro Ser Gln Ala Leu Gln Leu Ala Gly Cys Leu Ser
210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
            260                 265                 270

Gly Met Ala Pro Ala Leu Gln Pro Thr Gln Gly Ala Met Pro Ala Phe
        275                 280                 285

Ala Ser Ala Phe Gln Arg Arg Ala Gly Gly Val Leu Val Ala Ser His
        290                 295                 300

Leu Gln Ser Phe Leu Glu Val Ser Tyr Arg Val Leu Arg His Leu Ala
305                 310                 315                 320
```

Gln Pro (2) INFORMATION FOR SEQ ID NO:130:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:130:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
        130                 135                 140

Pro Asn Met Ala Thr Pro Leu Gly Pro Ala Ser Ser Leu Pro Gln Ser
145                 150                 155                 160

Phe Leu Leu Lys Cys Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
        195                 200                 205

Leu Ser Ser Cys Pro Ser Gln Ala Leu Gln Leu Ala Gly Cys Leu Ser
    210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
            260                 265                 270

Gly Met Ala Pro Ala Leu Gln Pro Thr Gln Gly Ala Met Pro Ala Phe
        275                 280                 285

Ala Ser Ala Phe Gln Arg Arg Ala Gly Gly Val Leu Val Ala Ser His
    290                 295                 300

Leu Gln Ser Phe Leu Glu Val Ser Tyr Arg Val Leu Arg His Leu Ala
305                 310                 315                 320

Gln Pro
```

(2) INFORMATION FOR SEQ ID NO:131:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:131:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Glu Pro Ser Gly Pro
        115                 120                 125

Ile Ser Thr Ile Asn Pro Ser Pro Ser Lys Glu Ser His Lys Ser
    130                 135                 140

Pro Asn Met Ala Asn Cys Ser Ile Met Ile Asp Glu Ile Ile His His
145                 150                 155                 160

Leu Lys Arg Pro Pro Asn Pro Leu Leu Asp Pro Asn Asn Leu Asn Ser
                165                 170                 175

Glu Asp Met Asp Ile Leu Met Glu Arg Asn Leu Arg Thr Pro Asn Leu
            180                 185                 190

Leu Ala Phe Val Arg Ala Val Lys His Leu Glu Asn Ala Ser Gly Ile
        195                 200                 205

Glu Ala Ile Leu Arg Asn Leu Gln Pro Cys Leu Pro Ser Ala Thr Ala
    210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln
```

(2) INFORMATION FOR SEQ ID NO:132:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:132:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
```

```
                     20                  25                  30

Met Asp Ile Leu Met Glu Arg Asn Leu Arg Thr Pro Asn Leu Leu Ala
                35                  40                  45

Phe Val Arg Ala Val Lys His Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Lys Ile Ser Pro Gly Glu Pro Ser Gly Pro
            115                 120                 125

Ile Ser Thr Ile Asn Pro Ser Pro Pro Ser Lys Glu Ser His Lys Ser
130                 135                 140

Pro Asn Met Ala Asn Cys Ser Ile Met Ile Asp Glu Ile Ile His His
145                 150                 155                 160

Leu Lys Arg Pro Pro Asn Pro Leu Leu Asp Pro Asn Asn Leu Asn Ser
                165                 170                 175

Glu Asp Met Asp Ile Leu Met Glu Arg Asn Leu Arg Thr Pro Asn Leu
            180                 185                 190

Leu Ala Phe Val Arg Ala Val Lys His Leu Glu Asn Ala Ser Gly Ile
        195                 200                 205

Glu Ala Ile Leu Arg Asn Leu Gln Pro Cys Leu Pro Ser Ala Thr Ala
    210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln (2) INFORMATION FOR SEQ ID NO:133:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:133:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
                35                  40                  45

Phe Val Arg Ala Val Lys His Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110
```

```
Gln Tyr Val Glu Gly Gly Gly Ser Pro Gly Pro Ser Gly Pro
        115                 120                 125

Ile Ser Thr Ile Asn Pro Ser Pro Ser Lys Glu Ser His Lys Ser
    130                 135                 140

Pro Asn Met Ala Asn Cys Ser Ile Met Ile Asp Glu Ile Ile His His
145                 150                 155                 160

Leu Lys Arg Pro Pro Asn Pro Leu Leu Asp Pro Asn Asn Leu Asn Ser
                165                 170                 175

Glu Asp Met Asp Ile Leu Met Glu Arg Asn Leu Arg Thr Pro Asn Leu
                180                 185                 190

Leu Ala Phe Val Arg Ala Val Lys His Leu Glu Asn Ala Ser Gly Ile
            195                 200                 205

Glu Ala Ile Leu Arg Asn Leu Gln Pro Cys Leu Pro Ser Ala Thr Ala
    210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln
```

(2) INFORMATION FOR SEQ ID NO:134:

(i) SEQUENCE CHARACTERISTICS:
       (A) LENGTH: 307 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:134:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
                35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
        115                 120                 125

Gly Ser Asn Met Ala Thr Pro Leu Gly Pro Ala Ser Ser Leu Pro Gln
        130                 135                 140

Ser Phe Leu Leu Lys Cys Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190
```

```
Pro Leu Ser Ser Cys Pro Ser Gln Ala Leu Gln Leu Ala Gly Cys Leu
            195                 200                 205

Ser Gln Leu His Ser Gly Leu Phe Leu Tyr Gln Gly Leu Leu Gln Ala
    210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
            260                 265                 270

Phe Ala Ser Ala Phe Gln Arg Arg Ala Gly Gly Val Leu Val Ala Ser
            275                 280                 285

His Leu Gln Ser Phe Leu Glu Val Ser Tyr Arg Val Leu Arg His Leu
    290                 295                 300

Ala Gln Pro
305

(2) INFORMATION FOR SEQ ID NO:135:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:135:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Ser Gly Gly Gly
        115                 120                 125

Gly Ser Asn Met Ala Thr Pro Leu Gly Pro Ala Ser Ser Leu Pro Gln
    130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
            165                 170                 175

Pro Glu Glu Leu Val Leu Leu Gly His Ser Leu Gly Ile Pro Trp Ala
            180                 185                 190

Pro Leu Ser Ser Cys Pro Ser Gln Ala Leu Gln Leu Ala Gly Cys Leu
            195                 200                 205

Ser Gln Leu His Ser Gly Leu Phe Leu Tyr Gln Gly Leu Leu Gln Ala
    210                 215                 220
```

```
Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
            260                 265                 270

Phe Ala Ser Ala Phe Gln Arg Arg Ala Gly Val Leu Val Ala Ser
        275                 280                 285

His Leu Gln Ser Phe Leu Glu Val Ser Tyr Arg Val Leu Arg His Leu
    290                 295                 300

Ala Gln Pro
305
```

(2) INFORMATION FOR SEQ ID NO:136:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:136:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
            115                 120                 125

Gly Ser Asn Met Ala Asn Cys Ser Ile Met Ile Asp Glu Ile Ile His
    130                 135                 140

His Leu Lys Arg Pro Pro Ala Pro Leu Leu Asp Pro Asn Asn Leu Asn
145                 150                 155                 160

Asp Glu Asp Val Ser Ile Leu Met Asp Arg Asn Leu Arg Leu Pro Asn
                165                 170                 175

Leu Glu Ser Phe Val Arg Ala Val Lys Asn Leu Glu Asn Ala Ser Gly
            180                 185                 190

Ile Glu Ala Ile Leu Arg Asn Leu Gln Pro Cys Leu Pro Ser Ala Thr
        195                 200                 205

Ala Ala Pro Ser Arg His Pro Ile Ile Ile Lys Ala Gly Asp Trp Gln
    210                 215                 220

Glu Phe Arg Glu Lys Leu Thr Phe Tyr Leu Val Thr Leu Glu Gln Ala
225                 230                 235                 240

Gln Glu Gln Gln
```

(2) INFORMATION FOR SEQ ID NO:137:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:137:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Glu Pro Ser Gly Pro
        115                 120                 125

Ile Ser Thr Ile Asn Pro Ser Pro Ser Lys Glu Ser His Lys Ser
    130                 135                 140

Pro Asn Met Ala Asn Cys Ser Ile Met Ile Asp Glu Ile Ile His His
145                 150                 155                 160

Leu Lys Arg Pro Pro Ala Pro Leu Leu Asp Pro Asn Asn Leu Asn Asp
                165                 170                 175

Glu Asp Val Ser Ile Leu Met Asp Arg Asn Leu Arg Leu Pro Asn Leu
            180                 185                 190

Glu Ser Phe Val Arg Ala Val Lys Asn Leu Glu Asn Ala Ser Gly Ile
        195                 200                 205

Glu Ala Ile Leu Arg Asn Leu Gln Pro Cys Leu Pro Ser Ala Thr Ala
    210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln
```

(2) INFORMATION FOR SEQ ID NO:138:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:138:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Asp Glu Asp
```

-continued

```
                    20                  25                  30
Val Ser Ile Leu Met Asp Arg Asn Leu Arg Leu Pro Asn Leu Glu Ser
         35                  40                  45
Phe Val Arg Ala Val Lys Asn Leu Glu Asn Ala Ser Gly Ile Glu Ala
     50                  55                  60
Ile Leu Arg Asn Leu Gln Pro Cys Leu Pro Ser Ala Thr Ala Ala Pro
 65                  70                  75                  80
Ser Arg His Pro Ile Ile Ile Lys Ala Gly Asp Trp Gln Glu Phe Arg
                 85                  90                  95
Glu Lys Leu Thr Phe Tyr Leu Val Thr Leu Glu Gln Ala Gln Glu Gln
            100                 105                 110
Gln Tyr Val Ile Glu Gly Arg Ile Ser Pro Gly Glu Pro Ser Gly Pro
            115                 120                 125
Ile Ser Thr Ile Asn Pro Ser Pro Pro Ser Lys Glu Ser His Lys Ser
130                 135                 140
Pro Asn Met Ala Thr Pro Leu Gly Pro Ala Ser Ser Leu Pro Gln Ser
145                 150                 155                 160
Phe Leu Leu Lys Ser Leu Glu Gln Val Arg Lys Ile Gln Gly Asp Gly
                165                 170                 175
Ala Ala Leu Gln Glu Lys Leu Cys Ala Thr Tyr Lys Leu Cys His Pro
            180                 185                 190
Glu Glu Leu Val Leu Leu Gly His Ser Leu Gly Ile Pro Trp Ala Pro
            195                 200                 205
Leu Ser Ser Cys Pro Ser Gln Ala Leu Gln Leu Ala Gly Cys Leu Ser
    210                 215                 220
Gln Leu His Ser Gly Leu Phe Leu Tyr Gln Gly Leu Leu Gln Ala Leu
225                 230                 235                 240
Glu Gly Ile Ser Pro Glu Leu Gly Pro Thr Leu Asp Thr Leu Gln Leu
                245                 250                 255
Asp Val Ala Asp Phe Ala Thr Thr Ile Trp Gln Gln Met Glu Glu Leu
            260                 265                 270
Gly Met Ala Pro Ala Leu Gln Pro Thr Gln Gly Ala Met Pro Ala Phe
            275                 280                 285
Ala Ser Ala Phe Gln Arg Arg Ala Gly Gly Val Leu Val Ala Ser His
    290                 295                 300
Leu Gln Ser Phe Leu Glu Val Ser Tyr Arg Val Leu Arg His Leu Ala
305                 310                 315                 320
Gln Pro
```

(2) INFORMATION FOR SEQ ID NO:139:

(i) SEQUENCE CHARACTERISTICS:
        (A) LENGTH: 349 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:139:

```
Met Ala Asn Cys Ser Ile Met Ile Asp Glu Ile Ile His His Leu Lys
 1               5                  10                  15
Arg Pro Pro Asn Pro Leu Leu Asp Pro Asn Asn Leu Asn Ser Glu Asp
                 20                  25                  30
Met Asp Ile Leu Met Glu Arg Asn Leu Arg Thr Pro Asn Leu Leu Ala
             35                  40                  45
```

-continued

```
Phe Val Arg Ala Val Lys His Leu Glu Asn Ala Ser Gly Ile Glu Ala
     50                  55                  60

Ile Leu Arg Asn Leu Gln Pro Cys Leu Pro Ser Ala Thr Ala Ala Pro
 65                  70                  75                  80

Ser Arg His Pro Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gln Pro Val Asn Ala
                115                 120                 125

Gly Gly Gly Ser Gly Gly Ser Gly Gly Gly Ser Glu Gly Gly
    130                 135                 140

Ser Glu Gly Gly Gly Ser Gly Gly Gly Ser Glu Gly Gly Gly Ser
145                 150                 155                 160

Gly Gly Gly Ser Gly Ser Gly Asp Phe Asp Tyr Glu Asn Met Ala Thr
                165                 170                 175

Pro Leu Gly Pro Ala Ser Ser Leu Pro Gln Ser Phe Leu Leu Lys Ser
                180                 185                 190

Leu Glu Gln Val Arg Lys Ile Gln Gly Asp Gly Ala Ala Leu Gln Glu
                195                 200                 205

Lys Leu Cys Ala Thr Tyr Lys Leu Cys His Pro Glu Glu Leu Val Leu
210                 215                 220

Leu Gly His Ser Leu Gly Ile Pro Trp Ala Pro Leu Ser Ser Cys Pro
225                 230                 235                 240

Ser Gln Ala Leu Gln Leu Ala Gly Cys Leu Ser Gln Leu His Ser Gly
                245                 250                 255

Leu Phe Leu Tyr Gln Gly Leu Leu Gln Ala Leu Glu Gly Ile Ser Pro
                260                 265                 270

Glu Leu Gly Pro Thr Leu Asp Thr Leu Gln Leu Asp Val Ala Asp Phe
                275                 280                 285

Ala Thr Thr Ile Trp Gln Gln Met Glu Glu Leu Gly Met Ala Pro Ala
    290                 295                 300

Leu Gln Pro Thr Gln Gly Ala Met Pro Ala Phe Ala Ser Ala Phe Gln
305                 310                 315                 320

Arg Arg Ala Gly Gly Val Leu Val Ala Ser His Leu Gln Ser Phe Leu
                325                 330                 335

Glu Val Ser Tyr Arg Val Leu Arg His Leu Ala Gln Pro
                340                 345
```

(2) INFORMATION FOR SEQ ID NO:140:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:140:

GGATCCACCA TGAGCCGCCT GCCCGTCCTG CTCCTGCTCC AACTCCTGGT CCGCCCCGCC    60

ATGG    64

(2) INFORMATION FOR SEQ ID NO:141:

(i) SEQUENCE CHARACTERISTICS:
    (A) LENGTH: 259 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:141:

```
Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ala Thr Ala Ala Pro
 65                 70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln Tyr Val Ile Glu Gly Arg Ile Ser Pro Gly Gly Gly Ser Gly Gly
           115                 120                 125

Gly Ser Asn Met Ala Pro Ala Arg Ser Pro Ser Pro Ser Thr Gln Pro
       130                 135                 140

Trp Glu His Val Asn Ala Ile Gln Glu Ala Arg Arg Leu Leu Asn Leu
145                 150                 155                 160

Ser Arg Asp Thr Ala Ala Glu Met Asn Glu Thr Val Glu Val Ile Ser
                165                 170                 175

Glu Met Phe Asp Leu Gln Glu Pro Thr Cys Leu Gln Thr Arg Leu Glu
               180                 185                 190

Leu Tyr Lys Gln Gly Leu Arg Gly Ser Leu Thr Lys Leu Lys Gly Pro
           195                 200                 205

Leu Thr Met Met Ala Ser His Tyr Lys Gln His Cys Pro Pro Thr Pro
       210                 215                 220

Glu Thr Ser Cys Ala Thr Gln Ile Ile Thr Phe Glu Ser Phe Lys Glu
225                 230                 235                 240

Asn Leu Lys Asp Phe Leu Leu Val Ile Pro Phe Asp Cys Trp Glu Pro
                245                 250                 255

Val Gln Glu
```

(2) INFORMATION FOR SEQ ID NO:142:

(i) SEQUENCE CHARACTERISTICS:
    (A) LENGTH: 301 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:142:

```
Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
                20                  25                  30
```

```
Met Asp Ile Leu Met Glu Arg Asn Leu Arg Thr Pro Asn Leu Leu Ala
         35                  40                  45

Phe Val Arg Ala Val Lys His Leu Glu Asn Ala Ser Gly Ile Glu Ala
         50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
             100                 105                 110

Gln Tyr Val Ile Glu Gly Arg Ile Ser Pro Gln Pro Val Asn Ala
             115                 120                 125

Gly Gly Gly Ser Gly Gly Gly Ser Gly Gly Gly Ser Glu Gly Gly Gly
    130                 135                 140

Ser Glu Gly Gly Gly Ser Glu Gly Gly Gly Ser Glu Gly Gly Gly Ser
145                 150                 155                 160

Gly Gly Gly Ser Gly Ser Gly Asp Phe Asp Tyr Glu Asn Met Ala Pro
                165                 170                 175

Ala Arg Ser Pro Ser Pro Ser Thr Gln Pro Trp Glu His Val Asn Ala
             180                 185                 190

Ile Gln Glu Ala Arg Arg Leu Leu Asn Leu Ser Arg Asp Thr Ala Ala
             195                 200                 205

Glu Met Asn Glu Thr Val Glu Val Ile Ser Glu Met Phe Asp Leu Gln
210                 215                 220

Glu Pro Thr Cys Leu Gln Thr Arg Leu Glu Leu Tyr Lys Gln Gly Leu
225                 230                 235                 240

Arg Gly Ser Leu Thr Lys Leu Lys Gly Pro Leu Thr Met Met Ala Ser
                245                 250                 255

His Tyr Lys Gln His Cys Pro Pro Thr Pro Glu Thr Ser Cys Ala Thr
             260                 265                 270

Gln Ile Ile Thr Phe Glu Ser Phe Lys Glu Asn Leu Lys Asp Phe Leu
             275                 280                 285

Leu Val Ile Pro Phe Asp Cys Trp Glu Pro Val Gln Glu
290                 295                 300

(2) INFORMATION FOR SEQ ID NO:143:

(i) SEQUENCE CHARACTERISTICS:
        (A) LENGTH: 335 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:143:

Met Ala Asn Cys Ser Ile Met Ile Asp Glu Ile Ile His Leu Lys
 1               5                  10                  15

Arg Pro Pro Asn Pro Leu Leu Asp Pro Asn Asn Leu Asn Ser Glu Asp
             20                  25                  30

Met Asp Ile Leu Met Glu Arg Asn Leu Arg Thr Pro Asn Leu Leu Ala
         35                  40                  45

Phe Val Arg Ala Val Lys His Leu Glu Asn Ala Ser Gly Ile Glu Ala
         50                  55                  60

Ile Leu Arg Asn Leu Gln Pro Cys Leu Pro Ser Ala Thr Ala Ala Pro
 65                  70                  75                  80
```

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Pro Val Asn Ala Gly Gly Ser Gly Gly Gly Ser Gly
        115                 120                 125

Gly Gly Ser Glu Gly Gly Ser Glu Gly Gly Ser Glu Gly Gly
    130                 135                 140

Gly Ser Glu Gly Gly Ser Gly Gly Ser Gly Ser Gly Asn Met
145                 150                 155                 160

Ala Thr Pro Leu Gly Pro Ala Ser Ser Leu Pro Gln Ser Phe Leu Leu
                165                 170                 175

Lys Cys Leu Glu Gln Val Arg Lys Ile Gln Gly Asp Gly Ala Ala Leu
            180                 185                 190

Gln Glu Lys Leu Cys Ala Thr Tyr Lys Leu Cys His Pro Glu Glu Leu
        195                 200                 205

Val Leu Leu Gly His Ser Leu Gly Ile Pro Trp Ala Pro Leu Ser Ser
    210                 215                 220

Cys Pro Ser Gln Ala Leu Gln Leu Ala Gly Cys Leu Ser Gln Leu His
225                 230                 235                 240

Ser Gly Leu Phe Leu Tyr Gln Gly Leu Leu Gln Ala Leu Glu Gly Ile
                245                 250                 255

Ser Pro Glu Leu Gly Pro Thr Leu Asp Thr Leu Gln Leu Asp Val Ala
            260                 265                 270

Asp Phe Ala Thr Thr Ile Trp Gln Gln Met Glu Glu Leu Gly Met Ala
        275                 280                 285

Pro Ala Leu Gln Pro Thr Gln Gly Ala Met Pro Ala Phe Ala Ser Ala
    290                 295                 300

Phe Gln Arg Arg Ala Gly Gly Val Leu Val Ala Ser His Leu Gln Ser
305                 310                 315                 320

Phe Leu Glu Val Ser Tyr Arg Val Leu Arg His Leu Ala Gln Pro
                325                 330                 335

(2) INFORMATION FOR SEQ ID NO:144:

(i) SEQUENCE CHARACTERISTICS:
        (A) LENGTH: 274 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:144:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95
```

```
Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Glu Pro Ser Gly Pro
            115                 120                 125

Ile Ser Thr Ile Asn Pro Ser Pro Pro Ser Lys Glu Ser His Lys Ser
            130                 135                 140

Pro Asn Met Ala Pro Ala Arg Ser Pro Ser Pro Ser Thr Gln Pro Trp
145                 150                 155                 160

Glu His Val Asn Ala Ile Gln Glu Ala Arg Arg Leu Leu Asn Leu Ser
                    165                 170                 175

Arg Asp Thr Ala Ala Glu Met Asn Glu Thr Val Glu Val Ile Ser Glu
            180                 185                 190

Met Phe Asp Leu Gln Glu Pro Thr Cys Leu Gln Thr Arg Leu Glu Leu
            195                 200                 205

Tyr Lys Gln Gly Leu Arg Gly Ser Leu Thr Lys Leu Lys Gly Pro Leu
            210                 215                 220

Thr Met Met Ala Ser His Tyr Lys Gln His Cys Pro Pro Thr Pro Glu
225                 230                 235                 240

Thr Ser Cys Ala Thr Gln Ile Ile Thr Phe Glu Ser Phe Lys Glu Asn
                    245                 250                 255

Leu Lys Asp Phe Leu Leu Val Ile Pro Phe Asp Cys Trp Glu Pro Val
            260                 265                 270

Gln Glu (2) INFORMATION FOR SEQ ID NO:145:

(i) SEQUENCE CHARACTERISTICS:
        (A) LENGTH: 317 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:145:

Met Ala Asn Cys Ser Ile Met Ile Asp Glu Ile Ile His His Leu Lys
1                   5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                    85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Gly Ser Gly Gly
            115                 120                 125

Gly Ser Asn Met Ala Pro Val Pro Pro Gly Glu Asp Ser Lys Asp Val
            130                 135                 140

Ala Ala Pro His Arg Gln Pro Leu Thr Ser Ser Glu Arg Ile Asp Lys
145                 150                 155                 160

Gln Ile Arg Tyr Ile Leu Asp Gly Ile Ser Ala Leu Arg Lys Glu Thr
```

```
                    165                 170                 175
Cys Asn Lys Ser Asn Met Cys Glu Ser Ser Lys Glu Ala Leu Ala Glu
            180                 185                 190
Asn Asn Leu Asn Leu Pro Lys Met Ala Glu Lys Asp Gly Cys Phe Gln
            195                 200                 205
Ser Gly Phe Asn Glu Glu Thr Cys Leu Val Lys Ile Ile Thr Gly Leu
    210                 215                 220
Leu Glu Phe Glu Val Tyr Leu Glu Tyr Leu Gln Asn Arg Phe Glu Ser
225                 230                 235                 240
Ser Glu Glu Gln Ala Arg Ala Val Gln Met Ser Thr Lys Val Leu Ile
                245                 250                 255
Gln Phe Leu Gln Lys Lys Ala Lys Asn Leu Asp Ala Ile Thr Thr Pro
            260                 265                 270
Asp Pro Thr Thr Asn Ala Ser Leu Leu Thr Lys Leu Gln Ala Gln Asn
            275                 280                 285
Gln Trp Leu Gln Asp Met Thr Thr His Leu Ile Leu Arg Ser Phe Lys
            290                 295                 300
Glu Phe Leu Gln Ser Ser Leu Arg Ala Leu Arg Gln Met
305                 310                 315

(2) INFORMATION FOR SEQ ID NO:146:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:146:

Met Ala Thr Pro Leu Gly Pro Ala Ser Ser Leu Pro Gln Ser Phe Leu
1               5                   10                  15
Leu Lys Cys Leu Glu Gln Val Arg Lys Ile Gln Gly Asp Gly Ala Ala
            20                  25                  30
Leu Gln Glu Lys Leu Cys Ala Thr Tyr Lys Leu Cys His Pro Glu Glu
        35                  40                  45
Leu Val Leu Leu Gly His Ser Leu Gly Ile Pro Trp Ala Pro Leu Ser
    50                  55                  60
Ser Cys Pro Ser Gln Ala Leu Gln Leu Ala Gly Cys Leu Ser Gln Leu
65              70                  75                  80
His Ser Gly Leu Phe Leu Tyr Gln Gly Leu Leu Gln Ala Leu Glu Gly
                85                  90                  95
Ile Ser Pro Glu Leu Gly Pro Thr Leu Asp Thr Leu Gln Leu Asp Val
            100                 105                 110
Ala Asp Phe Ala Thr Thr Ile Trp Gln Gln Met Glu Glu Leu Gly Met
            115                 120                 125
Ala Pro Ala Leu Gln Pro Thr Gln Gly Ala Met Pro Ala Phe Ala Ser
            130                 135                 140
Ala Phe Gln Arg Arg Ala Gly Gly Val Leu Val Ala Ser His Leu Gln
145                 150                 155                 160
Ser Phe Leu Glu Val Ser Tyr Arg Val Leu Arg His Leu Ala Gln Pro
                165                 170                 175
Tyr Val Ile Glu Gly Arg Ile Ser Pro Gly Gly Ser Gly Gly Gly
            180                 185                 190
Ser Asn Met Ala Asn Cys Ser Ile Met Ile Asp Glu Ile Ile His His
```

```
            195                 200                 205
Leu Lys Arg Pro Pro Asn Pro Leu Leu Asp Pro Asn Asn Leu Asn Ser
        210                 215                 220

Glu Asp Met Asp Ile Leu Met Glu Arg Asn Leu Arg Thr Pro Asn Leu
225                 230                 235                 240

Leu Ala Phe Val Arg Ala Val Lys His Leu Glu Asn Ala Ser Gly Ile
                245                 250                 255

Glu Ala Ile Leu Arg Asn Leu Gln Pro Cys Leu Pro Ser Ala Thr Ala
            260                 265                 270

Ala Pro Ser Arg His Pro Ile Ile Ile Lys Ala Gly Asp Trp Gln Glu
        275                 280                 285

Phe Arg Glu Lys Leu Thr Phe Tyr Leu Val Thr Leu Glu Gln Ala Gln
    290                 295                 300

Glu Gln Gln
305

(2) INFORMATION FOR SEQ ID NO:147:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:147:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
            85                  90                  95

Ile Ser Pro Glu Leu Gly Pro Thr Leu Asp Thr Leu Gln Leu Asp Val
        100                 105                 110

Ala Asp Phe Ala Thr Thr Ile Trp Gln Gln Met Glu Glu Leu Gly Met
    115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
            165                 170                 175

Tyr Val Ile Glu Gly Arg Ile Ser Pro Gly Gly Ser Gly Gly Gly
        180                 185                 190

Ser Asn Met Ala Asn Cys Ser Ile Met Ile Asp Glu Ile Ile His His
            195                 200                 205

Leu Lys Arg Pro Pro Ala Pro Leu Leu Asp Pro Asn Asn Leu Asn Asp
        210                 215                 220

Glu Asp Val Ser Ile Leu Met Asp Arg Asn Leu Arg Leu Pro Asn Leu
```

-continued

```
225                 230                 235                 240
Glu Ser Phe Val Arg Ala Val Lys Asn Leu Glu Asn Ala Ser Gly Ile
                245                 250                 255
Glu Ala Ile Leu Arg Asn Leu Gln Pro Cys Leu Pro Ser Ala Thr Ala
                260                 265                 270
Ala Pro Ser Arg His Pro Ile Ile Ile Lys Ala Gly Asp Trp Gln Glu
                275                 280                 285
Phe Arg Glu Lys Leu Thr Phe Tyr Leu Val Thr Leu Glu Gln Ala Gln
                290                 295                 300
Glu Gln Gln
305

(2) INFORMATION FOR SEQ ID NO:148:

(i) SEQUENCE CHARACTERISTICS:
        (A) LENGTH: 337 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:148:

Met Ala Thr Pro Leu Gly Pro Ala Ser Ser Leu Pro Gln Ser Phe Leu
1                   5                  10                  15
Leu Lys Cys Leu Glu Gln Val Arg Lys Ile Gln Gly Asp Gly Ala Ala
                20                  25                  30
Leu Gln Glu Lys Leu Cys Ala Thr Tyr Lys Leu Cys His Pro Glu Glu
                35                  40                  45
Leu Val Leu Leu Gly His Ser Leu Gly Ile Pro Trp Ala Pro Leu Ser
            50                  55                  60
Ser Cys Pro Ser Gln Ala Leu Gln Leu Ala Gly Cys Leu Ser Gln Leu
65                  70                  75                  80
His Ser Gly Leu Phe Leu Tyr Gln Gly Leu Leu Gln Ala Leu Glu Gly
                85                  90                  95
Ile Ser Pro Glu Leu Gly Pro Thr Leu Asp Thr Leu Gln Leu Asp Val
                100                 105                 110
Ala Asp Phe Ala Thr Thr Ile Trp Gln Gln Met Glu Glu Leu Gly Met
                115                 120                 125
Ala Pro Ala Leu Gln Pro Thr Gln Gly Ala Met Pro Ala Phe Ala Ser
                130                 135                 140
Ala Phe Gln Arg Arg Ala Gly Gly Val Leu Val Ala Ser His Leu Gln
145                 150                 155                 160
Ser Phe Leu Glu Val Ser Tyr Arg Val Leu Arg His Leu Ala Gln Pro
                165                 170                 175
Tyr Val Pro Gln Pro Pro Val Asn Ala Gly Gly Gly Ser Gly Gly Gly
                180                 185                 190
Ser Gly Gly Gly Ser Glu Gly Gly Gly Ser Glu Gly Gly Gly Ser Glu
                195                 200                 205
Gly Gly Gly Ser Glu Gly Gly Gly Ser Gly Gly Ser Gly Ser Gly
                210                 215                 220
Asp Phe Asp Tyr Glu Asn Met Ala Asn Cys Ser Ile Met Ile Asp Glu
225                 230                 235                 240
Ile Ile His His Leu Lys Arg Pro Pro Ala Pro Leu Leu Asp Pro Asn
                245                 250                 255
Asn Leu Asn Asp Glu Asp Val Ser Ile Leu Met Asp Arg Asn Leu Arg
```

```
                   260                 265                 270

Leu Val Arg Ala Val Lys Asn Leu Glu Asn Ala Ser Gly Ile Glu Ala
            275                 280                 285

Ile Leu Arg Asn Leu Gln Pro Cys Leu Pro Ser Ala Thr Ala Ala Pro
    290                 295                 300

Ser Arg His Pro Ile Ile Ile Lys Ala Gly Asp Trp Gln Glu Phe Arg
305                 310                 315                 320

Glu Lys Leu Thr Phe Tyr Leu Val Thr Leu Glu Gln Ala Gln Glu Gln
                325                 330                 335

Gln (2) INFORMATION FOR SEQ ID NO:149:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:149:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gly Glu Pro Ser Gly Pro Ile
            180                 185                 190

Ser Thr Ile Asn Pro Ser Pro Ser Lys Glu Ser His Lys Ser Pro
    195                 200                 205

Asn Met Ala Asn Cys Ser Ile Met Ile Asp Glu Ile His His Leu
210                 215                 220

Lys Arg Pro Pro Ala Pro Leu Leu Asp Pro Asn Asn Leu Asn Asp Glu
225                 230                 235                 240

Asp Val Ser Ile Leu Met Asp Arg Asn Leu Arg Leu Pro Asn Leu Glu
                245                 250                 255

Ser Phe Val Arg Ala Val Lys Asn Leu Glu Asn Ala Ser Gly Ile Glu
            260                 265                 270
```

```
Ala Ile Leu Arg Asn Leu Gln Pro Cys Leu Pro Ser Ala Thr Ala Ala
        275                 280                 285

Pro Ser Arg His Pro Ile Ile Ile Lys Ala Gly Asp Trp Gln Glu Phe
290                 295                 300

Arg Glu Lys Leu Thr Phe Tyr Leu Val Thr Leu Glu Gln Ala Gln Glu
305                 310                 315                 320

Gln Gln (2) INFORMATION FOR SEQ ID NO:150:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:150:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gly Glu Pro Ser Gly Pro Ile
            180                 185                 190

Ser Thr Ile Asn Pro Ser Pro Pro Ser Lys Glu Ser His Lys Ser Pro
        195                 200                 205

Asn Met Ala Asn Cys Ser Ile Met Ile Asp Glu Ile Ile His His Leu
210                 215                 220

Lys Arg Pro Pro Asn Pro Leu Leu Asp Pro Asn Asn Leu Asn Ser Glu
225                 230                 235                 240

Asp Met Asp Ile Leu Met Glu Arg Asn Leu Arg Thr Pro Asn Leu Leu
                245                 250                 255

Ala Phe Val Arg Ala Val Lys His Leu Glu Asn Ala Ser Gly Ile Glu
            260                 265                 270

Ala Ile Leu Arg Asn Leu Gln Pro Cys Leu Pro Ser Ala Thr Ala Ala
        275                 280                 285
```

Pro Ser Arg His Pro Ile Ile Ile Lys Ala Gly Asp Trp Gln Glu Phe
    290                 295                 300

Arg Glu Lys Leu Thr Phe Tyr Leu Val Thr Leu Glu Gln Ala Gln Glu
305                 310                 315                 320

Gln Gln (2) INFORMATION FOR SEQ ID NO:151:

(i) SEQUENCE CHARACTERISTICS:
        (A) LENGTH: 349 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:151:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gln Pro Val Asn Ala Gly
            180                 185                 190

Gly Gly Ser Gly Gly Gly Ser Gly Gly Gly Ser Glu Gly Gly Gly Ser
    195                 200                 205

Glu Gly Gly Gly Ser Glu Gly Gly Gly Ser Glu Gly Gly Gly Ser Gly
    210                 215                 220

Gly Gly Ser Gly Ser Gly Asp Phe Asp Tyr Glu Asn Met Ala Asn Cys
225                 230                 235                 240

Ser Ile Met Ile Asp Glu Ile Ile His His Leu Lys Arg Pro Pro Asn
                245                 250                 255

Pro Leu Leu Asp Pro Asn Asn Leu Asn Ser Glu Asp Met Asp Ile Leu
            260                 265                 270

Met Glu Arg Asn Leu Arg Thr Pro Asn Leu Leu Ala Phe Val Arg Ala
        275                 280                 285

Val Lys His Leu Glu Asn Ala Ser Gly Ile Glu Ala Ile Leu Arg Asn
    290                 295                 300

Leu Gln Pro Cys Leu Pro Ser Ala Thr Ala Ala Pro Ser Arg His Pro

```
305                 310                 315                 320
Ile Ile Ile Lys Ala Gly Asp Trp Gln Glu Phe Arg Glu Lys Leu Thr
                325                 330                 335

Phe Tyr Leu Val Thr Leu Glu Gln Ala Gln Glu Gln Gln
            340                 345
```

(2) INFORMATION FOR SEQ ID NO:152:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:152:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Gly Ser Gly Gly
            115                 120                 125

Gly Ser Asn Met Ala Thr Pro Leu Gly Pro Ala Ser Ser Leu Pro Gln
130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
            180                 185                 190

Pro Leu Ser Ser Cys Pro Ser Gln Ala Leu Gln Leu Ala Gly Cys Leu
        195                 200                 205

Ser Gln Leu His Ser Gly Leu Phe Leu Tyr Gln Gly Leu Leu Gln Ala
210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
            260                 265                 270

Phe Ala Ser Ala Phe Gln Arg Arg Ala Gly Gly Val Leu Val Ala Ser
        275                 280                 285

His Leu Gln Ser Phe Leu Glu Val Ser Tyr Arg Val Leu Arg His Leu
    290                 295                 300

Ala Gln Pro
```

(2) INFORMATION FOR SEQ ID NO:153:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:153:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Gly Gly Ser Gly Gly
            115                 120                 125

Gly Ser Asn Met Ala Asn Cys Ser Ile Met Ile Asp Glu Ile Ile His
    130                 135                 140

His Leu Lys Arg Pro Pro Ala Pro Leu Leu Asp Pro Asn Asn Leu Asn
145                 150                 155                 160

Asp Glu Asp Val Ser Ile Leu Met Asp Arg Asn Leu Arg Leu Pro Asn
                165                 170                 175

Leu Glu Ser Phe Val Arg Ala Val Lys Asn Leu Glu Asn Ala Ser Gly
            180                 185                 190

Ile Glu Ala Ile Leu Arg Asn Leu Gln Pro Cys Leu Pro Ser Ala Thr
        195                 200                 205

Ala Ala Pro Ser Arg His Pro Ile Ile Ile Lys Ala Gly Asp Trp Gln
    210                 215                 220

Glu Phe Arg Glu Lys Leu Thr Phe Tyr Leu Val Thr Leu Glu Gln Ala
225                 230                 235                 240

Gln Glu Gln Gln
```

(2) INFORMATION FOR SEQ ID NO:154:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:154:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
```

```
                20                  25                  30
Val Ser Ile Leu Met Asp Arg Asn Leu Arg Leu Pro Asn Leu Glu Ser
             35                  40                  45
Phe Val Arg Ala Val Lys Asn Leu Glu Asn Ala Ser Gly Ile Glu Ala
 50                  55                  60
Ile Leu Arg Asn Leu Gln Pro Cys Leu Pro Ser Ala Thr Ala Ala Pro
 65                  70                  75                  80
Ser Arg His Pro Ile Ile Ile Lys Ala Gly Asp Trp Gln Glu Phe Arg
                 85                  90                  95
Glu Lys Leu Thr Phe Tyr Leu Val Thr Leu Glu Gln Ala Gln Glu Gln
             100                 105                 110
Gln Tyr Val Ile Glu Gly Gly Gly Ser Pro Gly Glu Pro Ser Gly Pro
             115                 120                 125
Ile Ser Thr Ile Asn Pro Ser Pro Pro Ser Lys Glu Ser His Lys Ser
130                 135                 140
Pro Asn Met Ala Thr Pro Leu Gly Pro Ala Ser Ser Leu Pro Gln Ser
145                 150                 155                 160
Phe Leu Leu Lys Ser Leu Glu Gln Val Arg Lys Ile Gln Gly Asp Gly
                 165                 170                 175
Ala Ala Leu Gln Glu Lys Leu Cys Ala Thr Tyr Lys Leu Cys His Pro
             180                 185                 190
Glu Glu Leu Val Leu Leu Gly His Ser Leu Gly Ile Pro Trp Ala Pro
             195                 200                 205
Leu Ser Ser Cys Pro Ser Gln Ala Leu Gln Leu Ala Gly Cys Leu Ser
         210                 215                 220
Gln Leu His Ser Gly Leu Phe Leu Tyr Gln Gly Leu Leu Gln Ala Leu
225                 230                 235                 240
Glu Gly Ile Ser Pro Glu Leu Gly Pro Thr Leu Asp Thr Leu Gln Leu
                 245                 250                 255
Asp Val Ala Asp Phe Ala Thr Thr Ile Trp Gln Gln Met Glu Glu Leu
             260                 265                 270
Gly Met Ala Pro Ala Leu Gln Pro Thr Gln Gly Ala Met Pro Ala Phe
             275                 280                 285
Ala Ser Ala Phe Gln Arg Arg Ala Gly Gly Val Leu Val Ala Ser His
         290                 295                 300
Leu Gln Ser Phe Leu Glu Val Ser Tyr Arg Val Leu Arg His Leu Ala
305                 310                 315                 320
Gln Pro (2) INFORMATION FOR SEQ ID NO:155:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:155:

Met Ala Asn Cys Ser Ile Met Ile Asp Glu Ile Ile His Leu Lys
1               5                  10                  15
Arg Pro Pro Ala Pro Leu Leu Asp Pro Asn Asn Leu Asn Asp Glu Asp
             20                  25                  30
Val Ser Ile Leu Met Asp Arg Asn Leu Arg Leu Pro Asn Leu Glu Ser
             35                  40                  45
```

```
Phe Val Arg Ala Val Lys Asn Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln Tyr Val Glu Gly Gly Gly Ser Pro Gly Glu Pro Ser Gly Pro
        115                 120                 125
Ile Ser Thr Ile Asn Pro Ser Pro Pro Ser Lys Glu Ser His Lys Ser
    130                 135                 140
Pro Asn Met Ala Asn Cys Ser Ile Met Ile Asp Glu Ile Ile His His
145                 150                 155                 160
Leu Lys Arg Pro Pro Ala Pro Leu Leu Asp Pro Asn Asn Leu Asn Asp
                165                 170                 175
Glu Asp Val Ser Ile Leu Met Asp Arg Asn Leu Arg Leu Pro Asn Leu
            180                 185                 190
Glu Ser Phe Val Arg Ala Val Lys Asn Leu Glu Asn Ala Ser Gly Ile
        195                 200                 205
Glu Ala Ile Leu Arg Asn Leu Gln Pro Cys Leu Pro Ser Ala Thr Ala
    210                 215                 220
Ala Pro Ser Arg His Pro Ile Ile Ile Lys Ala Gly Asp Trp Gln Glu
225                 230                 235                 240
Phe Arg Glu Lys Leu Thr Phe Tyr Leu Val Thr Leu Glu Gln Ala Gln
                245                 250                 255
Glu Gln Gln (2) INFORMATION FOR SEQ ID NO:156:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:156:

Met Ala Thr Pro Leu Gly Pro Ala Ser Ser Leu Pro Gln Ser Phe Leu
1               5                   10                  15
Leu Lys Cys Leu Glu Gln Val Arg Lys Ile Gln Gly Asp Gly Ala Ala
            20                  25                  30
Leu Gln Glu Lys Leu Cys Ala Thr Tyr Lys Leu Cys His Pro Glu Glu
        35                  40                  45
Leu Val Leu Leu Gly His Ser Leu Gly Ile Pro Trp Ala Pro Leu Ser
    50                  55                  60
Ser Cys Pro Ser Gln Ala Leu Gln Leu Ala Gly Cys Leu Ser Gly Leu
65                  70                  75                  80
His Ser Gly Leu Phe Leu Tyr Gln Gly Leu Leu Gln Ala Leu Glu Gly
                85                  90                  95
Ile Ser Pro Glu Leu Gly Pro Thr Leu Asp Thr Leu Gln Leu Asp Val
            100                 105                 110
Ala Asp Phe Ala Thr Thr Ile Trp Gln Gln Met Glu Glu Leu Gly Met
        115                 120                 125
```

```
Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Glu Gly Gly Gly Ser Pro Gly Glu Pro Ser Gly Pro Ile
            180                 185                 190

Ser Thr Ile Asn Pro Ser Pro Pro Ser Lys Glu Ser His Lys Ser Pro
            195                 200                 205

Asn Met Ala Asn Cys Ser Ile Met Ile Asp Glu Ile His His Leu
    210                 215                 220

Lys Arg Pro Pro Ala Pro Leu Leu Asp Pro Asn Asn Leu Asn Asp Glu
225                 230                 235                 240

Asp Val Ser Ile Leu Met Asp Arg Asn Leu Arg Leu Pro Asn Leu Glu
                245                 250                 255

Ser Phe Val Arg Ala Val Lys Asn Leu Glu Asn Ala Ser Gly Ile Glu
                260                 265                 270

Ala Ile Leu Arg Asn Leu Gln Pro Cys Leu Pro Ser Ala Thr Ala Ala
            275                 280                 285

Pro Ser Arg His Pro Ile Ile Ile Lys Ala Gly Asp Trp Gln Glu Phe
    290                 295                 300

Arg Glu Lys Leu Thr Phe Tyr Leu Val Thr Leu Glu Gln Ala Gln Glu
305                 310                 315                 320

Gln Gln (2) INFORMATION FOR SEQ ID NO:157:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:157:

Met Ala Thr Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gly Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Gly Leu Gly Met
            115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
```

-continued

```
145                 150                 155                 160
Ser Phe Leu Glu Val Ser Tyr Arg Val Leu Arg His Leu Ala Gln Pro
                165                 170                 175
Tyr Val Glu Gly Gly Gly Ser Pro Gly Glu Pro Ser Gly Pro Ile
                180                 185                 190
Ser Thr Ile Asn Pro Ser Pro Pro Ser Lys Glu Ser His Lys Ser Pro
                195                 200                 205
Asn Met Ala Asn Cys Ser Ile Met Ile Asp Glu Ile His His Leu
            210                 215                 220
Lys Arg Pro Pro Ala Pro Leu Leu Asp Pro Asn Asn Leu Asn Asp Glu
225                 230                 235                 240
Asp Val Ser Ile Leu Met Asp Arg Asn Leu Arg Leu Pro Asn Leu Glu
                245                 250                 255
Ser Phe Val Arg Ala Val Lys Asn Leu Glu Asn Ala Ser Gly Ile Glu
                260                 265                 270
Ala Ile Leu Arg Asn Leu Gln Pro Cys Leu Pro Ser Ala Thr Ala Ala
            275                 280                 285
Pro Ser Arg His Pro Ile Ile Ile Lys Ala Gly Asp Trp Gln Glu Phe
    290                 295                 300
Arg Glu Lys Leu Thr Phe Tyr Leu Val Thr Leu Glu Gln Ala Gln Glu
305                 310                 315                 320
Gln Gln (2) INFORMATION FOR SEQ ID NO:158:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:158:

Met Ala Thr Pro Leu Gly Pro Ala Ser Ser Leu Pro Gln Ser Phe Leu
1               5                   10                  15
Leu Lys Cys Leu Glu Gln Val Arg Lys Ile Gln Gly Asp Gly Ala Ala
            20                  25                  30
Leu Gln Glu Lys Leu Cys Ala Thr Tyr Lys Leu Cys His Pro Glu Glu
        35                  40                  45
Leu Val Leu Leu Gly His Ser Leu Gly Ile Pro Trp Ala Pro Leu Ser
    50                  55                  60
Ser Cys Pro Ser Gln Ala Leu Gln Leu Ala Gly Cys Leu Ser Gly Leu
65                  70                  75                  80
His Ser Gly Leu Phe Leu Tyr Gln Gly Leu Leu Gln Ala Leu Glu Gly
                85                  90                  95
Ile Ser Pro Glu Leu Gly Pro Thr Leu Asp Thr Leu Gln Leu Asp Val
            100                 105                 110
Ala Asp Phe Ala Thr Thr Ile Trp Gln Gln Met Glu Glu Leu Gly Met
        115                 120                 125
Ala Pro Ala Leu Gln Pro Thr Gln Gly Ala Met Pro Ala Phe Ala Ser
    130                 135                 140
Ala Phe Gln Arg Arg Ala Gly Gly Val Leu Val Ala Ser His Leu Gln
145                 150                 155                 160
Ser Phe Leu Glu Val Ser Tyr Arg Val Leu Arg His Leu Ala Gln Pro
                165                 170                 175
```

-continued

```
Tyr Val Glu Gly Gly Gly Gly Ser Pro Gly Gly Ser Gly Gly Gly
            180                 185                 190

Ser Asn Met Ala Asn Cys Ser Ile Met Ile Asp Glu Ile Ile His His
            195                 200                 205

Leu Lys Arg Pro Pro Ala Pro Leu Leu Asp Pro Asn Asn Leu Asn Asp
            210                 215                 220

Glu Asp Val Ser Ile Leu Met Asp Arg Asn Leu Arg Leu Pro Asn Leu
225                 230                 235                 240

Glu Ser Phe Val Arg Ala Val Lys Asn Leu Glu Asn Ala Ser Gly Ile
                245                 250                 255

Glu Ala Ile Leu Arg Asn Leu Gln Pro Cys Leu Pro Ser Ala Thr Ala
                260                 265                 270

Ala Pro Ser Arg His Pro Ile Ile Ile Lys Ala Gly Asp Trp Gln Glu
            275                 280                 285

Phe Arg Glu Lys Leu Thr Phe Tyr Leu Val Thr Leu Glu Gln Ala Gln
            290                 295                 300

Glu Gln Gln
305
```

(2) INFORMATION FOR SEQ ID NO:159:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:159:

```
Met Ala Thr Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
            50                  55                  60

Ser Cys Pro Ser Gln Ala Leu Gln Leu Ala Gly Cys Leu Ser Gly Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
            130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Glu Gly Gly Gly Gly Ser Pro Gly Gly Ser Gly Gly Gly
            180                 185                 190

Ser Asn Met Ala Asn Cys Ser Ile Met Ile Asp Glu Ile Ile His His
            195                 200                 205
```

```
Leu Lys Arg Pro Pro Ala Pro Leu Leu Asp Pro Asn Asn Leu Asn Asp
    210                 215                 220

Glu Asp Val Ser Ile Leu Met Asp Arg Asn Leu Arg Leu Pro Asn Leu
225                 230                 235                 240

Glu Ser Phe Val Arg Ala Val Lys Asn Leu Glu Asn Ala Ser Gly Ile
                245                 250                 255

Glu Ala Ile Leu Arg Asn Leu Gln Pro Cys Leu Pro Ser Ala Thr Ala
                260                 265                 270

Ala Pro Ser Arg His Pro Ile Ile Ile Lys Ala Gly Asp Trp Gln Glu
                275                 280                 285

Phe Arg Glu Lys Leu Thr Phe Tyr Leu Val Thr Leu Glu Gln Ala Gln
290                 295                 300

Glu Gln Gln
305

(2) INFORMATION FOR SEQ ID NO:160:

(i) SEQUENCE CHARACTERISTICS:
        (A) LENGTH: 128 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:160:

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
                20                  25                  30

Thr Ala Ala Glu Met Asn Glu Thr Val Glu Val Ile Ser Glu Met Phe
                35                  40                  45

Asp Leu Gln Glu Pro Thr Cys Leu Gln Thr Arg Leu Glu Leu Tyr Lys
    50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
                100                 105                 110

Asp Phe Leu Leu Val Ile Pro Phe Asp Cys Trp Glu Pro Val Gln Glu
                115                 120                 125

(2) INFORMATION FOR SEQ ID NO:161:

(i) SEQUENCE CHARACTERISTICS:
        (A) LENGTH: 176 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:161:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
```

```
                    35                  40                  45
Leu Val Leu Leu Gly His Ser Leu Gly Ile Pro Trp Ala Pro Leu Ser
 50                  55                  60
Ser Cys Pro Ser Gln Ala Leu Gln Leu Ala Gly Cys Leu Ser Gln Leu
 65                  70                  75                  80
His Ser Gly Leu Phe Leu Tyr Gln Gly Leu Leu Gln Ala Leu Glu Gly
                     85                  90                  95
Ile Ser Pro Glu Leu Gly Pro Thr Leu Asp Thr Leu Gln Leu Asp Val
                    100                 105                 110
Ala Asp Phe Ala Thr Thr Ile Trp Gln Gln Met Glu Glu Leu Gly Met
                115                 120                 125
Ala Pro Ala Leu Gln Pro Thr Gln Gly Ala Met Pro Ala Phe Ala Ser
                130                 135                 140
Ala Phe Gln Arg Arg Ala Gly Gly Val Leu Val Ala Ser His Leu Gln
145                 150                 155                 160
Ser Phe Leu Glu Val Ser Tyr Arg Val Leu Arg His Leu Ala Gln Pro
                165                 170                 175

(2) INFORMATION FOR SEQ ID NO:162:

(i) SEQUENCE CHARACTERISTICS:
        (A) LENGTH: 176 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:162:

Met Ala Thr Pro Leu Gly Pro Ala Ser Ser Leu Pro Gln Ser Phe Leu
 1               5                  10                  15
Leu Lys Ser Leu Glu Gln Val Arg Lys Ile Gln Gly Asp Gly Ala Ala
                 20                  25                  30
Leu Gln Glu Lys Leu Cys Ala Thr Tyr Lys Leu Cys His Pro Glu Glu
                 35                  40                  45
Leu Val Leu Leu Gly His Ser Leu Gly Ile Pro Trp Ala Pro Leu Ser
 50                  55                  60
Ser Cys Pro Ser Gln Ala Leu Gln Leu Ala Gly Cys Leu Ser Gln Leu
 65                  70                  75                  80
His Ser Gly Leu Phe Leu Tyr Gln Gly Leu Leu Gln Ala Leu Glu Gly
                     85                  90                  95
Ile Ser Pro Glu Leu Gly Pro Thr Leu Asp Thr Leu Gln Leu Asp Val
                    100                 105                 110
Ala Asp Phe Ala Thr Thr Ile Trp Gln Gln Met Glu Glu Leu Gly Met
                115                 120                 125
Ala Pro Ala Leu Gln Pro Thr Gln Gly Ala Met Pro Ala Phe Ala Ser
                130                 135                 140
Ala Phe Gln Arg Arg Ala Gly Gly Val Leu Val Ala Ser His Leu Gln
145                 150                 155                 160
Ser Phe Leu Glu Val Ser Tyr Arg Val Leu Arg His Leu Ala Gln Pro
                165                 170                 175

(2) INFORMATION FOR SEQ ID NO:163:

(i) SEQUENCE CHARACTERISTICS:
        (A) LENGTH: 186 amino acids
        (B) TYPE: amino acid
        (C) STRANDEDNESS:
```

(D) TOPOLOGY: linear (ii) MOLECULE TYPE: protein (xi) SEQUENCE DESCRIPTION: SEQ ID NO:163:

Met Ala Pro Val Pro Pro Gly Glu Asp Ser Lys Asp Val Ala Ala Pro
1               5                   10                  15

His Arg Gln Pro Leu Thr Ser Ser Glu Arg Ile Asp Lys Gln Ile Arg
            20                  25                  30

Tyr Ile Leu Asp Gly Ile Ser Ala Leu Arg Lys Glu Thr Cys Asn Lys
        35                  40                  45

Ser Asn Met Cys Glu Ser Ser Lys Glu Ala Leu Ala Glu Asn Asn Leu
    50                  55                  60

Asn Leu Pro Lys Met Ala Glu Lys Asp Gly Cys Phe Gln Ser Gly Phe
65                  70                  75                  80

Asn Glu Glu Thr Cys Leu Val Lys Ile Ile Thr Gly Leu Leu Glu Phe
                85                  90                  95

Glu Val Tyr Leu Glu Tyr Leu Gln Asn Arg Phe Glu Ser Ser Glu Glu
            100                 105                 110

Gln Ala Arg Ala Val Gln Met Ser Thr Lys Val Leu Ile Gln Phe Leu
        115                 120                 125

Gln Lys Lys Ala Lys Asn Leu Asp Ala Ile Thr Thr Pro Asp Pro Thr
    130                 135                 140

Thr Asn Ala Ser Leu Leu Thr Lys Leu Gln Ala Gln Asn Gln Trp Leu
145                 150                 155                 160

Gln Asp Met Thr Thr His Leu Ile Leu Arg Ser Phe Lys Glu Phe Leu
                165                 170                 175

Gln Ser Ser Leu Arg Ala Leu Arg Gln Met
            180                 185

(2) INFORMATION FOR SEQ ID NO:164:

(i) SEQUENCE CHARACTERISTICS:
        (A) LENGTH: 155 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:164:

Met Ala Ser Pro Ala Pro Ala Cys Asp Leu Arg Val Leu Ser Lys
1               5                   10                  15

Leu Leu Arg Asp Ser His Val Leu His Ser Arg Leu Ser Gln Cys Pro
            20                  25                  30

Glu Val His Pro Leu Pro Thr Pro Val Leu Leu Pro Ala Val Asp Phe
        35                  40                  45

Ser Leu Gly Glu Trp Lys Thr Gln Met Glu Glu Thr Lys Ala Gln Asp
    50                  55                  60

Ile Leu Gly Ala Val Thr Leu Leu Glu Gly Val Met Ala Ala Arg
65                  70                  75                  80

Gln Gln Leu Gly Pro Thr Cys Leu Ser Ser Leu Leu Gly Gln Leu Ser
                85                  90                  95

Gly Gln Val Arg Leu Leu Leu Gly Ala Leu Gln Ser Leu Leu Gly Thr
            100                 105                 110

Gln Leu Pro Pro Gln Gly Arg Thr Thr Ala His Lys Asp Pro Asn Ala
        115                 120                 125

```
Ile Phe Leu Ser Phe Gln His Leu Leu Arg Gly Lys Val Arg Phe Leu
    130                 135                 140

Met Leu Val Gly Gly Ser Thr Leu Cys Val Arg
145             150             155
```

(2) INFORMATION FOR SEQ ID NO:165:

(i) SEQUENCE CHARACTERISTICS:
        (A) LENGTH: 286 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:165:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Gly Ser Gly Gly
        115                 120                 125

Gly Ser Asn Met Ala Ser Pro Ala Pro Ala Cys Asp Leu Arg Val
    130                 135                 140

Leu Ser Lys Leu Leu Arg Asp Ser His Val Leu His Ser Arg Leu Ser
145                 150                 155                 160

Gln Cys Pro Glu Val His Pro Leu Pro Thr Pro Val Leu Leu Pro Ala
                165                 170                 175

Val Asp Phe Ser Leu Gly Glu Trp Lys Thr Gln Met Glu Glu Thr Lys
            180                 185                 190

Ala Gln Asp Ile Leu Gly Ala Val Thr Leu Leu Leu Glu Gly Val Met
        195                 200                 205

Ala Ala Arg Gln Gln Leu Gly Pro Thr Cys Leu Ser Ser Leu Leu Gly
    210                 215                 220

Gln Leu Ser Gly Gln Val Arg Leu Leu Leu Gly Ala Leu Gln Ser Leu
225                 230                 235                 240

Leu Gly Thr Gln Leu Pro Pro Gln Gly Arg Thr Thr Ala His Lys Asp
                245                 250                 255

Pro Asn Ala Ile Phe Leu Ser Phe Gln His Leu Leu Arg Gly Lys Val
            260                 265                 270

Arg Phe Leu Met Leu Val Gly Gly Ser Thr Leu Cys Val Arg
        275                 280                 285
```

(2) INFORMATION FOR SEQ ID NO:166:

(i) SEQUENCE CHARACTERISTICS:
        (A) LENGTH: 286 amino acids
        (B) TYPE: amino acid (C) STRANDEDNESS:
(D) TOPOLOGY: linear (ii) MOLECULE TYPE: protein (xi) SEQUENCE DESCRIPTION: SEQ ID NO:166:

```
Met Ala Asn Cys Ser Ile Met Ile Asp Glu Ile Ile His His Leu Lys
  1               5                  10                  15

Arg Pro Pro Asn Pro Leu Leu Asp Pro Asn Asn Leu Asn Ser Glu Asp
                 20                  25                  30

Met Asp Ile Leu Met Glu Arg Asn Leu Arg Thr Pro Asn Leu Leu Ala
             35                  40                  45

Phe Val Arg Ala Val Lys His Leu Glu Asn Ala Ser Gly Ile Glu Ala
         50                  55                  60

Ile Leu Arg Asn Leu Gln Pro Cys Leu Pro Ser Ala Thr Ala Ala Pro
 65                  70                  75                  80

Ser Arg His Pro Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Gly Gly Ser Gly Gly
                115                 120                 125

Gly Ser Asn Met Ala Ser Pro Ala Pro Pro Ala Cys Asp Leu Arg Val
            130                 135                 140

Leu Ser Lys Leu Leu Arg Asp Ser His Val Leu His Ser Arg Leu Ser
145                 150                 155                 160

Gln Cys Pro Glu Val His Pro Leu Pro Thr Pro Val Leu Leu Pro Ala
                165                 170                 175

Val Asp Phe Ser Leu Gly Glu Trp Lys Thr Gln Met Glu Glu Thr Lys
            180                 185                 190

Ala Gln Asp Ile Leu Gly Ala Val Thr Leu Leu Leu Glu Gly Val Met
            195                 200                 205

Ala Ala Arg Gln Gln Leu Gly Pro Thr Cys Leu Ser Ser Leu Leu Gly
        210                 215                 220

Gln Leu Ser Gly Gln Val Arg Leu Leu Leu Gly Ala Leu Gln Ser Leu
225                 230                 235                 240

Leu Gly Thr Gln Leu Pro Pro Gln Gly Arg Thr Thr Ala His Lys Asp
                245                 250                 255

Pro Asn Ala Ile Phe Leu Ser Phe Gln His Leu Leu Arg Gly Lys Val
            260                 265                 270

Arg Phe Leu Met Leu Val Gly Gly Ser Thr Leu Cys Val Arg
        275                 280                 285
```

(2) INFORMATION FOR SEQ ID NO:167:

(i) SEQUENCE CHARACTERISTICS:
        (A) LENGTH: 286 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:167:

```
Met Ala Ser Pro Ala Pro Pro Ala Cys Asp Leu Arg Val Leu Ser Lys
  1               5                  10                  15

Leu Leu Arg Asp Ser His Val Leu His Ser Arg Leu Ser Gln Cys Pro
                 20                  25                  30
```

```
Glu Val His Pro Leu Pro Thr Pro Val Leu Leu Pro Ala Val Asp Phe
             35                  40                  45

Ser Leu Gly Glu Trp Lys Thr Gln Met Glu Glu Thr Lys Ala Gln Asp
 50                  55                  60

Ile Leu Gly Ala Val Thr Leu Leu Glu Gly Val Met Ala Ala Arg
 65                  70                  75                  80

Gln Gln Leu Gly Pro Thr Cys Leu Ser Ser Leu Leu Gly Gln Leu Ser
                 85                  90                  95

Gly Gln Val Arg Leu Leu Gly Ala Leu Gln Ser Leu Leu Gly Thr
                100                 105                 110

Gln Leu Pro Pro Gln Gly Arg Thr Thr Ala His Lys Asp Pro Asn Ala
                115                 120                 125

Ile Phe Leu Ser Phe Gln His Leu Leu Arg Gly Lys Val Arg Phe Leu
 130                 135                 140

Met Leu Val Gly Gly Ser Thr Leu Cys Val Arg Tyr Val Ile Glu Gly
 145                 150                 155                 160

Arg Ile Ser Pro Gly Gly Gly Ser Asn Met Ala Asn
                165                 170                 175

Cys Ser Ile Met Ile Asp Glu Ile Ile His His Leu Lys Arg Pro Pro
                180                 185                 190

Asn Pro Leu Leu Asp Pro Asn Asn Leu Asn Ser Glu Asp Met Asp Ile
                195                 200                 205

Leu Met Glu Arg Asn Leu Arg Thr Pro Asn Leu Leu Ala Phe Val Arg
 210                 215                 220

Ala Val Lys His Leu Glu Asn Ala Ser Gly Ile Glu Ala Ile Leu Arg
225                  230                 235                 240

Asn Leu Gln Pro Cys Leu Pro Ser Ala Thr Ala Ala Pro Ser Arg His
                245                 250                 255

Pro Ile Ile Ile Lys Ala Gly Asp Trp Gln Glu Phe Arg Glu Lys Leu
                260                 265                 270

Thr Phe Tyr Leu Val Thr Leu Glu Gln Ala Gln Glu Gln Gln
 275                 280                 285

(2) INFORMATION FOR SEQ ID NO:168:

(i) SEQUENCE CHARACTERISTICS:
        (A) LENGTH: 290 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:168:

Met Ala Ser Pro Ala Pro Pro Ala Cys Asp Leu Arg Val Leu Ser Lys
1                5                  10                  15

Leu Leu Arg Asp Ser His Val Leu His Ser Arg Leu Ser Gln Cys Pro
                 20                  25                  30

Glu Val His Pro Leu Pro Thr Pro Val Leu Leu Pro Ala Val Asp Phe
             35                  40                  45

Ser Leu Gly Glu Trp Lys Thr Gln Met Glu Glu Thr Lys Ala Gln Asp
 50                  55                  60

Ile Leu Gly Ala Val Thr Leu Leu Glu Gly Val Met Ala Ala Arg
 65                  70                  75                  80

Gln Gln Leu Gly Pro Thr Cys Leu Ser Ser Leu Leu Gly Gln Leu Ser
                 85                  90                  95
```

Gly Gln Val Arg Leu Leu Leu Gly Ala Leu Gln Ser Leu Leu Gly Thr
                100                 105                 110

Gln Leu Pro Pro Gln Gly Arg Thr Thr Ala His Lys Asp Pro Asn Ala
        115                 120                 125

Ile Phe Leu Ser Phe Gln His Leu Leu Arg Gly Lys Val Arg Phe Leu
        130                 135                 140

Met Leu Val Gly Gly Ser Thr Leu Cys Val Arg Glu Phe His Ala Tyr
145                 150                 155                 160

Val Glu Gly Gly Gly Ser Pro Gly Gly Ser Gly Gly Ser
                165                 170                 175

Asn Met Ala Asn Cys Ser Ile Met Ile Asp Glu Ile Ile His His Leu
        180                 185                 190

Lys Arg Pro Pro Asn Pro Leu Leu Asp Pro Asn Asn Leu Asn Ser Glu
        195                 200                 205

Asp Met Asp Ile Leu Met Glu Arg Asn Leu Arg Thr Pro Asn Leu Leu
        210                 215                 220

Ala Phe Val Arg Ala Val Lys His Leu Glu Asn Ala Ser Gly Ile Glu
225                 230                 235                 240

Ala Ile Leu Arg Asn Leu Gln Pro Cys Leu Pro Ser Ala Thr Ala Ala
                245                 250                 255

Pro Ser Arg His Pro Ile Ile Ile Lys Ala Gly Asp Trp Gln Glu Phe
                260                 265                 270

Arg Glu Lys Leu Thr Phe Tyr Leu Val Thr Leu Glu Gln Ala Gln Glu
        275                 280                 285

Gln Gln
   290

(2) INFORMATION FOR SEQ ID NO:169:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:169:

ACGTCCATGG CNTCNCCNGC NCCNCCTGCT TGTGACCTCC GAGTC                45

(2) INFORMATION FOR SEQ ID NO:170:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:170:

AATAGCTGAA TTCTTACCCT TCCTGAGACA GATT                            34

(2) INFORMATION FOR SEQ ID NO:171:

(i) SEQUENCE CHARACTERISTICS:
        (A) LENGTH: 33 base pairs
        (B) TYPE: nucleic acid
        (C) STRANDEDNESS: single (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:171:

TGACAAGCTT ACCTGACGCA GAGGGTGGAC CCT                                    33

(2) INFORMATION FOR SEQ ID NO:172:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:172:

ATGCACGAAT TCCCTGACGC AGAGGGTGGA                                        30

(2) INFORMATION FOR SEQ ID NO:173:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:173:

AATTCCATGC ATAC                                                         14

(2) INFORMATION FOR SEQ ID NO:174:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:174:

GGTACGTATG                                                              10

(2) INFORMATION FOR SEQ ID NO:175:

(i) SEQUENCE CHARACTERISTICS:
      (A) LENGTH: 561 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:175:

ATGGCTCCAG TACCACCAGG TGAAGATTCC AAAGATGTGG CCGCCCCACA CAGACAGCCA        60

CTCACCTCTT CAGAACGAAT TGACAAACAA ATTCGGTACA TCCTCGACGG GATATCAGCC       120

CTGAGAAAGG AGACATGTAA CAAGAGTAAC ATGTGTGAAA GCAGCAAAGA GGCGCTAGCA       180

GAAAACAACC TGAACCTTCC AAAGATGGCT GAAAAGATG GATGCTTCCA ATCCGGATTC        240

AATGAGGAGA CTTGCCTGGT GAAAATCATC ACTGGTCTTT TGGAGTTTGA GGTATACCTC       300

```
GAGTACCTCC AGAACAGATT TGAGAGTAGT GAGGAACAAG CCAGAGCTGT GCAGATGTCG    360

ACAAAAGTCC TGATCCAGTT CCTGCAGAAA AAGGCAAAGA ATCTAGATGC AATAACCACC    420

CCTGACCCAA CCACAAATGC ATCCCTGCTG ACGAAGCTGC AGGCACAGAA CCAGTGGCTG    480

CAGGACATGA CAACTCATCT CATTCTGCGC AGCTTTAAGG AGTTCCTGCA GTCCAGCCTG    540

AGGGCTCTTC GGCAAATGTA G                                              561
```

(2) INFORMATION FOR SEQ ID NO:176:

(i) SEQUENCE CHARACTERISTICS:
        (A) LENGTH: 402 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:176:

```
ATGGCACCGG CTCGTTCCCC GTCCCCGTCT ACCCAGCCGT GGGAACACGT GAATGCCATC    60

CAGGAGGCCC GGCGTCTCCT GAACCTGAGT AGAGACACTG CTGCTGAGAT GAATGAAACA    120

GTAGAAGTGA TATCAGAAAT GTTTGACCTC CAGGAGCCGA CTTGCCTACA GACCCGCCTG    180

GAGCTGTACA AGCAGGGCCT GCGGGGCAGC CTCACCAAGC TCAAGGGCCC CTTGACCATG    240

ATGGCCAGCC ACTACAAGCA GCACTGCCCT CCAACCCCGG AAACTTCCTG TGCAACCCAG    300

ATTATCACCT TTGAAAGTTT CAAAGAGAAC CTGAAGGACT TCCTGCTTGT CATCCCCTTT    360

GACTGCTGGG AGCCAGTCCA GGAGTGATAA GGATCCGAAT TC                       402
```

(2) INFORMATION FOR SEQ ID NO:177:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:177:

```
ATGGCTACAC CATTAGGCCC TGCCAGCTCC CTGCCCCAGA GCTTCCTGCT CAAGTGCTTA    60

GAGCAAGTGA GGAAGATCCA GGGCGATGGC GCAGCGCTCC AGGAGAAGCT GTGTGCCACC    120

TACAAGCTGT GCCACCCCGA GGAGCTGGTG CTGCTCGGAC ACTCTCTGGG CATCCCCTGG    180

GCTCCCCTGA GCTCCTGCCC CAGCCAGGCC CTGCAGCTGG CAGGCTGCTT GAGCCAACTC    240

CATAGCGGCC TTTTCCTCTA CCAGGGGCTC CTGCAGGCCC TGGAAGGGAT ATCCCCCGAG    300

TTGGGTCCCA CCTTGGACAC ACTGCAGCTG GACGTCGCCG ACTTTGCCAC CACCATCTGG    360

CAGCAGATGG AAGAACTGGG AATGGCCCCT GCCCTGCAGC CCACCCAGGG TGCCATGCCG    420

GCCTTCGCCT CTGCTTTCCA GCGCCGGGCA GGAGGGGTCC TGGTTGCTAG CCATCTGCAG    480

AGCTTCCTGG AGGTGTCGTA CCGCGTTCTA CGCCACCTTG CGCAGCCCTG ATAAGGATCC    540

GAATTC                                                               546
```

(2) INFORMATION FOR SEQ ID NO:178:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:178:

| | | | | | |
|---|---|---|---|---|---|
| ATGGCTACAC | CATTAGGACC | TGCCAGCTCC | CTGCCCCAGA | GCTTCCTGCT | CAAGTGCTTA | 60 |
| GAGCAAGTGA | GGAAGATCCA | GGGCGATGGC | GCAGCGCTCC | AGGAGAAGCT | GTGTGCCACC | 120 |
| TACAAGCTGT | GCCACCCCGA | GGAGCTGGTG | CTGCTCGGAC | ACTCTCTGGG | CATCCCCTGG | 180 |
| GCTCCCCTGA | GCTCCTGCCC | CAGCCAGGCC | CTGCAGCTGG | CAGGCTGCTT | GAGCCAACTC | 240 |
| CATAGCGGCC | TTTTCCTCTA | CCAGGGGCTC | CTGCAGGCCC | TGGAAGGGAT | ATCCCCCGAG | 300 |
| TTGGGTCCCA | CCTTGGACAC | ACTGCAGCTG | GACGTCGCCG | ACTTTGCCAC | CACCATCTGG | 360 |
| CAGCAGATGG | AAGAACTGGG | AATGGCCCCT | GCCCTGCAGC | CCACCCAGGG | TGCCATGCCG | 420 |
| GCCTTCGCCT | CTGCTTTCCA | GCGCCGGGCA | GGAGGGGTCC | TGGTTGCTAG | CCATCTGCAG | 480 |
| AGCTTCCTGG | AGGTGTCGTA | CCGCGTTCTA | CGCCACCTTG | CGCAGCCCTG | ATAAGGATCC | 540 |
| GAATTC | | | | | | 546 |

(2) INFORMATION FOR SEQ ID NO:179:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:179:

| | | | | | |
|---|---|---|---|---|---|
| ATGGCTACAC | CATTGGGCCC | TGCCAGCTCC | CTGCCCCAGA | GCTTCCTGCT | CAAGTCTTTA | 60 |
| GAGCAAGTGA | GGAAGATCCA | GGGCGATGGC | GCAGCGCTCC | AGGAGAAGCT | GTGTGCCACC | 120 |
| TACAAGCTGT | GCCACCCCGA | GGAGCTGGTG | CTGCTCGGAC | ACTCTCTGGG | CATCCCCTGG | 180 |
| GCTCCCCTGA | GCTCCTGCCC | CAGCCAGGCC | CTGCAGCTGG | CAGGCTGCTT | GAGCCAACTC | 240 |
| CATAGCGGCC | TTTTCCTCTA | CCAGGGGCTC | CTGCAGGCCC | TGGAAGGGAT | ATCCCCCGAG | 300 |
| TTGGGTCCCA | CCTTGGACAC | ACTGCAGCTG | GACGTCGCCG | ACTTTGCCAC | CACCATCTGG | 360 |
| CAGCAGATGG | AAGAACTGGG | AATGGCCCCT | GCCCTGCAGC | CCACCCAGGG | TGCCATGCCG | 420 |
| GCCTTCGCCT | CTGCTTTCCA | GCGCCGGGCA | GGAGGGGTCC | TGGTTGCTAG | CCATCTGCAG | 480 |
| AGCTTCCTGG | AGGTGTCGTA | CCGCGTTCTA | CGCCACCTTG | CGCAGCCCTG | ATAAGGATCC | 540 |
| GAATTC | | | | | | 546 |

(2) INFORMATION FOR SEQ ID NO:180:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:180:

| | | | | | |
|---|---|---|---|---|---|
| ATGGCGTCTC | CGGCGCCGCC | TGCTTGTGAC | CTCCGAGTCC | TCAGTAAACT | GCTTCGTGAC | 60 |
| TCCCATGTCC | TTCACAGCAG | ACTGAGCCAG | TGCCCAGAGG | TTCACCCTTT | GCCTACACCT | 120 |
| GTCCTGCTGC | CTGCTGTGGA | CTTTAGCTTG | GGAGAATGGA | AAACCCAGAT | GGAGGAGACC | 180 |
| AAGGCACAGG | ACATTCTGGG | AGCAGTGACC | CTTCTGCTGG | AGGGAGTGAT | GGCAGCACGG | 240 |

```
GGACAACTGG GACCCACTTG CCTCTCATCC CTCCTGGGGC AGCTTTCTGG ACAGGTCCGT    300

CTCCTCCTTG GGGCCCTGCA GAGCCTCCTT GGAACCCAGC TTCCTCCACA GGGCAGGACC    360

ACAGCTCACA AGGATCCCAA TGCCATCTTC CTGAGCTTCC AACACCTGCT CCGAGGAAAG    420

GTGCGTTTCC TGATGCTTGT AGGAGGGTCC ACCCTCTGCG TCAGG                    465

(2) INFORMATION FOR SEQ ID NO:181:

(i) SEQUENCE CHARACTERISTICS:
        (A) LENGTH: 143 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:181:

CCTGTCAACC CGGGCGGCGG CTCTGGTGGT GGTTCTGGTG GCGGCTCTGA GGGTGGCGGC     60

TCTGAGGGTG GCGGTTCTGA GGGTGGCGGC TCTGAGGGTG GCGGTTCCGG TGGCGGCTCC    120

GGTTCCGGTA ACATGTATTA TGA                                           143

(2) INFORMATION FOR SEQ ID NO:182:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:182:

ATCGTCTGAC CTCCCGGGCC TCCTGTCAAT GCTGGCGGCG GCTCTGGTGG TGGTTCTGGT     60

GGCGGCTCTG AGGGTGGCGG CTCTGAGGGT GGCGGTTCTG AGGGTGGCGG CTCTGAGGGT    120

GGCGGTTCCG GTGGCGGCTC CGGTTCCGGT GATTTTGATT ATGAAAACAT GTCAAACGCT    180

(2) INFORMATION FOR SEQ ID NO:183:

(i) SEQUENCE CHARACTERISTICS:
        (A) LENGTH: 858 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:183:

ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAATCGA GGGAAGGATT    360

TCCCCGGGTG GTGGTTCTGG CGGCGGCTCC AACATGGCGT CTCCGGCGCC GCCTGCTTGT    420

GACCTCCGAG TCCTCAGTAA ACTGCTTCGT GACTCCCATG TCCTTCACAG CAGACTGAGC    480

CAGTGCCCAG AGGTTCACCC TTTGCCTACA CCTGTCCTGC TGCCTGCTGT GGACTTTAGC    540

TTGGGAGAAT GGAAAACCCA GATGGAGGAG ACCAAGGCAC AGGACATTCT GGGAGCAGTG    600
```

```
ACCCTTCTGC TGGAGGGAGT GATGGCAGCA CGGGGACAAC TGGGACCCAC TTGCCTCTCA      660

TCCCTCCTGG GGCAGCTTTC TGGACAGGTC CGTCTCCTCC TTGGGGCCCT GCAGAGCCTC      720

CTTGGAACCC AGCTTCCTCC ACAGGGCAGG ACCACAGCTC ACAAGGATCC CAATGCCATC      780

TTCCTGAGCT TCCAACACCT GCTCCGAGGA AAGGTGCGTT TCCTGATGCT TGTAGGAGGG      840

TCCACCCTCT GCGTCAGG                                                   858

(2) INFORMATION FOR SEQ ID NO:184:

(i) SEQUENCE CHARACTERISTICS:
        (A) LENGTH: 858 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:184:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCGT CTCCGGCGCC GCCTGCTTGT      420

GACCTCCGAG TCCTCAGTAA ACTGCTTCGT GACTCCCATG TCCTTCACAG CAGACTGAGC      480

CAGTGCCCAG AGGTTCACCC TTTGCCTACA CCTGTCCTGC TGCCTGCTGT GGACTTTAGC      540

TTGGGAGAAT GGAAAACCCA GATGGAGGAG ACCAAGGCAC AGGACATTCT GGGAGCAGTG      600

ACCCTTCTGC TGGAGGGAGT GATGGCAGCA CGGGGACAAC TGGGACCCAC TTGCCTCTCA      660

TCCCTCCTGG GGCAGCTTTC TGGACAGGTC CGTCTCCTCC TTGGGGCCCT GCAGAGCCTC      720

CTTGGAACCC AGCTTCCTCC ACAGGGCAGG ACCACAGCTC ACAAGGATCC CAATGCCATC      780

TTCCTGAGCT TCCAACACCT GCTCCGAGGA AAGGTGCGTT TCCTGATGCT TGTAGGAGGG      840

TCCACCCTCT GCGTCAGG                                                   858

(2) INFORMATION FOR SEQ ID NO:185:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:185:

ATGGCGTCTC CGGCGCCGCC TGCTTGTGAC CTCCGAGTCC TCAGTAAACT GCTTCGTGAC       60

TCCCATGTCC TTCACAGCAG ACTGAGCCAG TGCCCAGAGG TTCACCCTTT GCCTACACCT      120

GTCCTGCTGC CTGCTGTGGA CTTTAGCTTG GGAGAATGGA AAACCCAGAT GGAGGAGACC      180

AAGGCACAGG ACATTCTGGG AGCAGTGACC CTTCTGCTGG AGGGAGTGAT GGCAGCACGG      240

GGACAACTGG GACCCACTTG CCTCTCATCC CTCCTGGGGC AGCTTTCTGG ACAGGTCCGT      300

CTCCTCCTTG GGGCCCTGCA GAGCCTCCTT GGAACCCAGC TTCCTCCACA GGGCAGGACC      360

ACAGCTCACA AGGATCCCAA TGCCATCTTC CTGAGCTTCC AACACCTGCT CCGAGGAAAG      420
```

```
GTGCGTTTCC TGATGCTTGT AGGAGGGTCC ACCCTCTGCG TCAGGATCGA GGGAAGGATT      480

TCCCCGGGTG GTGGTTCTGG CGGCGGCTCC AACATGGCTA ACTGCTCTAT AATGATCGAT      540

GAAATTATAC ATCACTTAAA GAGACCACCT AACCCTTTGC TGGACCCGAA CAACCTCAAT      600

TCTGAAGACA TGGATATCCT GATGAACGA AACCTTCGAA CTCCAAACCT GCTCGCATTC       660

GTAAGGGCTG TCAAGCACTT AGAAAATGCA TCAGGTATTG AGGCAATTCT TCGTAATCTC      720

CAACCATGTC TGCCCTCTGC CACGGCCGCA CCCTCTCGAC ATCCAATCAT CATCAAGGCA      780

GGTGACTGGC AAGAATTCCG GGAAAAACTG ACGTTCTATC TGGTTACCCT TGAGCAAGCG      840

CAGGAACAAC AG                                                         852
```

(2) INFORMATION FOR SEQ ID NO:186:

(i) SEQUENCE CHARACTERISTICS:
        (A) LENGTH: 870 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:186:

```
ATGGCGTCTC CGGCGCCGCC TGCTTGTGAC CTCCGAGTCC TCAGTAAACT GCTTCGTGAC       60

TCCCATGTCC TTCACAGCAG ACTGAGCCAG TGCCCAGAGG TTCACCCTTT GCCTACACCT      120

GTCCTGCTGC CTGCTGTGGA CTTTAGCTTG GGAGAATGGA AAACCCAGAT GGAGGAGACC      180

AAGGCACAGG ACATTCTGGG AGCAGTGACC CTTCTGCTGG AGGGAGTGAT GGCAGCACGG      240

GGACAACTGG GACCCACTTG CCTCTCATCC CTCCTGGGGC AGCTTTCTGG ACAGGTCCGT      300

CTCCTCCTTG GGGCCCTGCA GAGCCTCCTT GGAACCCAGC TTCCTCCACA GGGCAGGACC      360

ACAGCTCACA AGGATCCCAA TGCCATCTTC CTGAGCTTCC AACACCTGCT CCGAGGAAAG      420

GTGCGTTTCC TGATGCTTGT AGGAGGGTCC ACCCTCTGCG TCAGGGAATT CCATGCATAC      480

GTAGAGGGCG GTGGAGGCTC CCCGGGTGGT GGTTCTGGCG GCGGCTCCAA CATGGCTAAC      540

TGCTCTATAA TGATCGATGA AATTATACAT CACTTAAAGA GACCACCTAA CCCTTTGCTG      600

GACCCGAACA ACCTCAATTC TGAAGACATG GATATCCTGA TGGAACGAAA CCTTCGAACT      660

CCAAACCTGC TCGCATTCGT AAGGGCTGTC AAGCACTTAG AAAATGCATC AGGTATTGAG      720

GCAATTCTTG GTAATCTCCA ACCATGTCTG CCCTCTGCCA CGGCCGCACC CTCTCGACAT      780

CCAATCATCA TCAAGGCAGG TGACTGGCAA GAATTCCGGG AAAAACTGAC GTTCTATCTG      840

GTTACCCTTG AGCAAGCGCA GGAACAACAG                                      870
```

(2) INFORMATION FOR SEQ ID NO:187:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:187:

```
Met Ser Arg Leu Pro Val Leu Leu Leu Gln Leu Leu Val Arg Pro
1               5                   10                  15
Ala Met
```

(2) INFORMATION FOR SEQ ID NO:188:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:188:

Tyr Val Ile Glu Gly Arg Ile Ser Pro Gly Gly Gly Ser Gly Gly Gly
1               5                   10                  15

Ser Asn (2) INFORMATION FOR SEQ ID NO:189:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:189:

Tyr Val Ile Glu Gly Lys Ile Ser Pro Gly Gly Gly Ser Gly Gly Gly
1               5                   10                  15

Ser Asn (2) INFORMATION FOR SEQ ID NO:190:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:190:

Tyr Val Glu Gly Gly Gly Gly Ser Pro Gly Gly Gly Ser Gly Gly Gly
1               5                   10                  15

Ser Asn (2) INFORMATION FOR SEQ ID NO:191:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:191:

Tyr Val Ile Glu Gly Arg Ile Ser Pro Gly Glu Pro Ser Gly Pro Ile
1               5                   10                  15

Ser Thr Ile Asn Pro Ser Pro Pro Ser Lys Glu Ser His Lys Ser Pro
            20                  25                  30

Asn (2) INFORMATION FOR SEQ ID NO:192:

(i) SEQUENCE CHARACTERISTICS:
        (A) LENGTH: 33 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:192:

Tyr Val Ile Glu Gly Lys Ile Ser Pro Gly Glu Pro Ser Gly Pro Ile
1               5                   10                  15

Ser Thr Ile Asn Pro Ser Pro Pro Ser Lys Glu Ser His Lys Ser Pro
            20                  25                  30

Asn (2) INFORMATION FOR SEQ ID NO:193:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:193:

Tyr Val Glu Gly Gly Gly Gly Ser Pro Gly Glu Pro Ser Gly Pro Ile
1               5                   10                  15

Ser Thr Ile Asn Pro Ser Pro Pro Ser Lys Glu Ser His Lys Ser Pro
            20                  25                  30

Asn (2) INFORMATION FOR SEQ ID NO:194:

(i) SEQUENCE CHARACTERISTICS:
        (A) LENGTH: 49 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:194:

Tyr Val Ile Glu Gly Arg Ile Ser Pro Gly Gly Gly Ser Gly Gly Gly
1               5                   10                  15

Ser Gly Gly Gly Ser Glu Gly Gly Ser Glu Gly Gly Ser Glu
            20                  25                  30

Gly Gly Gly Ser Glu Gly Gly Gly Ser Gly Gly Gly Ser Ser Gly
            35                  40                  45

Asn (2) INFORMATION FOR SEQ ID NO:195:

(i) SEQUENCE CHARACTERISTICS:
        (A) LENGTH: 60 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:195:

Tyr Val Ile Glu Gly Arg Ile Ser Pro Gln Pro Pro Val Asn Ala Gly
1               5                   10                  15

Gly Gly Ser Gly Gly Gly Ser Gly Gly Gly Ser Glu Gly Gly Gly Ser
            20                  25                  30

-continued

```
Glu Gly Gly Gly Ser Glu Gly Gly Gly Ser Glu Gly Gly Gly Ser Gly
         35                  40                  45

Gly Gly Ser Gly Ser Gly Asp Phe Asp Tyr Glu Asn
    50              55                  60
```

(2) INFORMATION FOR SEQ ID NO:196:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:196:

```
Glu Phe His Ala Tyr Val Glu Gly Gly Gly Ser Pro Gly Gly Gly
1               5                  10                  15

Ser Gly Gly Gly Ser Asn
             20
```

(2) INFORMATION FOR SEQ ID NO:197:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA other nucleic acid
        (A) DESCRIPTION: /desc = "synthetic DNA"

(xi) SEQUENCE DESCRIPTION: SEQ ID NO:197:

```
ATGGCTCCAA TGACTCAGAC TACTTCTCTT AAGACTTCTT GGGTTAACTG CTCTAACATG      60

ATCGATGAAA TTATAACACA CTTAAAGCAG CCACCTTTGC CTTTGCTGGA CTTCAACAAC     120

CTCAATGGGG AAGACCAAGA CATTCTGATG GAAAATAACC TTCGAAGGCC AAACCTGGAG     180

GCATTCAACA GGGCTGTCAA GAGTTTACAG AATGCATCAG CAATTGAGAG CATTCTTAAA     240

AATCTCCTGC CATGTCTGCC CCTGGCCACG GCCGCACCCA CGCGACATCC AATCCATATC     300

AAGGACGGTG ACTGGAATGA ATTCCGTCGT AAACTGACCT TCTATCTGAA AACCTTGGAG     360

AACGCGCAGG CTCAACAGAC CACTCTGTCG CTAGCGATCT TTTAATAA                  408
```